US008450525B2

(12) United States Patent
Rajagopal et al.

(10) Patent No.: US 8,450,525 B2
(45) Date of Patent: May 28, 2013

(54) HISTONE DEACETYLASE INHIBITORS

(75) Inventors: Sridharan Rajagopal, Chennai (IN);
Virendra Kachhadia, Chennai (IN);
Thanasekaran Ponpandian, Chennai
(IN); Abdul Raheem Keeri, Chennai
(IN); Karnambaram Anandhan,
Chennai (IN); Sriram Rajagopal,
Bangalore (IN); Rajendran Praveen,
Corvallis, OR (US); **Prabhu
Daivasigamani**, Tirupati (IN)

(73) Assignee: Orchid Chemicals & Pharmaceuticals Limited, Chennai (IN)

( * ) Notice: Subject to any disclaimer, the term of this patent is extended or adjusted under 35 U.S.C. 154(b) by 373 days.

(21) Appl. No.: 12/734,030

(22) PCT Filed: Oct. 21, 2008

(86) PCT No.: PCT/IB2008/002799
§ 371 (c)(1),
(2), (4) Date: Jun. 3, 2010

(87) PCT Pub. No.: WO2009/053808
PCT Pub. Date: Apr. 30, 2009

(65) Prior Publication Data
US 2010/0291003 A1 Nov. 18, 2010

(30) Foreign Application Priority Data
Oct. 22, 2007 (IN) ........................... 2384/CHE/2007
Apr. 21, 2008 (IN) ............................. 980/CHE/2008

(51) Int. Cl.
*C07C 233/65* (2006.01)
*A61K 31/16* (2006.01)
(52) U.S. Cl.
USPC ........... 564/156; 564/155; 562/622; 562/623; 549/441; 544/58.4; 544/168; 546/336; 546/337; 514/227.5; 514/237.5; 514/466; 514/575; 514/616
(58) Field of Classification Search
USPC ............... 564/155, 156; 514/616, 575, 227.2, 514/237.5, 466; 544/58.5, 168; 546/336, 546/337; 549/441; 562/622, 623
See application file for complete search history.

(56) References Cited

U.S. PATENT DOCUMENTS

| 5,369,108 | A | 11/1994 | Breslow et al. |
| 6,624,197 | B1 | 9/2003 | Nag et al. |
| 2004/0077726 | A1 | 4/2004 | Watkins et al. |
| 2005/0038125 | A1 | 2/2005 | Smit et al. |
| 2008/0139673 | A1 | 6/2008 | Hu et al. |

FOREIGN PATENT DOCUMENTS

| WO | WO 98/55449 | 12/1998 |
| WO | WO 01/38322 A1 | 5/2001 |
| WO | WO 2004/035525 A1 | 4/2004 |
| WO | WO 2005/034880 A2 | 4/2005 |
| WO | WO 2005/097747 A1 | 10/2005 |
| WO | WO 2005/121073 A1 | 12/2005 |
| WO | WO 2006/025683 A1 | 3/2006 |
| WO | WO 2008/021944 A2 | 2/2008 |
| WO | WO 2008/054154 A1 | 5/2008 |

OTHER PUBLICATIONS

Wolff, M.E. "Burger's Medicinal Chemistry 4th Ed. Part I", Wiley: New York, 1979, 336-337.*
Wolff, Manfred E. "Burger's Medicinal Chemistry, 5ed, Part I", John Wiley & Sons, 1995, pp. 975-977.*
Banker (Modern Pharmaceutics) Banker, G.S. et al, "Modern Pharmaceutics, 3ed.", Marcel Dekker, New York, 1996, pp. 451 and 596.*
West, Anthony R., Solid State Chemistry and its Applications, Wiley, New York, 1988, pp. 358 & 365.*
Bernard Testa "Predicting drug metabolism: Concepts and challenges" Pure and Applied Chemistry 2004, vol. 76, No. 5, pp. 907-914.*
Carter et al., Chemotherapy of Cancer, second edition, John Wiley & Sons, N.Y., N.Y., 1981, pp. 362-365.*
Paris et al., "Histone Deacetylase Inhibitors: From Bench to Clinic," *Journal of Medicinal Chemistry*, Mar. 27, 2008, pp. 1505-1529, vol. 51—No. 6.
Mosmann, "Rapid Colorimetic Assay for Cellular Growth and Survival: Application to Proliferation and Cytotoxicity Assays," *Journal of Immunological Methods*, 1983, pp. 55-63, vol. 65.
Marks et al., "Histone Deacetylase Inhibitors: Inducers of Differentiation of Apoptosis of Transformed Cells," *Journal of the National Cancer Institute*, Aug. 2, 2000, pp. 1210-1215, vol. 92—No. 15.
Monks et al., "Feasibility of a High-Flux Anticancer Drug Screen Using a Diverse Panel of Cultured Human Tumor Cell Lines," *Journal of National Cancer Institute*, Jun. 5, 1991, pp. 757-766, vol. 83—No. 11.
Wegener et al., "Improved fluorogenic histone deacetylase assay for high-throughput-screening applications," *Analytical Biochemistry*, 2003, pp. 202-208, vol. 321.
Rodrigues, "Use of In Vitro Human Metabolism Studies in Drug Development," *Biochemical Pharmacology*, 1994, pp. 2147-2156, vol. 48—No. 12.

(Continued)

*Primary Examiner* — Shailendra Kumar
(74) *Attorney, Agent, or Firm* — Oliff & Berridge, PLC

(57) ABSTRACT

Novel compounds of the general formula (I), having histone deacetylase (HDAC) inhibiting enzymatic activity, their derivatives, analogs, tautomeric forms, stereoisomers, polymorphs, hydrates, solvates, intermediates, pharmaceutically acceptable salts, pharmaceutical compositions, metabolites and prodrugs thereof. The present invention more particularly provides novel compounds of the general formula (I). Also included is a method for treatment of cancer, psoriasis, proliferative conditions and conditions mediated by HDAC, in a mammal comprising administering an effective amount of a novel compound of formula (I).

(I)

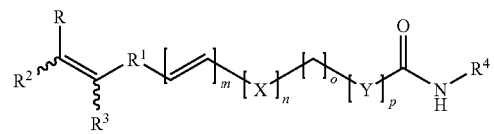

15 Claims, 1 Drawing Sheet

OTHER PUBLICATIONS

May 11, 2010 Search Report issued in International Patent Application No. PCT/IB2008/002799.
May 11, 2010 Written Opinion issued in International Patent Application No. PCT/IB2008/002799.

Greetje Elaut et al., "The Pharmaceutical Potential of Histone Deacetylase Inhibitors", *Current Pharmaceutical Design*, 2007, 13, 2584-2620.

* cited by examiner

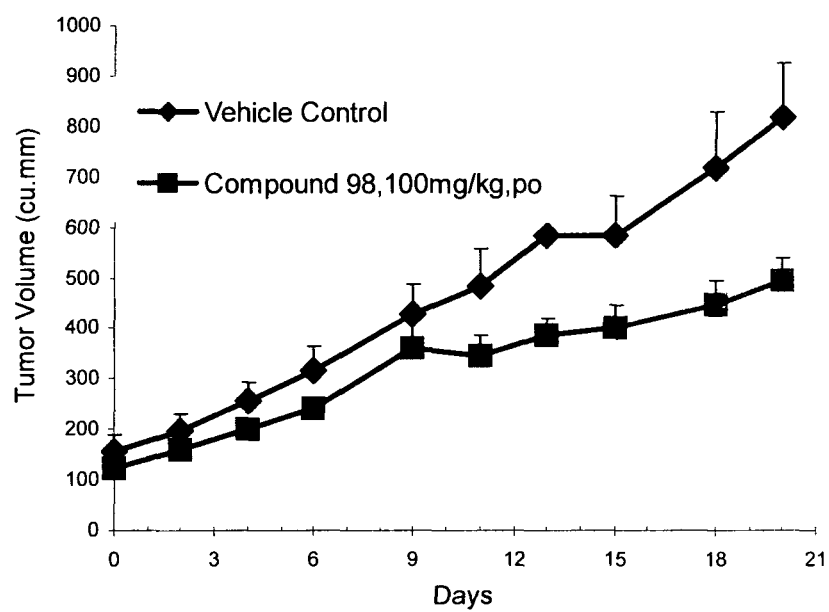
Xenograft study: In vivo anti-tumor effect of Compound 105 on HCT116 xenograft in SCID mice

HISTONE DEACETYLASE INHIBITORS

This application is a 371 of PCT/IB2008/002799, filed Oct. 21, 2008.

FIELD

Described are compounds of the formula (I), their derivatives, analogs, tautomeric forms, stereoisomers, geometrical isomers, polymorphs, hydrates, solvates, intermediates, pharmaceutically acceptable salts, pharmaceutical compositions, metabolites and prodrugs thereof.

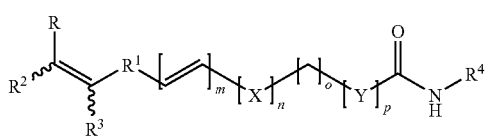

Described herein is the process for the preparation of the above said novel stilbene like compounds of the formula (I), their derivatives, analogs, stereoisomers, polymorphs, hydrates, solvates, pharmaceutically acceptable salts, pharmaceutical compositions, metabolites and prodrugs thereof.

The compounds described herein are inhibitors of Histone deacetylase (HDAC) and also arrest cell growth in neoplastic cells, thereby inhibiting proliferation. They can be used as therapeutic agents for diseases that are involved in cellular growth such as malignant tumors, autoimmune diseases, skin diseases, infections etc.

BACKGROUND

Transcriptional regulation is a major event in cell differentiation, proliferation and apoptosis. Transcriptional activation of a set of genes determines cell destination and for this reason transcription is tightly regulated by a variety of factors. One of its regulatory mechanisms involved in the process is an alteration in the tertiary structure of DNA, which affects transcription factors to their target DNA regiments. Nucleosomal integrity is regulated by the acetylating status of the core histone, with the result being permissiveness to transcription.

The regulations of transcription factor are thought to involve by changes in the structure of chromatin. Changing its affinity of histone proteins for coiled DNA in the nucleosome alters the structure of chromatin. Hypoacetylated histones are believed to have greater affinity to the DNA and form a tightly bound DNA-histone complex and render the DNA inaccessible to transcriptional regulation. The acetylating status of the histone is governed by the balance activities of the histone acetyl transferase (HAT) and histone deacetylase (HDAC).

The first isolation of histone deacetylase was described in 1964 from crude nuclear extracts of cells, but the molecular characterization of isoforms of the enzyme has been achieved recently. Inhibitors of histone deacetylase (HDACs) are zinc hydrolases responsible for the deacetylation of N-acetyl lysine residues of histone and non-histone protein substrates. Human HDACs are classified into two distinct classes, the HDACs and sirtuins. The HDACs are divided into two subclasses based on their similarity to yeast histone deacetylases, RPD 3 (class I includes HDAC 1, 2, 3, 8, and 11) and Hda 1 (class II includes HDAC 4, 6, 7, 9, and 10). All of the HDACs have a highly conserved zinc dependent catalytic domain. There is growing evidence that the acetylation state of proteins and thus the HDAC enzyme family plays a crucial role in the modulation of a number of biological processes, including transcription and cell cycle.

Recently, HDAC inhibitors have been found to arrest growth and apoptosis in several types of cancer cells, including colon cancer, t-cell lymphoma and erythroleukemic cells (M. Paris, et. al., *J. Med. Chem.*, 2008, 51, 1505-1529).

HDAC inhibitor MG3290 was found to be a potent, fungal selective potentiator of several azole antifungals in *Aspergillus* and *Candida* species including *C. glabrata* and also it was found to potentiate azole resistant *C-glabrata* mutant (WO 2008/021944 and US 2008/0139673).

Given that apoptosis is a crucial factor for cancer progression, HDAC inhibitors are promising reagents for cancer therapy as effective inducers of apoptosis.

Recently, suberoylanilide hydroxamic acid (SAHA) was launched as an antitumor agent for treating cutaneous T-cell lymphoma (CTCL) and is a known HDAC inhibitor. Several structural classes of HDAC inhibitors have been identified and are reviewed in Marks, P. A. et al., *J. Natl. Cancer Inst.*, 2000, 92, 1210-1215. More specifically WO 98/55449 and U.S. Pat. No. 5,369,108 patents report alkanoyl hydroxamates with HDAC inhibitory activity. Other compounds that are able to inhibit HDAC activity are Trichostatin A (TSA), PXD101, Tropoxin (TPX), Sodium butyrate (NaB), Sodium valproate (VPA), Cyclic hydroxamic acid containing peptides (CHAPs), Depsipeptide FK-228, MGCD0103 and MS-275 can derepress these genes, resulting in antiproliferative effects in vitro and anti tumor effects in vivo.

1) WO 2001038322 discloses the compounds and methods for inhibiting histone deacetylase enzymatic activity and have the following formulas I and II.

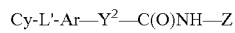

Cy-L'-Ar—Y$^2$—C(O)NH—Z      I

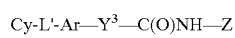

Cy-L'-Ar—Y$^3$—C(O)NH—Z      II wherein, Cy is cycloalkyl, aryl, heteroaryl, or heterocyclyl, any of which may be optionally substituted; L$^2$ is $C_1$-$C_6$ saturated alkylene or $C_1$-$C_6$ alkenylene, wherein the alkylene or alkenylene optionally may be substituted: Ar is arylene, wherein said arylene optionally may be additionally substituted. Y$^2$ is a chemical bond or a straight- or branched-chain saturated alkylene, which may be optionally substituted; Z is selected from the group consisting of anilinyl, pyridyl, thiadiazolyl, and —O-M, M being H. L$^3$ is selected from the group consisting of $C_1$-$C_6$ alkylene or $C_1$-$C_6$ alkenylene, wherein the alkylene or alkenylene optionally may be substituted; Y$^3$ is $C_{2-3}$ alkenylene or $C_{2-3}$ alkynylene;

2) U.S. Pat. No. 6,624,197 B1 discloses a class of diphenylethylenes of the formula A,

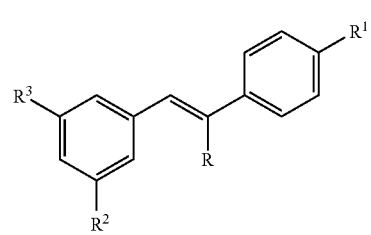

wherein, R is hydrogen or —CO$_2$Z, Z is hydrogen or a cation; and R$^1$, R$^2$ and R$^3$ are each independently H, —OH or —OR$^4$, wherein R$^4$ is linear or branched alkyl of 1-12 carbon atoms; with the condition that when R is hydrogen and R$^2$=R$^3$=

OMe, then $R^1$ is not —OH. The configuration around the double bond may be E/Z. A class of styrenes of the formula B is also provided;

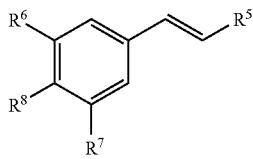

B wherein, $R^5$ is hydrogen or methyl; $R^6$ and $R^7$ are independently hydrogen or OMe; $R^8$ is hydrogen or hydroxy. The configuration around the double bond may be E/Z. Pharmaceutical compositions of compounds of the formula A or B are provided for the treatment of diabetes comprising of therapeutically effective amount of the compounds in a physiologically acceptable carrier. A method of treating diabetes is also provided comprising a step of orally administering to a subject suffering from a diabetic condition a therapeutically effective amount of a compound of formula A or B.

3) US 20050038125 describes a method for the treatment and/or prevention of disorders with elevated $PGE_2$ (such as arthritis, fybromyalgia and pain) and/or $LTB_4$ levels (such as asthma, allergy, arthritis, fybromyalgia and inflammation), comprising administering to a mammal an effective amount of pterostilbene component (PS component), a pharmaceutically acceptable salt of PS component or a precursor of PS component, wherein the PS component has the formula C.

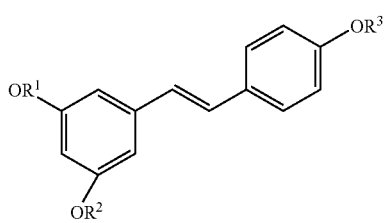

C

In which $R^1$, $R^2$ and $R^3$ are independently selected from hydrogen, $C_{1-50}$ hydrocarbyl, $C_{1-50}$ substituted hydrocarbyl, $C_{1-50}$ heterohydrocarbyl, $C_{1-50}$ substituted heterohydrocarbyl; and wherein at least one of $R^1$ and $R^2$ is not hydrogen.

4) US 2004/0077726 discloses certain active carbamic acid compounds, which inhibit HDAC activity and have the following formula D,

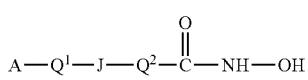

D wherein A is an aryl group; $Q^1$ is a covalent bond or an aryl leader group; J is a sulfonamide linkage selected from: —S(=O)$_2$NR$^1$— and —NR$^1$S(=O)$_2$—; $R^1$ is a sulfonamido substituent; and $Q^2$ is an acid leader group; with the proviso that if J is —S(=O)$_2$NR$^1$—, then $Q^1$ is an aryl leader group; and pharmaceutically acceptable salts, solvates, amides, esters, ethers, chemically protected forms and prodrugs thereof. Pharmaceutical compositions comprising such compounds, and their use to inhibit proliferative conditions are described. Compounds of formula E, wherein $Q^1$ is a covalent bond, J is —NR$^1$SO$_2$—, $Q^2$ is phenylene-meta-trans-ethylene are also described. $R^B$ represents fluoro, chloro, methyl, ethyl, isopropyl, t-butyl, trifluoromethyl, hydroxy, methoxy, ethoxy, isopropoxy, methylthio, amino, dimethylamino, diethylamino, morpholino, acetamido, nitro and phenyl. m is an integer from 0 to 4.

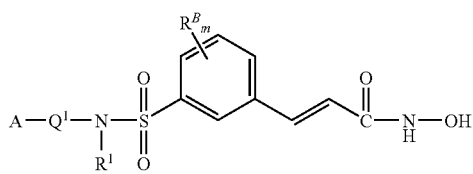

E

5) WO 2008/054154 discloses a napthalenyloxypropenyl derivative as HDAC inhibitors of the formula 1a-1d wherein $R^1$ is substituted or unsubstituted alkyl groups with one or more substituents.

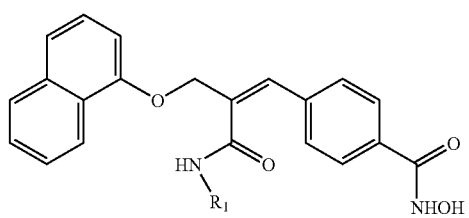

1a

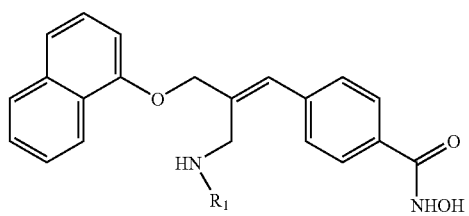

1b

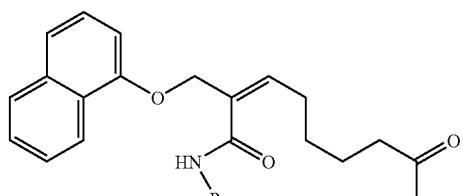

1c

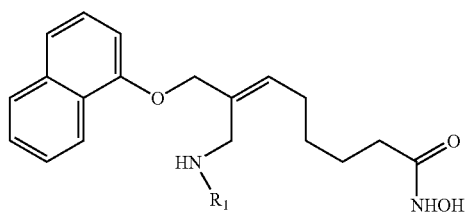

1d

SUMMARY

Novel substituted HDAC inhibitors of the formula (I),

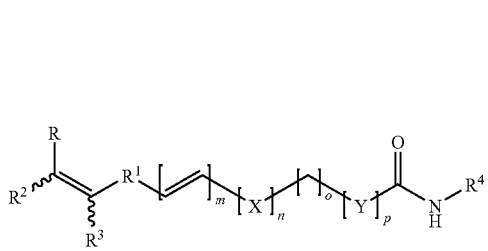

their derivatives, analogs, tautomeric forms, stereoisomers, polymorphs, solvates, intermediates, pharmaceutically acceptable salts, pharmaceutical compositions, metabolites and prodrugs thereof, wherein, the configuration around the double bonds may be E/Z;

R represents substituted or unsubstituted groups selected from aryl, cycloalkyl, heteroaryl, arylalkyl, arylalkenyl, arylalkynyl, heterocyclyl, heteroarylalkyl, heteroarylalkenyl and heteroarylalkynyl;

$R^1$ represents substituted or unsubstituted groups selected from aryl and heteroaryl groups;

$R^2$ and $R^3$ independently represents hydrogen, alkyl, —COOR$^5$, —CONR$^5$R$^6$, —CH$_2$NR$^5$R$^6$, —CH$_2$CH$_2$NR$^5$R$^6$, —CH$_2$CH$_2$OR$^5$, —CH$_2$OR$^5$, —CH$_2$OCONR$^5$R$^6$ and —CH$_2$NR$^5$COR$^6$; wherein when one of $R^2$ or $R^3$ is hydrogen or unsubstituted alkyl, the other is neither of hydrogen nor of unsubstituted alkyl.

$R^5$ and $R^6$ independently represents hydrogen, substituted or unsubstituted groups selected from alkyl, cycloalkyl, heterocyclyl, aryl, arylalkyl, arylalkenyl, arylalkynyl, heteroaryl, heteroarylalkyl, heteroarylalkenyl and heteroarylalkynyl or $R^5$ or $R^6$ may be combined to form 3-8 membered ring having 0-2 heteroatoms such as N, O or S;

$R^4$ represents OR$^7$, aryl, ortho substituted aniline, amino aryl and amino heteroaryl, which may be further substituted; wherein, $R^7$ represents hydrogen, —COR$^8$, substituted or unsubstituted groups selected from alkyl, cycloalkyl, aryl, heteroaryl and heterocyclyl; wherein, $R^8$ represents substituted or unsubstituted groups selected from alkyl, aryl, heteroaryl and heterocyclyl; X represents —O—, —NR$^7$—, —CONR$^7$—, —NR$^7$SO$_2$—, —SO$_2$NR$^7$—, —SO$_2$O—, O—SO$_2$—, —CH$_2$NR$^7$—, —NR$^7$CONR$^7$— and —NR$^7$CO—;

Y represents aryl, arylalkenyl and heteroaryl;

m is an integer from 0-3; n is an integer from 0-1; o is an integer from 0-7 and p is an integer from 0-1.

with the proviso that, if n, o and p=0, then m=0-1; and with the proviso that, if n=1, o=3-7 and p=0, then m=0-1; and with the proviso that, if n, o and p=1, then m=0-1.

BRIEF DESCRIPTION OF THE DRAWING

FIG. 1 shows the efficacy of compound 105 in HCT-116 xenograft model.

DETAILED DESCRIPTION

Novel compounds of the formula (I),

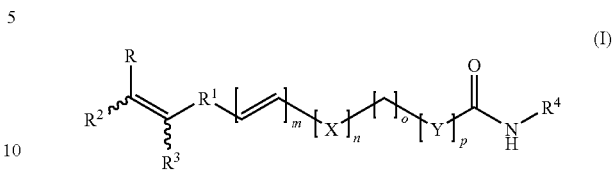

their derivatives, analogs, tautomeric forms, stereoisomers, polymorphs, solvates, intermediates, pharmaceutically acceptable salts, pharmaceutical compositions, metabolites and prodrugs thereof, wherein the configuration around the double bonds may be E/Z;

R represents substituted or unsubstituted groups selected from aryl, cycloalkyl, heteroaryl, arylalkyl, arylalkenyl, arylalkynyl, heterocyclyl, heteroarylalkyl, heteroarylalkenyl and heteroarylalkynyl;

$R^1$ represents substituted or unsubstituted groups selected from aryl and heteroaryl;

$R^2$ and $R^3$ independently represents hydrogen, alkyl, —COOR$^5$, —CONR$^5$R$^6$, —CH$_2$NR$^5$R$^6$, —CH$_2$CH$_2$NR$^5$R$^6$, —CH$_2$CH$_2$OR$^5$, —CH$_2$OR$^5$, —CH$_2$OCONR$^5$R$^6$ and —CH$_2$NR$^5$COR$^6$; wherein when one of $R^2$ or $R^3$ is hydrogen or unsubstituted alkyl the other is neither of hydrogen nor of unsubstituted alkyl.

$R^5$ and $R^6$ independently represents hydrogen, substituted or unsubstituted groups selected from alkyl, cycloalkyl, heterocyclyl, aryl, arylalkyl, arylalkenyl, arylalkynyl, heteroaryl, heteroarylalkyl, heteroarylalkenyl and heteroarylalkynyl; or $R^5$ and $R^6$ may be combined to form 3-8 membered saturated or unsaturated ring having 0-2 hetero atoms such as N, O or S;

$R^4$ represents OR$^7$, aryl, ortho substituted aniline, amino aryl and amino heteroaryl, which may be further substituted; wherein, $R^7$ represents hydrogen, —COR$^8$, optionally substituted alkyl, cycloalkyl, aryl, heteroaryl and heterocyclyl; wherein, $R^8$ represents optionally substituted alkyl, aryl, heteroaryl and heterocyclyl;

X represents —O—, —NR$^7$—, —CONR$^7$—, —NR$^7$SO$_2$—, —SO$_2$NR$^7$—, —SO$_2$O—, O—SO$_2$—, —CH$_2$NR$^7$—, —NR$^7$CONR$^7$— and —NR$^7$CO—;

Y represents aryl, arylalkenyl and heteroaryl;

m is an integer from 0-3; n is an integer from 0-1; o is an integer from 0-7 and p is an integer from 0-1.

when the groups R, $R^1$, $R^5$, $R^6$, $R^7$ and $R^8$ are substituted, the substituents which may be one or more selected from halogens such as fluorine, chlorine, bromine, iodine; hydroxy; nitro; cyano; oxo (=O); thioxo (=S); azido; nitroso; amino; hydrazino; formyl; alkyl; alkoxy; aryl; haloalkyl group such as trifluoromethyl, tribromomethyl and trichloromethyl; haloalkoxy comprising —OCH$_2$Cl; arylalkoxy comprising benzyloxy and phenylethoxy; cycloalkyl; —O-cycloalkyl; aryl; alkoxy; heterocyclyl; heteroaryl; alkylamino; —O—CH$_2$-cycloalkyl; —COOR$^a$; —C(O)R$^b$; —C(S)R$^a$; —C(O)NR$^2$R$^b$; —NR$^a$C(O)NR$^b$R$^c$; —N(R$^a$) SOR$^b$; —N(R$^a$)SO$_2$R$^b$; —NR$^a$C(O)OR$^b$; —NR$^a$R$^b$; —NR$^a$C(O)R$^b$—; NR$^a$C(S)R$^b$—; —SONR$^a$R$^b$—; —SO$_2$NR$^a$R$^b$—; —OR$^a$; —OR$^a$C(O)OR$^b$—; —OC(O) NR$^a$R$^b$; OC(O)R$^a$; —OC(O)NR$^a$R$^b$—; —R$^a$NR$^b$R$^c$; —R$^a$OR$^b$—; —SR$^a$; —SOR$^a$ and —SO$_2$R$^a$; R$^a$, R$^b$ and R$^c$ each independently represents hydrogen atom; substituted or unsubstituted groups selected from alkyl; aryl; arylalkyl; cycloalkyl; heterocyclyl; heteroaryl and hetroarylalkyl;

The substituents which in turn are further substituted by halogens such as fluorine, chlorine, bromine and iodine;

hydroxy; nitro; cycloalkyl; cyano; azido; nitroso, amino, hydrazino, formyl; alkyl; haloalkyl group such as trifluoromethyl and tribromoethyl;

with the proviso that, if n, o and p=0, then m=0-1; and
with the proviso that, if n=1, o=3-7 and p=0, then m=0-1; and
with the proviso that, if n, o and p=1, then m=0-1.

The term "alkyl" refers to straight or branched aliphatic hydrocarbon groups having the specified number of carbon atoms, which are attached to the rest of the molecule by a single atom. Examples of such alkyl groups include but are not limited to, methyl, ethyl, n-propyl, isopropyl, butyl, isobutyl, t-butyl, pentyl, hexyl, heptyl and octyl.

The term "aryl" refers to aromatic radicals having 6 to 14 carbon atoms such as phenyl, naphthyl, biphenyl, indanyl, substituted or unsubstituted arylene group such as phenylene, biphenylene, naphthylene, anthracenylene, phenathrylene and indanylene.

The term "arylalkyl" refers to an aryl group directly bonded to an alkyl group, examples of such alkyl groups include but are not limited to, benzyl and phenylethyl.

The term "heterocyclyl" refers to a stable 3- to 15 membered rings radical, which consists of carbon atoms and from one to five heteroatoms selected from nitrogen, phosphorus, oxygen and sulfur. For purposes of this invention the heterocyclic ring radical may be monocyclic, bicyclic or tricyclic ring systems, and the nitrogen, phosphorus, carbon, oxygen or sulfur atoms, in the heterocyclic ring radical may be optionally oxidized to various oxidation states. In addition, the nitrogen atom may be optionally quaternized; and the ring radical may be partially or fully saturated. Examples of such heterocyclic ring radicals include but are not limited to, azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, qunioxalinyl, quinolinyl, isoquinolinyl, tetrazolyl, imidazolyl, tetrahydroisoquinolyl, piperidinyl, piperazinyl, homopiperazinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, triazolyl, indanyl, isoxazolyl, isoxazolidinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, thienyl, morpholinyl, thiomorpholinyl, thiamorpholinyl sulfoxide, furyl, tetrahydrofuryl, tetrahydropyranyl, chromanyl and isochromanyl. The heterocyclyl ring radical may be attached to the main structure at any heteroatom or carbon atom that results in the creation of a stable structure.

The term "heteroaryl" refers to an aromatic heterocyclic ring radical as defined above. The heteroaryl ring radical may be attached to the main structure at any heteroatom or carbon atom that results in the creation of stable structure.

The term "heteroarylalkyl" refers to a heteroaryl ring radical as defined above directly bonded to an alkyl group. The heteroarylalkyl radical may be attached to the main structure at any carbon atom from an alkyl group.

The term "cycloalkyl" refers to non-aromatic mono or polycyclic ring system of about 3 to 12 carbon atoms. Examples of cycloalkyl groups include but are not include to cyclopropyl, cyclobutyl, cyclopentyl, cyclohexyl, cyclooctanyl and examples of polycyclic rings include perhydronaphthyl, adamantyl, and norbonyl groups, bridged cyclic groups or spirobicyclic groups e.g Spiro[4.4]-non-2-yl.

The term "alkenyl" refers to an aliphatic hydrocarbon group containing a carbon-carbon double bond and which may be straight or branched chain having about 2 to 10 carbon atoms, and examples of alkenyl groups include but are not include to, ethenyl, 1-propenyl, 2-propenyl, iso-propenyl, 2-methyl-1-propenyl, 1-butenyl and 2-butenyl.

The term "arylalkenyl" refers to an aromatic ring radical directly bonded to an alkenyl group. The aryl radical may be attached to the main structure at any carbon from the alkenyl group. Examples of such arylalkenyl groups include but are not limited to, phenylethenyl and phenylpropenyl.

The term "heteroarylalkenyl" refers to a heteroaryl ring radical directly bonded to an alkenyl group. The heteroaryl radical may be attached to the main structure at any carbon from the alkenyl group. Examples of such heteroarylalkenyl groups include but are not limited to, thienylpropenyl, indolylpropenyl, pyridinylethenyl and indolypropenyl.

The term "alkoxy" refers to an alkyl group attached via an oxygen linkage to the rest of the molecule. Representative examples of those groups include but are not limited to —OCH$_3$ and —OC$_2$H$_5$.

The term "aryloxy" refers to an aryl group attached via an oxygen linkage to the rest of the molecule. Representative examples of those groups include but are not limited to, —O-phenyl and —O-biphenyl.

The term "alkylamino" refers to an alkyl group as defined above attached via amino linkage to the rest of the molecule. Representative examples of those groups include but are not limited to —NHCH$_3$ and —N(CH$_3$)$_2$.

The term "alkynyl" refers to a straight or branched hydrocarbyl radicals having at least one carbon-carbon triple bond and having in the range of 2-12 carbon atoms. Representative examples of those groups include but are not limited to, ethynyl, propynyl and butynyl.

The term "arylalkynyl" refers to an aromatic ring, radical directly bonded to an alkynyl group. The aryl radical may be attached to the main structure at any carbon, from the alkynyl group.

The term "heteroarylalkynyl" refers to a heteroaryl radical directly bonded to an alkynyl group. The heteroaryl radical may be attached to the main structure at any carbon from the alkynyl group.

Furthermore, the compound of formula (I) can be its derivatives, analogs, tautomeric forms, stereoisomers, geometrical isomers, polymorphs, solvates, intermediates, pharmaceutically acceptable salts, pharmaceutical compositions, metabolites and prodrugs.

Pharmaceutically acceptable solvates may be hydrates or comprising of other solvents of crystallization such as alcohols.

The compounds described herein can be either in E or Z geometrical isomers and in some cases mixtures can also be present. In cases where two or more double bonds are present in formula 1, can give rise to more than two geometrical isomers and in these cases the invention is said to cover all the isomers.

It is understood that included in the family of compounds of formula (I) are isomeric forms including tautomers and stereoisomers (diastereoisomers, enantiomers and geometrical isomers in "E" or "Z" configurational isomer or a mixture of E and Z isomers). It is also understood that some isomeric form such as diastereomers, enantiomers and geometrical isomers can be separated by physical and/or chemical methods and by those skilled in the art.

Compounds disclosed herein may exist as single stereoisomers, racemates and or mixtures of enantiomers and or/diastereomers. All such single stereoisomers, racemates and mixtures thereof are intended to be within the scope of the subject matter described.

The phrase "pharmaceutically acceptable" refers to compounds or compositions that are physiologically tolerable and do not typically produce allergic or similar untoward reaction, including but are not limited to, gastric upset or dizziness when administered to mammal.

Pharmaceutically acceptable salts include salts derived from inorganic bases such as like Li, Na, K, Ca, Mg, Fe, Cu, Zn and Mn; salts of organic bases such as N,N'-diacetylethylenediamine, glucamine, triethylamine, choline, dicyclohexylamine, benzylamine, trialkylamine and thiamine, guanidine, diethanolamine, α-phenylethylamine, piperidine, morpholine, pyridine, hydroxyethylpyrrolidine, hydroxyethylpiperidine, and the like, ammonium or substituted ammonium salts, aluminum salts. Salts also include amino acid salts such as glycine, alanine, cystine, cysteine, lysine, arginine, phenylalanine, guanidine etc. Salts may include acid addition salts where appropriate which are sulphates, nitrates, phosphates, perchlorates, borates, hydrohalides, acetates, tartrates, maleates, citrates, succinates, palmoates, methanesulphonates, tosylates, benzoates, salicylates, hydroxynaphthoates, benzenesulfonates, ascorbates, glycerophosphates and ketoglutarates.

Described herein are prodrugs of the compound of formula (I), which on administration undergoes chemical conversion by metabolic processes before becoming active pharmacological substances. In general, such prodrugs will be functional derivatives of a compound of the invention, which are readily convertible in vivo into a compound of the invention.

"Prodrug" means a compound, which is convertible in vivo by metabolic means (that is by hydrolysis, reduction or oxidation) to a compound of formula (I). For example an ester prodrug of a compound of formula (I) containing hydroxyl group may be convertible by hydrolysis in vivo to the parent molecule.

The active compounds disclosed can also be prepared in any solid or liquid physical form, for example the compound can be in a crystalline form, in amorphous form and have any particle size. Furthermore, the compound particles may be micronized or nanoized, or may be agglomerated, particulate granules, powders, oils, oily suspensions or any other form of solid or liquid physical forms.

Described herein are also pharmaceutical compositions, containing one or more of the compounds of the general formula (I) as defined above, their derivatives, analogs, tautomeric forms, stereoisomers, polymorphs, hydrates, metabolites, prodrugs, pharmaceutically acceptable salts, pharmaceutically acceptable solvates in combination with the usual pharmaceutically employed carriers, diluents and the like, useful for the treatment of and/or proliferative disorders.

The pharmaceutical composition may be in the forms normally employed, such as tablets, capsules, powders, syrups, solutions, suspensions and the like, may contain flavorants, sweeteners etc. in suitable solid or liquid carriers or diluents, or in suitable sterile media to form injectable solutions or suspensions. The compositions may be prepared by processes known in the art. Suitable pharmaceutically acceptable carriers include solid fillers or diluents and sterile aqueous or organic solutions. The active compound will be present in such pharmaceutical compositions in the amounts sufficient to provide the desired dosage in the range as described above. Suitable routes of administration include systemic, such as orally or by parenteral administration such as subcutaneous, intramuscular, intravenous and intradermal routes. Thus for oral administration, the compounds can be combined with a suitable solid or liquid carrier or diluent to form capsules, tablets, powders, syrups, solutions, suspensions and the like. The pharmaceutical compositions, may, if desired, contain additional components such as flavorants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or alkali or alkaline earth metal salts of the compounds. The injectable solutions prepared in this manner can then be, administered intravenously, intraperitoneally, subcutaneously, or intramuscularly.

The compounds of formula (I) can also be administered as a pharmaceutical composition in a pharmaceutically acceptable carrier, preferably formulated for oral administration.

The compounds described herein may also exhibit polymorphism. This invention further includes different polymorphs of the compounds. The term polymorph refers to a particular crystalline state of a substance, having particular physical properties such as X-ray diffraction, IR spectra, melting point and the like.

This invention, in addition to the above listed compounds, is intended to encompass the use of homologs and analogs of such compounds. In this context, homologs are molecules having substantial structural similarities to the above-described compounds and analogs are molecules having substantial biological similarities regardless of structural similarities.

The term 'histone deacetylase inhibitor' or 'inhibitor of histone deacetylas' is used to identify a compound, which is capable of interacting with a histone deacetylase and inhibiting its activity, more particularly its enzymatic activity. Inhibiting histone deacetylase enzymatic activity means reducing the ability of a histone deacetylase to remove an acetyl group from a histone. Preferably, such inhibition is specific, i.e. the histone deacetylase inhibitor reduces the ability of histone deacetylase to remove an acetyl group from a histone at a concentration that is lower than the concentration of the inhibitor that is required to produce some other, unrelated biological effect.

The term 'histone deacetylase' and 'HDAC' are intended to refer to any one of a family of enzymes that remove acetyl groups from the s-amino groups of lysine residues at the N-terminus of a histone. Unless otherwise indicated by context, the term "histone" is meant to refer to any histone protein, including H1, H2A, H2B, H3, H4 and H5, from any species. Human HDAC proteins or gene products include but are not limited to, HDAC-1, HDAC-2, HDAC-3, HDAC-4, HDAC-5, HDAC-6, HDAC-7, HDAC-8, HDAC-9 and HDAC-10. The histone deacetylase can also be derived from a protozoal or fungal source.

The invention also provides a method of treatment of cancer in patient including administration of a therapeutically effective amount of a compound formula (I).

The present invention provides a method of treatment of a disorder caused by, associated with or accompanied by disruptions of cell proliferation and/or angiogenesis including administration of a therapeutically effective amount of a compound of formula (I).

The disorder is either a proliferative disorder or is selected from the group consisting of but is not limited to, cancer, inflammatory diseases/immune disorder, fibrotic diseases (e.g liver fibrosis), diabetes, autoimmune disease, chronic and acute neurodegenerative disease, Huntington's disease and infectious disease.

The compounds described herein are used in the treatment or prevention of cancer. The cancer can include solid tumors or hematologic malignancies.

The present, invention provides a method of treatment of a disorder, disease or condition that can be treated by the inhibition of HDAC enzymes including administration of therapeutically effective amount of compound of formula (I).

The invention provides a method of treatment of cancer in patient including administration of effective amount of formula (I). The cancer can be either hematologic malignancy and this form of malignancy is selected from the group consisting of B-cell lymphoma, T-cell lymphoma and leukemia. In the case of solid tumors, the tumors are selected from the group consisting of breast cancer, lung cancer, ovarian cancer, prostate cancer, head cancer, neck cancer, renal cancer, gastric cancer, colon cancer, pancreatic cancer and brain cancer.

The term "therapeutically effective amount" or "effective amount" is an amount sufficient to effect beneficial or desired results. An effective amount can be administered in one or more administrations. An effective amount is typically sufficient to palliate, ameliorate, stabilize, reverse, slow or delay the progression of the disease state.

In another aspect, the compound may be administered in combination therapy by combining the compound of formula (I) with one or more separate agents, not limited to targets such as HDAC, DNA methyltransferase, heat shock proteins (e.g. HSP90) kinase and other matrix metalloproteinases.

"Combination therapy" includes the administration of the subject compounds in further combination with other biologically active ingredients (such as, but are not limited to, different antineoplastic agent) and non-drug therapies (such as, but are not limited to, surgery or radiation treatment). The compounds described herein can be used in combination with other pharmaceutically active compounds, preferably, which will enhance the effect of the compounds of, the invention. The compounds can be administered simultaneously or sequentially to the other drug therapy.

In another aspect, the subject compounds may be combined with the antineoplastic agents (e.g. small molecules, monoclonal antibodies, antisense RNA and fusion proteins) that inhibit one or more biological targets. Such combination may enhance therapeutic efficacy over the efficacy achieved by any of the agents alone and may prevent or delay the appearance of resistant variants.

In another aspect, the subject compounds may be combined with the antifungal agents (e.g. azoles) that inhibit one or more biological targets. Such combination may enhance therapeutic efficacy over the efficacy achieved by any of the agents alone and may prevent or delay the appearance of resistant variants.

The compounds of the invention are administered in combination with chemotherapeutic agents. Chemotherapeutic agents consist of a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment.

The term "subject" as used herein is meant to include all mammals, and in particular humans, in need of treatment. The therapeutically effective amount will vary depending upon the subject and disease condition being treated, the weight and age of the subject, the severity of the disease condition, the particular compound of formula (I) chosen, the dosing regimen to be followed, timing of administration, the manner of administration and the like, all of which can readily be determined by one of ordinary skill in the art.

Representative compounds include:
1. N-Cyclopropyl-2-(4-fluorophenyl)-3-(4-((1E)-3-(hydroxyamino)-3-oxoprop-1-en-1-yl)phenyl)acrylamide;
2. N-Methyl-2-(4-fluorophenyl)-3-(4-((1E)-3-(hydroxyamino)-3-oxoprop-1-en-1-yl)phenyl)acrylamide;
3. N,N-Dimethyl-2-(4-fluorophenyl)-3-(4-((1E)-3-(hydroxyamino)-3-oxoprop-1-en-1-yl)phenyl)acrylamide;
4. 2-Phenyl-3-(4-((1E)-3-(hydroxyamino)-3-oxoprop-1-en-1-yl)phenyl) acrylamide;
5. N-Cyclopropyl-2-(thiophen-2-yl)-3-(4-((1E)-3-(hydroxyamino)-3-oxoprop-1-en-1-yl)phenyl)acrylamide;
6. N-Cyclopropyl-2-phenyl-3-(4-((1E)-3-(hydroxyamino)-3-oxoprop-1-en-1-yl)phenyl)acrylamide;
7. N-Cyclopropyl-2-(4-trifluoromethylphenyl)-3-(4-((1E)-3-(hydroxyamino)-3-oxoprop-1-en-1-yl)phenyl)acrylamide;
8. N-Cyclopropyl-2-(pyridin-3-yl)-3-(4-((1E)-3-(hydroxyamino)-3-oxoprop-1-en-1-yl)phenyl)acrylamide;
9. N-Cyclopropyl-2-(4-methoxyphenyl)-3-(4-((1E)-3-(hydroxyamino)-3-oxoprop-1-en-1-yl)phenyl)acrylamide;
10. N-Cyclopropyl-2-(2-chlorophenyl)-3-(4-((1E)-3-(hydroxyamino)-3-oxoprop-1-en-1-yl)phenyl)acrylamide;
11. N-Cyclopropyl-2-(2-fluorophenyl)-3-(4-((1E)-3-(hydroxyamino)-3-oxoprop-1-en-1-yl)phenyl)acrylamide;
12. N-Cyclopropyl-2-(3-chlorophenyl)-3-(4-((1E)-3-(hydroxyamino)-3-oxoprop-1-en-1-yl)phenyl)acrylamide;
13. N-Cyclopropyl-2-[benzodioxol-5-yl]-3-(4-((1E)-3-(hydroxyamino)-3-oxoprop-1-en-1-yl)phenyl)acrylamide;
14. N-Cyclopropyl-2-(4-methylphenyl)-3-(4-((1E)-3-(hydroxyamino)-3-oxoprop-1-en-1-yl)phenyl)acrylamide;
15. N-Morpholino-2-(4-fluorophenyl)-3-(4-((1E)-3-(hydroxyamino)-3-oxoprop-1-en-1-yl)phenyl)acrylamide;
16. N-Morpholino-2-(2-fluorophenyl)-3-(4-((1E)-3-(hydroxyamino)-3-oxoprop-1-en-1-yl)phenyl)acrylamide;
17. N-Morpholino-2-(3-methoxyphenyl)-3-(4-((1E)-3-(hydroxyamino)-3-oxoprop-1-en-1-yl)phenyl)acrylamide;
18. N-Thiomorpholino-2-(4-fluorophenyl)-3-(4-((1E)-3-(hydroxyamino)-3-oxoprop-1-en-1-yl)phenyl)acrylamide;
19. N-Cyclooctyl-2-(4-fluorophenyl)-3-(4-((1E)-3-(hydroxyamino)-3-oxoprop-1-en-1-yl)phenyl)acrylamide;
20. N-Cyclopropyl-2-(3-methoxyphenyl)-3-(4-((1E)-3-(hydroxyamino)-3-oxoprop-1-en-1-yl)phenyl)acrylamide;
21. N-Cyclopropyl-2-(3-fluorophenyl)-3-(4-((1E)-3-(hydroxyamino)-3-oxoprop-1-en-1-yl)phenyl)acrylamide;
22. N-Isopropyl-2-(3-fluorophenyl)-3-(4-((1E)-3-(hydroxyamino)-3-oxoprop-1-en-1-yl)phenyl)acrylamide;
23. N-Isopropyl-2-(4-fluorophenyl)-3-(4-((1E)-3-(hydroxyamino)-3-oxoprop-1-en-1-yl)phenyl)acrylamide;
24. N-Isopropyl-2-(3,4-difluorophenyl)-3-(4-((1E)-3-(hydroxyamino)-3-oxoprop-1-en-1-yl)phenyl)acrylamide;
25. N-Cyclopropyl-2-(3-fluoro-4-methoxyphenyl)-3-(4-((1E)-3-(hydroxyamino)-3-oxoprop-1-en-1-yl)phenyl) acrylamide;
26. N-Isopropyl-2-(3-fluoro-4-methoxyphenyl)-3-(4-((1E)-3-(hydroxyamino)-3-oxoprop-1-en-1-yl)phenyl)acrylamide;
27. N-Cyclopropyl-2-(3,4-difluorophenyl)-3-(4-((1E)-3-(hydroxyamino)-3-oxoprop-1-en-1-yl)phenyl)acrylamide;
28. 2-(4-Fluorophenyl)-3-(4-((1E)-3-(hydroxyamino)-3-oxoprop-1-en-1-yl)phenyl)acrylamide;
29. 2-(4-Fluorophenyl)-3-(4-((1E)-3-(hydroxyamino)-3-oxoprop-1-en-1-yl)phenyl)-N-phenylacrylamide;
30. N-Pyrrolidino-2-(4-fluorophenyl)-3-(4-((1E)-3-(hydroxyamino)-3-oxoprop-1-en-1-yl)phenyl)acrylamide;
31. N-Cyclopropyl-2-(4-cyclopropylmethoxyphenyl)-3-(4-((1E)-3-(hydroxyamino)-3-oxoprop-1-en-1-yl)phenyl) acrylamide;

32. N-Cyclopropyl-2-(4-benzyloxyphenyl)-3-(4-((1E)-3-(hydroxyamino)-3-oxoprop-1-en-1-yl)phenyl)acrylamide;
33. N-Cyclopropyl-2-(4-cyclopentyloxyphenyl)-3-(4-((1E)-3-(hydroxyamino)-3-oxoprop-1-en-1-yl)phenyl)acrylamide;
34. N-(4-Fluorobenzyl)-2-(4-fluorophenyl)-3-(4-((1E)-3-(hydroxyamino)-3-oxoprop-1-en-1-yl)phenyl)acrylamide;
35. N-Cyclopropyl-2-(2,4-dimethoxyphenyl)-3-(4-((1E)-3-(hydroxyamino)-3-oxoprop-1-en-1-yl)phenyl)acrylamide;
36. N-Cyclopropyl-2-(3,4-dimethoxyphenyl)-3-(4-((1E)-3-(hydroxyamino)-3-oxoprop-1-en-1-yl)phenyl)acrylamide;
37. N-Cyclopropyl-2-(indol-3-yl)-3-(4-((1E)-3-(hydroxyamino)-3-oxoprop-1-en-1-yl)phenyl)acrylamide;
38. N-Cyclopropyl-2-(thiophen-3-yl)-3-(4-((1E)-3-(hydroxyamino)-3-oxoprop-1-en-1-yl)phenyl)acrylamide;
39. N-Cyclopropyl-3-(4-fluorophenyl)-2-(4-((1E)-3-(hydroxyamino)-3-oxoprop-1-en-1-yl)phenyl)acrylamide;
40. N-Cyclopropyl-3-(4-fluorophenyl)-2-(3-((1E)-3-(hydroxyamino)-3-oxoprop-1-en-1-yl)phenyl)acrylamide;
41. N-Cyclopropyl-2-(3-cyclopropylmethoxyphenyl)-3-(4-((1E)-3-(hydroxyamino)-3-oxoprop-1-en-1-yl)phenyl)acrylamide;
42. 2-(3-Cyclopropylmethoxyphenyl)-3-(4-((1E)-3-(hydroxyamino)-3-oxoprop-1-en-1-yl)phenyl)-N-phenylacrylamide;
43. N-Cyclopropyl-2-(3-cyclopentyloxyphenyl)-3-(4-((1E)-3-(hydroxyamino)-3-oxoprop-1-en-1-yl)phenyl)acrylamide;
44. 2-(3-Cyclopentyloxyphenyl)-3-(4-((1E)-3-(hydroxyamino)-3-oxoprop-1-en-1-yl)phenyl)-N-phenylacrylamide;
45. N-Cyclopropyl-2-(biphenyl-4-yl)-3-(4-((1E)-3-(hydroxyamino)-3-oxoprop-1-en-1-yl)phenyl)acrylamide;
46. 2-(4-Cyclopropylmethoxyphenyl)-3-(4-((1E)-3-(hydroxyamino)-3-oxoprop-1-en-1-yl)phenyl)-N-phenylacrylamide;
47. N-Cyclopropyl-3-(3,4-dimethoxyphenyl)-2-(3-((1E)-3-(hydroxyamino)-3-oxoprop-1-en-1-yl)phenyl)acrylamide;
48. N-Cyclopropyl-3-(4-methoxyphenyl)-2-(4-((1E)-3-(hydroxyamino)-3-oxoprop-1-en-1-yl)phenyl)acrylamide;
49. N-Cyclopropyl-3-(4-cyclopropylmethoxyphenyl)-2-(4-((1E)-3-(hydroxyamino)-3-oxoprop-1-en-1-yl)phenyl)acrylamide;
50. N-Cyclopropyl-3-(4-cyclopentyloxyphenyl)-2-(4-((1E)-3-(hydroxyamino)-3-oxoprop-1-en-1-yl)phenyl)acrylamide;
51. N-Cyclopropyl-2-(4-fluorophenyl)-3-(4-((1E)-3-(hydroxyamino)-3-oxoprop-1-en-1-yl)phenyl)but-2-enamide;
52. 2-[4-(Dimethylamino)phenyl]-3-(4-((1E)-3-(hydroxyamino)-3-oxoprop-1-en-1-yl)phenyl)-N-cyclopropylacrylamide;
53. N-Cyclopropyl-3-(4-fluorophenyl)-2-(4-(3-(hydroxyamino)-3-oxopropyl)phenyl)acrylamide;
54. N-Cyclopropyl-2-(4-fluorophenyl)-3-(3-((1E)-3-(hydroxyamino)-3-oxoprop-1-en-1-yl)phenyl)acrylamide
55. 3-(4-((1E)-3-(Cyclopropylamino)-2-(4-fluorophenyl)prop-1-en-1-yl)phenyl)-N-hydroxyacrylamide;
56. 3-(4-((1E)-3-(Cyclopropylamino)-2-phenylprop-1-en-1-yl)phenyl)-N-hydroxy acrylamide;
57. 3-(4-((1E)-2-(3-Cyclopentyloxyphenyl)-3-(cyclopropylamino)prop-1-en-1-yl)phenyl)-N-hydroxyacrylamide;
58. 3-(4-((1E)-2-(3-Chlorophenyl)-3-(cyclopropylamino)prop-1-en-1-yl)phenyl)-N-hydroxyacrylamide;
59. N-Cyclopropyl-3-(4-(3-(2-aminophenylamino)-3-oxoprop-1-en-1-ylphenyl)-2-(4-fluorophenyl)acrylamide;
60. 3-(4-((1E)-3-(2-Aminophenylamino)-3-oxoprop-1-en-1-yl)phenyl)-2-(4-fluorophenyl)-N,N-dimethylacrylamide;
61. N-Cyclopropyl-3-(4-((1E)-3-(2-aminophenylamino)-3-oxoprop-1-en-1-yl}phenyl)-2-(4-(trifluoromethyl)phenyl)acrylamide;
62. N-Cyclopropyl-3-(4-((1E)-3-(2-aminophenylamino)-3-oxoprop-1-en-1-yl}phenyl)-2-(pyridin-3-yl)acrylamide;
63. N-Cyclopropyl-3-(4-((1E)-3-(2-aminophenylamino)-3-oxoprop-1-en-1-yl}phenyl)-2-(2-chlorophenyl)acrylamide;
64. N-Cyclopropyl-3-(4-((1E)-3-(2-aminophenylamino)-3-oxoprop-1-en-1-yl}phenyl)-2-[benzodioxol-5-yl]-acrylamide;
65. N-Cyclopropyl-3-(4-((1E)-3-(2-aminophenylamino)-3-oxoprop-1-en-1-yl}phenyl)-2-(2-fluorophenyl)acrylamide;
66. N-Cyclopropyl-3-(4-((1E)-3-(2-aminophenylamino)-3-oxoprop-1-en-1-yl}phenyl)-2-(3-chlorophenyl)acrylamide;
67. (E)-N-Cyclopropyl-3-(4-((1E)-3-(2-aminophenylamino)-3-oxoprop-1-en-1-yl}phenyl)-2-(4-methylphenyl)acrylamide;
68. N-Morpholino-3-(4-((1E)-3-(2-aminophenylamino)-3-oxoprop-1-en-1-yl}phenyl)-2-(4-fluorophenyl)acrylamide;
69. N-Cyclopropyl-3-(4-((1E)-3-(2-aminophenylamino)-3-oxoprop-1-en-1-yl}phenyl)-2-(3-methoxyphenyl)acrylamide;
70. N-Cyclopropyl-3-(4-((1E)-3-(2-aminophenylamino)-3-oxoprop-1-en-1-yl}phenyl)-2-phenylacrylamide;
71. N-Cyclopropyl-3-(4-((1E)-3-(2-aminophenylamino)-3-oxoprop-1-en-1-yl}phenyl)-2-(thiophen-2-yl)acrylamide;
72. N-Morpholino-3-(4-((1E)-3-(2-aminophenylamino)-3-oxoprop-1-en-1-yl}phenyl)-2-(2-fluorophenyl)acrylamide;
73. N-Cyclopropyl-3-(4-((1E)-3-(2-aminophenylamino)-3-oxoprop-1-en-1-yl}phenyl)-2-(3,4-difluorophenyl)acrylamide;
74. N-Cyclopropyl-3-(4-((1E)-3-(2-aminophenylamino)-3-oxoprop-1-en-1-yl}phenyl)-2-(3,4-dimethoxyphenyl)acrylamide;
75. 6-((1E)-3-(4-(3-(Cyclopropylamino)-2-(4-fluorophenyl)-3-oxoprop-1-en-1-yl)phenyl)acrylamido)-N-hydroxyhexanamide;
76. 6-((1E)-3-(4-(3-(N,N-Dimethylamino)-2-(4-fluorophenyl)-3-oxoprop-1-en-1-yl)phenyl)acrylamido)-N-hydroxyhexanamide;
77. 6-((1E)-3-(4-(3-(Cyclopropylamino)-2-(2-chlorophenyl)-3-oxoprop-1-en-1-yl)phenyl)acrylamido)-N-hydroxyhexanamide;
78. 6-((1E)-3-(4-(3-(Cyclopropylamino)-2-(2-fluorophenyl)-3-oxoprop-1-en-1-yl)phenyl)acrylamido)-N-hydroxyhexanamide;
79. 6-((1E)-3-(4-(3-(Cyclopropylamino)-2-[benzodioxol-5-yl]-3-oxoprop-1-en-1-yl)phenyl)acrylamido)-N-hydroxyhexanamide;
80. 6-((1E)-3-(4-(3-(Cyclopropylamino)-2-(3-chlorophenyl)-3-oxoprop-1-en-1-yl)phenyl)acrylamido)-N-hydroxyhexanamide;
81. 6-((1E)-3-(4-(3-(Cyclopropylamino)-2-(4-methylphenyl)-3-oxoprop-1-en-1-yl)phenyl)acrylamido)-N-hydroxyhexanamide;

82. 6-((1E)-3-(4-(3-(cyclopropylamino)-2-phenyl-3-oxoprop-1-enyl)phenyl)acrylamido)-N-hydroxyhexanamide;
83. 6-((1E)-3-(4-(3-(Cyclopropylamino)-2-(thiophen-2-yl)-3-oxoprop-1-enyl)phenyl)acrylamido)-N-hydroxyhexanamide;
84. 6-((1E)-3-(4-(3-(Cyclopropylamino)-2-(4-methoxyphenyl)-3-oxoprop-1-en-1-yl)phenyl)acrylamido)-N-hydroxyhexanamide;
85. 6-((1E)-3-(4-(3-(Cyclopropylamino)-2-(3-methoxyphenyl)-3-oxoprop-1-en-1-yl)phenyl)acrylamido)-N-hydroxyhexanamide;
86. 6-((1E)-3-(4-(3-(Morpholino)-2-(4-fluorophenyl)-3-oxoprop-1-enyl)phenyl)acrylamido)-N-hydroxyhexanamide;
87. 6-((1E)-3-(4-(3-(Morpholino)-2-(2-fluorophenyl)-3-oxoprop-1-en-1-yl)phenyl)acrylamido)-N-hydroxyhexanamide;
88. 6-((1E)-3-(4-(3-(Cyclopropylamino)-2-(3-fluoro-4-methoxyphenyl)-3-oxoprop-1-en-1-yl)phenyl)acrylamido)-N-hydroxyhexanamide;
89. 4-(((1E)-3-(4-(3-(Cyclopropylamino)-2-(4-fluorophenyl)-3-oxoprop-1-en-1-yl)phenyl)acrylamido)methyl)-N-hydroxybenzamide;
90. 4-(((1E)-3-(4-(3-(Cyclopropylamino)-2-(2-chlorophenyl)-3-oxoprop-1-en-1-yl)phenyl)acrylamido)methyl)-N-hydroxybenzamide;
91. 4-(((1E)-3-(4-(3-(Cyclopropylamino)-2-(3-chlorophenyl)-3-oxoprop-1-en-1-yl)phenyl)acrylamido)methyl)-N-hydroxybenzamide;
92. 4-(((1E)-3-(4-(3-(Cyclopropylamino)-2-(4-methylphenyl)-3-oxoprop-1-en-1-yl)phenyl)acrylamido)methyl)-N-hydroxybenzamide;
93. 4-(((1E)-3-(4-(3-(Cyclopropylamino)-2-phenyl-3-oxoprop-1-en-1-yl)phenyl)acrylamido)methyl)-N-hydroxybenzamide;
94. 4-(((1E)-3-(4-(3-(Cyclopropylamino)-2-(thiophen-2-yl)-3-oxoprop-1-en-1-yl)phenyl)acrylamido)methyl)-N-hydroxybenzamide;
95. 4-(((1E)-3-(4-(3-(Cyclopropylamino)-2-(4-methoxyphenyl)-3-oxoprop-1-en-1-yl)phenyl)acrylamido)methyl)-N-hydroxybenzamide;
96. 4-(((1E)-3-(4-(3-(Morpholino)-2-(4-fluorophenyl)-3-oxoprop-1-en-1-yl)phenyl)acrylamido)methyl)-N-hydroxybenzamide;
97. 4-(((1E)-3-(4-(3-(Cyclopropylamino)-2-(3-methoxyphenyl)-3-oxoprop-1-en-1-yl)phenyl)acrylamido)methyl)-N-hydroxybenzamide;
98. 4-(((1E)-3-(4-(3-(Morpholino)-2-(2-fluorophenyl)-3-oxoprop-1-en-1-yl)phenyl)acrylamido)methyl)-N-hydroxybenzamide;
99. 4-(3-(Cyclopropylamino)-2-(4-methylphenyl)-3-oxoprop-1-en-1-yl)-N-hydroxy benzamide;
100. 4-(3-(Cyclopropylamino)-2-(4-methoxyphenyl)-3-oxoprop-1-en-1-yl)-N-hydroxy benzamide;
101. 4-(3-(Cyclopropylamino)-2-(3-methoxyphenyl)-3-oxoprop-1-en-1-yl)-N-hydroxy benzamide;
102. 4-(3-(Cyclopropylamino)-2-phenyl-3-oxoprop-1-en-1-yl)-N-hydroxybenzamide;
103. 4-(3-(Cyclopropylamino)-2-(2-fluorophenyl)-3-oxoprop-1-en-1-yl)-N-hydroxy benzamide;
104. N-(2-Aminophenyl)-4-(3-(cyclopropylamino)-2-(4-methylphenyl)-3-oxoprop-1-en-1-yl)benzamide;
105. (E)-N-(2-Aminophenyl)-4-(3-(cyclopropylamino)-2-(4-fluorophenyl)-3-oxoprop-1-en-1-yl)benzamide;
106. N-(2-Aminophenyl)-4-(3-(cyclopropylamino)-2-(4-trifluoromethylphenyl)-3-oxo prop-1-en-1-yl)benzamide;
107. N-(2-Aminophenyl)-4-(3-(cyclopropylamino)-2-phenyl-3-oxoprop-1-en-1-yl)benzamide;
108. N-(2-Aminophenyl)-4-(3-(cyclopropylamino)-2-(3-methoxyphenyl)-3-oxoprop-1-en-1-yl)benzamide;
109. N-(2-Aminophenyl)-4-(3-(cyclopropylamino)-2-(2-fluorophenyl)-3-oxoprop-1-en-1-yl)benzamide;
110. N-(2-Aminophenyl)-4-(3-(cyclopropylamino)-2-(3-fluorophenyl)-3-oxoprop-1-en-1-yl)benzamide;
111. N-(2-Aminophenyl)-4-(3-(cyclopropylamino)-2-(1,3-benzodioxol-5-yl)-3-oxoprop-1-en-1-yl)benzamide;
112. N-(2-Aminophenyl)-4-(3-(cyclopropylamino)-2-(2-chlorophenyl)-3-oxoprop-1-en-1-yl)benzamide;
113. N-(2-Aminophenyl)-4-(3-(cyclopropylamino)-2-(thiophen-2-yl)-3-oxoprop-1-en-1-yl)benzamide;
114. N-(2-Aminophenyl)-4-(3-(cyclopropylamino)-2-(3-chlorophenyl)-3-oxoprop-1-en-1-yl)benzamide;
115. N-(2-Aminophenyl)-4-(3-(cyclopropylamino)-2-(3,4-difluorophenyl)-3-oxoprop-1-en-1-yl)benzamide;
116. N-(2-Aminophenyl)-4-(3-(cyclopropylamino)-2-(4-methoxyphenyl)-3-oxoprop-1-en-1-yl)benzamide;
117. N-(2-Aminophenyl)-4-(3-(cyclopropylamino)-2-(2-chloro-4-fluorophenyl)-3-oxoprop-1-en-1-yl)benzamide;
118. N-(2-Aminophenyl)-4-(3-(phenylamino)-2-(3,4-dimethoxyphenyl)-3-oxoprop-1-en-1-yl)benzamide;
119. N-(2-Aminophenyl)-4-(3-(cyclopropylamino)-2-(3,4-dimethoxyphenyl)-3-oxoprop-1-en-1-yl)benzamide;
120. N-(2-Aminophenyl)-4-(3-(cyclopropylamino)-2-(2,4-dimethoxyphenyl)-3-oxoprop-1-en-1-yl)benzamide;
121. N-(2-Aminophenyl)-4-(3-(cyclopropylamino)-2-(2-naphthyl)-3-oxoprop-1-en-1-yl)benzamide;
122. N-(2-Aminophenyl)-4-(3-phenylamino-2-(2,4-dimethoxyphenyl)-3-oxoprop-1-en-1-yl)benzamide;
123. N-(2-Amino-4-fluorophenyl)-4-(2-(4-fluorophenyl)-3-(cyclopropylamino)-3-oxoprop-1-en-1-yl)benzamide;
124. N-(2-Aminophenyl)-4-(3-(cyclopropylamino)-3-oxo-2-(1H-indol-3-yl)prop-1-en-1-yl)benzamide;
125. N-(2-Aminophenyl)-4-(3-(cyclopropylamino)-3-oxo-2-biphenyl-4-yl-prop-1-en-1-yl)benzamide;
126. 4-(2-(4-Fluorophenyl)-3-(cyclopropylamino)-3-oxoprop-1-en-1-yl)-N-(2-hydroxyphenyl)benzamide;
127. N-(2-Aminophenyl)-4-[3-(cyclopropylamino)-3-oxo-2-pyridin-3-yl-prop-1-en-1-yl]benzamide;
128. N-(2-Aminophenyl)-4-(2-(4-hydroxyphenyl)-3-(cyclopropylamino)-3-oxoprop-1-en-1-yl)benzamide;
129. N-(2-Aminophenyl)-4-(2-(2,6-difluorophenyl)-3-(cyclopropylamino)-3-oxoprop-1-en-1-yl)benzamide;
130. N-(2-Aminophenyl)-4-(2-(2,5-difluorophenyl)-3-(cyclopropylamino)-3-oxoprop-1-en-1-yl)benzamide;
131. N-(2-Aminophenyl)-4-(2-(4-fluorophenyl)-3-(isopropylamino)-3-oxoprop-1-en-1-yl)benzamide;
132. N-(2-N-(4-Aminobiphenyl-3-yl)-4-(3-(cyclopropylamino)-2-(4-fluorophenyl)-3-oxoprop-1-enyl)benzamide;
133. N-(2-Aminophenyl)-4-(3-(cyclopropylamino)-2-(2-methylphenyl)-3-oxoprop-1-en-1-yl)benzamide;
134. N-(2-Aminophenyl)-4-(3-(methylamino)-2-(4-fluorophenyl)-3-oxoprop-1-en-1-yl)benzamide;
135. (Z)—N-(2-Aminophenyl)-4-(2-(4-fluorophenyl)-3-(cyclopropylamino)-3-oxoprop-1-en-1-yl)benzamide;
136. N-(2-Aminophenyl)-4-[2-(4-fluorophenyl)-3-morpholin-4-yl-3-oxoprop-1-en-1-yl]benzamide;
137. N-(2-Aminophenyl)-4-(3-(cyclopropylamino)-1-(4-fluorophenyl)-3-oxoprop-1-en-1-yl)benzamide;
138. N-(2-Aminophenyl)-3-(3-(cyclopropylamino)-1-(4-fluorophenyl)-3-oxoprop-1-en-1-yl)benzamide;
139. N-(2-Aminophenyl)-4-(3-(phenylamino)-2-(4-fluorophenyl)-3-oxoprop-1-en-1-yl)benzamide;

140. 4-[3-Amino-2-(4-fluorophenyl)-3-oxoprop-1-en-1-yl]-N-(2-aminophenyl)benzamide;
141. N-(2-Aminophenyl)-4-(2-(4-cyclopentyloxyphenyl)-3-(cyclopropylamino)-3-oxoprop-1-en-1-yl)benzamide;
142. N-(2-Aminophenyl)-4-(2-(4-cyclopropylmethoxyphenyl)-3-(cyclopropylamino)-3-oxoprop-1-en-1-yl)benzamide;
143. N-(2-Aminophenyl)-4-(3-(benzylamino)-2-(4-fluorophenyl)-3-oxoprop-1-en-1-yl)benzamide;
144. N-(2-Aminophenyl)-4-(3-(cyclopropylamino)-2-(4-fluorophenyl)prop-1-en-1-yl)benzamide;
145. 4-(3-(Cyclopropylamino)-2-(4-fluorophenyl)-3-oxoprop-1-en-1-yl)-N-(4-((E)-3-(hydroxyamino)-3-oxoprop-1-en-1-yl)benzyl)benzamide;
146. 4-(3-(Cyclopropylamino)-2-phenyl-3-oxoprop-1-en-1-yl)-N-(4-((E)-3-(hydroxyamino)-3-oxoprop-1-en-1-yl)benzyl)benzamide;
147. 4-(3-(Cyclopropylamino)-2-[benzodioxol-5-yl]-3-oxoprop-1-en-1-yl)-N-(4-((E)-3-(hydroxyamino)-3-oxoprop-1-en-1-yl)benzyl)benzamide;
148. 4-(3-(Cyclopropylamino)-2-(4-methylphenyl)-3-oxoprop-1-en-1-yl)-N-(4-(hydroxycarbamoyl)benzyl)benzamide;
149. 4-(3-(Cyclopropylamino)-2-phenyl-3-oxoprop-1-en-1-yl)-N-(4-(hydroxy carbamoyl)benzyl)benzamide;
150. 4-(3-(Cyclopropylamino)-2-(2-fluorophenyl)-3-oxoprop-1-en-1-yl)-N-(4-(hydroxycarbamoyl)benzyl)benzamide;
151. 4-(3-(Cyclopropylamino)-2-(2-chlorophenyl)-3-oxoprop-1-en-1-yl)-N-(4-(hydroxycarbamoyl)benzyl)benzamide;
152. 4-(3-(Cyclopropylamino)-2-(4-fluorophenyl)-3-oxoprop-1-en-1-yl)-N-(4-(hydroxycarbamoyl)benzyl)benzamide;
153. 4-(3-(Cyclopropylamino)-2-(3-chlorophenyl)-3-oxoprop-1-en-1-yl)-N-(4-(hydroxycarbamoyl)benzyl)benzamide;
154. 4-(3-(Cyclopropylamino)-2-(4-methoxyphenyl)-3-oxoprop-1-en-1-yl)-N-(4-(hydroxycarbamoyl)benzyl)benzamide;
155. 4-(3-(Cyclopropylamino)-2-(2-chloro-4-fluorophenyl)-3-oxoprop-1-en-1-yl)-N-(4-(hydroxycarbamoyl)benzyl)benzamide
156. 4-(3-(Cyclopropylamino)-2-(3-fluorophenyl)-3-oxoprop-1-en-1-yl)-N-(4-(hydroxycarbamoyl)benzyl)benzamide;
157. 4-(3-(Cyclopropylamino)-2-[benzodioxol-5-yl]-3-oxoprop-1-en-1-yl)-N-(4-(hydroxycarbamoyl)benzyl)benzamide;
158. 4-(3-(Cyclopropylamino)-2-(4-trifluoromethylphenyl)-3-oxoprop-1-en-1-yl)-N-(4-(hydroxycarbamoyl)benzyl)benzamide;
159. 4-(3-(Cyclopropylamino)-2-(3,4-difluorophenyl)-3-oxoprop-1-en-1-yl)-N-(4-(hydroxycarbamoyl)benzyl)benzamide;
160. 4-(3-(Cyclopropylamino)-2-(4-fluorophenyl)-3-oxoprop-1-en-1-yl)-N-(6-(hydroxyamino)-6-oxohexyl)benzamide;
161. 4-(3-(Cyclopropylamino)-2-phenyl-3-oxoprop-1-en-1-yl)-N-(6-hydroxyamino)-6-oxohexyl)benzamide;
162. 4-(3-(Cyclopropylamino)-2-(4-methylphenyl)-3-oxoprop-1-en-1-yl)-N-(6-(hydroxyamino)-6-oxohexyl)benzamide;
163. 4-(3-(Cyclopropylamino)-2-(2-fluorophenyl)-3-oxoprop-1-en-1-yl)-N-(6-(hydroxyamino)-6-oxohexyl)benzamide;
164. 4-(3-(Cyclopropylamino)-2-(3-fluorophenyl)-3-oxoprop-1-en-1-yl)-N-(6-(hydroxyamino)-6-oxohexyl)benzamide;
165. N-(4-(3-(Cyclopropylamino)-2-(4-fluorophenyl)-3-oxoprop-1-en-1-yl)phenyl)-N'-hydroxyoctanediamide and
166. N-(2-Aminophenyl)-4-((4-(3-(cyclopropylamino)-1-(4-fluorophenyl)-3-oxoprop-1-en-2-yl)phenylamino)methyl)benzamide.

There is also provided a process as shown in the following scheme-1, for the preparation of compounds of the formula (1), wherein all the groups are as defined earlier.

The said process for the preparation of compound of formula (I) wherein, $R^2$=COOH, comprises the steps of:

A) Condensing the compound of formula 1a with the compound of formula 1b in acetic anhydride in the presence of an organic base to yield compound of formula 1c, wherein $R^3$=H or unsubstituted alkyl, R, $R^1$, X, Y, m, n, o and p are as defined earlier;

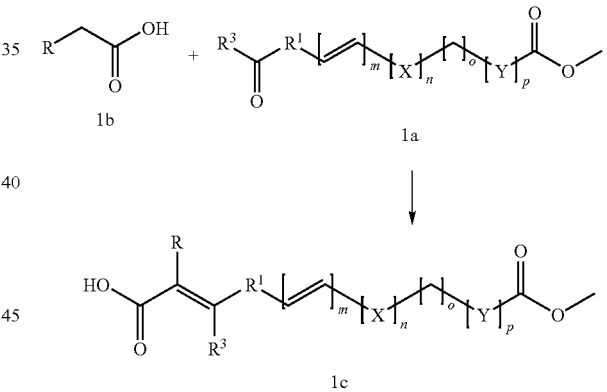

B) 1) Reacting the compound of formula 1c with an acid activating agent such as 1-ethyl-3-(3-dimethylaminopropyl)-carbodiimide hydrochloride (EDCI), 1-hydroxy benzotriazole (HOBt) and the like and with amine $NHR^5R^6$ to yield the compound of formula 2a, wherein R, $R^1$, X, Y, m, n, o and p are as defined earlier.

2) Reacting the compound of formula 1c with a suitable carboxylic acid activating reagent and base to yield the anhydride in situ, which on reduction with a suitable reducing agent yields compound of formula 2b, wherein R, $R^1$, $R^3$, X, Y, m, n, o and p are as defined earlier.

3) Oxidation of 2b with a suitable oxidizing agent yields the corresponding aldehyde, which on reductive amination with $HNR^5R^6$ yields compound of formula 2c, wherein R. $R^1$, X, Y, m, n, o and p are as defined earlier.

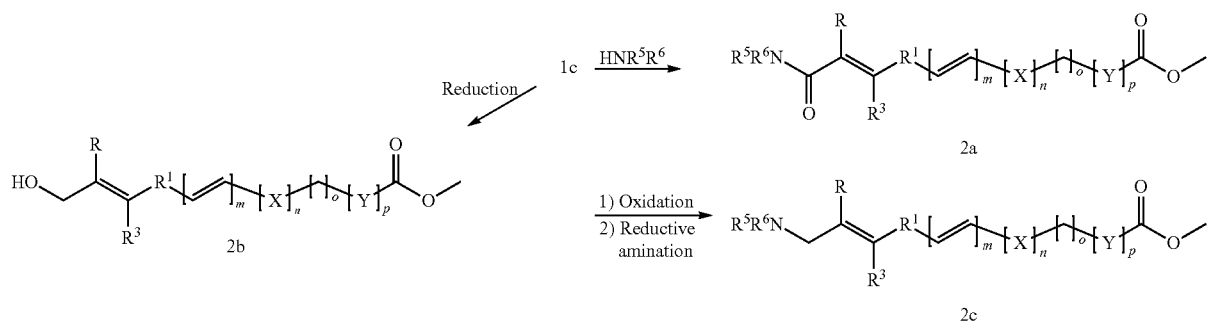

C) Hydrolyzing the compound of formulae 2a or 2b or 2c with a base to give the corresponding acid. Coupling the acid with activating agents such as EDCI, HOBt and the like in the presence of the respective amine $R^4NH_2$ to yield the compound of general formula (I) or reacting the compound of formulae 2a or 2b or 2c with $R^4NH_2$ in the presence of a base to yield the compound of general formula (1) wherein R, $R^1$, $R^2$, $R^3$, $R^4$, $R^5$, $R^6$, X, Y, m, n, o and p are as defined earlier.

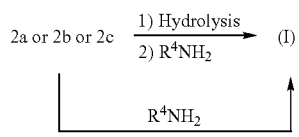

Also provided herein is a process for the preparation of compound of formula (I), from the compound of formula (II), wherein, when one of $R^2$ or $R^3$ is hydrogen or unsubstituted alkyl, the other is neither of hydrogen nor of unsubstituted alkyl, $R^4$, $R^3$, $R^2$, $R^1$, R, X, Y, m, n, o and p are as defined earlier.

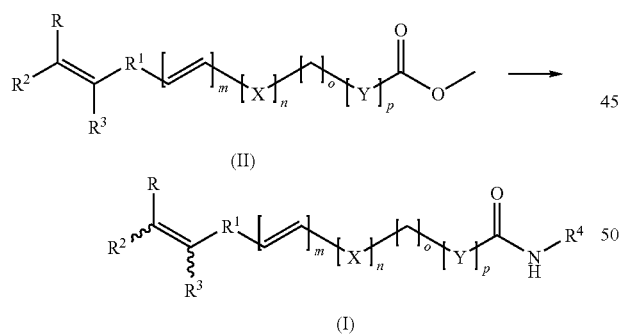

The same process was followed for the synthesis of the compound of formula (I), wherein, $R^2$=H or unsubstituted alkyl and $R^3$=COON by appropriately choosing the acids and the carbonyl compounds using the steps A-C, of the above-mentioned synthetic scheme.

All the above-mentioned alternative reactions may be carried out at 0° C. to room temperature and the duration of the reactions may range from 2 to 24 hours.

The pharmaceutically acceptable salts of the compounds of formula (I) are prepared. Acid addition salts are prepared by treatment with acids such as hydrochloric acid, hydrobromic acid, nitric acid, sulfuric acid, phosphoric acid, p-toluene- sulfonic acid, methanesulfonic acid, acetic acid, citric acid, maleic acid, salicylic acid, hydroxynaphthoic acid, ascorbic acid, palmitic acid, succinic acid, benzoic acid, benzene- sulfonic acid, tartaric acid and the like in solvents like ethyl acetate, ether, alcohols, acetone, tetrahydrofuran (THF), dioxane, etc. Mixture of solvents may also be used.

The examples given below are provided by way of illustration only and therefore should not be construed to limit the scope of the invention.

Example 1

Synthesis of N-cyclopropyl-2-(4-fluorophenyl)-3-(4-((E)-3-(hydroxyamino)-3-oxoprop-1-en-1-yl)phenyl)acrylamide

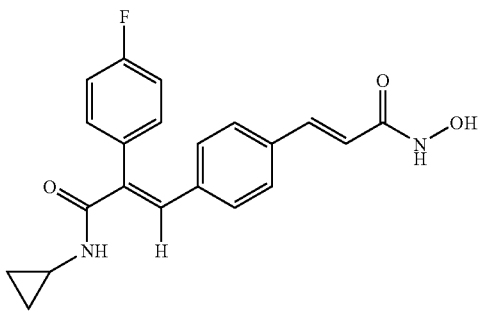 [SMILES: O=C(/C=C/c1ccc(/C=C(/C(=O)NC2CC2)c2ccc(F)cc2)cc1)NO]

Step-I

Preparation of methyl (E)-3-(4-formylphenyl)acrylate

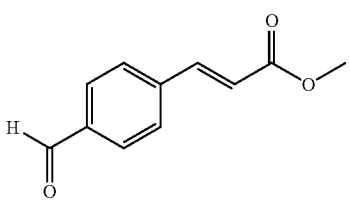

A suspension of (E)-3-(4-formylphenyl)acrylic acid (2 g, 10.5 mmol) in methanol (30 mL) was cooled to 5° C. and then concentrated $H_2SO_4$ (3 mL) was added under stirring and heated at 60° C. for 2 hours. The solvent was removed by evaporation and the obtained compound was stirred with water (100 mL) for 15 minutes. The precipitated white solid was filtered, washed with water (300 mL) and dried to get the pure product (1.9 g, 86% yield).

Step-II

Preparation of 2-(4-fluorophenyl)-3-(4-((E)-3-methoxy-3-oxoprop-1-en-1-yl)phenyl)acrylic acid

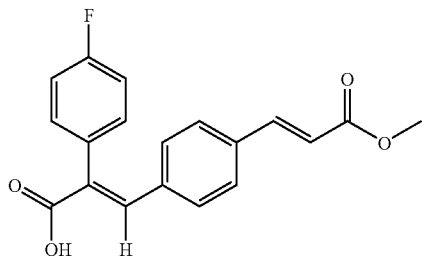 [SMILES: COC(=O)/C=C/c1ccc(/C=C(/C(=O)O)c2ccc(F)cc2)cc1]

A mixture of 4-fluorophenylacetic acid (2.5 g, 13.2 mmol) and methyl (E)-3-(4-formylphenyl)acrylate (2.03 g, 13.2 mmol) were dissolved under stirring with acetic anhydride (8 mL). To this mixture, diisopropylethylamine (DIPEA) (3.4 mL, 19.7 mmol) was added and stirred at 30° C. for 2 hours. Upon completion (as monitored by TLC using 100% ethyl acetate as eluent), the reaction mixture was poured into water and the pH adjusted to 1 using dilute HCl (1:1). The aqueous layer was extracted with ethyl acetate (2×150 mL). The combined ethyl acetate layer was washed with water till the washings were neutral and dried over anhydrous $Na_2SO_4$. The ethyl acetate layer was evaporated to dryness to obtain a sticky compound and further triturated with cold dichloromethane (DCM) to furnish a white solid. The solid obtained was filtered and dried under vacuum to afford the title compound (2 g, 47% yield).

Step-III

Preparation of methyl 3-(E) (4-(3-(cyclopropylamino)-2-(4-fluorophenyl)-3-oxoprop-1-en-1-yl)phenyl)acrylate

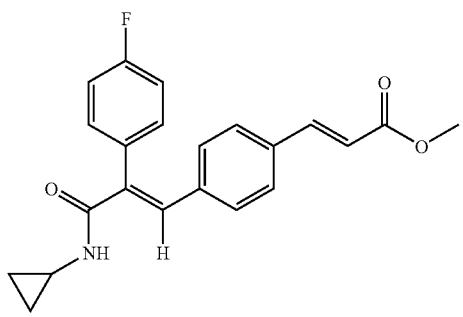 [SMILES: COC(=O)/C=C/c1ccc(/C=C(/C(=O)NC2CC2)c2ccc(F)cc2)cc1]

A mixture of 2-(4-fluorophenyl)-3-(4-((E)-3-methoxy-3-oxoprop-1-en-1-yl)phenyl)acrylic acid (0.23 g, 0.71 mmol) and cyclopropylamine (0.03 g, 0.60 mmol), EDCI (0.27 g, 1.4 mmol), HOBt (0.10 g, 0.71 mmol) was dissolved in N,N-dimethylformamide (DMF) (6 mL) under stirring. Triethylamine (TEA) (0.75 mL, 36 mmol) was added dropwise with constant stirring to the above reaction mixture and it was stirred at 30° C. for 2 hours. Subsequently the reaction mixture was diluted with ethyl acetate and washed successively with water (3×50 mL) and brine (3×50 mL). The organic layer was dried over anhydrous $Na_2SO_4$ and concentrated to afford the pure compound (0.25 g, 96% yield).

Step-IV

Preparation of N-cyclopropyl-2-(4-fluorophenyl)-3-(4-((E)-3-(hydroxyamino)-3-oxoprop-1-en-1-yl)phenyl)acrylamide

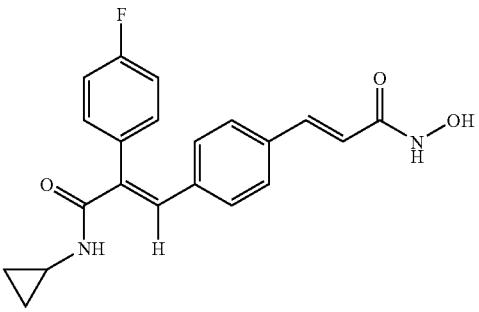 [SMILES: O=C(/C=C/c1ccc(/C=C(/C(=O)NC2CC2)c2ccc(F)cc2)cc1)NO]

Hydroxylamine hydrochloride (0.86 g, 12.3 mmol) in methanol (3 mL) was mixed with KOH (0.69 g, 12.3 mmol) in methanol (3 mL) at 0° C., and sonicated for 2 minutes, the white precipitate formed was filtered. The filtrate was added to methyl 3-(E)(4-(3-(cyclopropylamino)-2-(4-fluorophenyl)-3-oxoprop-1-en-1-yl)phenyl)acrylate (0.25 g, 0.68 mmol) in DCM (1.5 mL) and the mixture was stirred at room temperature, for 30 minutes. The reaction mixture was diluted with water (200 mL) and extracted with ethyl acetate (2×150 mL). The ethyl acetate layer was dried over anhydrous $Na_2SO_4$ and concentrated to obtain a sticky compound, which was triturated with DCM (15 mL). The pale brown solid obtained was filtered and washed with DCM (3×5 mL) to afford the title compound (0.07 g, 28% yield). $^1$H NMR (DMSO-$d_6$) δ (ppm): 0.49-0.53 (2H, dd, —$CH_2$), 0.61-0.66 (2H, m, —$CH_2$), 2.72-2.77 (1H, m, —CH), 6.38-6.42 (1H, d, =CH), 7.00-7.02 (2H, d, Ar—H), 7.16-7.27 (5H, m, Ar—H and =CH), 7.33-7.43 (3H, m, Ar—H and =CH), 7.81-7.82 (1H, d, —NH), 9.04 (1H, s, —OH), 10.73 (1H, s, —NH). MS m/z: 367.1 ($M^+$+1).

The following compounds were prepared according to the procedure given in Example 1

| Ex. No | Structure | Analytical data |
|---|---|---|
| 2 | (4-fluorophenyl compound with N-methyl amide and hydroxamic acid) | $^1$H NMR (DMSO-d$_6$) δ (ppm): 2.66 (3H, s, —CH$_3$), 6.38-6.42 (1H, d, =CH), 6.99-7.01 (2H, d, Ar—H), 7.21-7.27 (4H, m, Ar—H), 7.33-7.37 (1H, d, =CH), 7.34-7.43 (4H, m, Ar—H, =CH and —NH), 9.03 (1H, s, —OH), 10.73 (1H, s, —NH). MS m/z: 339.1 (M$^+$ − 1). |
| 3 | (4-fluorophenyl compound with N,N-dimethyl amide and hydroxamic acid) | $^1$H NMR (DMSO-d$_6$) δ (ppm): 2.9 (3H, s, —CH$_3$), 3.04 (3H, s, —CH$_3$), 6.39-6.43 (1H, d, =CH), 6.69 (1H, s, =CH), 7.10-7.12 (2H, d, Ar—H), 7.20-7.22 (2H, d, Ar—H), 7.29-7.33 (1H, d, =CH), 7.29-7.43 (4H, m, Ar—H), 9.03 (1H, s, —OH), 10.73 (1H, s, —NH); MS m/z: 353.1 (M$^+$ − 1). |
| 4 | (phenyl compound with primary amide and hydroxamic acid) | $^1$H NMR (DMSO-d$_6$) δ (ppm): 6.37-6.41 (1H, d, =CH), 6.94-7.00 (3H, m, Ar—H), 7.17-7.19 (2H, d, Ar—H), 7.33-7.42 (8H, m, Ar—H, =CH, —NH$_2$), 9.04 (1H, s, —OH), 10.73 (1H, s, —NH); MS m/z: 309.1 (M$^+$ + 1). |
| 5 | (thiophenyl compound with N-cyclopropyl amide and hydroxamic acid) | $^1$H NMR (DMSO-d$_6$) δ (ppm): 0.52-0.53 (2H, t, —CH$_2$), 0.63-0.66 (2H, m, —CH$_2$), 2.74-2.76 (1H, m, —CH), 6.41-6.45 (1H, d, =CH), 6.94-6.95 (1H, d, Ar—H), 7.04-7.06 (1H, t, Ar—H), 7.14-7.15 (2H, d, Ar—H), 7.24 (1H, s, =CH), 7.37-7.41 (1H, d, =CH), 7.43-7.45 (2H, d, Ar—H), 7.59-7.61 (1H, d, Ar—H), 7.98-7.99 (1H, d, —NH), 9.1 (1H, s, —OH), 10.8 (1H, s, —NH); MS m/z: 355.1 (M$^+$ + 1). |
| 6 | (phenyl compound with N-cyclopropyl amide and hydroxamic acid) | $^1$H NMR (DMSO-d$_6$) δ (ppm): 0.51-0.53 (2H, t, —CH$_2$), 0.63-0.65 (2H, m, —CH$_2$), 2.74-2.76 (1H, m, —CH), 6.37-6.41 (1H, d, =CH), 6.99-7.01 (2H, d, Ar—H), 7.16-7.23 (3H, m, Ar—H and =CH), 7.35-7.37 (6H, m, =CH and Ar—H), 7.79 (1H, s, —NH), 9.05 (1H, s, —OH), 10.74 (1H, s, —NH). MS m/z: 349.1 (M$^+$ + 1). |

| Ex. No | Structure | Analytical data |
|---|---|---|
| 7 | (4-CF3-phenyl substituted cyclopropylamide acrylohydroxamic acid) | ¹H NMR (DMSO-d₆) δ (ppm): 0.52-0.53 (2H, t, —CH₂), 0.63-0.66 (2H, t, —CH₂), 2.74-2.76 (1H, m, —CH), 6.39-6.43 (1H, d, =CH), 6.99-7.01 (2H, d, Ar—H), 7.33-7.40 (6H, m, Ar—H and =CH), 7.72-7.74 (2H, d, Ar—H), 8.03-8.04 (1H, d, —NH), 9.1 (1H, s, —OH), 10.73 (1H, s, —NH); MS m/z: 417.1 (M⁺ + 1). |
| 8 | (pyridin-3-yl substituted cyclopropylamide acrylohydroxamic acid) | ¹H NMR (DMSO-d₆) δ (ppm): 0.52-0.53 (2H, t, —CH₂), 0.64-0.65 (2H, t, —CH₂), 2.75-2.76 (1H, m, —CH), 6.39-6.43 (1H, d, =CH), 6.99-7.01 (2H, d, Ar—H), 7.34-7.43 (5H, d, Ar—H and =CH), 7.59-7.61 (1H, d, Ar—H), 8.05-8.06 (1H, t, —NH), 8.26-8.27 (1H, d, Ar—H), 8.53-8.55 (1H, m, Ar—H), 9.1 (1H, s, —OH), 10.76 (1H, s, —NH); MS m/z: 350.1 (M⁺ + 1). |
| 9 | (4-OMe-phenyl substituted cyclopropylamide acrylohydroxamic acid) | ¹H NMR (DMSO-d₆) δ (ppm): 0.49-0.50 (2H, d, —CH₂), 0.62-0.63 (2H, m, —CH₂), 2.72-2.74 (1H, m, —CH), 3.78 (3H, s, —CH₃), 6.37-6.41 (1H, d, =CH), 6.93-6.95 (2H, d, Ar—H), 7.03-7.08 (4H, m, Ar—H), 7.19 (1H, s, =CH), 7.34-7.39 (3H, m, =CH and Ar—H), 7.66-7.67 (1H, d, —NH), 9.1 (1H, s, —OH), 10.75 (1H, s, —NH); MS m/z: 379.1; (M⁺ + 1). |
| 10 | (2-Cl-phenyl substituted cyclopropylamide acrylohydroxamic acid) | ¹H NMR (DMSO-d₆) δ (ppm): 0.51 (2H, m, —CH₂), 0.62-0.64 (2H, m, —CH₂), 2.71-2.76 (1H, m, —CH), 6.38-6.42 (1H, d, =CH), 6.94-6.96 (2H, d, Ar—H), 7.12-7.14 (1H, d, Ar—H), 7.31-7.55 (7H, m, Ar—H and =CH), 7.82-7.83 (1H, d, —NH) 9.32 (1H, s, —OH), 10.76 (1H, s, —NH); MS m/z: 383.1 (M⁺ + 1). |
| 11 | (2-F-phenyl substituted cyclopropylamide acrylohydroxamic acid) | ¹H NMR (DMSO-d₆) δ (ppm): 0.51-0.52 (2H, m, —CH₂), 0.63-0.66 (2H, m, —CH₂), 2.74-2.75 (1H, m, —CH), 6.38-6.42 (1H, d, =CH), 7.01-7.03 (2H, d, Ar—H), 7.12-7.44 (8H, m, Ar—H and =CH), 7.97-7.98 (1H, d, —NH) 9.05 (1H, s, —OH), 10.75 (1H, s, —NH); MS m/z: 367.1; (M⁺ + 1). |

| Ex. No | Structure | Analytical data |
|---|---|---|
| 12 | 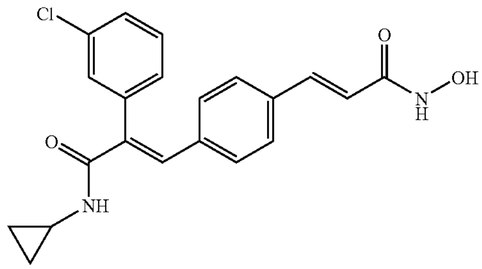 | ¹H NMR (DMSO-d₆) δ (ppm): 0.51-0.52 (2H, m, —CH₂), 0.63-0.66 (2H, m, —CH₂), 2.74-2.76 (1H, m, —CH), 6.38-6.42 (1H, d, =CH), 7.00-7.02 (2H, d, Ar—H), 7.09-7.10 (1H, d, Ar—H), 7.19 (1H, s, =CH), 7.28 (1H, s, Ar—H), 7.34 (1H, s, Ar—H), 7.38-7.44 (4H, m, Ar—H and =CH), 7.94 (1H, d, —NH) 9.05 (1H, s, —OH), 10.74 (1H, s, —NH); MS m/z: 383.1 (M⁺ + 1). |
| 13 | 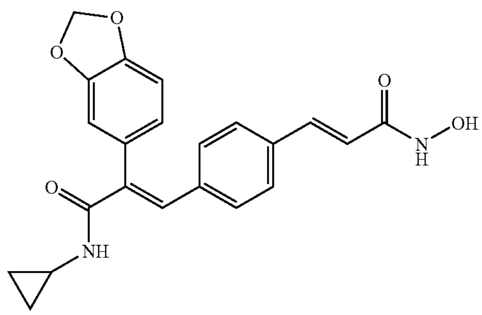 [SMILES: O=C(/C=C/c1ccc(/C=C(/C(=O)NC2CC2)c2ccc3c(c2)OCO3)cc1)NO] | ¹H NMR (DMSO D6) δ (ppm): 0.50 (2H, m, —CH₂), 0.61-0.63 (2H, m, —CH₂), 2.73-2.74 (1H, m, —CH), 6.05 (2H, s, —CH₂), 6.38-6.42 (1H, d, =CH), 6.58-6.60 (1H, d, Ar—H), 6.68 (1H, s, Ar—H), 6.90-6.92 (1H, d, Ar—H), 7.05-7.07 (2H, d, Ar—H), 7.23 (1H, s, =CH), 7.34-7.41 (3H, d, Ar—H and =CH), 7.61 (1H, d, NH) 9.05 (1H, s, —OH), 10.75 (1H, s, —NH). MS m/z: 393.1; (M⁺ + 1). |
| 14 | 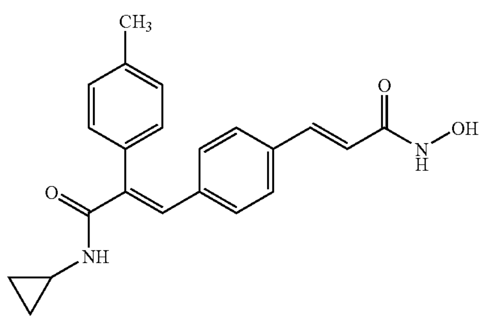 [SMILES: Cc1ccc(/C(=C\c2ccc(/C=C/C(=O)NO)cc2)C(=O)NC2CC2)cc1] | ¹H NMR (DMSO-d₆) δ (ppm): 0.49 (2H, m, —CH₂), 0.61-0.63 (2H, m, —CH₂), 2.33 (3H, s, —CH₃), 2.73 (1H, m, —CH), 6.37-6.41 (1H, d, =CH), 7.02-7.03 (4H, m, Ar—H and =CH), 7.17-7.19 (3H, m, Ar—H and =CH), 7.33-7.37 (3H, m, Ar—H and =CH), 7.69 (1H, d, —NH), 9.05 (1H, s, —OH), 10.73 (1H, s, —NH); MS m/z: 363.1 (M⁺ + 1) |
| 15 | 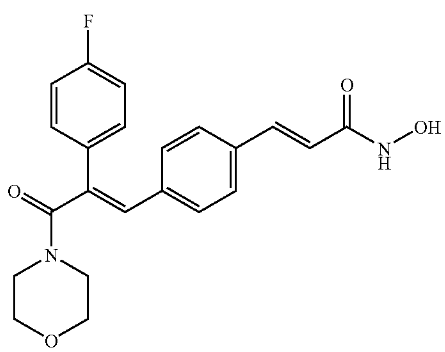 | ¹H NMR (DMSO-d₆) δ (ppm): 3.56 (8H, s, Morpholine-H), 6.39-6.43 (1H, d, =CH), 6.73 (1H, s, =CH), 7.10-7.12 (2H, d, Ar—H), 7.19-7.23 (2H, t, =CH and Ar—H), 7.29-7.32 (3H, t, Ar—H), 7.39-7.41 (2H, d, Ar—H). MS m/z: 397.2 (M⁺ + 1). |
| 16 | 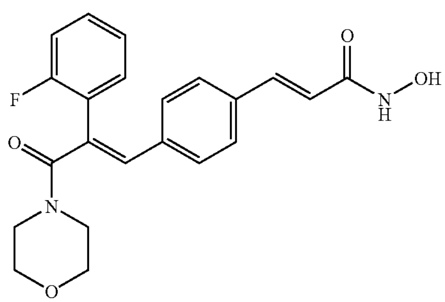 [SMILES: O=C(/C=C/c1ccc(/C=C(/C(=O)N2CCOCC2)c2ccccc2F)cc1)NO] | ¹H NMR (DMSO-d₆) δ (ppm): 3.58 (8H, s, Morpholine-H), 6.39-6.43 (1H, d, =CH), 6.93 (1H, s, =CH), 7.10-7.12 (2H, d, Ar—H), 7.21-7.26 (2H, q, Ar—H), 7.30-7.35 (2H, q, Ar—H), 7.40-7.46 (3H, d, =CH and Ar—H). MS m/z: 397.2 (M⁺ + 1). |

| Ex. No | Structure | Analytical data |
| --- | --- | --- |
| 17 | [Structure: 3-methoxyphenyl substituted acrylamide with morpholine amide and hydroxamic acid] | ¹H NMR (DMSO-d₆) δ (ppm): 3.55 (8H, s, Morpholine-H), 3.68 (3H, s, —CH₃), 6.39-6.43 (1H, d, =CH), 6.71 (1H, s, =CH), 6.80-6.83 (2H, t, Ar—H), 6.91-6.94 (1H, q, Ar—H), 7.14-7.16 (2H, d, Ar—H), 7.27-7.31 (1H, t, Ar—H), 7.35-7.42 (3H, t, =CH and Ar—H), 9.06 (1H, s, —OH), 10.74 (1H, s, —NH). MS m/z: 409.4 (M⁺ + 1). |
| 18 | [Structure: 4-fluorophenyl substituted acrylamide with thiomorpholine amide and hydroxamic acid] | ¹H NMR (DMSO-d₆) δ (ppm): 2.58 (4H, m, —CH₂), 3.79 (4H, m, —CH₂), 6.39-6.43 (1H, d, =CH), 6.75 (1H, s, =CH), 7.10-7.12 (2H, d, Ar—H), 7.19-7.23 (2H, m, Ar—H), 7.29-7.32 (3H, m, Ar—H and =CH), 7.39-7.41 (2H, d, Ar—H). MS m/z: 413.1 (M⁺ + 1) |
| 19 | [Structure: 4-fluorophenyl substituted acrylamide with cyclooctyl amide and hydroxamic acid] | ¹H NMR (DMSO-d₆) δ (ppm): 1.45-1.68 (14H, m, —CH₂), 3.88-3.89 (1H, m, —CH), 6.38-6.42 (1H, d, =CH), 7.01-7.03 (2H, d, Ar—H), 7.19-7.24 (5H, m, Ar—H and =CH), 7.33 (1H, s, =CH), 7.38-7.40 (2H, d, Ar—H), 7.55-7.57 (1H, d, NH) 9.05 (1H, s, —OH), 10.73 (1H, s, —NH). MS m/z: 437.1 (M⁺ + 1). |
| 20 | [Structure: 3-methoxyphenyl substituted acrylamide with cyclopropyl amide and hydroxamic acid] | ¹H NMR (DMSO-d₆) δ (ppm): 0.50-0.57 (2H, m, —CH₂), 0.62-0.64 (2H, m, —CH₂), 2.73-2.74 (1H, m, —CH), 3.70 (3H, s, —OCH₃) 6.38-6.42 (1H, d, =CH), 6.70 (2H, m, Ar—H), 6.93-6.95 (1H, d, Ar—H), 7.02-7.04 (2H, d, Ar—H), 7.24 (1H, s, =CH), 7.28-7.38 (4H, m, Ar—H and =CH), 7.70 (1H, d, —NH) 9.06 (1H, s, —OH), 10.74 (1H, s, —NH). MS m/z: 379.4 (M⁺ + 1). |
| 21 | [Structure: 3-fluorophenyl substituted acrylamide with cyclopropyl amide and hydroxamic acid] | ¹H NMR (DMSO-d₆) δ (ppm): 0.51-0.53 (2H, m, —CH₂), 0.62-0.65 (2H, m, —CH₂), 2.73-2.76 (1H, m, —CH), 6.38-6.42 (1H, d, =CH), 6.96-7.02 (4H, m, Ar—H), 7.20-7.23 (1H, t, Ar—H), 7.29 (1H, s, =CH), 7.34-7.38 (1H, d, =CH), 7.39-7.45 (3H, m, Ar—H), 7.88-7.89 (1H, d, —NH), 9.06 (1H, s, —OH), 10.75 (1H, s, —NH). MS m/z: 367.0. |

| Ex. No | Structure | Analytical data |
|---|---|---|
| 22 | 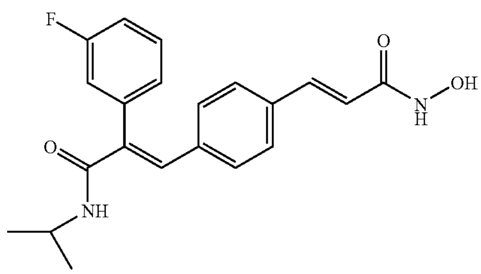 [SMILES: CC(C)NC(=O)/C(=C/c1ccc(/C=C/C(=O)NO)cc1)c1cccc(F)c1] | $^1$H NMR (DMSO-d$_6$) δ (ppm): 1.10-1.11 (6H, d, —CH$_3$), 3.94-4.01 (1H, m, —CH), 6.39-6.43 (1H, d, =CH), 6.98-7.04 (4H, m, Ar—H), 7.19-7.23 (1H, t, Ar—H), 7.30 (1H, s, =CH), 7.34-7.46 (4H, m, =CH and Ar—H), 7.59-7.61 (1H, d, —NH), 9.06 (1H, s, —OH), 10.75 (1H, s, —NH). MS m/z: 369.0; (M$^+$ + 1). |
| 23 | 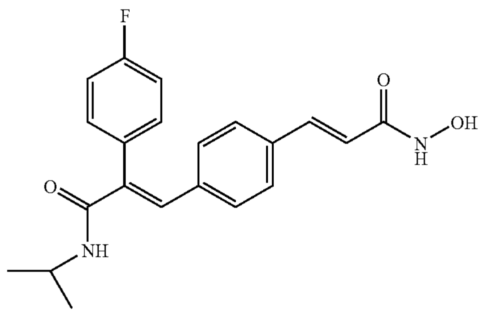 [SMILES: CC(C)NC(=O)/C(=C/c1ccc(/C=C/C(=O)NO)cc1)c1ccc(F)cc1] | $^1$H NMR (DMSO-d$_6$) δ (ppm): 1.09-1.11 (6H, d, —CH$_3$), 3.94-4.04 (1H, m, —CH), 6.38-6.42 (1H, d, =CH), 7.01-7.03 (2H, d, Ar—H), 7.20-7.28 (5H, m, Ar—H and =CH), 7.34-7.40 (3H, m, =CH and Ar—H), 7.52-7.54 (1H, d, —NH), 9.29 (1H, s, —OH), 10.75 (1H, s, —NH). MS m/z: 369.2 (M$^+$ + 1). |
| 24 | 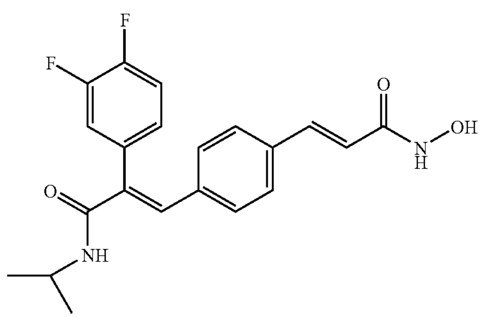 [SMILES: CC(C)NC(=O)/C(=C/c1ccc(/C=C/C(=O)NO)cc1)c1ccc(F)c(F)c1] | $^1$H NMR (DMSO-d$_6$) δ (ppm): 1.09-1.11 (6H, d, —CH$_3$), 3.95-4.02 (1H, m, —CH), 6.39-6.43 (1H, d, =CH), 6.98-7.05 (3H, m, Ar—H), 7.22-7.27 (1H, t, Ar—H), 7.35-7.48 (5H, m, =CH and Ar—H), 7.57-7.59 (1H, d, —NH), 9.06 (1H, s, —OH), 10.76 (1H, s, —NH). MS m/z: 387.0 (M$^+$ + 1). |
| 25 | 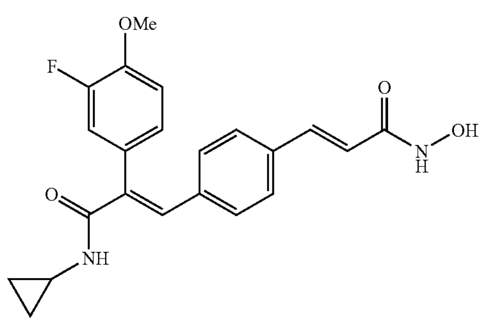 [SMILES: COc1ccc(/C(=C\c2ccc(/C=C/C(=O)NO)cc2)C(=O)NC2CC2)cc1F] | $^1$H NMR (DMSO-d$_6$) δ (ppm): 0.50-0.56 (2H, m, —CH$_2$), 0.62-0.63 (2H, m, —CH$_2$), 2.73-2.74 (1H, m, —CH), 3.86 (3H, s, —OCH$_3$), 6.38-6.42 (1H, d, =CH), 6.88-6.92 (1H, d, Ar—H), 6.96-7.06 (4H, m, Ar—H and =CH), 7.14-7.18 (1H, m, Ar—H), 7.26 (1H, s, =CH), 7.34-7.41 (2H, m, Ar—H), 7.73-7.74 (1H, d, —NH), 9.06 (1H, s, —OH), 10.76 (1H, s, —NH); MS m/z: 397.0 (M$^+$ + 1). |
| 26 | 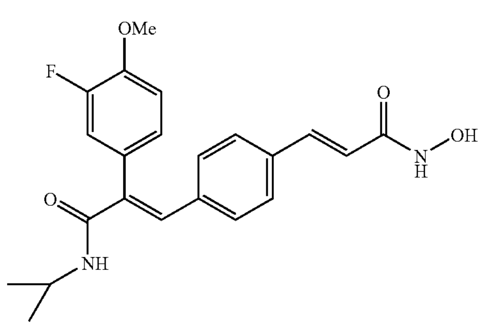 [SMILES: COc1ccc(/C(=C\c2ccc(/C=C/C(=O)NO)cc2)C(=O)NC(C)C)cc1F] | $^1$H NMR (DMSO-d$_6$) δ (ppm): 1.08-1.09 (6H, d, —CH$_3$), 3.86 (3H, s, —OCH$_3$), 3.97-4.03 (1H, m, —CH), 6.38-6.42 (1H, d, =CH), 6.91-7.06 (4H, m, Ar—H and =CH), 7.15-7.20 (1H, m, Ar—H), 7.27 (1H, s, =CH), 7.34-7.39 (1H, m, Ar—H), 7.41-7.45 (2H, m, Ar—H), 7.53-7.55 (1H, d, —NH) 9.05 (1H, s, —OH), 10.75 (1H, s, —NH). MS m/z: 399.1 (M$^+$ + 1). |

| Ex. No | Structure | Analytical data |
|---|---|---|
| 27 | 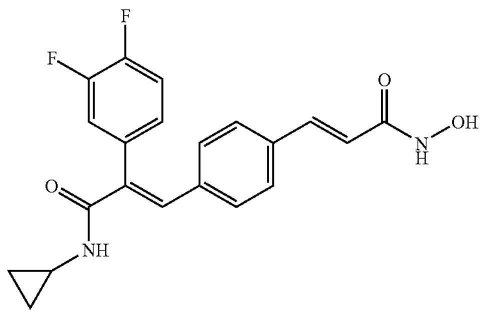 [SMILES: O=C(/C=C/c1ccc(/C=C(/C(=O)NC2CC2)c2ccc(F)c(F)c2)cc1)NO] | ¹H NMR (DMSO-d₆) δ (ppm): 0.49-0.52 (2H, m, —CH₂), 0.61-0.64 (2H, m, —CH₂), 2.72-2.76 (1H, m, —CH), 6.38-6.42 (1H, d, =CH), 6.96 (1H, d, Ar—H), 7.01-7.03 (2H, d, Ar—H), 7.22-7.27 (1H, m, Ar—H), 7.34-7.35 (2H, d, Ar—H and =CH), 7.38-7.47 (3H, m, Ar—H and =CH), 7.80-7.81 (1H, d, —NH) 9.06 (1H, s, —OH), 10.76 (1H, s, —NH); MS m/z: 385.1 (M⁺ + 1). |
| 28 | 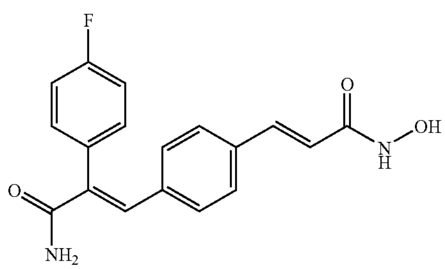 [SMILES: NC(=O)/C(=C/c1ccc(/C=C/C(=O)NO)cc1)c1ccc(F)cc1] | ¹H NMR (DMSO-d₆) δ (ppm): 6.39-6.43 (1H, d, =CH), 7.00-7.06 (3H, m, Ar—H and —NH), 7.18-7.26 (5H, m, Ar—H and —NH), 7.31-7.35 (1H, d, =CH), 7.39-7.43 (2H, t, Ar—H), 7.47 (1H, s, =CH), 9.06 (1H, s, —OH), 10.76 (1H, s, —NH); MS m/z: 327.0 (M⁺ + 1). |
| 29 | 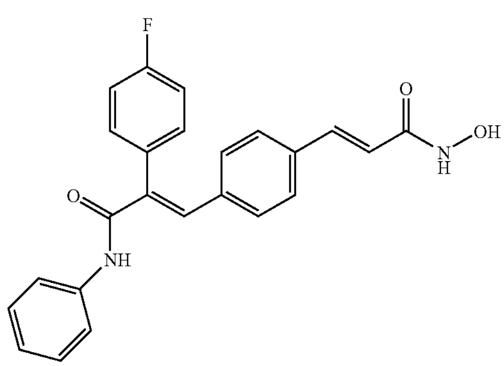 [SMILES: O=C(/C=C/c1ccc(/C=C(/C(=O)Nc2ccccc2)c2ccc(F)cc2)cc1)NO] | ¹H NMR (DMSO-d₆) δ (ppm): 6.40-6.44 (1H, d, =CH), 7.06-7.22 (3H, m, Ar—H), 7.24-7.45 (10H, m, Ar—H and =CH), 7.67-7.69 (2H, m, Ar—H), 9.08 (1H, d, —NH), 10.01 (1H, s, OH), 10.78 (1H, s, —NH). MS m/z: 403.1 (M⁺ + 1). |
| 30 | 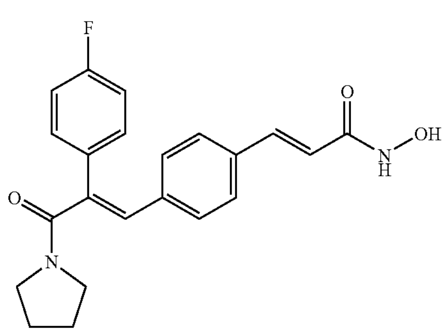 [SMILES: O=C(/C=C/c1ccc(/C=C(/C(=O)N2CCCC2)c2ccc(F)cc2)cc1)NO] | ¹H NMR (DMSO-d₆) δ (ppm): 1.81 (4H, m, —CH₂), 3.38-3.40 (4H, m, —CH₂), 6.38-6.42 (1H, d, =CH), 6.82 (1H, s, =CH), 7.09-7.11 (2H, d, Ar—H), 7.17-7.22 (2H, d, Ar—H), 7.27-7.31 (2H, m, Ar—H), 7.35-7.42 (3H, m, Ar—H, =CH), 9.05 (1H, s, —OH), 10.76 (1H, s, —NH); MS m/z: 381.1 (M⁺ + 1). |

| Ex. No | Structure | Analytical data |
| --- | --- | --- |
| 31 | 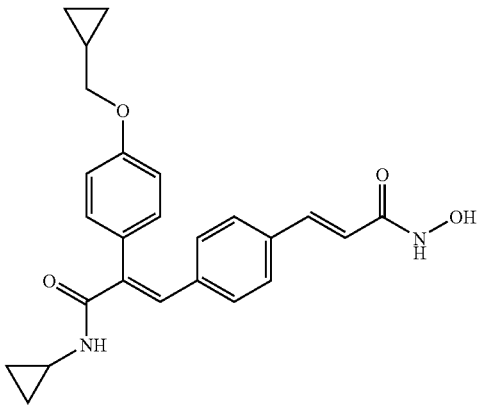 [SMILES: O=C(/C=C/c1ccc(/C=C(/C(=O)NC2CC2)c2ccc(OCC3CC3)cc2)cc1)NO] | $^1$H NMR (DMSO-d$_6$) δ (ppm): 0.49-0.51 (2H, m, —CH$_2$), 0.57-0.63 (6H, m, —CH$_2$), 1.22-1.28 (1H, m, —CH), 2.73-2.74 (1H, m, —CH), 3.81-3.83 (2H, d, —CH$_2$), 6.37-6.41 (1H, d, =CH), 6.90-6.92 (2H, d, Ar—H), 7.03-7.05 (4H, d, Ar—H), 7.18 (1H, s, =CH), 7.33-7.38 (3H, m, Ar—H and =CH), 7.65-7.66 (1H, d, —NH) 9.05 (1H, s, —OH), 10.75 (1H, s, —NH). MS m/z: 418.9 (M$^+$ + 1). |
| 32 | 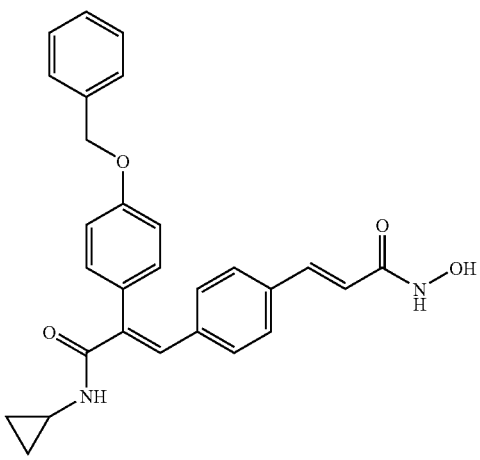 [SMILES: O=C(/C=C/c1ccc(/C=C(/C(=O)NC2CC2)c2ccc(OCc3ccccc3)cc2)cc1)NO] | $^1$H NMR (DMSO-d$_6$) δ (ppm): 0.50 (2H, m, —CH$_2$), 0.62-0.63 (2H, m, —CH$_2$), 2.74-2.75 (1H, m, —CH), 5.12 (2H, s, —CH$_2$), 6.37-6.41 (1H, d, =CH), 7.00-7.08 (6H, m, Ar—H), 7.18 (1H, s, =CH), 7.34-7.36 (4H, m, Ar—H), 7.38-7.43 (2H, m, Ar—H and =CH), 7.46-7.48 (2H, m, Ar—H), 7.70-7.71 (1H, d, —NH) 9.06 (1H, s, —OH), 10.77 (1H, s, —NH); MS m/z: 454.9 (M$^+$ + 1). |
| 33 | 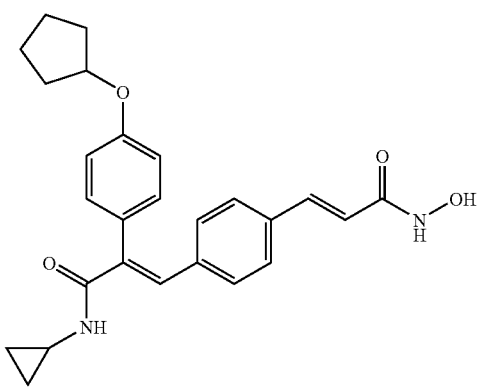 [SMILES: O=C(/C=C/c1ccc(/C=C(/C(=O)NC2CC2)c2ccc(OC3CCCC3)cc2)cc1)NO] | $^1$H NMR (DMSO-d$_6$) δ (ppm): 0.50 (2H, m, —CH$_2$), 0.62-0.63 (2H, m, —CH$_2$), 1.59 (2H, t, —CH$_2$), 1.71 (4H, m, —CH$_2$), 1.92-1.93 (2H, t, —CH$_2$), 2.73-2.74 (1H, m, —CH), 4.82 (1H, m, —CH), 6.37-6.41 (1H, d, =CH), 6.87-6.89 (2H, d, Ar—H), 7.02-7.04 (4H, d, Ar—H), 7.16 (1H, s, =CH), 7.33-7.38 (3H, m, Ar—H and =CH), 7.70-7.71 (1H, d, —NH) 9.05 (1H, s, —OH), 10.74 (1H, s, —NH); MS m/z: 432.9 (M$^+$ + 1). |
| 34 | 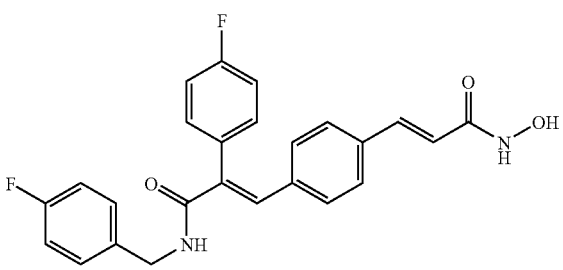 [SMILES: O=C(/C=C/c1ccc(/C=C(/C(=O)NCc2ccc(F)cc2)c2ccc(F)cc2)cc1)NO] | $^1$H NMR (DMSO-d$_6$) δ (ppm): 4.31-4.33 (2H, d, —CH$_2$), 6.39-6.43 (1H, d, =CH), 7.01-7.03 (2H, d, Ar—H), 7.12-7.16 (2H, t, Ar—H), 7.22-7.27 (4H, m, Ar—H), 7.29-7.34 (3H, m, Ar—H and =CH), 7.38-7.40 (2H, d, Ar—H), 7.48 (1H, s, =CH), 8.08-8.11 (1H, t, NH), 9.05 (1H, s, —OH), 10.75 (1H, s, —NH); MS m/z: 434.8 (M$^+$ + 1). |

| Ex. No | Structure | Analytical data |
|---|---|---|
| 35 | 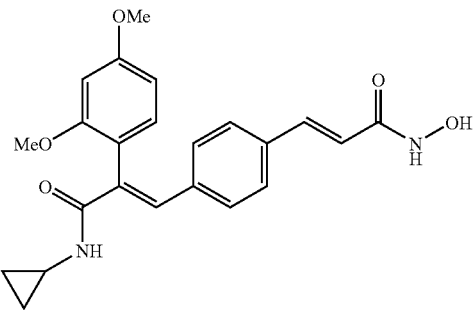 [SMILES: COc1ccc(/C(=C\c2ccc(/C=C/C(=O)NO)cc2)C(=O)NC2CC2)c(OC)c1] | $^1$H NMR (DMSO-d$_6$) δ (ppm): 0.47-0.48 (2H, m, —CH$_2$), 0.60-0.61 (2H, m, —CH$_2$), 2.67-2.71 (1H, m, —CH), 3.66 (3H, s, —OCH$_3$), 3.79 (3H, s, —OCH$_3$), 6.37-6.41 (1H, d, =CH), 6.48-6.51 (2H, dd, Ar—H), 6.63-6.64 (1H, d, Ar—H), 6.81-6.83 (1H, d, Ar—H), 7.02-7.04 (2H, d, Ar—H), 7.27 (1H, s, =CH), 7.33-7.38 (3H, m, Ar—H and —NH), 9.04 (1H, s, —OH), 10.79 (1H, s, —NH). MS m/z: 408.9 (M$^+$ + 1). |
| 36 | 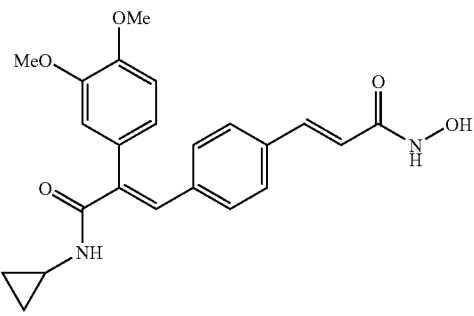 [SMILES: COc1ccc(/C(=C\c2ccc(/C=C/C(=O)NO)cc2)C(=O)NC2CC2)cc1OC] | $^1$H NMR (DMSO-d$_6$) δ (ppm): 0.50-0.51 (2H, m, —CH$_2$), 0.55-0.56 (2H, m, —CH$_2$), 2.71-2.76 (1H, m, —CH), 3.62 (3H, s, —OCH$_3$), 3.78 (3H, s, —OCH$_3$), 6.38-6.42 (1H, d, =CH), 6.66-6.70 (2H, m, Ar—H), 6.95-6.97 (1H, d, Ar—H), 7.04-7.06 (2H, d, Ar—H), 7.24 (1H, s, =CH), 7.34-7.40 (3H, m, Ar—H), 7.52-7.53 (1H, d, —NH) 9.04 (1H, s, —OH), 10.75 (1H, s, —NH). MS m/z: 408.9 (M$^+$ + 1). |
| 37 | 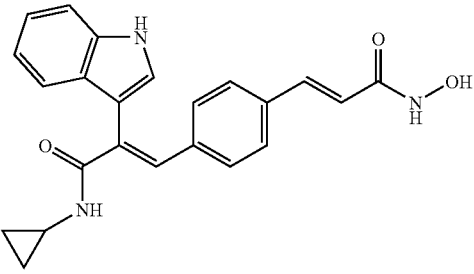 [SMILES: O=C(/C=C/c1ccc(/C=C(/C(=O)NC2CC2)c2c[nH]c3ccccc23)cc1)NO] | $^1$H NMR (DMSO-d$_6$) δ (ppm): 0.460-0.48 (2H, m, —CH$_2$), 0.58-0.62 (2H, m, —CH$_2$), 2.73-2.76 (1H, m, —CH), 6.32-6.36 (1H, d, =CH), 6.84-6.88 (1H, t, Ar—H), 6.95-6.97 (1H, d, Ar—H), 7.05-7.12 (3H, m, Ar—H), 7.28-7.33 (3H, m, Ar—H), 7.35 (1H, s, =CH), 7.40-7.42 (1H, d, Ar—H), 7.52-7.53 (1H, d, —NH), 9.02 (1H, s, —OH), 10.70 (1H, s, —NH), 11.35 (1H, s, —NH); MS m/z: 387.9 (M$^+$ + 1). |
| 38 | 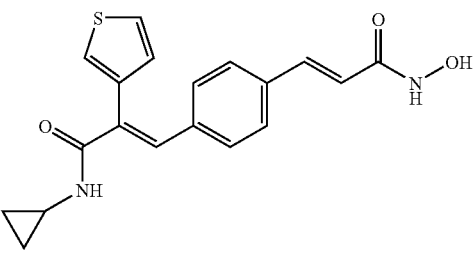 [SMILES: O=C(/C=C/c1ccc(/C=C(/C(=O)NC2CC2)c2ccsc2)cc1)NO] | $^1$H NMR (DMSO-d$_6$) δ (ppm): 0.51 (2H, m, —CH$_2$), 0.63-0.65 (2H, m, —CH$_2$), 2.73-2.75 (1H, m, —CH), 6.40-6.43 (1H, d, =CH), 6.84-6.85 (1H, d, Ar—H), 7.06-7.08 (2H, d, Ar—H), 7.22 (1H, s, =CH), 7.35-7.42 (4H, m, Ar—H), 7.57-7.58 (1H, d, —NH), 7.72 (1H, s, Ar—H), 9.04 (1H, s, —OH), 10.74 (1H, s, —NH); MS m/z: 354.9 (M$^+$ + 1). |
| 39 | 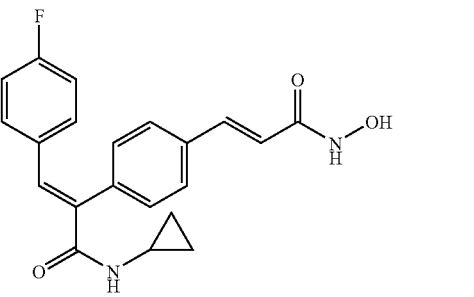 [SMILES: O=C(/C=C/c1ccc(/C(=C\c2ccc(F)cc2)C(=O)NC2CC2)cc1)NO] | $^1$H NMR (DMSO-d$_6$) δ (ppm): 0.50-0.51 (2H, d, —CH$_2$), 0.61-0.66 (2H, q, —CH$_2$), 2.73-2.76 (1H, q, —CH), 6.46-6.50 (1H, d, =CH), 7.05-7.06 (4H, d, Ar—H), 7.16-7.18 (2H, d, Ar—H), 7.25 (1H, s, =CH), 7.45-7.49 (1H, d, =CH), 7.55-7.57 (2H, d, Ar—H), 7.81-7.82 (1H, d, —NH), 9.07 (1H, s, —OH), 10.78 (1H, s, —NH). MS m/z: 366.9 (M$^+$ + 1). |

| Ex. No | Structure | Analytical data |
| --- | --- | --- |
| 40 | 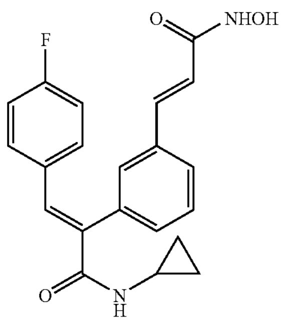 | ¹H NMR (DMSO-d₆) δ (ppm): 0.51-0.53 (2H, q, —CH₂), 0.63-0.65 (2H, t, —CH₂), 2.74-2.75 (1H, d, —CH), 6.40-6.44 (1H, d, =CH), 7.03-7.05 (4H, d, Ar—H), 7.11-7.13 (1H, d, Ar—H), 7.28 (1H, s, =CH), 7.34 (1H, s, Ar—H), 7.39-7.45 (2H, q, Ar—H and =CH), 7.54-7.56 (1H, d, Ar—H), 7.83-7.84 (1H, d, —NH), 9.07 (1H, s, —OH), 10.73 (1H, s, —NH). MS m/z: 366.9 (M⁺ + 1). |
| 41 | 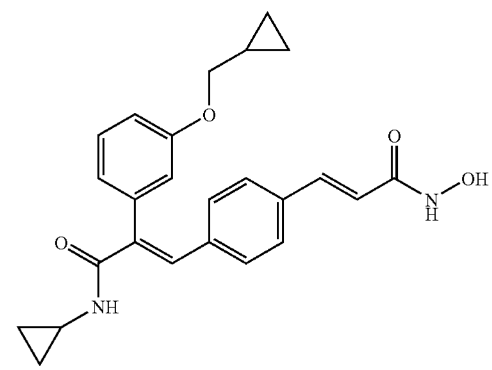 [SMILES: O=C(/C=C/c1ccc(/C=C(/C(=O)NC2CC2)c2cccc(OCC3CC3)c2)cc1)NO] | ¹H NMR (DMSO-d₆) δ: 0.26-0.28 (2H, m, —CH₂), 0.49-0.51 (4H, m, —CH₂), 0.63-0.66 (2H, t, —CH₂), 1.11-1.13 (1H, m, —CH), 2.73-2.75 (1H, m, —CH), 3.73-3.75 (2H, s, —CH₂), 6.37-6.41 (1H, d, =CH), 6.67-6.70 (2H, d, Ar—H), 6.91-6.93 (1H, d, Ar—H), 7.02-7.04 (2H, d, —Ar H), 7.23-7.29 (2H, m, =CH and Ar—H), 7.33-7.38 (3H, m, =CH and Ar—H), 7.67-7.68 (1H, d, —NH), 9.04 (1H, s, —OH) 10.73 (1H, s, —NH); MS m/z: 418.9 (M⁺ + 1). |
| 42 | 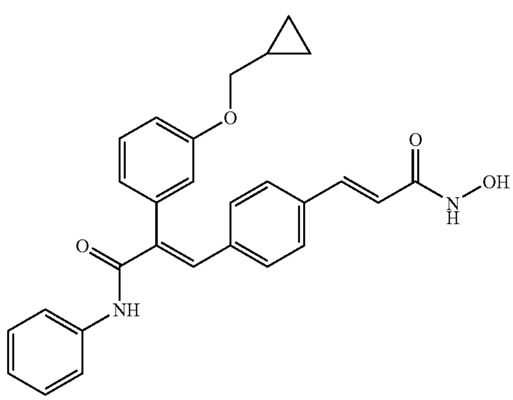 [SMILES: O=C(/C=C/c1ccc(/C=C(/C(=O)Nc2ccccc2)c2cccc(OCC3CC3)c2)cc1)NO] | ¹H NMR (DMSO-d₆) δ: 0.26-0.28 (2H, m, —CH₂), 0.49-0.51 (2H, m, —CH₂), 1.12 (1H, m, —CH), 3.75-3.76 (2H, s, —CH₂), 6.40-6.44 (1H, d, =CH), 6.78-6.82 (2H, d, Ar—H), 6.93-6.95 (1H, d, Ar—H), 7.06-7.14 (3H, m, =CH and Ar—H), 7.30-7.35 (5H, m, =CH and Ar—H), 7.41-7.43 (2H, d, Ar—H) 7.66-7.68 (2H, d, Ar—H) 9.05 (1H, d, —NH), 9.88 (1H, s, —OH) 10.75 (1H, s, —NH); MS m/z: 454.9 (M⁺ + 1). |
| 43 | 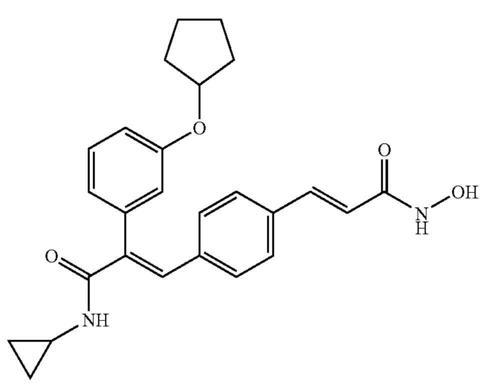 [SMILES: O=C(/C=C/c1ccc(/C=C(/C(=O)NC2CC2)c2cccc(OC3CCCC3)c2)cc1)NO] | ¹H NMR (DMSO-d₆) δ: 0.50-0.51 (2H, d, —CH₂), 0.63-0.65 (2H, d, —CH₂), 1.52 (2H, m, —CH₂), 1.63 (4H, m, —CH₂) 1.77-1.79 (2H, m, —CH₂), 2.73-2.74 (1H, m, —CH), 4.71 (1H, m, —CH), 6.38-6.41 (1H, d, =CH), 6.61 (1H, s, Ar—H), 6.68-6.70 (1H, d, Ar—H), 6.87-6.89 (1H, d, Ar—H) 7.01-7.03 (2H, m, =CH and Ar—H), 7.22-7.29 (2H, m, =CH and Ar—H), 7.34-7.38 (3H, d, Ar—H), 7.70-7.71 (1H, d, —NH), 9.04 (1H, s, —OH) 10.74 (1H, s, —NH); MS m/z: 432.9 (M⁺ + 1). |

-continued

| Ex. No | Structure | Analytical data |
| --- | --- | --- |
| 44 | 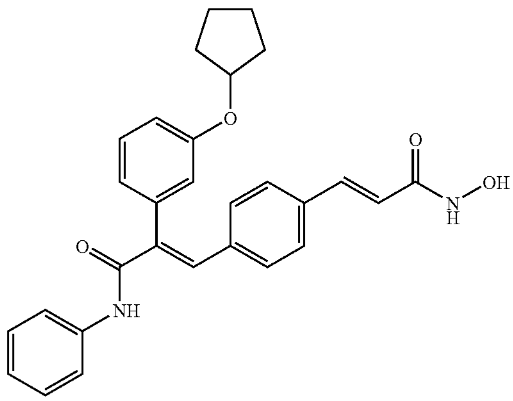 [SMILES: O=C(/C=C/c1ccc(/C=C(/C(=O)Nc2ccccc2)c2cccc(OC3CCCC3)c2)cc1)NO] | ¹H NMR (DMSO-d₆) δ: 1.51 (2H, m, —CH₂), 1.63 (4H, m, —CH₂), 1.78-1.79 (2H, m, —CH₂), 4.73 (1H, m, —CH), 6.41-6.45 (1H, d, =CH), 6.73 (1H, s, Ar—H), 6.80-6.81 (1H, d, Ar—H), 6.90-6.92 (1H, d, Ar—H), 7.06-7.09 (1H, t, Ar—H), 7.11-7.13 (2H, m, =CH and Ar—H), 7.28-7.35 (5H, m, Ar—H), 7.41-743 (2H, d, Ar—H), 7.67-7.69 (2H, d, Ar—H), 9.50 (1H, d, —NH), 9.92 (1H, s, —OH) 10.78 (1H, s, —NH); MS m/z: 468.9 (M⁺ + 1). |
| 45 | 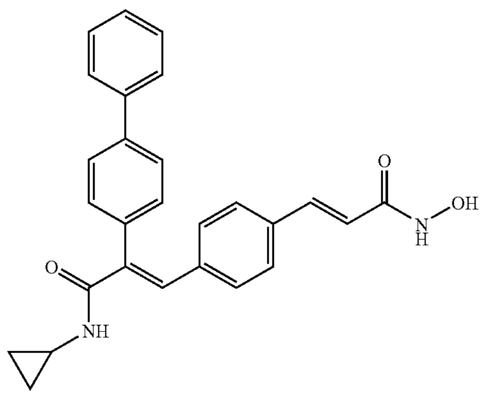 [SMILES: O=C(/C=C/c1ccc(/C=C(/C(=O)NC2CC2)c2ccc(-c3ccccc3)cc2)cc1)NO] | ¹H NMR (DMSO-d₆) δ: 0.52-0.53 (2H, m, —CH₂), 0.63-0.65 (2H, m, —CH₂), 2.73-2.78 (1H, m, —CH), 6.37-6.41 (1H, d, =CH), 7.07-7.09 (2H, d, Ar—H), 7.23-7.25 (3H, m, =CH and Ar—H), 7.33-7.39 (4H, m, =CH and Ar—H), 7.46-7.50 (2H, t, Ar—H), 7.69-7.73 (4H, t, Ar—H), 7.89-7.90 (1H, d, —NH), 9.04 (1H, s, —OH) 10.74 (1H, s, —NH); MS m/z: 424.9 (M⁺ + 1). |
| 46 | 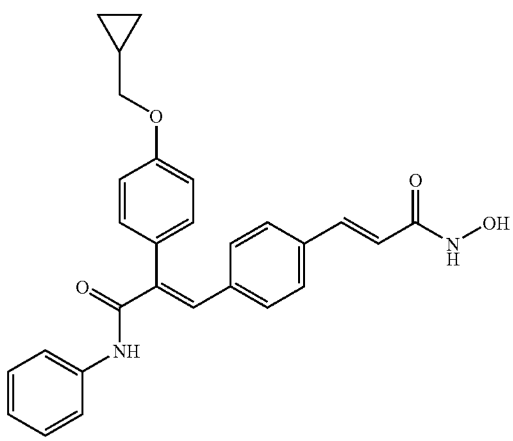 [SMILES: O=C(/C=C/c1ccc(/C=C(/C(=O)Nc2ccccc2)c2ccc(OCC3CC3)cc2)cc1)NO] | ¹H NMR (DMSO-d₆) δ: 0.33-0.35 (2H, m, —CH₂), 0.57-0.59 (2H, m, —CH₂), 1.12 (1H, m, —CH), 3.83-3.84 (2H, s, —CH₂), 6.40-6.43 (1H, d, =CH), 6.93-6.95 (2H, d, Ar—H), 7.07-7.16 (5H, m, Ar—H), 7.29-7.36 (3H, m, =CH and Ar—H), 7.41-7.43 (3H, m, =CH and Ar—H), 7.66-7.68 (2H, d, Ar—H), 9.05 (1H, d, —NH), 9.85 (1H, s, —OH) 10.75 (1H, s, —NH); MS m/z: 454.8 (M⁺ + 1). |
| 47 | 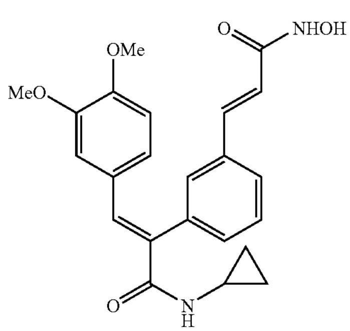 | ¹H NMR (DMSO-d₆) δ: 0.50-0.51 (2H, m, —CH₂), 0.60-0.63 (2H, m, —CH₂), 2.73-2.74 (1H, m, —CH), 3.28 (3H, s, —OCH₃), 3.70 (3H, s, —OCH₃), 6.41-6.46 (2H, t, Ar—H and =CH), 6.70-6.72 (1H, d, Ar—H), 6.80-6.82 (1H, m, Ar—H), 7.15-7.17 (1H, d, Ar—H), 7.28 (1H, s, =CH), 7.37-7.48 (3H, m, Ar—H and =CH), 7.56-7.58 (1H, d, Ar—H), 7.63-7.64 (1H, d, —NH), 9.05 (1H, s, —OH) 10.8 (1H, s, —NH); MS m/z: 408.9 (M⁺ + 1). |

| Ex. No | Structure | Analytical data |
|---|---|---|
| 48 | 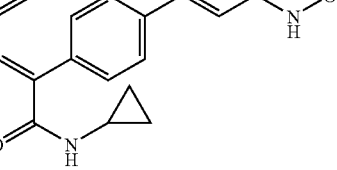 | $^1$H NMR (DMSO-d$_6$) δ: 0.49-0.50 (2H, d, —CH$_2$), 0.60-0.64 (2H, q, —CH$_2$), 2.73-2.75 (1H, t, —CH), 3.69 (3H, s, —OCH$_3$), 6.47-6.51 (1H, d, =CH), 6.75-6.77 (2H, d, Ar—H), 6.94-6.96 (2H, d, Ar—H), 7.17-7.19 (2H, d, Ar—H), 7.24 (1H, s, =CH), 7.46-7.50 (1H, d, =CH), 7.56-7.58 (2H, d, Ar—H), 7.64-7.65 (1H, d, —NH), 9.07 (1H, s, —OH), 10.78 (1H, s, —NH). MS m/z: 379.2 (M$^+$ + 1). |
| 49 | 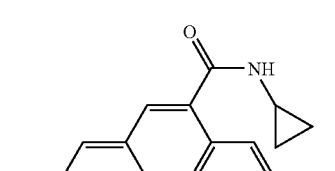 | $^1$H NMR (DMSO-d$_6$) δ: 0.32-0.34 (2H, d, —CH$_2$), 0.41-0.42 (2H, m, —CH$_2$), 0.56-0.58 (2H, m, —CH$_2$), 0.64-0.66 (2H, t, —CH), 1.22 (1H, m, —CH), 2.79-2.88 (1H, m, —CH), 3.83-3.85 (2H, d, —CH$_2$), 6.45-6.49 (1H, d, =CH), 6.92-6.94 (2H, d, Ar—H), 7.06 (1H, s, =CH), 7.43-7.47 (3H, m, Ar—H), 7.50-7.52 (1H, d, Ar—H), 7.57 7.59 (1H, d, Ar—H), 8.47-8.48 (1H, s, —NH), 9.06 (1H, s, —OH), 10.77 (1H, s, —NH) MS m/z: 420.1 (M$^+$ + 1). |
| 50 | 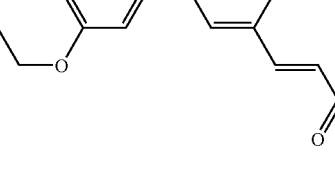 | $^1$H NMR (DMSO-d$_6$) δ: 0.49-0.50 (2H, m, —CH$_2$), 0.60-0.62 (2H, m, —CH$_2$), 1.54-1.56 (3H, t, —CH$_2$), 1.64-1.66 (3H, m, —CH$_2$), 1.86-1.87 (2H, d, —CH$_2$), 2.72-2.74 (1H, m, —CH), 4.74-4.75 (1H, m, —CH), 6.47-6.51 (1H, d, =CH), 6.70-6.72 (2H, d, Ar—H), 6.91-6.94 (2H, d, Ar—H), 7.17-7.19 (2H, d, Ar—H), 7.23 (1H, s, =CH), 7.46-7.50 (1H, d, =CH), 7.56-7.61 (3H, m, Ar—H and —NH), 9.07 (1H, s, —OH), 10.78 (1H, s, —NH); MS m/z: 433.2 (M$^+$ + 1). |
| 51 | 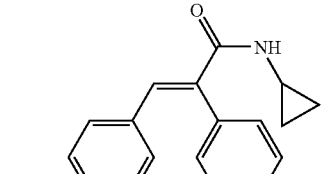 | $^1$H NMR (DMSO-d$_6$) δ (ppm): −0.10 (2H, m, —CH$_2$), 0.40-0.42 (2H, m, —CH$_2$), 2.33-2.35 (1H, m, —CH), 6.46-6.50 (1H, d, =CH), 7.22-7.27 (2H, m, Ar—H), 7.32-7.39 (4H, m, Ar—H), 7.44-7.48 (1H, d, =CH), 7.52-7.54 (2H, d, Ar—H), 7.84-7.85 (1H, d, —NH), 9.06 (1H, s, —OH), 10.77 (1H, s, —NH). MS m/z: 381.1 (M$^+$ + 1). |
| 52 | 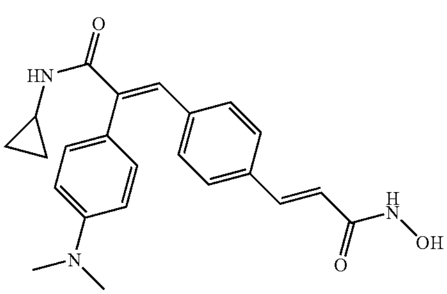 [SMILES: CN(C)c1ccc(/C(=C\c2ccc(/C=C/C(=O)NO)cc2)C(=O)NC2CC2)cc1] | $^1$H NMR (DMSO-d$_6$) δ (ppm): 0.48-0.49 (2H, d, —CH$_2$), 0.62-0.63 (2H, d, —CH$_2$), 2.73-2.75 (1H, q, —CH), 2.93 (6H, s, —NCH$_3$), 6.38-6.42 (1H, d, =CH), 6.68-6.70 (2H, d, Ar—H), 6.95-6.97 (2H, d, Ar—H), 7.09-7.10 (3H, d, Ar—H and =CH), 7.34-7.39 (3H, m, Ar—H and =CH), 7.53-7.54 (1H, d, —NH), 9.05 (1H, s, —OH), 10.74 (1H, s, —NH). MS m/z: 392.1 (M$^+$ + 1). |

| Ex. No | Structure | Analytical data |
|---|---|---|
| 53 | 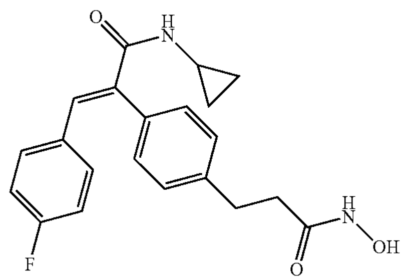 [SMILES: O=C(CCc1ccc(/C(=C\c2ccc(F)cc2)C(=O)NC2CC2)cc1)NO] | $^1$H NMR (DMSO-d$_6$) δ (ppm): 0.50 (2H, m, —CH$_2$), 0.61-0.64 (2H, q, —CH$_2$), 2.26-2.30 (2H, t, —CH$_2$), 2.70-2.75 (1H, m, —CH), 2.82-2.85 (2H, t, —CH$_2$), 7.01-7.05 (6H, m, Ar—H), 7.17-7.21 (3H, t, Ar—H and =CH), 7.22-7.23 (1H, d, —NH), 8.74 (1H, s, —OH), 10.39 (1H, s, —NH). MS m/z: 369.1 (M$^+$ + 1). |
| 54 | 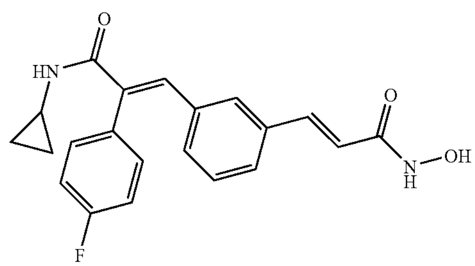 [SMILES: O=C(/C=C/c1cccc(/C=C(/C(=O)NC2CC2)c2ccc(F)cc2)c1)NO] | $^1$H NMR (DMSO-d$_6$) δ (ppm): 0.51-0.52 (2H, d, —CH$_2$), 0.62-0.65 (2H, t, —CH$_2$), 2.75-2.77 (1H, m, —CH), 6.27-6.31 (1H, d, =CH), 6.90-6.92 (1H, d, Ar—H), 7.18-7.29 (8H, m, Ar—H and =CH), 7.38-740 (1H, d, Ar—H), 7.8-7.83 (1H, d, —NH), 9.05 (1H, s, —OH), 10.76 (1H, s, —NH). MS m/z: 367.0 (M$^+$ + 1). |

Example 55

Synthesis of (1E)-3-(4-(3-(cyclopropylamino)-2-(4-fluorophenyl)prop-1-en-1-yl)phenyl)-N-hydroxy-acrylamide

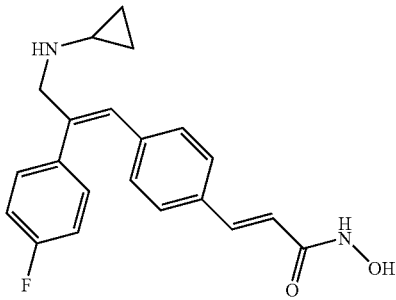 [SMILES: O=C(/C=C/c1ccc(/C=C(/CNC2CC2)c2ccc(F)cc2)cc1)NO]

Step-I

Preparation of methyl 3-(1E)-(4-(2-(4-fluorophenyl)-3-hydroxyprop-1-en-1-yl)phenyl)acrylate

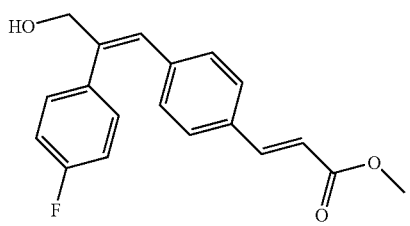 [SMILES: COC(=O)/C=C/c1ccc(/C=C(/CO)c2ccc(F)cc2)cc1]

To a suspension of 2-(4-fluorophenyl)-3-(4-(3-(E)-methoxy-3-oxoprop-1-en-1-yl)phenyl)acrylic acid (2 g, 6.1 mmol, prepared according to the procedure described in Example 1, step-II) in THF (10 mL), triethylamine was added (0.85 mL, 6.67 mmol) under constant stirring at 5° C. To this solution, methyl chloroformate (0.53 mL, 6.67 mmol) was added dropwise over a period of 30 minutes at 5° C. and stirred at the same temperature for 30 minutes. To this reaction mixture, sodium borohydride (0.9 g, 24.5 mmol) was added at one portion and methanol (5 mL) was added dropwise under stirring and the reaction mixture was stirred at 30° C. for 2 hours. After completion of the reaction, the reaction mixture was diluted with ethyl acetate (300 mL) and washed successively with water (2×100 mL) and brine (1×100 mL). The organic layer was dried over anhydrous Na$_2$SO$_4$ and concentrated to afford the crude compound, which was purified by column chromatography using 12% ethylacetate/hexanes as the eluent to afford a pure compound as a white solid (1.5 g, 79% yield).

Step-II

Preparation of methyl 3-(1E)(4-(2-(4-fluorophenyl)-3-oxoprop-1-en-1-yl)phenyl)acrylate

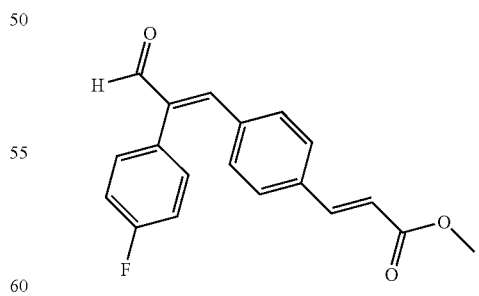

To a suspension of pyridinium chlorochromate (PCC, 0.75 g, 3.5 mmol) in dichloromethane (20 mL) a dropwise solution of methyl 3-(E)(4-(2-(4-fluorophenyl)-3-hydroxyprop-1-en-1-yl)phenyl)acrylate (0.9 g, 2.9 mmol) in dichloromethane (5 mL) was added under constant stirring and the reaction mixture was stirred at room temperature for 1 hour. The reaction mass was diluted with diethyl ether (200 mL) and filtered through a celite bed, the filtrate was successively washed with saturated aqueous NaHCO₃ solution (3×100 mL) and water (1×100 mL). The organic layer was dried over anhydrous Na₂SO₄ and concentrated to afford the pure title compound as a white solid (0.5 g, 56% yield).

Step-III

Preparation of methyl 3-(1E)-(4-(3-(cyclopropylamino)-2-(4-fluorophenyl) prop-1-en-1-yl)phenyl) acrylate

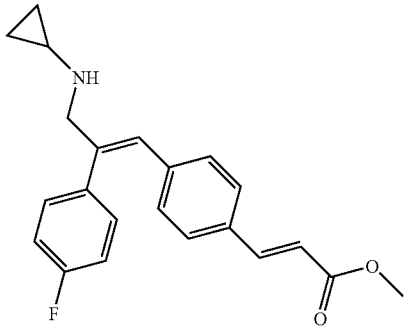 [SMILES: COC(=O)/C=C/c1ccc(/C=C(/CNC2CC2)c2ccc(F)cc2)cc1]

A mixture of methyl 3-(1E)(4-(2-(4-fluorophenyl)-3-hydroxyprop-1-en-1-yl)phenyl)acrylate (0.44 g, 1.4 mmol) and cyclopropylamine (0.14 g, 2.4 mmol) was stirred with MeOH (40 mL) for 3 hours. To the reaction mixture, sodium borohydride (0.09 g, 2.3 mmol) was added and stirred for 30 minutes. Subsequently the reaction mixture was diluted with ethyl acetate (300 mL) and washed successively with water (2×100 ml) and brine (1×100 mL). The organic layer was dried over anhydrous Na₂SO₄ and concentrated to afford the pure title compound as a pale yellow sticky compound (0.4 g, 80% yield).

Step-IV

Preparation of (1E)-3-(4-((3-(cyclopropylamino)-2-(4-fluorophenyl)prop-1-en-1-yl)phenyl)-N-hydroxyacrylamide

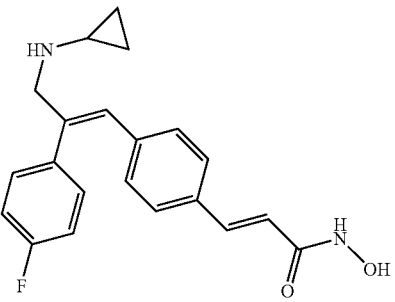 [SMILES: O=C(/C=C/c1ccc(/C=C(/CNC2CC2)c2ccc(F)cc2)cc1)NO]

Hydroxylamine hydrochloride (5 g, 71.8 mmol) in methanol (20 mL) was mixed with KOH (4 g, 71.8 mmol) in methanol (18 mL) at 0° C. and sonicated for 2 minutes and filtered. The filtrate was added to methyl 3-(1E)(4-(3-(cyclopropylamino)-2-(4-fluorophenyl)-prop-1-en-1-yl)phenyl)acrylate (1.4 g, 4 mmol) in dichloromethane (5 mL) and KOH (0.67 g, 12 mmol) was added. The reaction mixture was stirred at room temperature for 30 minutes. The reaction mixture was concentrated to obtain the yellow sticky compound, which was dissolved in water (200 mL) and adjusted to pH 8 using dilute acetic acid, extracted with ethyl acetate (2×150 mL). The ethyl acetate layer was dried over anhydrous Na₂SO₄ and concentrated to obtain the crude compound, which was purified by flash chromatography using 0.4% DCM: MeOH as eluent to afford the pure title compound as a yellow solid (0.56 g, 40% yield). $^1$H NMR (DMSO-$d_6$) δ (ppm): 0.74-0.76 (2H, d, —CH₂), 0.85 (2H, s, —CH₂), 2.73 (1H, s, —CH), 4.13 (2H, s, —CH₂), 6.38-6.42 (1H, d, =CH), 6.96-6.98 (3H, d, Ar—H), 7.23-7.28 (2H, t, Ar—H and =CH), 7.34-7.40 (5H, m, Ar—H and =CH), 9.00 (2H, d, —NH and —OH), 10.79 (1H, s, —NH). MS m/z: 352.9 (M⁺+1).

The following compounds were prepared according to the procedure given in Example 55.

| Ex. No | Structure | Analytical data |
|---|---|---|
| 56 | 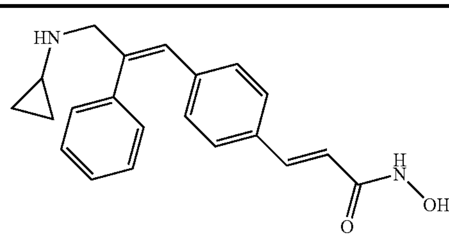 | $^1$H NMR (DMSO-$d_6$) δ (ppm): 0.26-0.27 (2H, d, —CH₂), 0.37-0.39 (2H, d, —CH₂), 2.11-2.1 (1H, m, —CH), 3.55 (2H, s, —CH₂), 6.32-6.426 (1H, d, =CH), 6.62 (1H, s, =CH), 6.93-6.95 (2H, d, Ar—H), 7.19-7.21 (2H, d, Ar—H), 7.28-7.37 (6H, m, Ar—H and =CH), 9.01 (1H, d, —OH), 10.69 (1H, s, —NH). MS m/z: 335.1 (M⁺ + 1). |
| 57 | 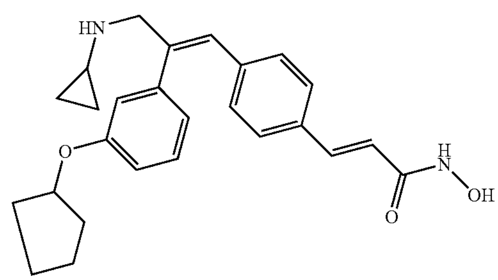 [SMILES: O=C(/C=C/c1ccc(/C=C(/CNC2CC2)c2cccc(OC3CCCC3)c2)cc1)NO] | $^1$H NMR (DMSO-$d_6$) δ (ppm): 0.23-0.24 (2H, m, —CH₂), 0.36-0.37 (2H, d, —CH₂), 1.50-1.60 (6H, m, —CH), 1.74-1.77 (2H, t, —CH₂), 2.12-2.16 (1H, m, —CH), 3.54 (2H, s, —CH₂), 4.68-4.70 (1H, t, —CH), 6.33-6.37 (1H, d, =CH), 6.60 (1H, s, =CH), 6.66 (1H, s, Ar—H), 6.73-6.75 (1H, d, Ar—H), 6.80-6.83 (1H, dd, Ar—H), 6.95-6.97 (2H, d, Ar—H), 7.21-7.25 (1H, t, Ar—H), 7.30-7.36 (3H, t, Ar—H and =CH), 9.05 (1H, s, —OH), 10.70 (1H, s, —NH). MS m/z: 419.1 (M⁺ + 1). |

| Ex. No | Structure | Analytical data |
|---|---|---|
| 58 | 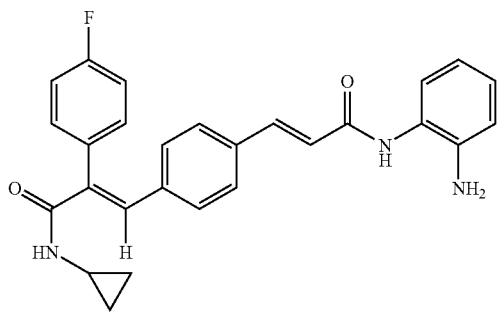 [SMILES: Nc1ccccc1NC(=O)/C=C/c1ccc(/C=C(/C(=O)NC2CC2)c2ccc(F)cc2)cc1] | $^1$H NMR (DMSO-d$_6$) δ (ppm): 0.23-0.24 (2H, d, —CH$_2$), 0.36-0.37 (2H, s, —CH$_2$), 2.09-2.13 (1H, s, —CH), 3.56 (2H, s, —CH$_2$), 6.34-6.38 (1H, d, =CH), 6.66 (1H, s, =CH), 6.95-6.97 (2H, d, Ar—H), 7.14-7.15 (1H, t, Ar—H), 7.27-7.37 (6H, m, Ar—H and =CH), 9.02 (2H, s, —OH), 10.70 (1H, s, —NH). MS m/z: 369.0 (M$^+$ + 1). |

Example 59

Synthesis of N-cyclopropyl-3-(4-((1E)-3-(2-aminophenylamino)-3-oxoprop-1-en-1-ylphenyl)-2-(4-fluorophenyl)-acrylamide

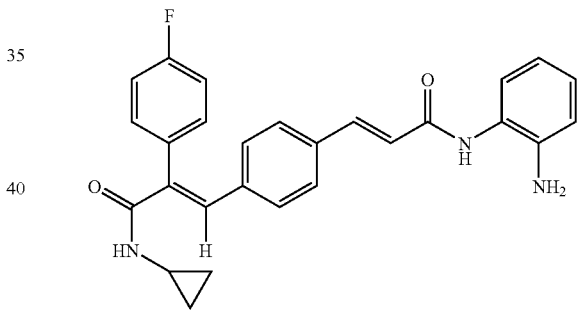

Step-I

Preparation of 3-(1E)-(4-(3-cyclopropylamino)-2-(4-fluorophenyl)-3-oxoprop-1-en-1-yl)phenyl)acrylic acid

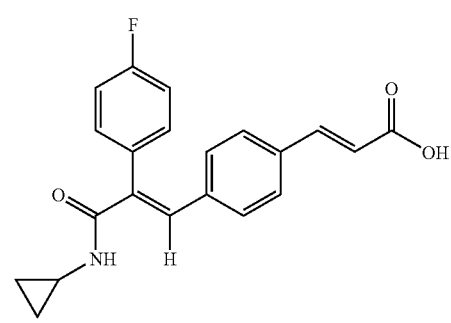 [SMILES: O=C(O)/C=C/c1ccc(/C=C(/C(=O)NC2CC2)c2ccc(F)cc2)cc1]

To a solution of methyl 3-(1E)-(4-(3-(cyclopropylamino)-2-(4-fluorophenyl)-3-oxoprop-1-en-1-yl)phenyl)acrylate (1 g, 2.7 mmol) in methanol (20 mL), a solution of NaOH (0.44 g, 4.4 mmol) in water (1 mL) was added. The reaction mixture was stirred for 2 hours at 70° C. Subsequently the solvent was completely removed by evaporation, diluted with water (50 mL) and extracted with ethyl acetate (2×50 mL). The aqueous layer was acidified to pH 2 with dilute aqueous HCl (1:1) and allowed to stand at 4° C. for 30 minutes, the solid precipitated out was filtered and dried under vacuum to give the expected product as a white solid (0.67 g, 70% yield).

Step-II

Preparation of N-cyclopropyl-3-(4-((1E)-3-(2-aminophenylamino)-3-oxoprop-1-en-1-ylphenyl)-2-(4-fluorophenyl)-acrylamide To a suspension of 3-(1E)-(4-(3-cyclopropylamino)-2-(4-fluorophenyl)-3-oxoprop-1-enyl)phenyl)acrylic acid (0.21 g, 0.6 mmol) in DMF (5 mL), EDCI (0.23 g, 1.2 mmol), HOBt (0.08 g, 0.6 mmol), o-phenylenediamine (0.06 g, 0.54 mmol), were added followed by triethylamine (0.25 mL, 1.8 mmol). The reaction mixture was stirred for 1 hour after which the mixture was added to cold water (20 mL). The aqueous layer was extracted with ethyl acetate (1×150 mL), washed with water (2×50 mL) and brine (1×100 mL). The organic layer was dried over anhydrous Na$_2$SO$_4$ and concentrated to get the crude compound. The crude yellow colored compound was triturated with ethyl acetate (20 mL) to afford the title compound as a yellow solid (0.06 g, 24% yield). $^1$H NMR (DMSO-d$_6$) δ (ppm): 0.52 (2H, m, —CH$_2$), 0.64-0.65 (1H, d, —CH$_2$), 2.75 (1H, m, —CH), 4.93 (2H, s, —NH$_2$), 6.57 (1H, t, =CH), 6.75 (1H, d, Ar—H), 6.82-6.86 (1H, d, =CH), 6.91 (1H, t, Ar—H), 7.03-7.05 (2H, d, Ar—H), 7.19-7.22 (4H, m. Ar—H), 7.29 (1H, s, =CH), 7.31-7.33 (1H, d, Ar—H), 7.43-7.47 (3H, t, Ar—H), 7.97-7.98 (1H, d, —NH), 9.35 (1H, s, —NH). MS m/z: 442.2 (M$^+$+1).

The following compounds were prepared according to the procedure given in Example 59.

| Ex. No | Structure | Analytical data |
|---|---|---|
| 60 | 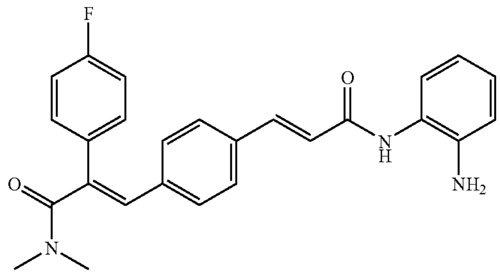 [SMILES: CN(C)C(=O)/C(=C/c1ccc(/C=C/C(=O)Nc2ccccc2N)cc1)c1ccc(F)cc1] | $^1$H NMR (DMSO-d$_6$) δ (ppm): 2.92 (3H, s, —CH$_3$), 3.05 (3H, s, —CH$_3$), 4.94 (2H, s, —NH$_2$), 6.56-6.58 (1H, t, Ar—H), 6.71 (1H, s, =CH), 6.73-9.75 (1H, d, Ar—H), 6.86-6.90 (1H, d, =CH), 6.91-6.93 (1H, m, Ar—H), 7.14-7.23 (4H, m, Ar—H and =CH), 7.31-7.34 (3H, t, Ar—H), 7.48-7.49 (3H, d, Ar—H), 9.37 (1H, s, —NH). MS m/z: 430.2 (M$^+$ + 1). |
| 61 | 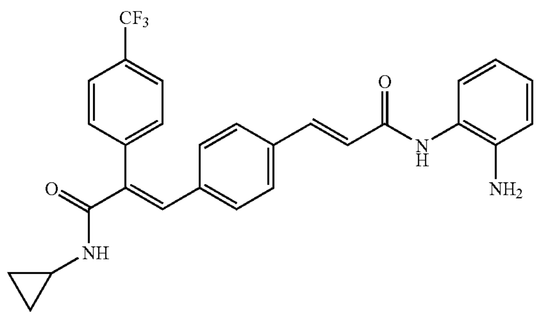 [SMILES: Nc1ccccc1NC(=O)/C=C/c1ccc(/C=C(/C(=O)NC2CC2)c2ccc(C(F)(F)F)cc2)cc1] | $^1$H NMR (DMSO-d$_6$) δ (ppm): 0.52-0.55 (2H, q, —CH$_2$), 0.63-0.66 (2H, q, —CH$_2$), 2.76-2.77 (1H, m, —CH), 4.93 (2H, s, —NH$_2$), 6.57 (1H, t, =CH), 6.73-6.75 (1H, d, Ar—H), 6.82-6.86 (1H, d, =CH), 6.91 (1H, t, Ar—H), 7.02-7.04 (2H, d, Ar—H), 7.31-7.47 (7H, m, =CH and Ar—H), 7.73-7.75 (2H, d, Ar—H), 8.05 (1H, s, —NH), 9.34 (1H, s, —NH). MS m/z: 492.2 (M$^+$ + 1). |
| 62 | 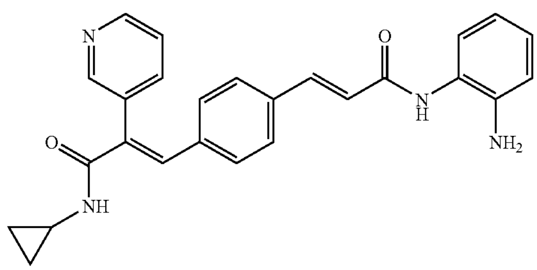 | $^1$H NMR (DMSO-d$_6$) δ (ppm): 0.53 (2H, m, —CH$_2$), 0.65-0.66 (2H, d, —CH$_2$), 2.77 (1H, m, —CH), 4.93 (2H, s, —NH$_2$), 6.57 (1H, t, =CH), 6.73-6.75 (1H, d, Ar—H), 6.82-6.86 (1H, d, =CH), 6.89-6.91 (1H, t, Ar—H), 7.03-7.05 (2H, d, Ar—H), 7.31-7.33 (1H, d, Ar—H), 7.41-7.48 (4H, m, =CH and Ar—H), 7.60-7.62 (1H, d, Ar—H), 8.05-8.06 (1H, d, Ar—H), 8.28 (1H, s, Ar—H), 8.54-8.55 (1H, d, —NH), 9.36 (1H, s, —NH). MS m/z: 425.2 (M$^+$ + 1). |
| 63 | 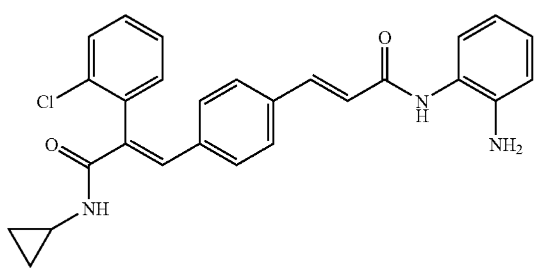 [SMILES: Nc1ccccc1NC(=O)/C=C/c1ccc(/C=C(/C(=O)NC2CC2)c2ccccc2Cl)cc1] | $^1$H NMR (DMSO-d$_6$) δ (ppm): 0.52 (2H, m, —CH$_2$), 0.63-0.65 (2H, d, —CH$_2$), 2.75 (1H, m, —CH), 4.93 (2H, s, —NH$_2$), 6.57 (1H, t, =CH), 6.73-6.75 (1H, d, Ar—H), 6.82-6.86 (1H, d, =CH), 6.91 (1H, t, Ar—H), 6.98-7.00 (2H, d, Ar—H), 7.14-7.16 (1H, d, Ar—H), 7.31-7.34 (2H, m, =CH and Ar—H), 7.42-7.46 (5H, t, Ar—H), 7.55-7.57 (1H, d, Ar—H), 7.84 (1H, s, —NH), 9.35 (1H, s, —NH). MS m/z: 458.1 (M$^+$ + 1). |
| 64 | 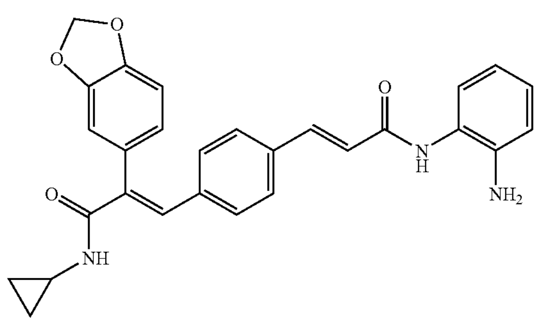 [SMILES: Nc1ccccc1NC(=O)/C=C/c1ccc(/C=C(/C(=O)NC2CC2)c2ccc3c(c2)OCO3)cc1] | $^1$H NMR (DMSO-d$_6$) δ (ppm): 0.51-0.52 (2H, d, —CH$_2$), 0.63-0.64 (2H, d, —CH$_2$), 2.75 (1H, m, —CH), 4.93 (2H, s, —NH$_2$), 6.06 (2H, s, —CH$_2$), 6.57 (1H, t, =CH), 6.60-6.62 (1H, d, Ar—H), 6.70 (1H, s, Ar—H), 6.73-6.75 (1H, d, Ar—H), 6.83-6.87 (1H, d, =CH), 6.92-6.94 (2H, d, Ar—H), 7.09-7.11 (2H, d, Ar—H), 7.26 (1H, s, =CH), 7.31 (1H, d, Ar—H), 7.45-7.48 (3H, t, Ar—H), 7.62-7.63 (1H, d, —NH), 9.36 (1H, s, —NH). MS m/z: 468.1 (M$^+$ + 1). |

| Ex. No | Structure | Analytical data |
| --- | --- | --- |
| 65 | 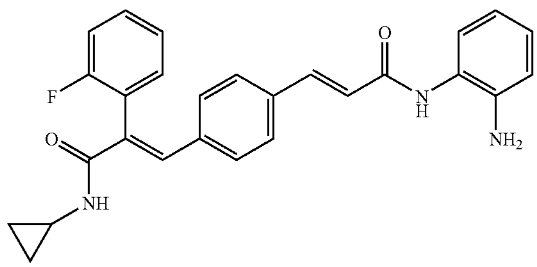 [SMILES: Nc1ccccc1NC(=O)/C=C/c1ccc(/C=C(/C(=O)NC2CC2)c2ccccc2F)cc1] | $^1$H NMR (DMSO-d$_6$) δ (ppm): 0.53 (2H, m, —CH$_2$), 0.64-0.65 (2H, d, —CH$_2$), 2.75-2.76 (1H, m, —CH), 4.93 (2H, s, —NH$_2$) 6.57 (1H, t, =CH), 6.73-6.75 (1H, d, Ar—H), 6.82-6.86 (1H, d, =CH), 6.91 (1H, t, Ar—H), 7.05-7.07 (2H, d, Ar—H), 7.16-7.24 (3H, m, =CH and Ar—H), 7.31-7.33 (1H, d, Ar—H), 7.43-7.47 (5H, m, Ar—H), 7.97-7.98 (1H, d, —NH), 9.35 (1H, s, —NH). MS m/z: 442.2 (M$^+$ + 1). |
| 66 | 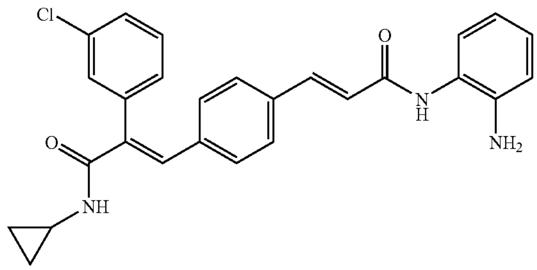 | $^1$H NMR (DMSO-d$_6$) δ (ppm): 0.53 (2H, m, —CH$_2$), 0.64-0.66 (2H, d, —CH$_2$), 2.75-2.76 (1H, m, —CH), 4.93 (2H, s, —NH$_2$), 6.57 (1H, t, =CH), 6.73-6.75 (1H, d, Ar—H), 6.83-6.87 (1H, d, =CH), 6.89-6.91 (1H, t, Ar—H), 7.04-7.06 (2H, d, Ar—H), 7.11-7.13 (1H, d, Ar—H), 7.21 (1H, s, =CH), 7.31-7.33 (2H, d, Ar—H), 7.42-7.48 (5H, m, Ar—H), 7.96-7.97 (1H, d, —NH), 9.36 (1H, s, —NH). MS m/z: 458.1 (M$^+$ + 1). |
| 67 | 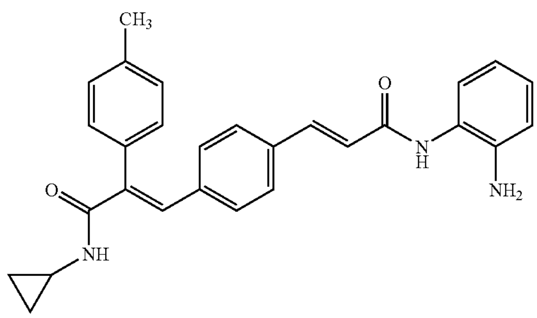 [SMILES: Cc1ccc(/C(=C\c2ccc(/C=C/C(=O)Nc3ccccc3N)cc2)C(=O)NC2CC2)cc1] | $^1$H NMR (DMSO-d$_6$) δ (ppm): 0.50 (2H, m, —CH$_2$), 0.62-0.64 (2H, d, —CH$_2$), 2.34 (3H, s, —CH$_3$), 2.74-2.75 (1H, m, —CH), 4.94 (2H, s, —NH$_2$), 6.57 (1H, t, =CH), 6.73-6.75 (1H, d, Ar—H), 6.81-6.85 (1H, d, =CH), 6.89-6.91 (1H, t, Ar—H), 7.04-7.06 (4H, m, Ar—H), 7.19-7.22 (3H, t, =CH and Ar—H), 7.31-7.33 (1H, d, Ar—H), 7.41-7.47 (3H, t, Ar—H), 7.70-7.71 (1H, d, —NH), 9.35 (1H, s, —NH). MS m/z: 438.2 (M$^+$ + 1). |
| 68 | 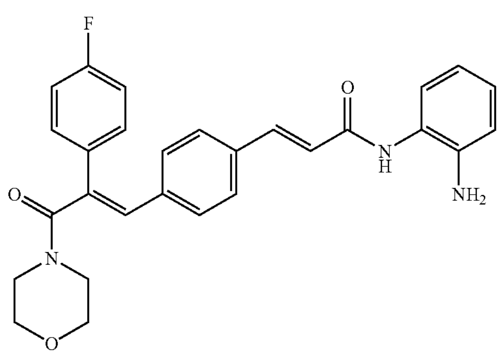 [SMILES: Nc1ccccc1NC(=O)/C=C/c1ccc(/C=C(/C(=O)N2CCOCC2)c2ccc(F)cc2)cc1] | $^1$H NMR (DMSO-d$_6$) δ (ppm): 3.17 (8H, s, Morpholine-H), 4.93 (2H, s, —NH$_2$), 6.57-6.59 (1H, t, =CH), 6.73-6.75 (2H, m, Ar—H and =CH), 6.83-6.87 (1H, d, =CH), 6.89-6.91 (1H, t, Ar—H), 7.15-7.17 (2H, d, Ar—H), 7.20-7.24 (2H, t, Ar—H), 7.31-7.32 (3H, d, Ar—H), 7.45-7.49 (3H, t, Ar—H), 9.37 (1H, s, —NH). MS m/z: 472.3 (M$^+$ + 1). |
| 69 | 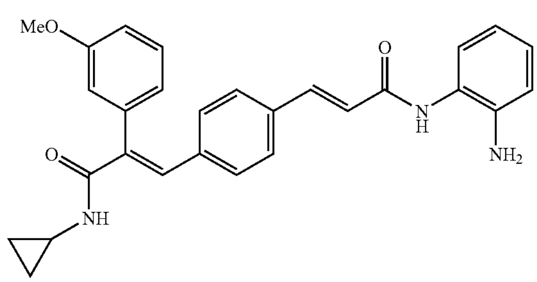 [SMILES: COc1cccc(/C(=C\c2ccc(/C=C/C(=O)Nc3ccccc3N)cc2)C(=O)NC2CC2)c1] | $^1$H NMR (DMSO-d$_6$) δ (ppm): 0.51 (2H, m, —CH$_2$), 0.63-0.65 (2H, d, —CH$_2$), 2.74-2.75 (1H, m, —CH), 3.71 (3H, s, —OCH$_3$), 4.93 (2H, s, —NH$_2$), 6.57 (1H, t, =CH), 6.71-6.75 (3H, m, Ar—H), 6.82-6.86 (1H, d, =CH), 6.89-6.91 (2H, m, Ar—H), 6.94-6.96 (2H, d, Ar—H), 7.26 (1H, s, =CH), 7.30-7.32 (2H, d, Ar—H), 7.42-7.47 (3H, t, Ar—H), 7.70 (1H, s, —NH), 9.36 (1H, s, —NH). MS m/z: 454.2 (M$^+$ + 1). |

-continued

| Ex. No | Structure | Analytical data |
|---|---|---|
| 70 | 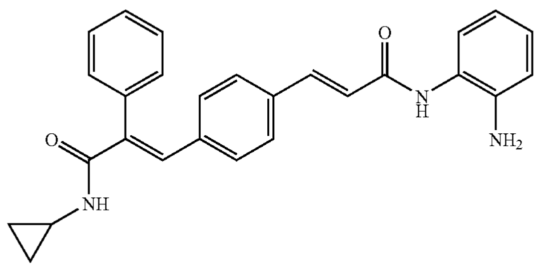 [SMILES: Nc1ccccc1NC(=O)/C=C/c1ccc(/C=C(/C(=O)NC2CC2)c2ccccc2)cc1] | ¹H NMR (DMSO-d₆) δ (ppm): 0.50-0.53 (2H, q, —CH₂), 0.62-0.65 (2H, q, —CH₂), 2.74-2.77 (1H, q, —CH), 4.93 (2H, s, —NH₂), 6.57 (1H, t, =CH), 6.73-6.75 (1H, d, Ar—H), 6.81-6.85 (1H, d, =CH), 6.91 (1H, t, Ar—H), 7.02-7.04 (2H, d, Ar—H), 7.16-7.18 (2H, t, Ar—H), 7.25 (1H, s, =CH), 7.31 (1H, d, Ar—H), 7.38-7.47 (6H, m, Ar—H), 7.80-7.81 (1H, d, —NH), 9.35 (1H, s, —NH). MS m/z: 424.1 (M⁺ + 1). |
| 71 | 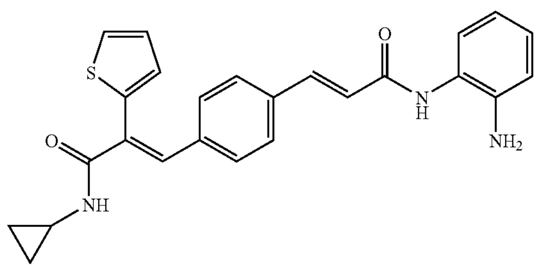 [SMILES: Nc1ccccc1NC(=O)/C=C/c1ccc(/C=C(/C(=O)NC2CC2)c2cccs2)cc1] | ¹H NMR (DMSO-d₆) δ (ppm): 0.53 (2H, m, —CH₂), 0.66-0.67 (2H, d, —CH₂), 2.76-2.77 (1H, m, —CH), 4.95 (2H, s, —NH₂), 6.58 (1H, t, =CH), 6.74-6.76 (1H, d, Ar—H), 6.89-6.97 (3H, m, Ar—H), 7.07 (1H, t, Ar—H), 7.18-7.19 (2H, d, Ar—H), 7.26 (1H, s, =CH), 7.32 (1H, d, Ar—H), 7.47-7.51 (3H, m, Ar—H), 7.61-7.62 (1H, d, Ar—H), 8.01-8.02 (1H, d, —NH), 9.39 (1H, s, —NH). MS m/z: 430.3 (M⁺ + 1). |
| 72 | 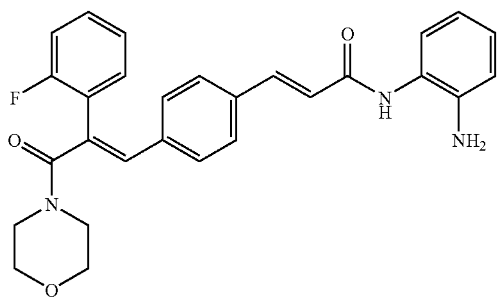 [SMILES: Nc1ccccc1NC(=O)/C=C/c1ccc(/C=C(/C(=O)N2CCOCC2)c2ccccc2F)cc1] | ¹H NMR (DMSO-d₆) δ (ppm): 3.59 (8H, s, Morpholine-H), 4.94 (2H, s, —NH₂), 6.57 (1H, t, =CH), 6.73-6.75 (1H, d, Ar—H), 6.83-6.87 (1H, d, =CH), 6.91 (1H, t, Ar—H), 6.95 (1H, s, =CH), 7.14-7.16 (2H, d, Ar—H), 7.22-7.27 (2H, q, Ar—H), 7.31-7.33 (2H, d, Ar—H), 7.45-7.49 (4H, t, Ar—H), 9.62 (1H, s, —NH). MS m/z: 472.0 (M⁺ + 1). |
| 73 | 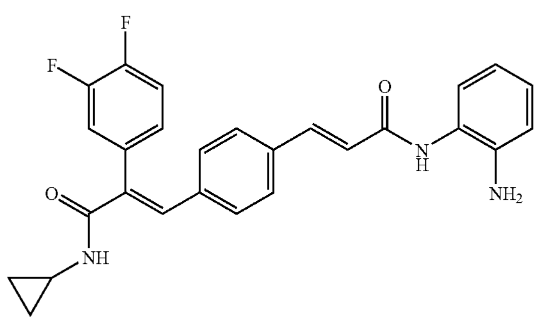 [SMILES: Nc1ccccc1NC(=O)/C=C/c1ccc(/C=C(/C(=O)NC2CC2)c2ccc(F)c(F)c2)cc1] | ¹H NMR (DMSO-d₆) δ (ppm): 0.52-0.54 (2H, t, —CH₂), 0.62-0.65 (2H, q, —CH₂), 2.73-2.76 (1H, q, —CH), 4.95 (2H, s, —NH₂), 6.57-6.59 (1H, t, =CH), 6.73-6.75 (1H, d, Ar—H), 6.85-6.91 (2H, t, =CH and Ar—H), 6.98 (1H, s, Ar—H), 7.05-7.07 (2H, d, Ar—H), 7.26 (1H, s, =CH), 7.32-7.48 (5H, m, Ar—H), 7.82-7.83 (1H, d, —NH), 9.41 (1H, s, —NH). MS m/z: 460.1 (M⁺ + 1). |
| 74 | 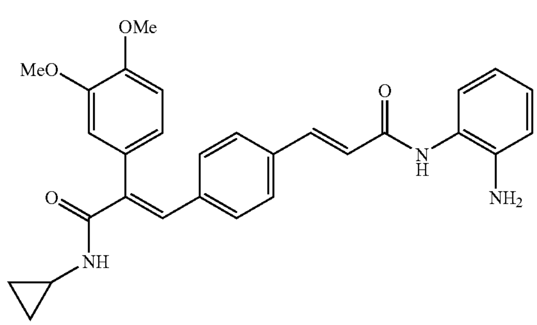 [SMILES: COc1ccc(/C(=C\c2ccc(/C=C/C(=O)Nc3ccccc3N)cc2)C(=O)NC2CC2)cc1OC] | ¹H NMR (DMSO-d₆) δ: 0.50-0.52 (2H, m, —CH₂), 0.61-0.65 (2H, m, —CH₂), 2.73-2.78 (1H, m, —CH), 3.62 (3H, s, —OCH₃), 3.78 (3H, s, —OCH₃), 4.93 (2H, s, —NH₂), 6.55-6.59 (1H, t, =CH), 6.68-6.75 (3H, m, Ar—H), 6.82-6.86 (1H, d, =CH), 6.89-6.93 (1H, t, Ar—H), 6.96-6.98 (1H, d, Ar—H), 7.08-7.10 (2H, d, Ar—H), 7.25 (1H, s, =CH), 7.30-7.32 (1H, d, Ar—H), 7.43-7.47 (3H, m, Ar—H), 7.54 (1H, d, —NH), 9.35 (1H, s, —NH); m/z: (M⁺ + 1) 483.9 |

Example 75

Synthesis of 6-(3-(1E)-(4-(3-(cyclopropylamino)-2-(4-fluorophenyl)-3-oxoprop-1-en-1-yl)phenyl)acrylamido)-N-hydroxyhexanamide

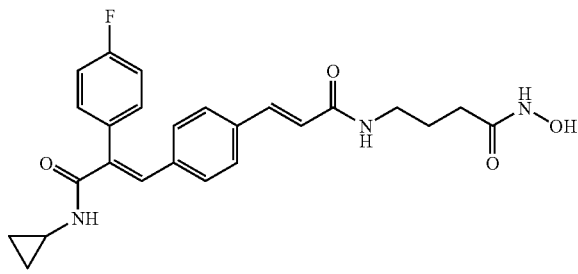 [SMILES: O=C(/C=C/c1ccc(/C=C(/C(=O)NC2CC2)c2ccc(F)cc2)cc1)NCCCC(=O)NO]

Step-I

Preparation of methyl 6-(3-(1E)-(4-(3-(cyclopropylamino)-2-(4-fluorophenyl)-3-oxoprop-1-en-1-yl)phenyl)acrylamido)hexenoate

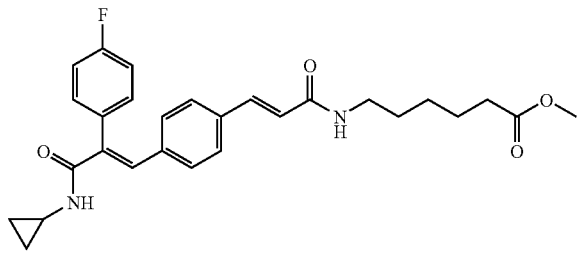 [SMILES: COC(=O)CCCCCNC(=O)/C=C/c1ccc(/C=C(/C(=O)NC2CC2)c2ccc(F)cc2)cc1]

To a suspension of 3-(1E)-(4-(2-(4-fluorophenyl)-3-(cyclopropylamino)-3-oxoprop-1-en-1-yl)phenyl)acrylic acid (prepared according to the procedure described in Example 59, step-I) (0.35 g, 1 mmol) in DMF (15 mL) EDCI (0.83 g, 2 mmol), HOBt (0.13 g, 1 mmol), methyl 6-aminocaproate (0.16 g, 0.9 mmol), were added, followed by triethylamine (0.4 mL, 3 mmol). The reaction mixture was stirred for 2 hours after which the mixture was added to cold water (50 mL). The aqueous layer was extracted with ethyl organic layer was dried over anhydrous $Na_2SO_4$ and concentrated to get the crude compound. The crude yellow colored compound was washed with ethyl acetate/hexane (0.5/9.5, 2×20 mL) to afford the title compound as a yellow solid (0.25 g, 52% yield).

Step-II

Preparation of 6-(3-(1E)-(4-(3-(cyclopropylamino)-2-(4-fluorophenyl)-3-oxoprop-1-en-1-yl)phenyl)acrylamido)-N-hydroxyhexanamide

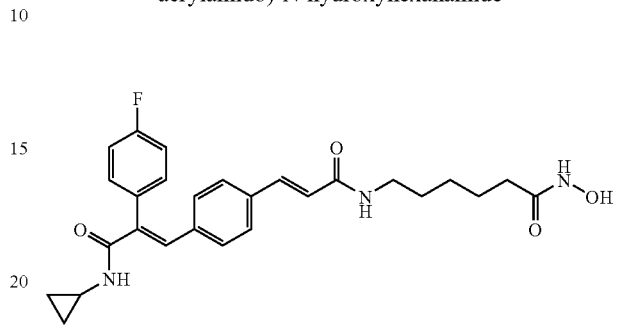

Hydroxylamine hydrochloride (0.63 g, 9 mmol) in methanol (3 mL) was mixed with KOH (0.51 g, 12.3 mmol) in methanol (3 mL) at 0° C., and sonicated for. 2 minutes and the white precipitate formed was filtered. The filtrate was added to the methyl 6-(3-(E)-(4-(3-(cyclopropylamino)-2-(4-fluorophenyl)-3-oxoprop-1-en-1-yl) phenyl)acrylamido)hexenoate (0.24 g, 0.5 mmol) in DCM (1.5 mL) and the mixture was stirred at room temperature for 30 minutes. The reaction mixture was diluted with water (200 mL) and extracted with ethyl acetate (1×200 mL). The ethyl acetate layer was washed with water (100 mL), dried over anhydrous $Na_2SO_4$ and concentrated to obtain a sticky compound, subsequently triturated with DCM (15 mL), to obtain a solid. The solid obtained was filtered and washed with DCM (5 mL) to afford the title compound (0.075 g, 32% yield). $^1$H NMR (DMSO-$d_6$) δ (ppm): 0.51 (2H, m, —$CH_2$), 0.62-0.64 (2H, t, —$CH_2$), 1.24 (2H, m, —$CH_2$), 1.40-1.49 (4H, m, —$CH_2$), 1.91-1.93 (2H, d, —$CH_2$), 2.74-2.76 (1H, m, —CH), 3.12-3.13 (2H, d, —$CH_2$) 6.53-6.57 (1H, d, =CH), 6.99-7.01 (2H, d, Ar—H), 7.18-7.22 (4H, m, Ar—H), 7.27 (1H, s, =CH), 7.28-7.32 (1H, d, =CH), 7.37-7.39 (2H, d, Ar—H), 7.82-7.83 (1H, d, —NH), 8.06 (1H, s, —NH), 8.67 (1H, s, —OH), 10.34 (1H, s, —NH). MS m/z: 480.3 ($M^+$+1).

The following compounds were prepared according to the procedure given in Example 75.

| Ex. No | Structure | Analytical data |
|---|---|---|
| 76 | 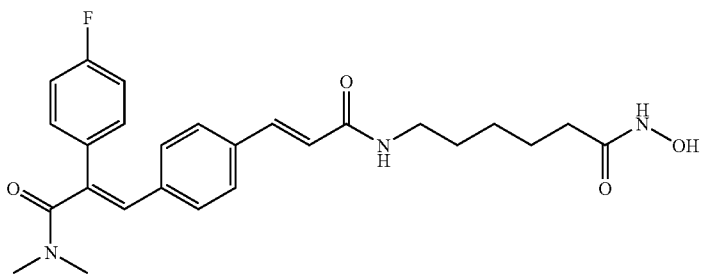 | $^1$H NMR (DMSO-$d_6$) δ (ppm): 1.24-1.26 (2H, m, —$CH_2$), 1.41-1.45 (2H, m, —$CH_2$), 1.47-1.51 (2H, m, —$CH_2$), 1.92-1.95 (2H, t, —$CH_2$), 2.91 (3H, s, —$CH_3$), 3.04 (3H, s, —$CH_3$), 3.11-3.16 (2H, q, —$CH_2$) 6.54-6.58 (1H, d, =CH), 6.69 (1H, s, =CH), 7.10-7.12 (2H, d, Ar—H), 7.18-7.22 (2H, t, =CH, Ar—H), 7.29-7.34 (3H, m, Ar—H), 7.40-7.42 (2H, d, Ar—H), 8.06-8.08 (1H, t, —NH), 8.67 (1H, s, —OH), 10.34 (1H, s, —NH). MS m/z: 496.2 ($M^+$ + 1). |

| Ex. No | Structure | Analytical data |
|---|---|---|
| 77 | 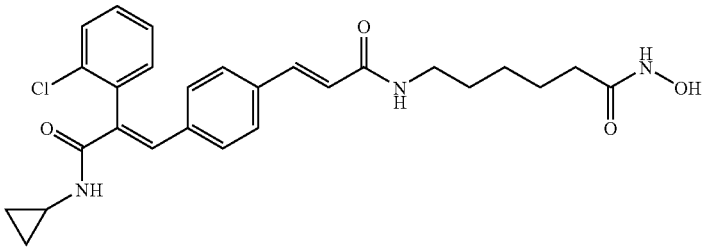 [SMILES: O=C(/C=C/c1ccc(/C=C(/C(=O)NC2CC2)c2ccccc2F)cc1)NCCCCCC(=O)NO] | $^1$H NMR (DMSO-$d_6$) δ (ppm): 0.50-0.52 (2H, t, —CH$_2$), 0.62-0.64 (2H, t, —CH$_2$), 1.25-1.50 (6H, m, —CH$_2$), 1.91-1.93 (2H, t, —CH$_2$), 2.74-2.76 (1H, m, —CH), 3.12-3.14 (2H, d, —CH$_2$) 6.53-6.57 (1H, d, =CH), 6.94-6.96 (2H, d, Ar—H), 7.14-7.15 (1H, d, Ar—H), 7.28-7.35 (2H, t, =CH, Ar—H), 7.38-7.40 (2H, t, Ar—H), 7.54-7.55 (2H, t, =CH and Ar—H), 7.55-7.57 (1H, d, Ar—H), 7.82 (1H, d, —NH), 8.05 (1H, t, —NH), 8.67 (1H, s, —OH), 10.34 (1H, s, —NH). MS m/z: 496.2 (M$^+$ + 1). |
| 78 | 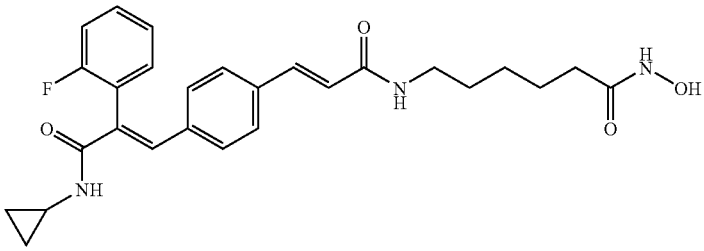 | $^1$H NMR (DMSO-$d_6$) δ (ppm): 0.50-0.52 (2H, t, —CH$_2$), 0.64-0.65 (2H, t, —CH$_2$), 1.24-1.25 (2H, m, —CH$_2$), 1.40-1.50 (4H, m, —CH$_2$), 1.91-1.95 (2H, t, —CH$_2$), 2.74-2.76 (1H, m, —CH), 3.12-3.13 (2H, d, —CH$_2$) 6.53-6.57 (1H, d, =CH), 7.02-7.04 (1H, d, Ar—H), 7.14-7.23 (4H, m, Ar—H), 7.28-7.32 (1H, d, =CH), 7.37-7.43 (4H, m, Ar—H and =CH), 7.96-7.97 (1H, d, —NH), 8.06 (1H, t, —NH), 8.66 (1H, s, —OH), 10.34 (1H, s, —NH). MS m/z: 480.2 (M$^+$ + 1). |
| 79 | 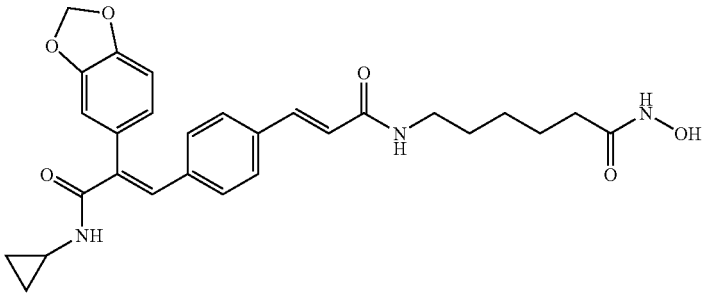 [SMILES: O=C(/C=C/c1ccc(/C=C(/C(=O)NC2CC2)c2ccc3c(c2)OCO3)cc1)NCCCCCC(=O)NO] | $^1$H NMR (DMSO-$d_6$) δ (ppm): 0.50-0.52 (2H, t, —CH$_2$), 0.61-0.63 (2H, t, —CH$_2$), 1.24 (2H, m, —CH$_2$), 1.43-1.49 (4H, m, —CH$_2$), 1.91-1.93 (2H, t, —CH$_2$), 2.74-2.76 (1H, m, —CH), 3.12-3.14 (2H, d, —CH$_2$), 6.06 (2H, s, —CH$_2$) 6.54-6.61 (2H, q, =CH and Ar—H), 6.68 (1H, s, Ar—H), 6.91-6.93 (1H, d, Ar—H), 7.05-7.07 (2H, d, Ar—H), 7.24 (1H, s, =CH), 7.29-7.33 (1H, d, =CH), 7.38-7.40 (2H, d, Ar—H), 7.60 (1H, s, —NH), 8.06 (1H, s, —NH), 8.67 (1H, s, —OH), 10.33 (1H, s, —NH). MS m/z: 506.2 (M$^+$ + 1). |
| 80 | 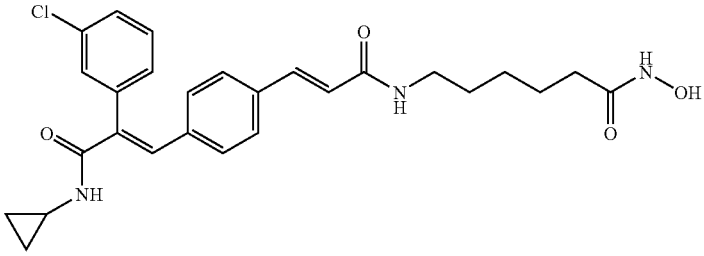 [SMILES: O=C(/C=C/c1ccc(/C=C(/C(=O)NC2CC2)c2cccc(Cl)c2)cc1)NCCCCCC(=O)NO] | $^1$H NMR (DMSO-$d_6$) δ (ppm): 0.52 (2H, s, —CH$_2$), 0.63-0.65 (2H, t, —CH$_2$), 1.24-1.26 (2H, m, —CH$_2$), 1.41-1.50 (4H, m, —CH$_2$), 1.91-1.95 (2H, t, —CH$_2$), 2.74 (1H, m, —CH), 3.12-3.14 (2H, d, —CH$_2$) 6.54-6.58 (1H, d, =CH) 7.00-7.02 (2H, d, Ar—H), 7.09-7.11 (1H, d, Ar—H), 7.19 (1H, s, =CH), 7.29-7.33 (2H, t, =CH and Ar—H), 7.38-7.44 (4H, m, Ar—H), 7.94-7.95 (1H, d, —NH), 8.04-8.05 (1H, d, —NH), 8.67 (1H, s, —OH), 10.33 (1H, s, —NH). MS m/z: 496.1 (M$^+$ + 1). |
| 81 | 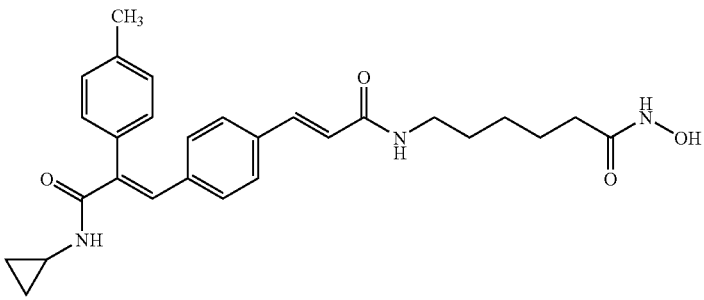 [SMILES: Cc1ccc(/C(=C\c2ccc(/C=C/C(=O)NCCCCCC(=O)NO)cc2)C(=O)NC2CC2)cc1] | $^1$H NMR (DMSO-$d_6$) δ (ppm): 0.49-0.50 (2H, d, —CH$_2$), 0.62-0.63 (2H, d, —CH$_2$), 1.24-1.25 (2H, m, —CH$_2$), 1.40-1.49 (4H, m, —CH$_2$), 1.91-1.95 (2H, t, —CH$_2$), 2.34 (3H, s, —CH$_3$), 2.74-2.76 (1H, m, —CH), 3.12-3.14 (2H, d, —CH$_2$), 6.53-6.57 (1H, d, =CH), 7.01-7.05 (4H, t, Ar—H), 7.18-7.20 (3H, d, Ar—H and =CH), 7.28-7.32 (1H, d, =CH), 7.34-7.36 (2H, d, Ar—H), 7.68-7.69 (1H, d, —NH), 8.05 (1H, s, —NH), 8.67 (1H, s, —OH), 10.34 (1H, s, —NH). MS m/z: 476.2 (M$^+$ + 1). |

| Ex. No | Structure | Analytical data |
|---|---|---|
| 82 | 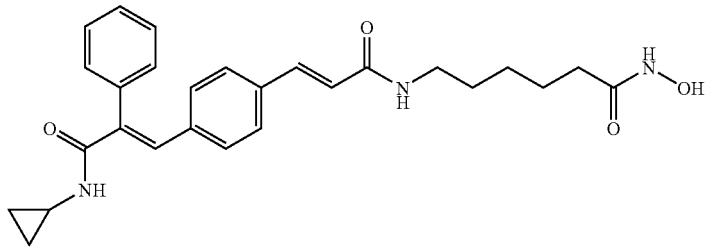 [SMILES: O=C(/C=C/c1ccc(/C=C(/C(=O)NC2CC2)c2ccccc2)cc1)NCCCCCC(=O)NO] | $^1$H NMR (DMSO-d$_6$) δ (ppm): 0.51 (2H, s, —CH$_2$), 0.63-0.64 (2H, d, —CH$_2$), 1.23-1.25 (2H, m, —CH$_2$), 1.40-1.48 (4H, m, —CH$_2$), 1.91-1.93 (2H, t, —CH$_2$), 2.74-2.76 (1H, m, —CH), 3.12-3.13 (2H, d, —CH$_2$) 6.52-6.56 (1H, d, =CH), 6.99-7.01 (2H, d, Ar—H), 7.15-7.16 (2H, d, Ar—H), 7.22 (1H, s, =CH), 7.27-7.31 (1H, d, =CH), 7.33-7.39 (5H, m, Ar—H), 7.78-7.79 (1H, d, —NH), 8.05 (1H, s, —NH), 867 (1H, s, —OH), 10.34 (1H, s, —NH). MS m/z: 462.4 (M$^+$ + 1). |
| 83 | 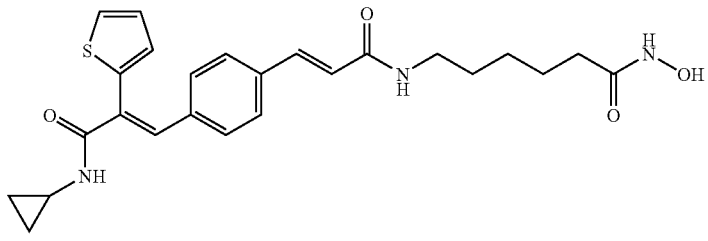 [SMILES: O=C(/C=C/c1ccc(/C=C(/C(=O)NC2CC2)c2cccs2)cc1)NCCCCCC(=O)NO] | $^1$H NMR (DMSO-d$_6$) δ (ppm): 0.52-0.53 (2H, t, —CH$_2$), 0.64-0.66 (2H, t, —CH$_2$), 1.24 (2H, m, —CH$_2$), 1.4H,49 (4H, m, —CH$_2$), 1.92-1.93 (2H, t, —CH$_2$), 2.74-2.76 (1H, m, —CH), 3.13-3.14 (2H, d, —CH$_2$), 6.56-6.60 (1H, d, =CH), 6.94-6.95 (1H, m, Ar—H), 7.05-7.06 (1H, t, Ar—H), 7.14-7.16 (2H, d, Ar—H), 7.24 (1H, s, =CH), 7.32-7.36 (1H, d, =CH), 7.42-7.44 (2H, d, Ar—H), 7.60-7.61 (1H, d, Ar—H), 7.80 (1H, s, —NH), 7.96-7.98 (1H, d, —NH), 8.66 (1H, s, —OH), 10.33 (1H, s, —NH). MS m/z: 468.2 (M$^+$ + 1). |
| 84 | 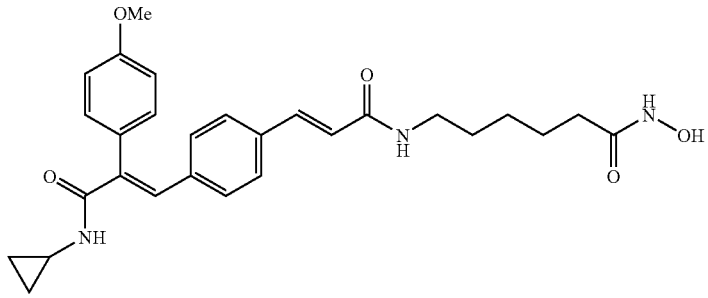 | $^1$H NMR (DMSO-d$_6$) δ (ppm): 0.49-0.51 (2H, q, —CH$_2$), 0.62-0.64 (2H, d, —CH$_2$), 1.24-1.25 (2H, m, —CH$_2$), 1.43-1.49 (4H, m, —CH$_2$), 1.93-1.95 (2H, m, —CH$_2$), 2.74-2.76 (1H, m, —CH), 3.12-3.14 (2H, d, —CH$_2$), 3.78 (3H, s, —OCH$_3$), 6.53-6.57 (1H, d, =CH), 6.93-6.96 (2H, t, Ar—H), 7.03-7.09 (4H, m, Ar—H), 7.20 (1H, s, =CH), 7.29-7.33 (1H, d, =CH), 7.36-7.38 (2H, d, Ar—H), 7.66 (1H, s, —NH), 8.05-8.06 (1H, d, —NH), 8.68 (1H, s, —OH), 10.35 (1H, s, —NH). MS m/z: 492.5 (M$^+$ + 1). |
| 85 | 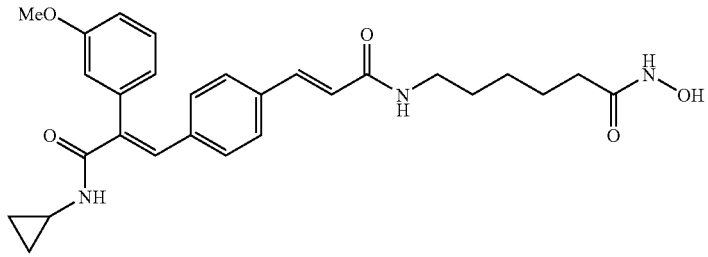 | $^1$H NMR (DMSO-d$_6$) δ (ppm): 0.50-0.52 (2H, t, —CH$_2$), 0.63-0.65 (2H, q, —CH$_2$), 1.24-1.25 (2H, m, —CH$_2$), 1.43-1.49 (4H, m, —CH$_2$), 1.94 (2H, m, —CH$_2$), 2.74-2.76 (1H, m, —CH), 3.12-3.14 (2H, d, —CH$_2$), 3.71 (3H, s, —OCH$_3$), 6.54-6.58 (1H, d, =CH), 6.70-6.73 (2H, t, Ar—H), 6.93-6.95 (1H, d, Ar—H), 7.03-7.05 (2H, d, Ar—H), 7.25-7.38 (5H, m, =CH and Ar—H), 7.69 (1H, s, —NH), 8.06 (1H, s, —NH), 8.68 (1H, s, —OH), 10.34 (1H, s, —NH). MS m/z: 492.0 (M$^+$ + 1). |
| 86 | 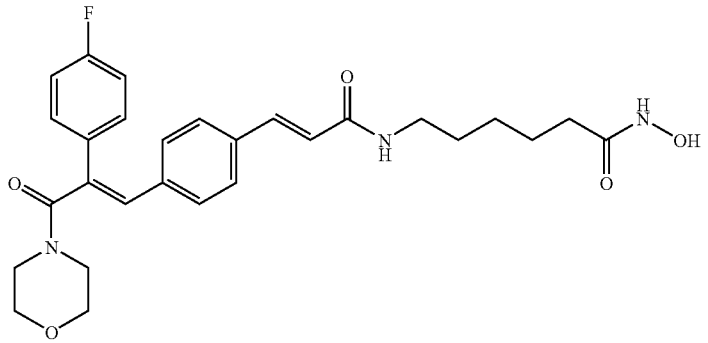 [SMILES: O=C(/C=C/c1ccc(/C=C(/C(=O)N2CCOCC2)c2ccc(F)cc2)cc1)NCCCCCC(=O)NO] | $^1$H NMR (DMSO-d$_6$) δ (ppm): 1.24 (2H, m, —CH$_2$), 1.42-1.49 (4H, m, —CH$_2$), 1.92-1.95 (2H, t, —CH$_2$), 3.12-3.14 (2H, d, —CH$_2$), 3.56 (8H, s, Morpholine-H), 6.54-6.58 (1H, d, =CH), 6.74 (1H, s, =CH), 7.11-7.13 (2H, t, Ar—H), 7.19-7.24 (2H, t, Ar—H), 7.30-7.34 (3H, m, Ar—H and =CH), 7.40-7.42 (2H, d, Ar—H), 8.06-8.09 (1H, t, —NH), 9.01 (1H, s, —OH), 10.35 (1H, s, —NH). MS m/z: 510.0 (M$^+$ + 1). |

| Ex. No | Structure | Analytical data |
|---|---|---|
| 87 | 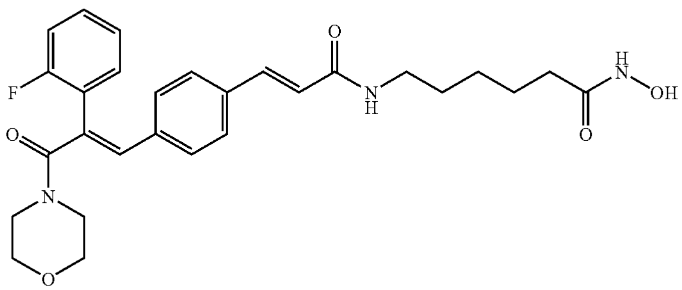 [SMILES: O=C(/C=C/c1ccc(/C=C(/C(=O)N2CCOCC2)c2ccccc2F)cc1)NCCCCCC(=O)NO] | $^1$H NMR (DMSO-$d_6$) δ (ppm): 1.24-1.26 (2H, m, —CH$_2$), 1.41-1.51 (4H, m, —CH$_2$), 1.91-1.95 (2H, t, —CH$_2$), 3.12-3.14 (2H, d, —CH$_2$), 3.58 (8H, s, Morpholine-H), 6.54-6.58 (1H, d, =CH), 6.93 (1H, s, =CH), 7.11-7.13 (2H, d, Ar—H), 7.21-7.26 (2H, m, Ar—H), 7.30-7.34 (2H, q, Ar—H and =CH), 7.40-7.45 (3H, m, Ar—H), 8.07-8.08 (1H, d, —NH), 8.67 (1H, s, —OH), 10.34 (1H, s, —NH). MS m/z: 510.0 (M$^+$ + 1). |
| 88 | 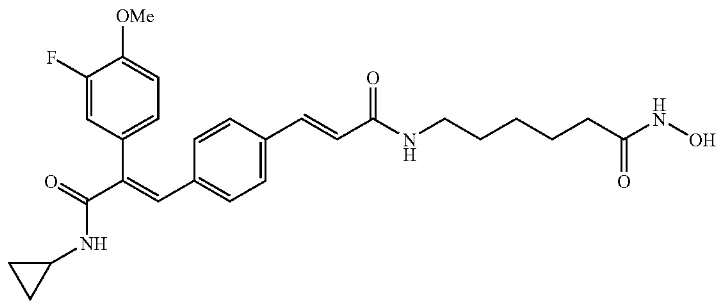 [SMILES: COc1ccc(/C(=C\c2ccc(/C=C/C(=O)NCCCCCC(=O)NO)cc2)C(=O)NC2CC2)cc1F] | $^1$H NMR (DMSO-$d_6$) δ (ppm): 0.50-0.51 (2H, t, —CH$_2$), 0.62-0.64 (2H, t, —CH$_2$), 1.24-1.25 (2H, m, —CH$_2$), 1.42-1.49 (4H, m, —CH$_2$), 1.91-1.93 (2H, m, —CH$_2$), 2.74-2.76 (1H, m, —CH), 3.12-3.14 (2H, d, —CH$_2$), 3.86 (3H, s, —OCH$_3$), 6.55-6.59 (1H, d, =CH), 6.93 (2H, m, Ar—H), 7.04-7.07 (2H, d, Ar—H), 7.18 (1H, t, Ar—H), 7.26 (1H, s, =CH), 7.30-7.34 (1H, d, =CH), 7.42-7.44 (2H, d, Ar—H), 7.81-7.82 (1H, d, —NH), 8.07-8.08 (1H, d, —NH), 8.67 (1H, s, —OH), 10.34 (1H, s, —NH). MS m/z: 510.2 (M$^+$ + 1). |

Example 89

Synthesis of 4-((3-(1E)-(4-(3-(cyclopropylamino)-2-(4-fluorophenyl)-3-oxoprop-1-en-1-yl)phenyl)acrylamido)methyl)-N-hydroxybenzamide

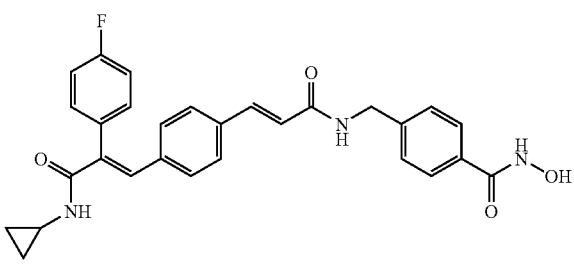 [SMILES: O=C(/C=C/c1ccc(/C=C(/C(=O)NC2CC2)c2ccc(F)cc2)cc1)NCc1ccc(C(=O)NO)cc1]

Step-I

Preparation of methyl 4-((3-(1E)-(4-(3-(cyclopropylamino)-2-(4-fluorophenyl)-3-oxoprop-1-en-1-yl)phenyl)acrylamido)methyl)benzoate To a suspension of (1E)-3-(4-(2-(4-fluorophenyl)-3-(cyclopropylamino)-3-oxoprop-1-en-1-yl)phenyl)acrylic acid (prepared according to the procedure described in Example 59, step-II, 0.35 g, 1 mmol) in DMF (15 mL) EDCI (0.83 g, 2 mmol), HOBt (0.13 g, 1 mmol) and methyl-4-aminomethyl-benzoate hydrochloride salt (0.18 g, 0.9 mmol), were added, followed by triethylamine (0.4 mL, 3 mmol). The reaction mixture was stirred at room temperature for 1.5 hours, after which the mixture was added to cold water (50 mL). The aqueous layer was extracted with ethyl acetate (1×150 mL) and washed with water (2×50 mL), 10% dilute HCl (50 mL) and brine (1×100 mL). The organic layer was dried over anhydrous Na$_2$SO$_4$ and concentrated to give the crude compound (0.225 g, 53.5% yield).

Step-II

Preparation of 4-((3-(1E)-(4-(3-(cyclopropylamino)-2-(4-fluorophenyl)-3-oxoprop-1-en-1-yl)phenyl)acrylamido)methyl)-N-hydroxybenzamide

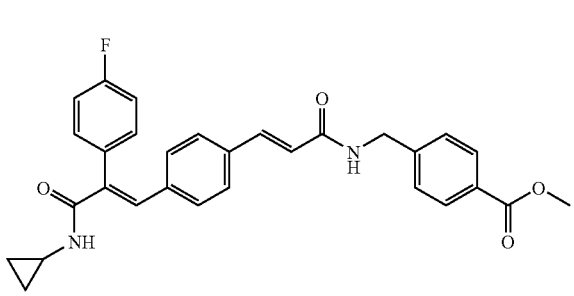 [SMILES: COC(=O)c1ccc(CNC(=O)/C=C/c2ccc(/C=C(/C(=O)NC3CC3)c3ccc(F)cc3)cc2)cc1]

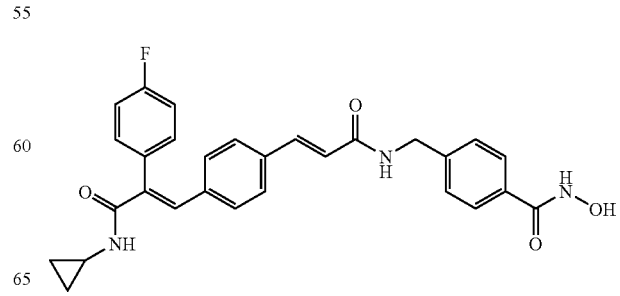

Hydroxylamine hydrochloride (0.55 g, 8 mmol) in methanol (2 mL) was mixed with KOH (0.45 g, 8 mmol) in methanol (2 mL) at 0° C. and sonicated for 2 minutes and the white precipitate formed was filtered. The filtrate was added to methyl 3-((3-(4-(3-(cyclopropylamino)-2-(4-fluorophenyl)-3-oxoprop-1-enyl)phenyl)acrylamido)methyl)benzoate (0.22 g, 0.44 mmol) in DCM (1.5 mL) and the mixture was stirred at room temperature for 1.5 hours. The reaction mixture was diluted with water (200 mL) and extracted with ethyl acetate (1×200 mL). The ethyl acetate layer was washed with water (100 mL), dried over anhydrous $Na_2SO_4$ and concentrated to obtain a crude compound followed by trituration with DCM (15 mL). The obtained solid was filtered and washed with DCM (5 mL) to afford the title compound (0.044 g, 20% yield). $^1$H NMR (DMSO-$d_6$) δ (ppm): 0.51 (2H, m, —$CH_2$), 0.62-0.65 (2H, m, —$CH_2$), 2.73-2.75 (1H, m, —CH), 4.37-4.38 (2H, d, —$CH_2$), 6.62-6.66 (1H, d, =CH), 7.00-7.02 (2H, d, Ar—H), 7.15-7.19 (3H, m, Ar—H), 7.21-7.27 (3H, d, Ar—H and =CH), 7.35 (2H, d, Ar—H), 7.38-7.40 (2H, m, Ar—H and NH), 7.69-7.71 (2H, d, Ar—H), 7.83-7.84 (1H, d, =CH), 8.63 (1H, t, NH). MS m/z: 500.1 ($M^+$+1).

The following compounds were prepared according to the procedure given in Example 89.

| Ex. No | Structure | Analytical data |
|---|---|---|
| 90 | 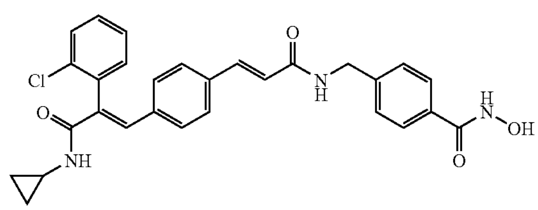 [SMILES: O=C(/C=C/c1ccc(/C=C(/C(=O)NC2CC2)c2ccccc2Cl)cc1)NCc1ccc(C(=O)NO)cc1] | $^1$H NMR (DMSO-$d_6$) δ (ppm): 0.51-0.52 (2H, m, —$CH_2$), 0.62-0.64 (2H, m, —$CH_2$), 2.72-2.75 (1H, m, —CH), 4.40-4.42 (2H, d, —$CH_2$), 6.61-6.65 (1H, d, =CH), 6.95-6.97 (2H, d, Ar—H), 7.14 (1H, d, =CH), 7.31-7.34 (3H, m, Ar—H, and =CH), 7.38-7.44 (5H, m, Ar—H), 7.54-7.56 (1H, d. Ar—H), 7.69-7.71 (2H, d, Ar—H), 7.82-7.83 (1H, d, —NH), 8.62-8.65 (1H, t, —NH) 9.0 (1H, s, —OH), 11.17 (1H, s, —NH), MS m/z: 516.1 ($M^+$ + 1). |
| 91 | 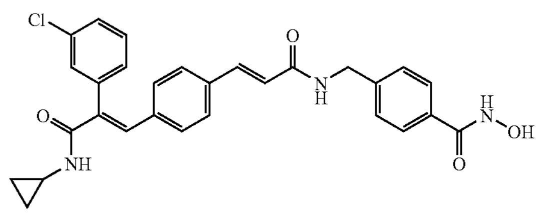 [SMILES: O=C(/C=C/c1ccc(/C=C(/C(=O)NC2CC2)c2cccc(Cl)c2)cc1)NCc1ccc(C(=O)NO)cc1] | $^1$H NMR (DMSO-$d_6$) δ (ppm): 0.52 (2H, m, —$CH_2$), 0.63-0.65 (2H, m, —$CH_2$), 2.74-2.75 (1H, m, —CH), 4.41-4.42 (2H. d, —$CH_2$), 6.62-6.66 (1H, d, =CH), 7.01-7.03 (2H, d, Ar—H), 7.09-7.11 (1H, d, Ar—H), 7.19 (1H, s, =CH), 7.29-7.42 (8H, m, Ar—H and =CH), 7.69-7.71 (2H, d, Ar—H) 7.95-7.96 (1H, d, —NH), 8.63-8.65 (1H, t, NH), 9.01 (1H, s, —OH), 11.18 (1H, s, —NH). MS m/z: 516.2 ($M^+$ + 1). |
| 92 | 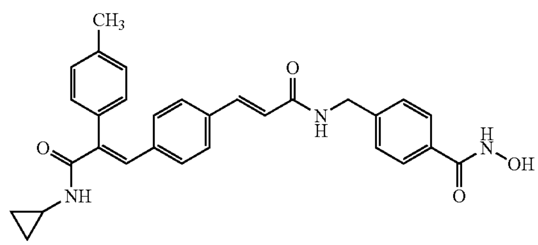 [SMILES: Cc1ccc(/C(=C\c2ccc(/C=C/C(=O)NCc3ccc(C(=O)NO)cc3)cc2)C(=O)NC2CC2)cc1] | $^1$H NMR (DMSO-$d_6$) δ (ppm): 0.49 (2H, m, —$CH_2$), 0.62-0.63 (2H, m, —$CH_2$), 2.33 (3H, s, —$CH_3$), 2.73 (1H, m, —CH), 4.40-4.41 (2H, d, —$CH_2$), 6.60-6.64 (1H, d, =CH), 7.02-7.04 (4H, d, Ar—H), 7.18-7.20 (3H, m, Ar—H and =CH), 7.31-7.39 (4H, m, Ar—H and =CH), 7.69-7.71 (3H, m, Ar—H, and —NH), 8.63 (2H, m, NH and Ar—H), 9.01 (1H, s, —OH), 11.18 (1H, s, —NH). MS m/z: 496.2 ($M^+$ + 1). |
| 93 | 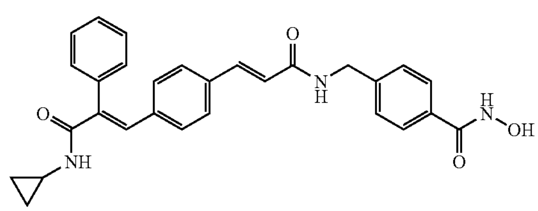 [SMILES: O=C(/C=C/c1ccc(/C=C(/C(=O)NC2CC2)c2ccccc2)cc1)NCc1ccc(C(=O)NO)cc1] | $^1$H NMR (DMSO-$d_6$) δ (ppm): 0.50 (2H, m, —$CH_2$), 0.63-0.64 (2H, m, —$CH_2$), 2.74-2.75 (1H, m, —CH), 4.40-4.41 (2H, d, —$CH_2$), 6.60-6.64 (1H, d, =CH), 6.99-7.01 (2H, d, Ar—H), 7.14-7.15 (2H, d, Ar—H), 7.22 (1H, s, =CH), 7.31-7.37 (8H, m, Ar—H and =CH), 7.69-7.71 (2H, d, Ar—H and =CH), 7.78 (1H, d, —NH), 8.64 (1H, t, —NH), 9.01 (1H, s, —OH), 11.18 (1H, s, —NH). MS m/z: 482.4 ($M^+$ + 1). |
| 94 | 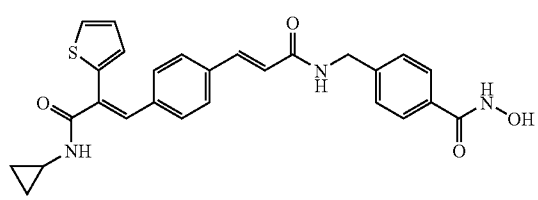 [SMILES: O=C(/C=C/c1ccc(/C=C(/C(=O)NC2CC2)c2cccs2)cc1)NCc1ccc(C(=O)NO)cc1] | $^1$H NMR (DMSO-$d_6$) δ (ppm): 0.52-0.53 (2H, m, —$CH_2$), 0.65-0.66 (2H, m, —$CH_2$), 2.73-2.75 (1H, m, —CH), 4.42-4.43 (2H, d, —$CH_2$), 6.62-6.66 (1H, d, =CH), 6.94-6.95 (1H, d, Ar—H), 7.15-7.17 (1H, m, Ar—H), 7.24 (2H, m, Ar—H and =CH), 7.32-7.34 (1H, d, Ar—H), 7.39-7.47 (5H, m, Ar—H and =CH), 7.60-7.61(1H, d, Ar—H), 7.69-7.71 (2H, d, Ar—H), 7.99 (1H, d, —NH), 8.66-8.69 (1H, t, —NH), 9.02 (1H, s, —OH), 11.18 (1H, s, —NH). MS m/z: 488.6 ($M^+$ + 1). |

| Ex. No | Structure | Analytical data |
|---|---|---|
| 95 | 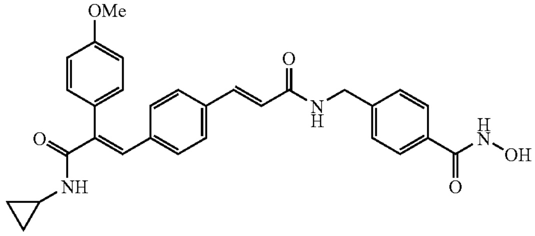 | ¹H NMR (DMSO-d₆) δ (ppm): 0.49-0.50 (2H, m, —CH₂), 0.62-0.63 (2H, m, —CH₂), 2.73-2.75 (1H, m, —CH), 3.77 (3H, s, —OCH₃), 4.41-4.42 (2H, d, —CH₂), 6.62-6.66 (1H, d, =CH), 6.92-6.95 (2H, d, Ar—H), 7.03-7.07 (4H, m, Ar—H), 7.19 (1H, s, =CH), 7.32-7.40 (5H, m, Ar—H and =CH), 7.69-7.71 (3H, m, Ar—H and —NH), 8.65 (1H, t, —NH), 9.01 (1H, s, —OH), 11.18 (1H, s, —NH). MS m/z: 512.6 (M⁺ + 1). |
| 96 | 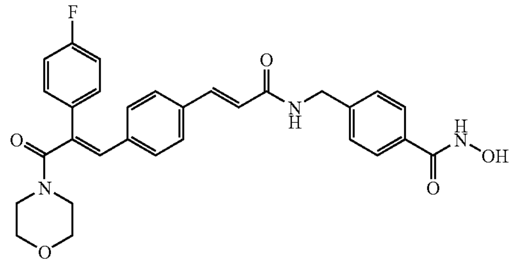 [SMILES: O=C(/C=C/c1ccc(/C=C(/C(=O)N2CCOCC2)c2ccc(F)cc2)cc1)NCc1ccc(C(=O)NO)cc1] | ¹H NMR (DMSO-d₆) δ (ppm): 3.56 (8H, m, —CH₂), 4.42-4.43 (2H, d, —CH₂), 6.67-6.75 (2H, s and d, =CH), 7.12-7.14 (2H, d, Ar—H), 7.22-7.45 (12H, m, Ar—H and =CH), 7.70-7.72 (2H, d, Ar—H), 8.65-8.67 (1H, t, —NH), 9.04 (1H, s, —OH), 11.19 (1H, s, —NH). MS m/z: 530.4 (M⁺ + 1). |
| 97 | 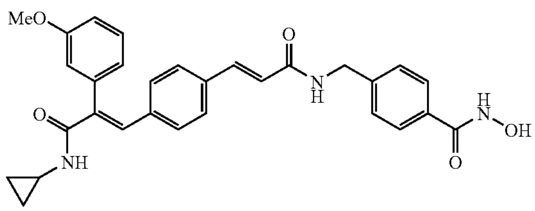 [SMILES: COc1cccc(/C(=C\c2ccc(/C=C/C(=O)NCc3ccc(C(=O)NO)cc3)cc2)C(=O)NC2CC2)c1] | ¹H NMR (DMSO-d₆) δ (ppm): 0.50-0.51 (2H, m, —CH₂), 0.62-0.64 (2H, m, —CH₂), 2.73-2.75 (1H, m, —CH), 3.70 (3H, s, —OCH₃), 4.41-4.42 (2H, d, —CH₂), 6.61-6.65 (1H, d, =CH), 6.70 (3H, m, Ar—H), 7.02-7.05 (2H, d, Ar—H), 7.24 (1H, s, =CH), 7.31-7.40 (5H, m, =CH and Ar—H), 7.69 (4H, m, Ar—H and NH), 8.63-8.6 (1H, t, NH), 9.01 (1H, s, —OH), 11.18 (1H, s, —NH). MS m/z: 512.6 (M⁺ + 1). |
| 98 | 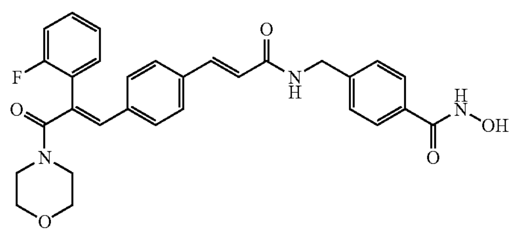 [SMILES: O=C(/C=C/c1ccc(/C=C(/C(=O)N2CCOCC2)c2ccccc2F)cc1)NCc1ccc(C(=O)NO)cc1] | ¹H NMR (DMSO-d₆) δ (ppm): 3.58 (8H, m, —CH₂), 4.41-4.42 (2H, d, —CH₂), 6.62-6.66 (1H, d, =CH), 6.93 (1H, s, =CH), 7.11-7.13 (2H, d, Ar—H), 7.21-7.45 (9H, m, Ar—H and =CH), 7.69-7.71 (2H, d, Ar—H), 8.64-8.67 (1H, t, NH), 10.65 (1H, s, —OH), 11.18 (1H, s, —NH). MS m/z: 529.9 (M⁺ + 1). |

Example 99

Synthesis of 4-(3-(cyclopropylamino)-2-(4-methylphenyl)-3-oxoprop-1-en-1-yl)-N-hydroxybenzamide

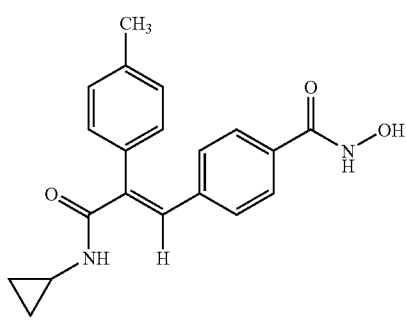 [SMILES: Cc1ccc(/C(=C\c2ccc(C(=O)NO)cc2)C(=O)NC2CC2)cc1]

Step-I

Preparation of 3-(4-(methoxycarbonyl)phenyl)-2-(4-methylphenyl)acrylic acid

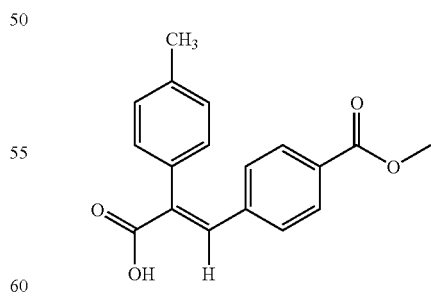

A mixture of 4-methylphenylacetic acid (3 g, 20 mmol) and methyl 4-formylbenzoate (3.3 g, 20 mmol) was dissolved under stirring with Ac₂O (8 mL). To this mixture, diisopropylethylamine (DIPEA) (5.2 mL, 30 mmol) was added and stirred at 30° C. for 6 hours. Upon completion, as monitored by TLC using 100% ethyl acetate as eluent, the reaction mixture was poured into water and pH was adjusted to 3 using aqueous dilute HCl (1:1). The aqueous layer was extracted with ethyl acetate (2×150 mL). The combined ethyl acetate layer was washed with water till the washings were neutral and dried over anhydrous $Na_2SO_4$. The ethyl acetate layer was evaporated to dryness to obtain a sticky compound, which was triturated with cold dichloromethane (DCM) to furnish a pale yellow solid. It was filtered and dried under vacuum to afford the title compound (3.88 g, 66% yield).
Step-II Preparation of methyl-4-(3-(cyclopropylamino)-2-(4-methylphenyl)-3-oxoprop-1-en-1-yl)benzoate

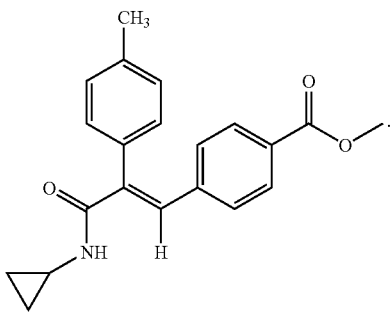 [SMILES: COC(=O)c1ccc(/C=C(/C(=O)NC2CC2)c2ccc(C)cc2)cc1]

A mixture of 3-(4-(methoxycarbonyl)phenyl)-2-(4-methylphenyl)acrylic acid (0.23 g, 0.71 mmol), cyclopropylamine (3.88 g, 13 mmol), EDCl (5 g, 26 mmol), HOBt (1.8 g, 13 mmol) was dissolved in N,N-dimethylformamide (DMF) (6 mL) under stirring. Triethylamine (TEA) (5.5 mL, 39 mmol) was added dropwise with constant stirring to the above reaction mixture. The reaction mixture was stirred at 30° C. for 4 hours. Subsequently the reaction mixture was poured into ice water (150 mL), upon standing at room temperature for 1 hour, the white precipitate formed was filtered and washed with hexane (100 mL) dried under vacuum to afford the pure compound (2.9 g, 66% yield).
Step-III Preparation of 4-(3-(cyclopropylamino)-2-(4-methylphenyl)-3-oxoprop-1-en-1-yl)benzoicacid

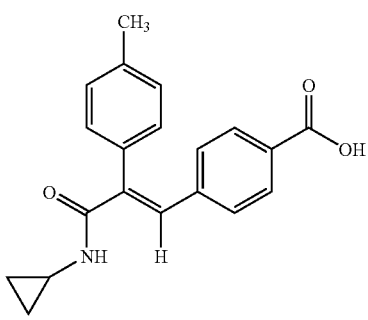 [SMILES: Cc1ccc(/C(=C\c2ccc(C(=O)O)cc2)C(=O)NC2CC2)cc1]

To a solution of methyl 4-(3-(cyclopropylamino)-2-(4-methylphenyl)-3-oxoprop-1-en-1-yl)benzoate (4 g, 12 mmol) in methanol (10 mL), a solution of NaOH (1.4 g, 36 mmol) in water (1 mL) was added. The reaction mixture was refluxed for two hours at 70° C. The solvent was removed by evaporation, poured to ice cold water. The aqueous layer was acidified to pH 3 with citric acid and allowed to stand at 4° C. for 30 minutes the solid precipitated out was filtered and dried under vacuum to get a pale yellow solid (3.2 g, 83% yield).
Step-IV Preparation of 4-(3-(cyclopropylamino)-2-(4-methylphenyl)-3-oxoprop-1-en-1-yl)-N-hydroxybenzamide

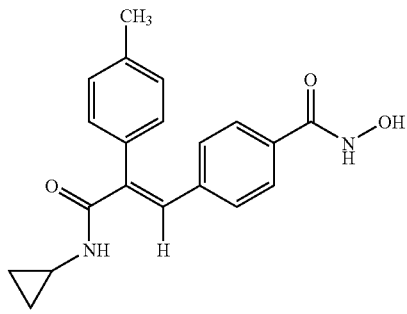 [SMILES: Cc1ccc(/C(=C\c2ccc(C(=O)NO)cc2)C(=O)NC2CC2)cc1]

To a suspension of 4-(3-(cyclopropylamino)-2-(p-tolyl)-3-oxoprop-1-en-1-yl)benzoic acid (0.1 g, 0.3 mmol) in DMF (3 mL), benzotriazol-1-yloxy-tris(dimethyl amino)phosphonium hexafluorophosphate (BOP reagent, 0.23 g, 0.55 mmol), HOBt (0.04 g, 0.3 mmol), hydroxylamine hydrochloride (0.03 g, 0.35 mmol), were added followed by DIPEA (0.16 mL, 0.9 mmol). The reaction mixture was stirred for 1 hour, after which the mixture was added to cold water (100 mL) and kept it for 1 hour at 0° C. the white solid formed. The obtained solid was filtered and washed with water (50 mL), dried under vacuum to afford the title compound as white solid (0.080 g, 77% yield). $^1$H NMR (DMSO-$d_6$) δ (ppm): 0.46-0.51 (2H, m, —$CH_2$), 0.58-0.60 (2H, m, —$CH_2$), 2.29 (3H, s, $CH_3$), 2.69-2.70 (1H, m, —CH), 6.81 (4H, m, Ar—H), 6.97-7.03 (3H, m, Ar—H), 7.36-7.38 (I+1H, d, Ar—H and =CH), 7.70 (1H, d, NH), 8.99 (1H, s, OH), 11.10 (1H, s, NH), MS m/z: 337.1 (M$^+$+1).

The following compounds were prepared according to the procedure given in Example 99.

| Ex. No | Structure | Analytical data |
|---|---|---|
| 100 | (structure: 4-methoxyphenyl variant) | $^1$H NMR (DMSO-d$_6$) δ (ppm): 0.50 (2H, m, —CH$_2$), 0.62-0.64 (2H, m, —CH$_2$), 2.74-2.75 (1H, m, —CH), 3.77 (3H, s, OCH$_3$), 6.91-6.93 (2H, d, Ar—H), 7.06 (4H, m, Ar—H), 7.20 (1H, s, =CH), 7.53 (2H, d, Ar—H). 7.71(1H, d, NH), 9.01 (1H, s, OH), 11.13 (1H, s, NH), MS m/z: 353.1 (M$^+$ + 1). |
| 101 | (structure: 3-methoxyphenyl variant) | $^1$H NMR (DMSO-d$_6$) δ (ppm): 0.50 (2H, m, —CH$_2$), 0.63-0.64 (2H, m, —CH$_2$), 2.67-2.74 (1H, m, —CH), 3.79 (3H, s, OCH$_3$), 6.68 (2H, m, Ar—H), 6.94 (1H, d, Ar—H), 7.06 (2H, m, Ar—H), 7.24-7.29 (2H, m, Ar—H and =CH), 7.53 (2H, d, Ar—H), 7.73-7.79 (1H, d, NH), 9.01 (1H, s, NH), 11.13 (114, s, OH), MS m/z: 353.1 (M$^+$ + 1). |
| 102 | (structure: phenyl variant) | $^1$H NMR (DMSO-d$_6$) δ (ppm): 0.50-0.55 (2H, m, —CH$_2$), 0.63-0.65 (2H, m, —CH$_2$), 2.73-2.75 (1H, m, —CH), 7.03 (2H, d, Ar—H), 7.14 (2H, d, Ar—H), 7.23 (1H, s, =CH), 7.36 (3H, m, Ar—H), 7.51 (2H, d, Ar—H), 7.84 (1H, d, NH), 9.01 (1H, s, OH), 11.13 (1H, s, NH), MS m/z: 323.1 (M$^+$ + 1). |
| 103 | (structure: 2-fluorophenyl variant) | $^1$H NMR (DMSO-d$_6$) δ (ppm): 0.51-0.57 (2H, m, —CH$_2$), 0.63-0.65 (2H, m, —CH$_2$), 2.73-2.75 (1H, m, —CH), 7.05-7.24 (5H, m, Ar—H), 7.36 (2H, m, =CH and Ar—H), 7.54 (2H, d, Ar—H). 7.95 (1H, d, NH), 8.90 (1H, s, OH), 11.16 (1H, s, NH), MS m/z: 339.0 (M$^+$ − 1). |

Example 104

Synthesis of N-(2-aminophenyl)-4-(3-(cyclopropylamino)-2-(4-methylphenyl)-3-oxoprop-1-en-1-yl)benzamide

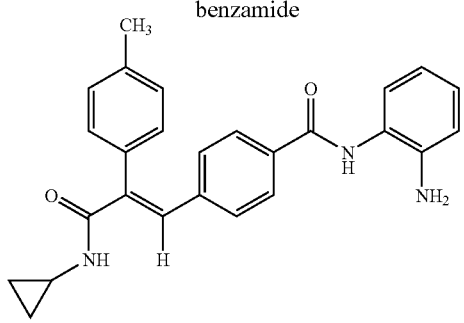

Step-I

Preparation of N-(2-aminophenyl)-4-(3-(cyclopropylamino)-2-(4-methylphenyl)-3-oxoprop-1-en-1-yl)benzamide

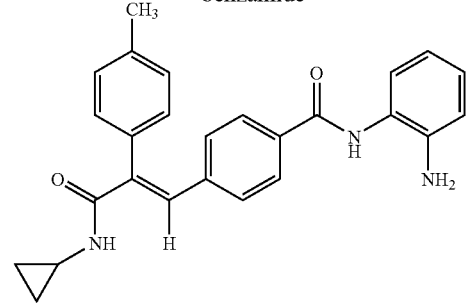 [SMILES: Cc1ccc(/C(=C\c2ccc(C(=O)Nc3ccccc3N)cc2)C(=O)NC2CC2)cc1]

To a suspension of 4-(3-(cyclopropylamino)-2-(4-methylphenyl)-3-oxoprop-1-en-1-yl)benzoic acid (0.2 g, 0.6 mmol, prepared according to the procedure described in Example 99, step I-III) in DMF (3 mL) EDCl (0.23 g, 1.1 mmol), HOBt (0.08 g, 5 mmol), o-phenylenediamine (0.08 g, 0.7 mmol), were added followed by TEA (0.23 mL, 15 mmol). The reaction mixture was stirred for 4 hours after which the mixture was added to cold water (100 mL) and kept 0° C. for 1 hour to obtain a pale yellow solid. The solid was filtered and washed with water (50 mL) dried under vacuum to afford the title compound (0.110 g, 45% yield). $^1$H NMR (DMSO-d$_6$) δ (ppm): 0.51 (2H, m, —CH$_2$), 0.63-0.65 (2H, m, —CH$_2$), 2.33 (3H, s, —CH$_3$), 2.67-2.75 (1H, m, —CH), 4.87 (2H, s, —NH$_2$), 6.55-6.58 (1H, m, Ar—H), 6.74-6.76 (1H, m, Ar—H), 6.93-6.97 (1H, m, Ar—H), 7.04 (2H, d, Ar—H), 7.11 (3H, m, Ar—H), 7.19 (2H, m, Ar—H), 7.25 (1H, s, =CH), 7.76-7.78 (3H, m, Ar—H and —NH), 9.57 (1H, s, —NH), MS m/z: 412.2 (M$^+$+1).

The following compounds were prepared according to the procedure given in Example 104.

| Ex. No | Structure | Analytical data |
|---|---|---|
| 105 | 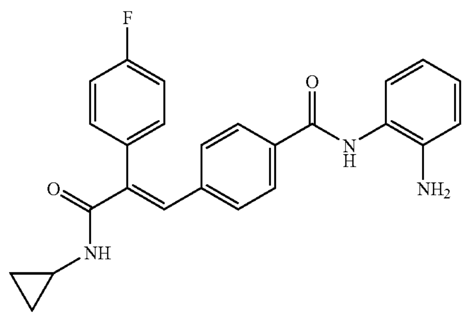 [SMILES: Nc1ccccc1NC(=O)c1ccc(/C=C(/C(=O)NC2CC2)c2ccc(F)cc2)cc1] | $^1$H NMR (DMSO-d$_6$) δ (ppm): 0.52-0.58 (2H, m, —CH$_2$), 0.63-0.65 (2H, m, —CH$_2$), 2.75-2.76 (1H, m, —CH), 4.87 (2H, s, —NH$_2$), 6.55-6.58 (1H, m, Ar—H), 6.75 (1H, d, Ar—H), 6.93-6.97 (1H, m, Ar—H), 7.09-7.11 (3H, m, Ar—H), 7.19-7.24 (4H, m, Ar—H), 7.32 (1H, s, =CH), 7.79 (2H, d, Ar—H). 7.91 (1H, d, —NH), 9.63 (1H, s, —NH), MS m/z: 416.1 (M$^+$ +1). |
| 106 | 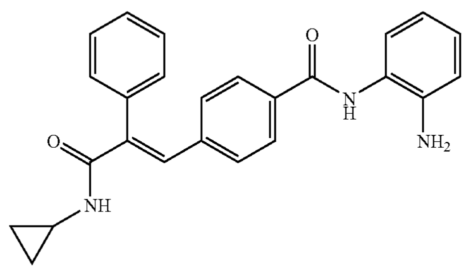 [SMILES: Nc1ccccc1NC(=O)c1ccc(/C=C(/C(=O)NC2CC2)c2ccccc2)cc1] | $^1$H NMR (DMSO-d$_6$) δ (ppm): 0.54 (2H, m, —CH$_2$), 0.65-0.66 (2H, m, —CH$_2$), 2.76 (1H, m, —CH), 4.87 (2H, s, —NH$_2$), 6.56 (1H, m, Ar—H), 6.75 (1H, d, Ar—H), 6.95 (1H, m, Ar—H), 7.09-7.11 (3H, m, Ar—H), 7.38 (2 + 1H, m, Ar—H and =CH), 7.74 (2H, d, Ar—H), 7.80 (2H, d, Ar—H), 8.11 (1H, d, —NH), 9.60 (1H, s, —NH), MS m/z: 466.1 (M$^+$ + 1). |
| 107 | 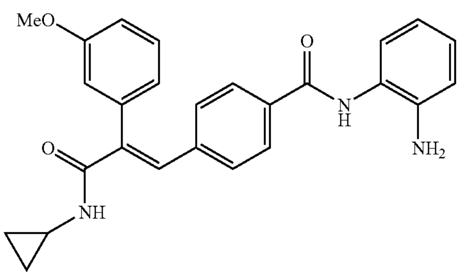 [SMILES: COc1cccc(/C(=C\c2ccc(C(=O)Nc3ccccc3N)cc2)C(=O)NC2CC2)c1] | $^1$H NMR (DMSO-d$_6$) δ (ppm): 0.52 (2H, m, —CH$_2$), 0.64-0.66 (2H, m, —CH$_2$), 2.75-2.76 (1H, m, —CH), 4.86 (2H, s, —NH$_2$), 6.55-6.59 (1H, m, Ar—H), 6.75 (1H, d, Ar—H), 6.94-6.97 (1H, m, Ar—H), 7.08-7.10 (3H, m, Ar—H), 7.15-7.17 (2H, d, Ar—H), 7.27 (1H, s, =CH), 7.38 (3H, m, Ar—H), 7.76 (2H, d, Ar—H), 7.90 (1H, d, —NH), 9.58 (1H, s, NH), MS m/z: 398.2 (M$^+$ + 1). |
| 108 | 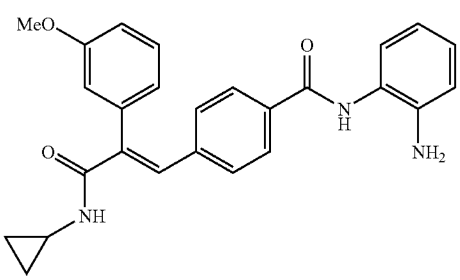 [SMILES: COc1cccc(/C(=C\c2ccc(C(=O)Nc3ccccc3N)cc2)C(=O)NC2CC2)c1] | $^1$H NMR (DMSO-d$_6$) δ (ppm): 0.51-0.53 (2H, m, —CH$_2$), 0.63-0.65 (2H, m, —CH$_2$), 2.75-2.76 (1H, m, —CH), 3.71 (3H, s, —OCH$_3$), 4.87 (2H, s, —NH$_2$), 6.56 (1H, m, Ar—H), 6.71-6.76 (3H, m, Ar—H), 6.93-6.96 (2H, m, Ar—H), 7.10-7.13 (3H, m, Ar—H), 7.28-7.33 (1 + 1H, Ar—H and =CH), 7.76-7.78 (3H, m, Ar—H and NH), 9.57 (1H, s, —NH), MS m/z: 428.2 (M$^+$ + 1). |

| Ex. No | Structure | Analytical data |
|---|---|---|
| 109 | 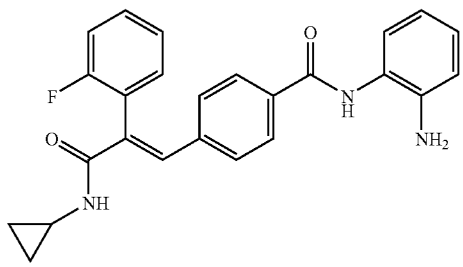 [SMILES: Nc1ccccc1NC(=O)c1ccc(/C=C(/C(=O)NC2CC2)c2ccccc2F)cc1] | $^1$H NMR (DMSO-d$_6$) δ (ppm): 0.53-0.58 (2H, m, —CH$_2$), 0.64-0.66 (2H, m, —CH$_2$), 2.75-2.76 (1H, m, —CH), 4.88 (2H, s, —NH$_2$), 6.56 (1H, m, Ar—H). 6.75 (1H, d, Ar—H), 6.95 (1H, m, Ar—H), 7.10-7.24 (6H, m, Ar—H and =CH), 7.45 (2H, d, Ar—H), 7.79 (2H, s, Ar—H), 8.06 (1H, d, —NH), 9.60 (1H, s, —NH), MS m/z: 416.0 (M$^+$ + 1). |
| 110 | 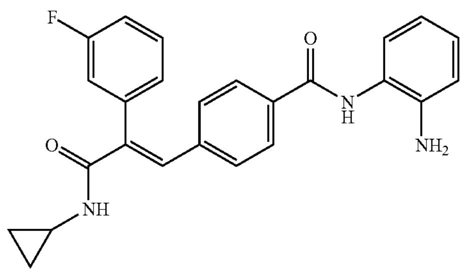 [SMILES: Nc1ccccc1NC(=O)c1ccc(/C=C(/C(=O)NC2CC2)c2cccc(F)c2)cc1] | $^1$H NMR (DMSO-d$_6$) δ (ppm): 0.53-0.54 (2H, m, —CH$_2$), 0.65-0.66 (2H, m, —CH$_2$), 2.75-2.76 (1H, m, —CH), 4.88 (2H, s, —NH$_2$), 6.57 (1H, m, Ar—H). 6.75 (1H, d, Ar—H), 6.93-6.99 (3H, m, Ar—H), 7.10-7.12 (3H, m, Ar—H), 7.21 (1H, t, Ar—H), 7.34 (1H, s, =CH), 7.43 (1H, s, Ar—H), 7.79 (2H, d, Ar—H), 7.97 (1H, d, —NH), 9.60 (1H, s, —NH), MS m/z: 416.1 (M$^+$ + 1). |
| 111 | 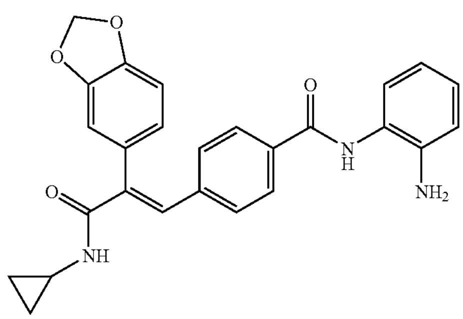 [SMILES: Nc1ccccc1NC(=O)c1ccc(/C=C(/C(=O)NC2CC2)c2ccc3c(c2)OCO3)cc1] | $^1$H NMR (DMSO-d$_6$) δ (ppm): 0.52 (2H, m, —CH$_2$), 0.63-0.64 (2H, m, —CH$_2$), 2.75-2.76 (1H, m, —CH), 4.89 (2H, s, —NH$_2$), 6.06 (2H, s, —CH$_2$), 6.58-6.60 (2H, m, Ar—H), 6.69 (2H, m, Ar—H), 6.92-6.94 (2H, m, Ar—H), 7.15-7.17 (3H, m, Ar—H), 7.29 (1H, s, =CH), 7.77 (1H, d, —NH), 7.79-7.81 (2H, d, Ar—H), 9.60 (1H, s, NH), MS m/z: 441.8 M$^+$ + 1). |
| 112 | 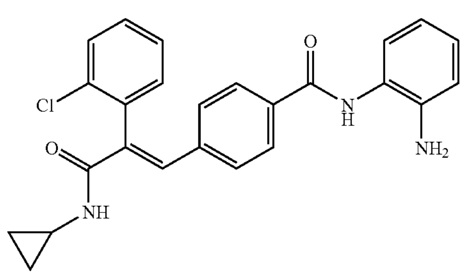 [SMILES: Nc1ccccc1NC(=O)c1ccc(/C=C(/C(=O)NC2CC2)c2ccccc2Cl)cc1] | $^1$H NMR (DMSO-d$_6$) δ (ppm): 0.52 (2H, m, —CH$_2$), 0.64-0.65 (2H, m, —CH$_2$), 2.73-2.75 (1H, m, —CH), 4.88 (2H, s, —NH$_2$), 6.56-6.58 (1H, m, Ar—H), 6.73-6.75 (1H, d, Ar—H), 6.92-6.94 (1H, m, Ar—H), 7.04-7.06 (2H, m, Ar—H), 7.09-7.15 (2H, m, Ar—H), 7.32-7.35 (1H, t, Ar—H), 7.41-7.45 (1H, t, Ar—H), 7.50 (1H, s, =CH), 7.55-7.57 (1H, d, Ar—H), 7.77-7.79 (2H, d, Ar—H), 7.93-7.94 (1H, d, —NH), 9.58 (1H, s, —NH), MS m/z: 431.8 (M$^+$ + 1). |
| 113 | 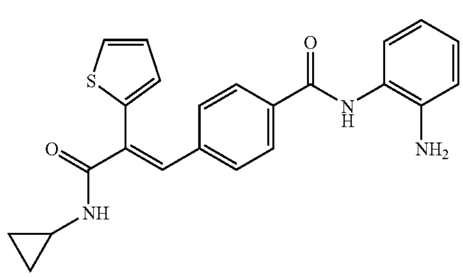 [SMILES: Nc1ccccc1NC(=O)c1ccc(/C=C(/C(=O)NC2CC2)c2cccs2)cc1] | $^1$H NMR (DMSO-d$_6$) δ (ppm): 0.53-0.55 (2H, m, —CH$_2$), 0.66-0.68 (2H, m, —CH$_2$), 2.75-2.76 (1H, m, —CH), 4.89 (2H, s, —NH$_2$), 6.58 (1H, m, Ar—H), 6.76 (1H, d, Ar—H), 6.94-6.96 (2H, d, Ar—H), 7.04-7.07 (1H, m, Ar—H), 7.13 (1H, d, Ar—H), 7.24-7.27 (3H, m, Ar—H and =CH), 7.60-7.61 (1H, d, Ar—H), 7.84-7.86 (2H, d, Ar—H), 8.09-8.10 (1H, d, —NH), 9.64 (1H, s, —NH), MS m/z: 403.8 (M$^+$ + 1). |

| Ex. No | Structure | Analytical data |
|---|---|---|
| 114 | 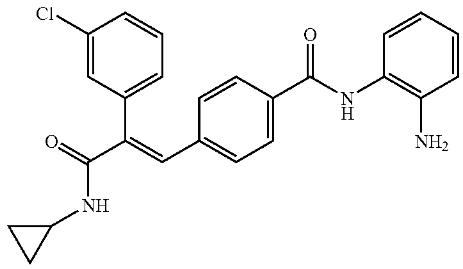 [SMILES: Nc1ccccc1NC(=O)c1ccc(/C=C(/C(=O)NC2CC2)c2cccc(Cl)c2)cc1] | ¹H NMR (DMSO-d₆) δ (ppm): 0.53-0.54 (2H, m, —CH₂), 0.65-0.66 (2H, m, —CH₂), 2.75 (1H, m, —CH), 4.88 (2H, s, —NH₂), 6.56 (1H, m, Ar—H), 6.74-6.76 (1H, d, Ar—H), 6.95 (1H, m, Ar—H), 7.10-7.12 (4H, m, Ar—H), 7.21 (1H, s, Ar—H), 7.34 (1H, s, =CH), 7.41-7.44 (2H, m, Ar—H), 7.79-7.81 (2H, d, Ar—H), 8.03-8.04 (1H, d, NH), 9.60 (1H, s, NH), MS m/z: 431.8 (M⁺ + 1). |
| 115 | 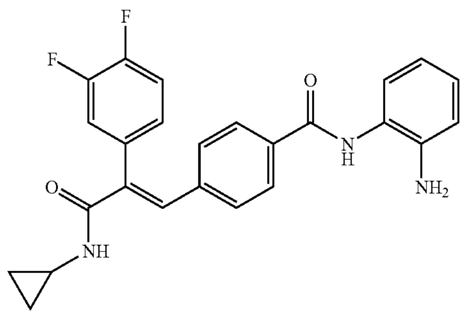 [SMILES: Nc1ccccc1NC(=O)c1ccc(/C=C(/C(=O)NC2CC2)c2ccc(F)c(F)c2)cc1] | 1H NMR (DMSO-d6) δ (ppm): 0.53 (2H, m, —CH₂), 0.64-0.65 (2H, m, —CH₂), 2.75-2.76 (1H, m, —CH), 4.88 (2H, s, —NH₂), 6.57-6.58 (1H, m, Ar—H), 6.75 (1H, d, Ar—H), 6.93-6.97 (2H, m, Ar—H), 7.11-7.13 (3H, m, Ar—H), 7.23-7.25 (1H, m, Ar—H), 7.41-7.45 (3H, m, Ar—H and =CH), 7.80-7.82 (2H, m, Ar—H) 7.88-7.89 (1H, d, NH), 9.59 (1H, s, —NH), MS m/z: 433.8 (M⁺ + 1). |
| 116 | 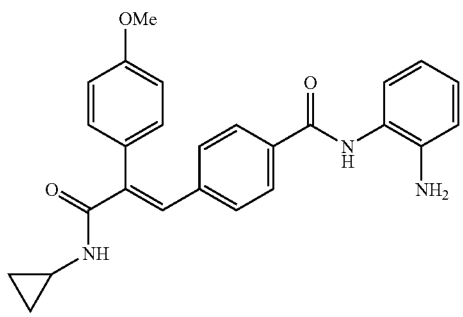 [SMILES: COc1ccc(/C(=C\c2ccc(C(=O)Nc3ccccc3N)cc2)C(=O)NC2CC2)cc1] | ¹H NMR (DMSO-d₆) δ (ppm): 0.51-0.52 (2H, m, —CH₂), 0.63-0.65 (2H, m, —CH₂), 2.75-2.76 (1H, m, —CH), 3.78 (3H, s, —OCH₃), 4.88 (2H, s, —NH₂), 6.56 (1H, m. Ar—H), 6.71-6.76 (1H, m, Ar—H), 6.93-6.95 (3H, m. Ar—H), 7.06-7.14 (5H, m, Ar—H), 7.23 (1H, s, =CH), 7.77-7.79 (3H, m, Ar—H and —NH), 9.58 (1H, s, —NH), MS m/z: 427.9 (M⁺ + 1). |
| 117 | 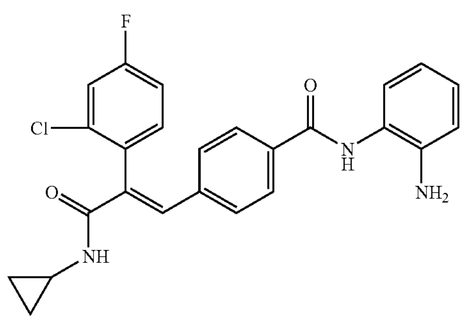 [SMILES: Nc1ccccc1NC(=O)c1ccc(/C=C(/C(=O)NC2CC2)c2ccc(F)cc2Cl)cc1] | ¹H NMR (DMSO-d₆) δ (ppm): 0.523-0.528 (2H, m, —CH₂), 0.64-0.65 (2H, m, —CH₂), 2.75 (1H, m, —CH), 4.88 (2H, s, —NH₂), 6.56 (1H, t, Ar—H), 6.75 (1H, d, Ar—H), 6.95 (1H, d, Ar—H), 7.05-7.12 (3H, m, Ar—H), 7.19-7.24 (1 + 1H, m, Ar—H and =CH), 7.57 (2H, t, Ar—H), 7.79-7.88 (2 + 1H, m, Ar—H and —NH), 9.59 (1H, s, —NH), MS m/z: 449.8 (M⁺ + 1). |
| 118 | 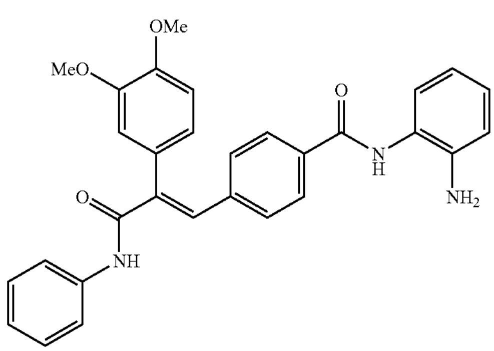 [SMILES: COc1ccc(/C(=C\c2ccc(C(=O)Nc3ccccc3N)cc2)C(=O)Nc2ccccc2)cc1OC] | ¹H NMR (DMSO-d₆) δ (ppm): 3.64 (3H, s, —OCH₃), 3.79 (3H, s, —OCH₃), 4.89 (2H, s, —NH₂), 6.59 (1H, t, Ar—H), 6.75-6.83 (3H, m, Ar—H), 6.94-7.01 (2H, m, Ar—H), 7.07-7.14 (2H, m, Ar—H), 7.24 (2H, d, Ar—H), 7.33 (2H, t, Ar—H), 7.39 (1H, s, =CH), 7.69 (2H, d, Ar—H), 7.83 (2H, d, Ar—H), 9.61 (1H, s, —NH), 9.80 (1H, s, —NH), MS m/z: 493.8 (M⁺ + 1). |

| Ex. No | Structure | Analytical data |
|---|---|---|
| 119 | 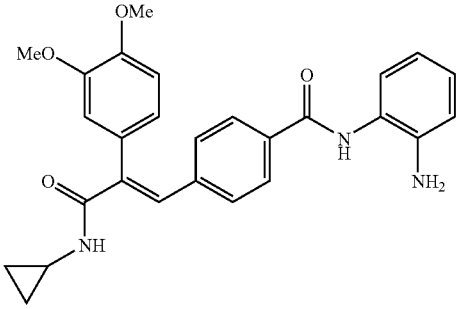 [SMILES: COc1ccc(/C(=C\c2ccc(C(=O)Nc3ccccc3N)cc2)C(=O)NC2CC2)cc1OC] | $^1$H NMR (DMSO-d$_6$) δ (ppm): 0.514—0.518 (2H, m, —CH$_2$), 0.63-0.65 (2H, m, —CH$_2$), 2.761-2.769 (1H, m, —CH), 3.63 (3H, s, —OCH$_3$), 3.77 (3H, s, —OCH$_3$), 4.87 (2H, s, —NH$_2$), 6.57 (1H, t, Ar—H), 6.67-6.76 (3H, m, Ar—H), 6.93-6.97 (2H, m, Ar—H), 7.11-7.15 (3H, m, Ar—H), 7.29 (1H, s, =CH), 7.62-7.63 (1H, t, —NH), 7.78-7.80 (2H, d, Ar—H), 9.58 (1H, s, —NH), MS m/z: 457.9 (M$^+$ + 1). |
| 120 | 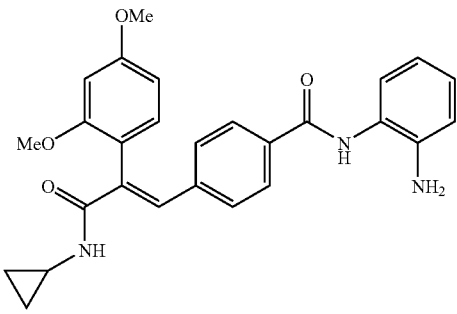 [SMILES: COc1ccc(/C(=C\c2ccc(C(=O)Nc3ccccc3N)cc2)C(=O)NC2CC2)c(OC)c1] | $^1$H NMR (DMSO-d$_6$) δ (ppm): 0.48 (2H, m, —CH$_2$), 0.61-0.63 (2H, m, —CH$_2$), 2.70-2.71 (1H, m, —CH), 3.67 (3H, s, —OCH$_3$), 3.79 (3H, s, —OCH$_3$), 4.87 (2H, s, —NH$_2$), 6.51 (1H, t, Ar—H), 6.57 (1H, t, Ar—H), 6.65 (1H, s, Ar—H), 6.76 (1H, d, Ar—H), 6.82 (1H, d, Ar—H), 6.95 (1H, t, Ar—H), 7.12—7.13 (3H, m, Ar—H), 7.32 (1H, s, =CH), 7.43 (1H, t, —NH), 7.77 (2H, d, Ar—H), 9.57 (1H, s, —NH), MS m/z: 457.9 (M$^+$+ 1). |
| 121 | 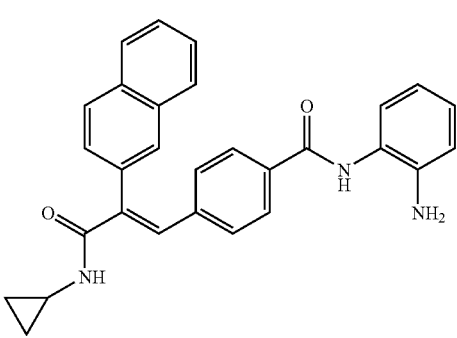 [SMILES: Nc1ccccc1NC(=O)c1ccc(/C=C(/C(=O)NC2CC2)c2ccc3ccccc3c2)cc1] | $^1$H NMR (DMSO-d$_6$) δ (ppm): 0.53 (2H, m, —CH$_2$), 0.65 (2H, m, —CH$_2$), 2.80 (1H, m, —CH), 4.84 (2H, s, —NH$_2$), 6.54-6.56 (1H, t, Ar—H), 6.72-6.73 (1H, d, Ar—H), 6.93-6.97 (1H, t, Ar—H), 7.07-7.12 (3H, m, Ar—H), 7.25-7.27 (2H, m, Ar—H), 7.42 (1H, s, =CH), 7.53 (1H, m, Ar—H), 7.71-7.76 (3H. m. Ar—H), 7.91-7.93 (4H, d, Ar—H and —NH), 9.52 (1H, s, —NH), MS m/z: 447.9 (M$^+$ + 1). |
| 122 | 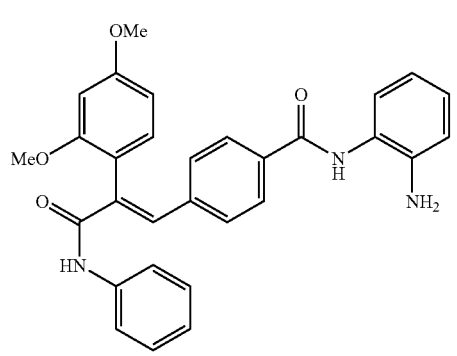 [SMILES: COc1ccc(/C(=C\c2ccc(C(=O)Nc3ccccc3N)cc2)C(=O)Nc2ccccc2)c(OC)c1] | $^1$H NMR (DMSO-d$_6$) δ (ppm): 3.71 (3H, s, —OCH$_3$), 3.81 (3H, s, —OCH$_3$), 4.89 (2H, s, —NH$_2$), 6.52-6.60 (2H, d, Ar—H), 6.69 (1H, s, Ar—H), 6.75-6.77 (1H, d, Ar—H), 6.90-6.92 (1H, d, Ar—H), 6.94-6.98 (1H, t, Ar—H), 7.05-7.08 (1H, t, Ar—H), 7.12-7.14 (1H, d, Ar—H), 7.23-7.24 (2H, d, Ar—H), 7.29-7.33 (2H, t, Ar—H), 7.43 (1H, s, =CH), 7.66-7.68 (2H, d, Ar—H), 7.80-7.82 (2H, d, Ar—H), 9.60 (1H, s, —NH), 9.67 (1H, s, —NH) MS m/z: 493.8 (M$^+$ + 1). |

-continued

| Ex. No | Structure | Analytical data |
|---|---|---|
| 123 | 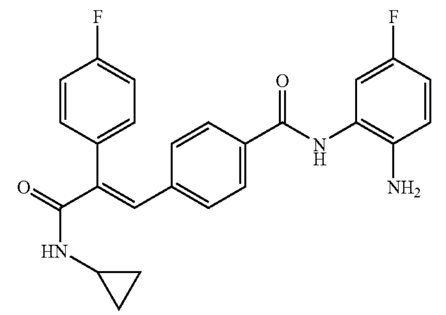 [SMILES: Nc1ccc(F)cc1NC(=O)c1ccc(/C=C(/C(=O)NC2CC2)c2ccc(F)cc2)cc1] | $^1$H NMR (DMSO-d$_6$) δ (ppm): 0.53 (2H, m, —CH$_2$), 0.64-0.65 (2H, m, —CH$_2$), 2.76-2.77 (1H, m, —CH), 5.21 (2H, s, —NH$_2$), 6.31-6.34 (1H, t, Ar—H), 6.49-6.52 (1H, d, Ar—H), 7.04-7.05 (1H, t, Ar—H), 7.09-7.11 (2H, d, Ar—H), 7.19-7.24 (4H, m, Ar—H), 7.32 (1H, s, =CH), 7.78-7.80 (2H, d, Ar—H), 7.90-7.91 (1H, d, Ar—H), 9.51 (1H, s, —NH), MS m/z: 433.8 (M$^+$ + 1). |
| 124 | 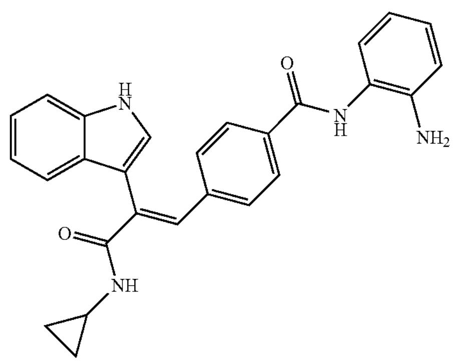 [SMILES: Nc1ccccc1NC(=O)c1ccc(/C=C(/C(=O)NC2CC2)c2c[nH]c3ccccc23)cc1] | $^1$H NMR (DMSO-d$_6$) δ (ppm): 0.47-0.49 (2H, m, —CH$_2$), 0.61-0.63 (2H, m, —CH$_2$), 2.75-2.76 (1H, s, —CH), 4.84 (2H, s, —NH$_2$), 6.76 (1H, t, Ar—H), 6.89 (1H, d, Ar—H), 6.99 (3H, m, Ar—H), 7.08-7.10 (2H, d, Ar—H), 7.20-7.22 (2H, d, Ar—H), 7.32-7.33 (1H, d, Ar—H), 7.40-7.44 (2H, t, Ar—H and =CH), 7.62-7.64 (1H, d, Ar—H), 7.70-7.72 (2H, d, Ar—H), 9.55 (1H, s, —NH), 11.38 (1H, s, —NH) MS m/z: 436.9 (M$^+$ + 1). |
| 125 | 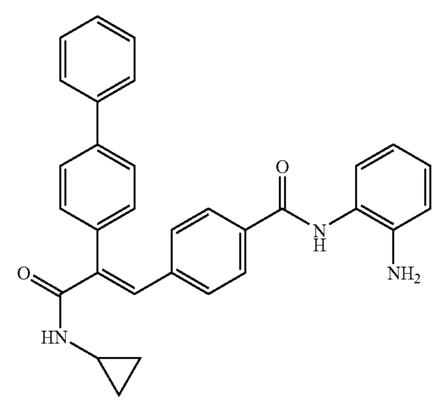 [SMILES: Nc1ccccc1NC(=O)c1ccc(/C=C(/C(=O)NC2CC2)c2ccc(-c3ccccc3)cc2)cc1] | $^1$H NMR (DMSO-d$_6$) δ (ppm): 0.54-0.55 (2H, m, —CH$_2$), 0.66-0.67 (2H, m, —CH$_2$), 2.78-2.79 (1H, m, —CH), 4.86 (2H, s, —NH$_2$), 6.56-6.57 (1H, t, Ar—H), 6.73-6.75 (1H, d, Ar—H), 6.95 (1H, t, Ar—H), 7.09-7.11 (1H, d, Ar—H), 7.17-7.19 (2H, d, Ar—H), 7.24-7.26 (2H, d, Ar—H), 7.31 (1H, s, =CH), 7.38-7.40 (1H, d, Ar—H), 7.46-7.50 (2H, t, Ar—H), 7.70-7.74 (4H, m, Ar—H), 7.78-7.80 (2H, d, Ar—H), 7.99-8.00 (1H, d, —NH), 9.59 (1H, s, —NH) MS m/z: 473.9 (M$^+$ + 1). |
| 126 | 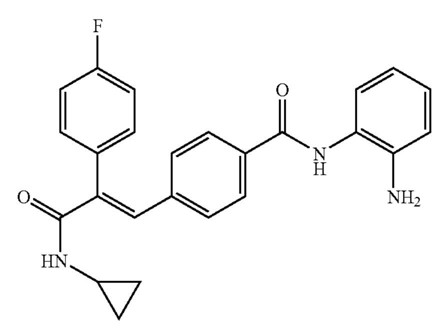 [SMILES: Nc1ccccc1NC(=O)c1ccc(/C=C(/C(=O)NC2CC2)c2ccc(F)cc2)cc1] | $^1$H NMR (DMSO-d$_6$) δ (ppm): 0.53 (2H, m, —CH$_2$), 0.64-0.65 (2H, m, —CH$_2$), 2.76-2.77 (1H, m, —CH), 6.79-6.81(1H, t, Ar—H), 6.89-6.91 (1H, d, Ar—H), 7.00-7.04 (1H, t, Ar—H), 7.11-7.13 (2H, d, Ar—H), 7.19-7.24 (4H, m, Ar—H), 7.32 (1H, s, =CH), 7.58-7.60 (1H, d, Ar—H), 7.77-7.79 (2H, d, Ar—H), 7.93-7.94 (1H, d, Ar—H), 9.49 (2H, s, —NH and —OH), MS m/z: 416.8 (M$^+$ + 1). |

| Ex. No | Structure | Analytical data |
|---|---|---|
| 127 | 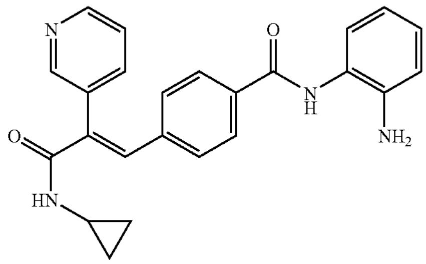 [SMILES: Nc1ccccc1NC(=O)c1ccc(/C=C(/C(=O)NC2CC2)c2cccnc2)cc1] | ¹H NMR (DMSO-d₆) δ (ppm): 0.54 (2H, m, —CH₂), 0.66-0.67 (2H, m, —CH₂), 2.77-2.78 (1H, m, —CH), 4.93 (2H, s, —NH₂), 6.56-6.59 (1H,t, Ar—H), 6.74-6.76 (1H, d, Ar—H), 6.93-6.97 (1H, t, Ar—H), 7.09-7.11 (3H, m, Ar—H), 7.40-7.45 (2H, m, Ar—H and =CH), 7.61-7.63 (1H, d, Ar—H), 7.79-7.81 (2H, d, Ar—H), 8.12-8.13 (1H, d, Ar—H), 8.27 (1H, s, Ar—H), 8.54-8.55 (1H, d, —NH), 9.57 (1H, s, —NH), MS m/z: 398.9 (M⁺ + 1). |
| 128 | 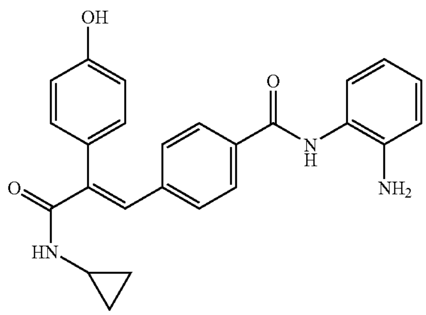 [SMILES: Nc1ccccc1NC(=O)c1ccc(/C=C(/C(=O)NC2CC2)c2ccc(O)cc2)cc1] | ¹H NMR (DMSO-d₆) δ (ppm): 0.51-0.52 (2H, m, —CH₂), 0.62-0.66 (2H, m, —CH₂), 2.73-2.77 (1H, m, —CH), 4.88 (2H, s, —NH₂), 6.55-6.58 (1H, t, Ar—H), 6.75-6.77 (3H, d, Ar—H), 6.94-6.96 (3H, d, Ar—H), 7.11-7.13 (3H, t, Ar—H), 7.19 (1H, s, =CH), 7.67-7.68 (1H, d, Ar—H), 7.77-7.79 (2H, d, Ar—H), 9.57 (2H, s, —NH and OH), MS m/z: 413.9 (M⁺ + 1). |
| 129 | 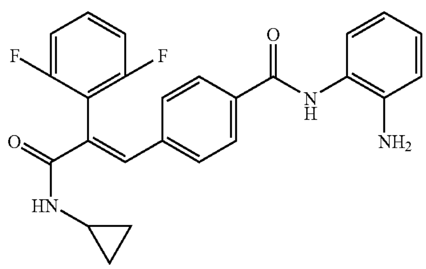 [SMILES: Nc1ccccc1NC(=O)c1ccc(/C=C(/C(=O)NC2CC2)c2c(F)cccc2F)cc1] | ¹H NMR (DMSO—d₆) δ (ppm): 0.52-0.54 (2H, m, —CH₂), 0.65-0.67 (2H, m, —CH₂), 2.75-2.76 (1H, m, —CH), 4.89 (2H, s, —NH), 6.57 (1H, t, Ar—H), 6.74-6.76 (1H, m, Ar—H), 6.95 (1H, t, Ar—H), 7.11-7.18 (5H, m, Ar—H), 7.51 (1H, m, Ar—H), 7.64 (1H, s, =CH), 7.82-7.84 (2H, d, Ar—H), 8.24-8.25 (1H, d, —NH), 9.62 (1H, s, —NH) MS m/z: 433.8 (M⁺ + 1). |
| 130 | 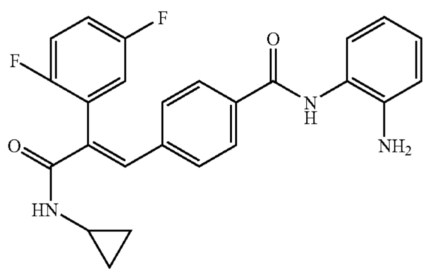 [SMILES: Nc1ccccc1NC(=O)c1ccc(/C=C(/C(=O)NC2CC2)c2cc(F)ccc2F)cc1] | ¹H NMR (DMSO-d₆) δ (ppm): 0.53-0.54 (2H, m, —CH₂), 0.63-0.66 (2H, m, —CH₂), 2.75-2.77 (1H, m, —CH), 4.89 (2H, s, —NH₂), 6.55-6.58 (1H, t, Ar—H), 6.74-6.76 (1H, d, Ar—H), 6.93-6.97 (1H, t, Ar—H), 7.03-7.06 (1H, t, Ar—H), 7.11-7.17 (3H, m, Ar—H), 7.28-7.31 (2H, t, Ar—H), 7.54 (1H, s, =CH), 7.82-7.84 (2H, d, Ar—H), 8.08-8.09 (1H, d, —NH), 9.61 (1H, s, —NH). MS m/z: 433.8 (M⁺ + 1). |
| 131 | 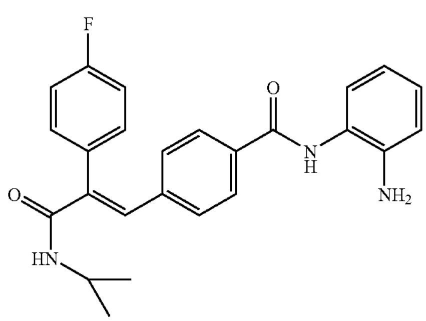 [SMILES: CC(C)NC(=O)/C(=C/c1ccc(C(=O)Nc2ccccc2N)cc1)c1ccc(F)cc1] | ¹H NMR (DMSO-d₆) δ (ppm): 1.11 (6H, s, —CH₃), 3.96-4.02 (1H, m, —CH), 4.88 (2H, s, —NH₂), 6.55-6.58 (1H, t, Ar—H), 6.74-6.76 (1H, d, Ar—H), 6.93-6.97 (1H, d, Ar—H), 7.11-7.13 (3H, d, Ar—H), 7.18-7.26 (4H, m, Ar—H), 7.33 (1H, s, =CH), 7.63-7.65 (1H, d, Ar—H), 7.79-7.81 (2H, d, Ar—H), 9.58 (1H, s, —NH), MS m/z: 417.9 (M⁺ + 1). |

-continued

| Ex. No | Structure | Analytical data |
|---|---|---|
| 132 | 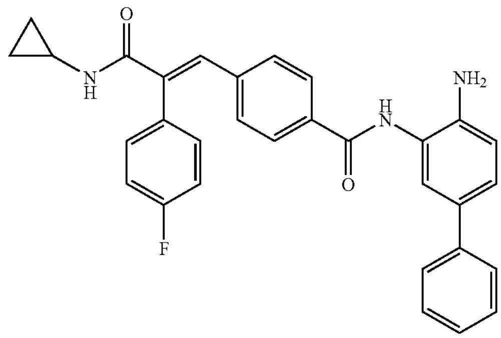 [SMILES: Nc1ccc(-c2ccccc2)cc1NC(=O)c1ccc(/C=C(/C(=O)NC2CC2)c2ccc(F)cc2)cc1] | $^1$H NMR (DMSO-d$_6$) δ (ppm): 0.53-0.54 (2H, m, —CH$_2$), 0.65-0.66 (2H, m, —CH$_2$), 2.76-2.77 (1H, m, —CH), 4.08 (2H, s, —NH$_2$), 6.83-6.85 (1H, d, Ar—H), 7.11-7.13 (2H, d, Ar—H), 7.21-7.25 (5H, m, Ar—H), 7.31-7.33 (2H, m, Ar—H), 7.36-7.40 (2H, m, Ar—H), 7.48 (1H, s, =CH), 7.52-7.54 (2H, d, Ar—H), 7.82-7.84 (2H, d, Ar—H), 7.92-7.93 (1H, d, Ar—H), 9.68 (1H, s, —NH) MS m/z: 491.8 (M$^+$ + 1). |
| 133 | 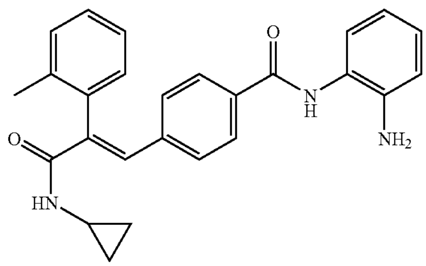 [SMILES: Cc1ccccc1/C(=C\c1ccc(C(=O)Nc2ccccc2N)cc1)C(=O)NC1CC1] | $^1$H NMR (DMSO-d$_6$) δ (ppm): 0.50-0.51 (2H, m, —CH$_2$), 0.63-0.66 (2H, m, —CH$_2$), 2.08 (3H, s, —CH$_3$), 2.73-2.76 (1H, s, —CH), 4.87 (2H, s, —NH$_2$), 6.55-6.58 (1H, t, Ar—H), 6.73-6.75 (1H, d, Ar—H), 6.93-6.96 (1H, t, Ar—H), 7.01-7.03 (3H, m, Ar—H), 7.09-7.11 (1H, d, Ar—H), 7.21-7.24 (1H, m, Ar—H), 7.30 (2H, m, Ar—H), 7.41 (1H, s, =CH), 7.70-7.76 (3H, m, Ar—H and NH), 9.55 (1H, s, —NH). MS m/z: 411.9 (M$^+$ + 1). |
| 134 | 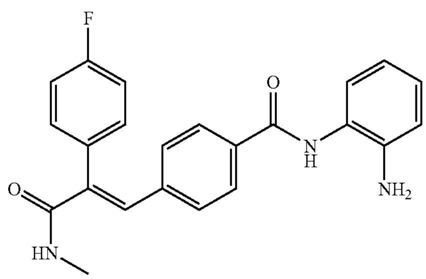 [SMILES: CNC(=O)/C(=C/c1ccc(C(=O)Nc2ccccc2N)cc1)c1ccc(F)cc1] | $^1$H NMR (DMSO-d$_6$) δ (ppm): 2.68 (3H, s, —CH$_3$), 4.87 (2H, s, —NH$_2$), 6.55-6.59 (1H, t, Ar—H), 6.74-6.76 (1H, d, Ar—H), 6.93-6.97 (1H, t, Ar—H), 7.08-7.12 (3H, d, Ar—H), 7.22-7.28 (4H, m, Ar—H and =CH), 7.49-7.51 (2H, d, Ar—H), 7.78-7.80 (2H, d, Ar—H), 9.58 (1H, s, —NH), MS m/z: 390.2(M$^+$ + 1). |
| 135 | 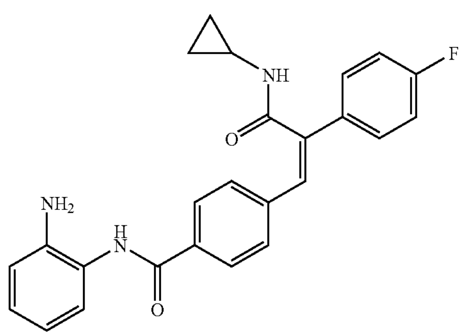 [SMILES: Nc1ccccc1NC(=O)c1ccc(/C=C(\C(=O)NC2CC2)c2ccc(F)cc2)cc1] | $^1$H NMR (DMSO-d$_6$) δ (ppm): 0.42 (2H, m, —CH$_2$), 0.66-0.67 (2H, m, —CH$_2$), 2.80-2.81 (1H, m, —CH), 4.92 (2H, s, —NH$_2$), 6.59-6.62 (1H, t, Ar—H), 6.78-6.80 (1H, d, Ar—H), 6.96-7.00 (1H, t, Ar—H), 7.12 (1H, s, =CH), 7.16-7.18 (1H, d, Ar—H), 7.25-7.29 (2H, t, Ar—H), 7.59-7.61 (4H, d, Ar—H), 7.97-7.99 (2H, d, Ar—H), 8.59-8.60 (1H, d, Ar—H), 9.69 (1H, s, —NH), MS m/z: 416.2 (M$^+$ + 1). |
| 136 | 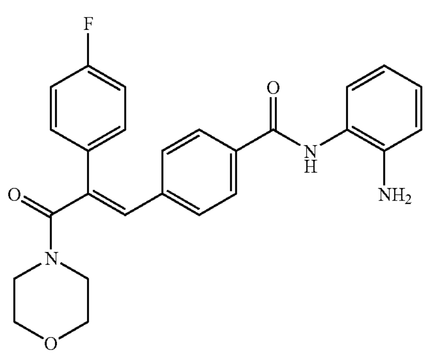 [SMILES: Nc1ccccc1NC(=O)c1ccc(/C=C(/C(=O)N2CCOCC2)c2ccc(F)cc2)cc1] | $^1$H NMR (DMSO-d$_6$) δ (ppm): 3.58 (8H, s, —CH$_2$), 4.88 (2H, s, —NH$_2$), 6.58 (1H, t, Ar—H), 6.75-6.77 (1H, d, Ar—H), 6.81 (1H, d, Ar—H), 6.95 (1H, t, Ar—H), 7.11 (1H, d, Ar—H), 7.20-7.22 (3H, m, Ar—H), 7.24 (1H, s, =CH), 7.30-7.34 (2H, m, Ar—H), 7.82-7.84 (2H, d, Ar—H), 9.61 (1H, s, —NH), MS m/z: 446.2(M$^+$ + 1). |

| Ex. No | Structure | Analytical data |
|---|---|---|
| 137 | 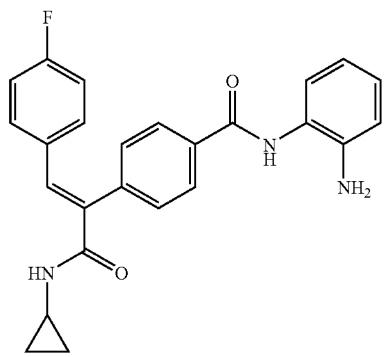 [SMILES: Nc1ccccc1NC(=O)c1ccc(/C(=C\c2ccc(F)cc2)C(=O)NC2CC2)cc1] | ¹H NMR (DMSO-d₆) δ (ppm): 0.67 (2H, m, —CH₂), 0.82-0.85 (2H, m, —CH₂), 2.73-2.77 (1H, m, —CH), 4.90 (2H, s, —NH₂), 6.59-6.62 (1H, t, Ar—H), 6.78-6.80 (1H, d, Ar—H), 6.96-7.00 (1H, t, Ar—H), 7.07-7.09 (4H, d, Ar—H), 7.15-7.17 (1H, d, Ar—H), 7.26 (1H, s, =CH), 7.28-7.29 (2H, d, Ar—H), 7.86-7.87 (1H, d, Ar—H), 7.98-8.00 (2H, d, Ar—H), 9.73 (1H, s, —NH), MS m/z: 416.0 (M⁺ + 1). |
| 138 | 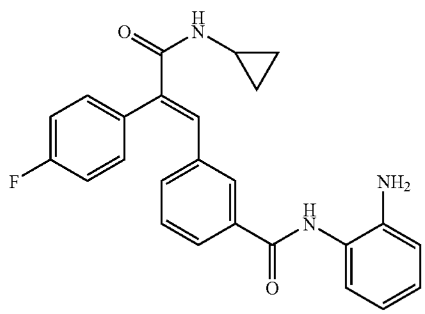 [SMILES: Nc1ccccc1NC(=O)c1cccc(/C=C(/C(=O)NC2CC2)c2ccc(F)cc2)c1] | ¹H NMR (DMSO-d₆) δ (ppm): 0.49-0.53 (2H, m, —CH₂), 0.62-0.66 (2H, m, —CH₂), 2.74-2.78 (1H, m, —CH), 4.87 (2H, s, —NH₂), 6.57-6.60 (1H, t, Ar—H), 6.76-6.78 (1H, d, Ar—H), 6.95-6.98 (1H, t, Ar—H), 7.01-7.02 (1H, d, Ar—H), 7.10-7.12 (1H, d, Ar—H), 7.13-7.22 (4H, m, Ar—H), 7.27-7.30 (1H, t, Ar—H), 7.35 (1H, s, =CH), 7.75-7.81 (2H, d, Ar—H), 7.84-7.86 (1H, d, Ar—H), 9.58 (1H, s, —NH), MS m/z: 416.0 (M⁺ + 1). |
| 139 | 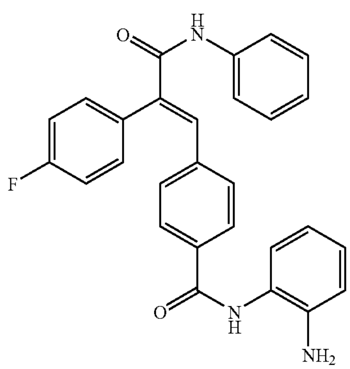 [SMILES: Nc1ccccc1NC(=O)c1ccc(/C=C(/C(=O)Nc2ccccc2)c2ccc(F)cc2)cc1] | ¹H NMR (DMSO-d₆) δ (ppm): 4.89 (2H, s, —NH₂), 6.55-6.57 (1H, t, Ar—H), 6.60-6.62 (1H, d, Ar—H), 6.78-6.80 (1H, d, Ar—H), 6.99 2H, t, Ar—H), 7.12-7.14 (2H, m, Ar—H), 7.20-7.37 (6H, m, Ar—H), 7.46 (1H, s, =CH), 7.69-7.71 (2H, d, Ar—H), 7.83-7.85 (2H, d, Ar—H), 9.62 (1H, s, —NH), 10.07 (1H, s, —NH), MS m/z: 452.0 (M⁺ + 1). |
| 140 | 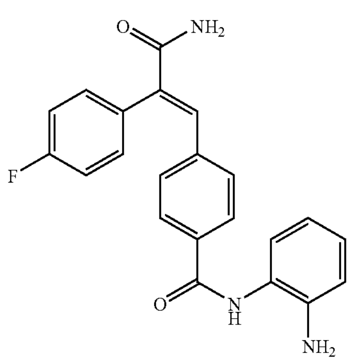 [SMILES: NC(=O)/C(=C/c1ccc(C(=O)Nc2ccccc2N)cc1)c1ccc(F)cc1] | ¹H NMR (DMSO-d₆) δ (ppm): 4.87 (2H, s, —NH₂), 6.57 (1H, t, Ar—H), 6.74-6.76 (1H, d, Ar—H), 6.95 (1H, t, Ar—H), 7.10-7.12 (4H, m, Ar—H), 7.22-7.24 (4H, m, Ar—H and NH₂), 7.38 (1H, s, —NH₂), 7.50 (1H, s, =CH), 7.79-7.81 (2H, d, Ar—H), 9.58 (1H, s, —NH), MS m/z: 376.0 (M⁺ + 1). |

| Ex. No | Structure | Analytical data |
|---|---|---|
| 141 | 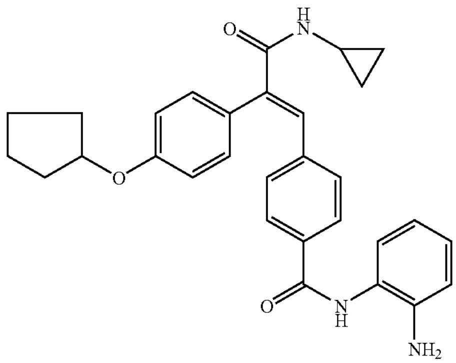 [SMILES: Nc1ccccc1NC(=O)c1ccc(/C=C(/C(=O)NC2CC2)c2ccc(OC3CCCC3)cc2)cc1] | $^1$H NMR (DMSO-d$_6$) δ (ppm): 0.51-0.52 (2H, m, —CH$_2$), 0.64-0.65 (2H, m, —CH$_2$), 1.59 (2H, m, —CH$_2$), 1.72 (4H, m, —CH$_2$), 1.92-1.93 (2H, m, —CH$_2$), 2.74-2.76 (1H, m, —CH), 4.83-4.88 (3H, t, —NH$_2$ and —CH), 6.57 (1H, t, Ar—H), 6.74-6.76 (1H, d, Ar—H), 6.88-6.90 (2H, d, Ar—H), 6.95 (1H, t, Ar—H), 7.04-7.06 (2H, d, Ar—H), 7.12-7.14 (3H, m, Ar—H), 7.22 (1H, s, =CH), 7.78-7.80 (3H, t, Ar—H and —NH), 9.58 (1H, s, —NH), MS m/z: 482.1(M$^+$ + 1). |
| 142 | 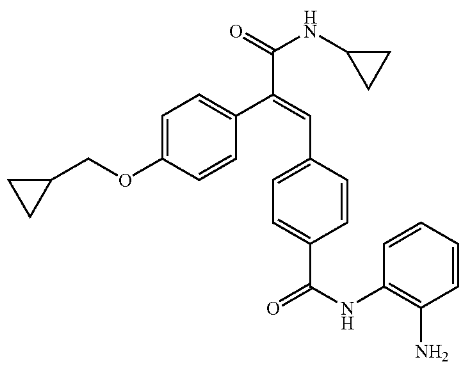 [SMILES: Nc1ccccc1NC(=O)c1ccc(/C=C(/C(=O)NC2CC2)c2ccc(OCC3CC3)cc2)cc1] | $^1$H NMR (DMSO-d$_6$) δ (ppm): 0.32-0.33 (2H, d, —CH$_2$), 0.51-0.52 (2H, d, —CH$_2$), 0.57-0.59 (2H, d, —CH$_2$), 0.63-0.65 (2H, d. —CH$_2$), 1.22-1.25 (1H, m, —CH), 2.75-2.78 (1H, m, —CH), 3.82-3.83 (2H, d, —CH$_2$), 4.88 (2H, s, —NH$_2$), 6.57 (1H, t, Ar—H), 6.74-6.76 (1H, d, Ar—H), 6.91-6.95 (3H, m, Ar—H), 7.04-7.06 (2H, d, Ar—H), 7.11-7.14 (3H, m, Ar—H), 7.23 (1H, s, =CH), 7.74-7.79 (3H, m, Ar—H and —NH), 9.58 (1H, s, —NH), MS m/z: 468.1 (M$^+$ + 1). |
| 143 | 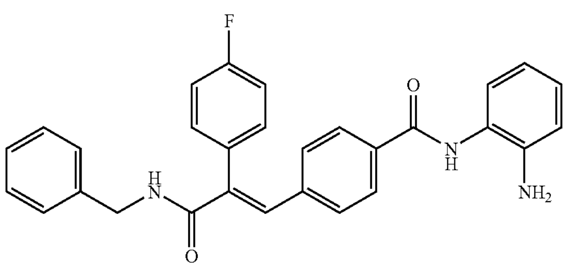 [SMILES: Nc1ccccc1NC(=O)c1ccc(/C=C(/C(=O)NCc2ccccc2)c2ccc(F)cc2)cc1] | $^1$H NMR (DMSO-d$_6$) δ (ppm): 4.36-4.37 (2H, d, —CH$_2$), 4.88 (2H, s, —NH$_2$), 6.55-6.59 (1H, t, Ar—H), 6.74-6.76 (1H, d, Ar—H), 6.93-6.97 (1H, t, Ar—H), 7.11-7.13 (3H, d, Ar—H), 7.24-7.35 (9H, m, Ar—H), 7.53 (1H, s, =CH), 7.79-7.81 (2H, d, Ar—H), 8.17-8.20 (1H, t, —NH), 9.58 (1H, s, —NH), MS m/z: 466.0 (M$^+$ + 1). |

Example 144

Synthesis of N-(2-aminophenyl)-4-(3-(cyclopropylamino)-2-(4-fluorophenyl)prop-1-enyl)benzamide

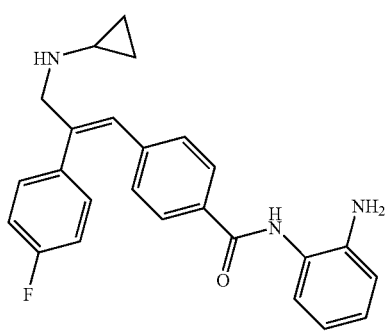 [SMILES: Nc1ccccc1NC(=O)c1ccc(/C=C(/CNC2CC2)c2ccc(F)cc2)cc1]

Step-I

Preparation of methyl 3-(4-(2-(4-fluorophenyl)-3-hydroxyprop-1-en-1-yl)phenyl)benzoate

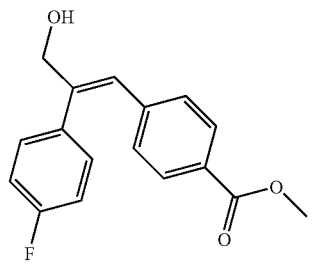 [SMILES: COC(=O)c1ccc(/C=C(/CO)c2ccc(F)cc2)cc1]

To a suspension of 2-(4-fluorophenyl)-3-(4-(methoxycarbonyl)phenyl)acrylic acid (3 g, 10 mmol) (prepared according to the procedure described in Example 99, step-I) in THF (30 mL) was added triethylamine (1.5 mL, 12 mmol) under constant stirring at 5° C. To this solution methyl chloroformate (0.86 mL, 12 mmol) was added dropwise at 5° C. and stirred for 30 minutes at the same temperature. To this reaction mixture sodium borohydride (1.5 g, 40 mmol) was added at once and methanol (20 mL) was added dropwise under stirring and the reaction mixture was stirred at 30° C. for 1 hour. After completion of the reaction, the reaction mixture was diluted with ethyl acetate (200 mL) and washed with water (100 mL) and brine (100 mL). The organic layer was dried over anhydrous $Na_2SO_4$ and concentrated to afford the crude compound. The crude product was purified by column chromatography using 10% ethylacetate/hexane as the eluent to afford a pure compound as a white solid (1.4 g, 51% yield).

Step-II

Preparation of methyl 4-(2-(4-fluorophenyl)-3-oxo-prop-1-en-1-yl)benzoate

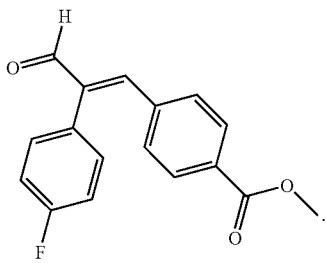 [SMILES: COC(=O)c1ccc(/C=C(/C=O)c2ccc(F)cc2)cc1]

Pyridinium chlorochromate (PCC) (1.12 g, 5.2 mmol) was dissolved in dichloromethane (20 mL). The solution of methyl 3-(4-(2-(4-fluorophenyl)-3-hydroxyprop-1-en-1-yl)phenyl)benzoate (1.14 g, 4 mmol) in dichloromethane (4 mL) was added dropwise under constant stirring and the reaction mixture was stirred at room temperature for 1 hour. The reaction mixture was diluted with diethyl ether (100 mL) and filtered through celite; the filtrate was washed with saturated aqueous $NaHCO_3$ solution (2×100 mL) and water (100 mL). The organic layer was dried over anhydrous $Na_2SO_4$ and concentrated to afford the pure title compound as a white solid (0.58 g, 53% yield)

Step-III

Preparation of methyl 4-(3-(cyclopropylamino)-2-(4-fluorophenyl)prop-1-en-1-yl)benzoate

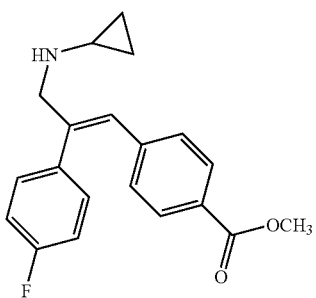 [SMILES: COC(=O)c1ccc(/C=C(/CNC2CC2)c2ccc(F)cc2)cc1]

A mixture of methyl 4-(2-(4-fluorophenyl)-3-oxoprop-1-en-1-yl)benzoate (0.568 g. 2 mmol) and cyclopropylamine (0.17 g, 3 mmol) were stirred with MeOH (50 mL) for 3 hours. $NaBH_4$ (0.114 g, 3 mmol) was added to the reaction mixture and it was stirred for 30 minutes. Subsequently the reaction mixture was diluted with ethyl acetate (300 mL) and washed with water (3×50 mL) and brine (100 mL). The organic layer was dried over anhydrous $Na_2SO_4$ and concentrated to afford the pure title compound as a pale yellow sticky compound (0.51 g, 76% yield).

Step-IV

Preparation of 4-(3-(cyclopropylamino)-2-(4-fluorophenyl) prop-1-en-1-yl)benzoic acid

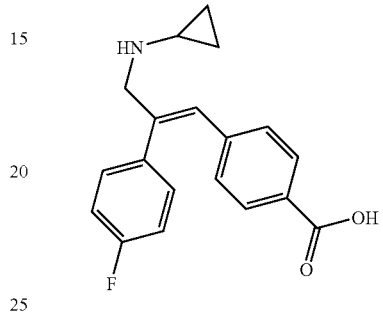

To a solution methyl 4-((4-(3-(cyclopropylamino)-1-(4-fluorophenyl)-3-oxo prop-1-en-2-yl)phenylamino)methyl) benzoate (0.5 g, 1.5 mmol) in methanol (10 mL) a solution of NaOH (0.088 g, 3.8 mmol) in water (0.5 mL) was added. The reaction mixture was refluxed for 1 hour at 70° C. The solvent was removed by evaporation, and the remainder was poured to ice cold water. The aqueous layer was acidified to pH 3 with citric acid, the solid precipitated out was filtered and dried under vacuum to get a pale yellow solid (0.4 g, 77% yield).

Step-V

Preparation of N-(2-aminophenyl)-4-(3-(cyclopropylamino)-2-(4-fluorophenyl)prop-1-enyl)benzamide

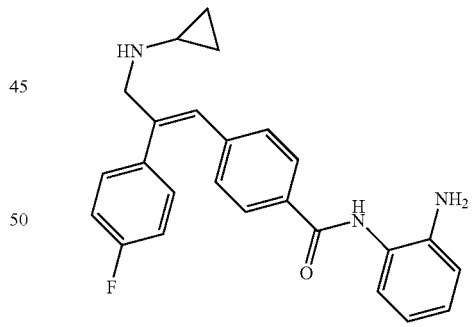

To a solution of 4-(3-(cyclopropylamino)-2-(4-fluorophenyl)prop-1-en-1-yl)benzoic acid (0.4 g, 1.3 mmol) in DMF (5 mL), EDCl (0.49 g, 2.6 mmol), HOBt (0.175 g. 1.3 mmol) and TEA (0.54 mL, 3.9 mmol), were added, followed by n-phenylenediamine (0.280 g, 2.6 mmol). The reaction mixture was stirred at room temperature for 2 hours, subsequently the residue was poured into water and extracted with ethyl acetate (300 mL) and washed with water (3×50 mL) and brine (100 mL). The organic layer was dried over anhydrous $Na_2SO_4$ and concentrated to afford the crude compound. The obtained compound was purified with flash chromatography using 15% ethyl acetate/hexane as the eluent, pure fraction evaporated to afford title compound (0.040 g, 9% yield). $^1$H NMR (DMSO-$d_6$) δ (ppm): 0.24-0.25 (2H, m, —CH$_2$), 0.37-0.39 (2H, m, —CH$_2$), 2.13-2.14 (1H, m, —CH), 3.57 (2H, s, —CH$_2$), 4.86 (2H, s, —NH$_2$), 6.55-6.59 (1H, t, Ar—H), 6.70 (1H, s, =CH), 6.74-6.76 (1H, d, Ar—H), 6.93-6.95 (1H, t, Ar—H), 7.02-7.04 (2H, m, Ar—H), 7.10-7.12 (1H, d, Ar—H), 7.16-7.26 (4H, m, Ar—H), 7.74-7.76 (2H, d, Ar—H), 9.52 (1H, s, —NH), MS m/z: 402.2 (M$^+$+1).

Example 145

Synthesis of 4-(3-(cyclopropylamino)-2-(4-fluorophenyl)-3-oxoprop-1-enyl)-N-(4-((1E)-3-(hydroxyamino)-3-oxoprop-1-en-1-yl)benzyl)benzamide

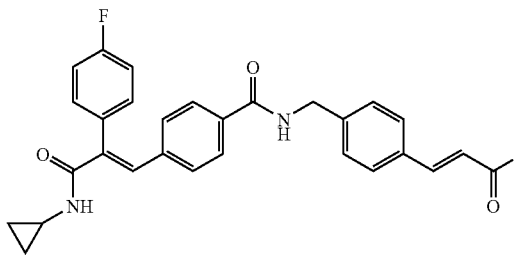

Step-I

Preparation of methyl 3(4-((4-((1E)-3-(cyclopropylamino)-2-(4-fluorophenyl)-3-oxoprop-1-en-1-yl)benzamido)methyl)phenyl)acrylate

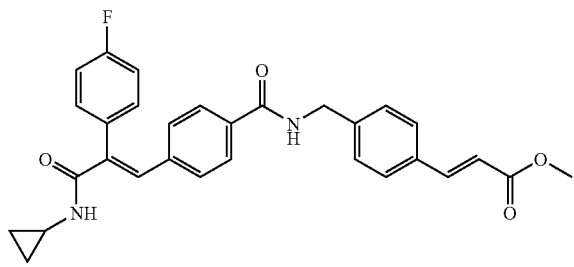 [SMILES: COC(=O)/C=C/c1ccc(CNC(=O)c2ccc(/C=C(/C(=O)NC3CC3)c3ccc(F)cc3)cc2)cc1]

To a suspension of 4-((1E)-3-(cyclopropylamino)-2-(4-fluorophenyl)-3-oxoprop-1-en-1-yl)benzoic acid (0.3 g, 0.9 mmol, prepared according to the procedure described in Example 99, step-III) in DMF (5 mL) EDCl (0.35 g, 1.8 mmol), HOBt (0.12 g, 0.9 mmol), methyl 4-aminomethylcinnamate (0.237 g, 1.1 mmol), were added followed by triethylamine (0.4 mL, 3 mmol). The reaction mixture was stirred for 8 hours after which the mixture was poured to cold water (100 mL), the white precipitate formed was filtered, washed with water (1×150 mL), dried under vacuum to afford the title compound as a yellow solid (0.4 g, 87% yield).

Step-II

Preparation of 4-(3-(cyclopropylamino)-2-(4-fluorophenyl)-3-oxoprop-1-enyl)-N-(4-((1E)-3-(hydroxyamino)-3-oxoprop-1-en-1-yl)benzyl)benzamide

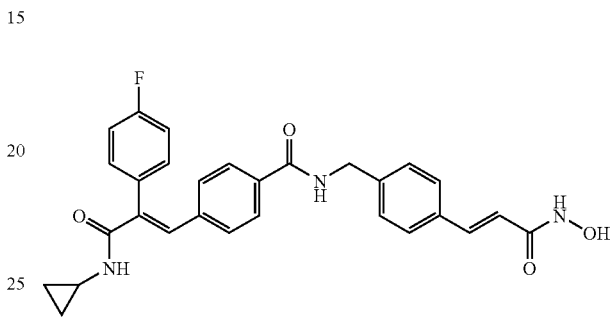

Hydroxylamine hydrochloride (0.5 g, 7.2 mmol) in methanol (2 mL) was mixed with KOH (0.4 g, 7.2 mmol) in methanol (2 mL) at 0° C., and sonicated for 2 minutes and the white precipitate formed was filtered. The filtrate was added to methyl 3(4-((4-((1E)-(3-(cyclopropylamino)-2-(4-fluorophenyl)-3-oxoprop-1-enyl)benzamido)methyl)phenyl)acrylate (0.20 g, 0.4 mmol) in DCM (1.5 mL) and the mixture stirred at room temperature for 30 minutes. The reaction mixture was diluted with water (200 mL) and extracted with ethyl acetate (3×100 mL). The ethyl acetate layers were washed with water (100 mL), dried over anhydrous Na$_2$SO$_4$ and concentrated to obtain a crude compound, which was triturated with DCM (15 mL) to obtain a solid which was filtered and washed with DCM (5 mL) to afford the title compound (0.050 g, 25% yield). $^1$H NMR (DMSO-$d_6$) δ (ppm): 0.51-052 (2H, m, —CH$_2$), 0.63-0.65 (2H, m, —CH$_2$), 2.74-2.75 (1H, m, —CH), 4.43-4.44 (2H, d, CH$_2$), 6.39-6.43 (1H, d, =CH), 7.05-7.07 (2H, d, Ar—H), 7.16-7.22 (4H, m, Ar—H), 7.29-7.32 (3H, m, Ar—H and =CH), 7.40-7.44 (1H, d, =CH), 7.49-7.51 (2H, d, Ar—H), 7.68-7.70 (2H, d, Ar—H), 7.89-7.90 (1H, d, —NH), 9.00 (2H, m, NH and OH), 10.73 (1H, s, NH), MS m/z: 498.1 (M$^+$–1).

The following compounds were prepared according to the procedure given in Example 145.

| Ex. No | Structure | Analytical data |
|---|---|---|
| 146 | 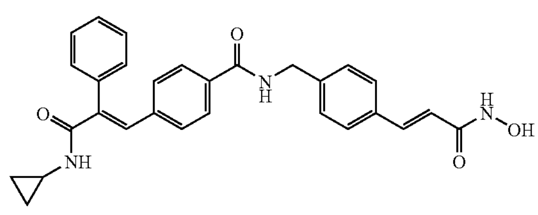 [SMILES: O=C(/C=C/c1ccc(CNC(=O)c2ccc(/C=C(/C(=O)NC3CC3)c3ccccc3)cc2)cc1)NO] | $^1$H NMR (DMSO-$d_6$) δ (ppm): 0.51 (2H, m, —CH$_2$), 0.63-0.65 (2H, m, —CH$_2$), 2.74 (1H, m, —CH), 4.42 (2H, s, CH$_2$), 6.43 (1H, d, =CH), 7.05 (2H, d, Ar—H), 7.14 (2H, d, Ar—H), 7.24 (1H, s, =CH), 7.30 (2H, d, Ar—H), 7.36 (3H, m, Ar—H), 7.38 (1H, d, =CH), 7.49 (2H, d, Ar—H), 7.66 (2H, d, Ar—H), 7.87 (1H, d, —NH), 8.99 (2H, m, NH and OH), 10.75 (1H, s, NH), MS m/z: 480.1 (M$^+$ – 1). |

| Ex. No | Structure | Analytical data |
|---|---|---|
| 147 | 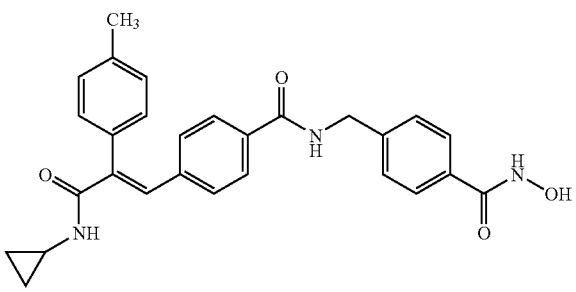 | $^1$H NMR (DMSO-d$_6$) δ (ppm): 0.51-0.52 (2H, m, —CH$_2$), 0.64 (2H, m, —CH$_2$), 2.74-2.75 (1H, m, —CH), 4.44 (2H, s, CH$_2$), 6.05 (2H, s, —CH$_2$), 6.46 (1H, d, =CH), 6.61-6.66 (2H, m, Ar—H), 6.91-6.93 (1H, d, Ar—H), 7.14-7.16 (2H, d, Ar—H), 7.27 (1H, s, =CH), 7.34-7.36 (2H, d, Ar—H), 7.43-7.46 (1H, d, =CH), 7.55-7.56 (2H, d, Ar—H), 7.68-7.70 (2H, d, Ar—H), 7.80 (1H, s, NH), 9.04 (2H, t, NH and OH), 10.75 (1H, s, NH), MS m/z: 525.8 (M$^+$ + 1). |

Example 148

Synthesis of 4-3-(cyclopropylamino)-2-(4-methylphenyl)-3-oxoprop-1-en-1-yl)-N-(4-(hydroxycarbamoyl)benzyl)benzamide

Step-I

Preparation of 4-((4-3-(cyclopropylamino)-2-(4-methylphenyl)-3-oxo prop-1-en-1-yl)benzamido)methyl)benzoic acid

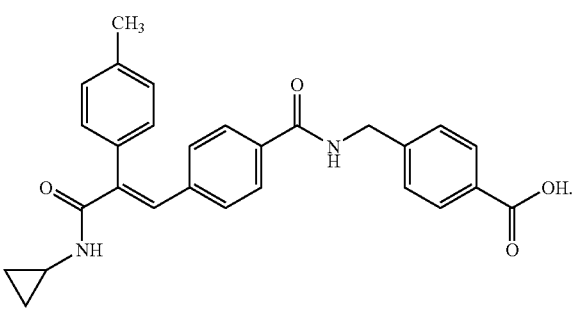 [SMILES: Cc1ccc(/C(=C\c2ccc(C(=O)NCc3ccc(C(=O)O)cc3)cc2)C(=O)NC2CC2)cc1]

To a solution of 3-(4-((2-(4-methylphenyl)-3-(cyclopropylamino)-3-oxoprop-1-en-1-yl)phenyl)benzoic acid methyl ester (0.26 g, 0.5 mmol, prepared similar to the procedure described in Example 145, step-II with appropriate reactants) in methanol (10 mL) a solution of NaOH (0.06 g, 1.6 mmol) in water (0.5 mL) was added. The reaction mixture was stirred for 3 hours at 70° C. The solvent was completely removed by evaporation, diluted with water (50 mL) and extracted with ethyl acetate (2×50 mL). The aqueous layer was acidified to pH 3 with dilute aqueous HCl (1:1) and allowed to stand at 4° C. for 30 minutes, the solid precipitated out was filtered and dried under vacuum to give a white solid (0.22 g, 88% yield).

Step-II

Preparation of 4-3-(cyclopropylamino)-2-(4-methylphenyl)-3-oxoprop-1-en-1-yl)-N-(4-(hydroxycarbamoyl)benzyl)benzamide

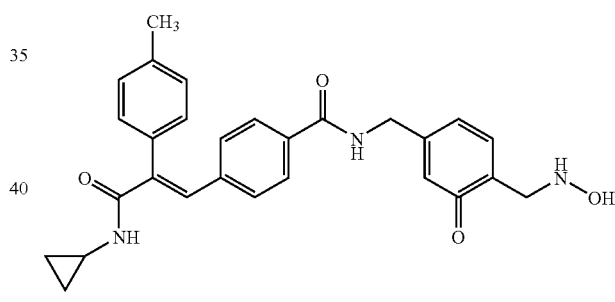

To a suspension of 4-3-(cyclopropylamino)-2-(4-methylphenyl)-3-oxoprop-1-enyl)-benzoic acid (0.22 g, 0.5 mmol) in DMF (5 mL) EDCl (0.4 g, 0.9 mmol), HOBt (0.06 g, 0.5 mmol), hydroxylamine hydrochloride (0.05 g, 0.7 mmol), were added followed by triethylamine (0.25 mL, 1.4 mmol). The reaction mixture was stirred for 1 hour, after which the mixture was added to cold water (20 mL). Upon standing at room temperature for 10 minutes, the precipitate formed was filtered, washed with (20 mL) water and dried under vacuum to afford the title compound. (0.14 g, 61% yield). $^1$H NMR (DMSO-d$_6$) δ (ppm): 0.51 (2H, m, —CH$_2$), 0.62-0.64 (2H, m, —CH$_2$), 2.32 (3H, s, —CH$_3$), 2.74-2.75 (1H, m, —CH), 4.45 (2H, d, —CH$_2$), 7.02 (2H, s, Ar—H), 7.06 (2H, d, Ar—H), 7.18 (2H, d, Ar—H), 7.22 (1H, s, =CH), 7.33 (2H, d, Ar—H), 7.67-7.77 (4H, m, Ar—H), 7.78 (1H, d, NH), 9.02 (2H, m, NH and OH), 11.17 (1H, s, NH), MS m/z: 470.4 (M$^+$+1).

The following compounds were prepared according to the procedure given in Example 148.

| Ex. No | Structure | Analytical data |
|---|---|---|
| 149 | 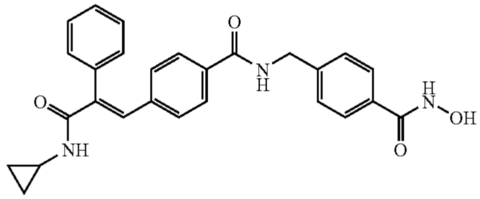 [SMILES: O=C(NC1CC1)/C(=C/c1ccc(C(=O)NCc2ccc(C(=O)NO)cc2)cc1)c1ccccc1] | ¹H NMR (DMSO-d₆) δ (ppm): 0.51 (2H, m, —CH₂), 0.63-0.65 (2H, m, —CH₂), 2.74-2.75 (1H, m, —CH), 4.45 (2H, d, —CH2), 7.06 (2H, d, Ar—H), 7.14 (2H, d, Ar—H), 7.25 (1H, s, =CH), 7.32-7.37(5H, m, Ar—H) 7.66-7.69 (4H, m, Ar—H), 7.88 (1H, d, NH), 9.02 (2H, m, NH and OH), 11.17 (1H, s, NH), MS m/z: 456.2 (M⁺ + 1). |
| 150 | 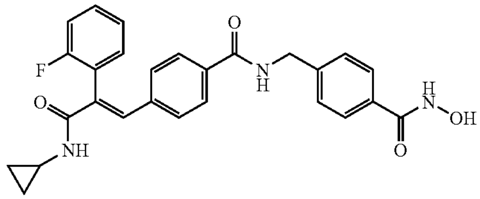 | ¹H NMR (DMSO-d₆) δ (ppm): 0.52 (2H, m, —CH₂), 0.64-0.65 (2H, m, —CH₂), 2.74-2.75 (1H, m, —CH), 4.45 (2H, d, —CH₂), 7.08-7.22 (5H, m, Ar—H), 7.33 (2H, d, Ar—H and =CH), 7.43 (2H, d, Ar—H), 7.67-7.70 (4H, m, Ar—H), 8.06 (1H, d, NH), 9.04 (2H, t, OH), 11.18 (1H, s, NH), MS m/z: 472.1 (M⁺ + 1). |
| 151 | 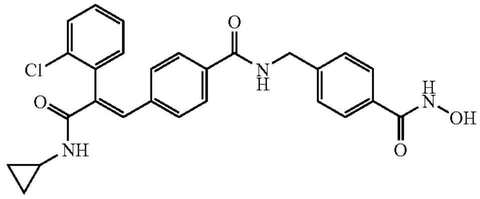 [SMILES: O=C(NC1CC1)/C(=C/c1ccc(C(=O)NCc2ccc(C(=O)NO)cc2)cc1)c1ccccc1Cl] | ¹H NMR (DMSO-d₆) δ (ppm): 0.51-0.52 (2H, m, —CH₂), 0.63-0.64 (2H, m, —CH₂), 2.73-2.74 (1H, m, —CH), 4.45 (2H, d, —CH₂), 7.02 (2H, d, Ar—H), 7.11-7.13 (1H, d, Ar—H), 7.32 (3H, m, Ar—H), 7.41 (1H, t, Ar—H), 7.47 (1H, s, =CH), 7.54 (1H, d, Ar—H), 7.68 (4H, m, Ar—H), 7.92-7.93 (1H, d, NH), 9.03 (2H, m, OH), 11.17 (1 H, s, NH), MS m/z: 488.0 (M⁺ – 1). |
| 152 | 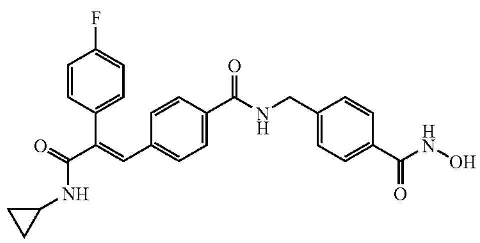 [SMILES: O=C(NC1CC1)/C(=C/c1ccc(C(=O)NCc2ccc(C(=O)NO)cc2)cc1)c1ccc(F)cc1] | ¹H NMR (DMSO-d₆) δ (ppm): 0.52 (2H, m, —CH₂), 0.63-0.64 (2H, m, —CH₂), 2.75 (1H, m, —CH), 4.44-4.45 (2H, d, —CH), 7.05 (2H, d, Ar—H), 7.17-7.18 (4H, d, Ar—H), 7.20-7.34 (3H, m, Ar—H and =CH), 7.68-7.89 (4H, m, Ar—H), 7.89 (1H, d, NH), 9.01 (2H, m, —NH and —OH), 11.01 (1H.s, —NH); MS m/z: 474.2 (M⁺ + 1). |
| 153 | 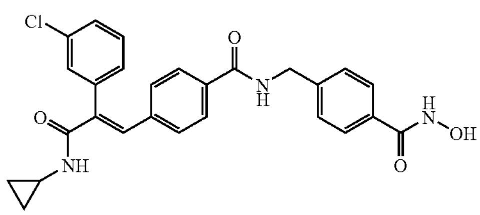 [SMILES: O=C(NC1CC1)/C(=C/c1ccc(C(=O)NCc2ccc(C(=O)NO)cc2)cc1)c1cccc(Cl)c1] | ¹H NMR (DMSO-d₆) δ (ppm): 0.52-0.53 (2H, m, —CH₂), 0.63-0.65 (2H, m, —CH₂), 2.50 (1H, m, —CH), 4.45-4.46 (2H, d, —CH₂), 7.07-7.10 (3H, m, Ar—H), 7.19 (1H, s, =CH), 7.32-7.35 (3H, m, Ar—H), 7.41-7.42 (2H, m, Ar—H), 7.67-7.72 (4H, t, Ar—H), 8.10-8.20 (1H, d, —NH), 8.99 (1H, s, —OH), 9.05 (1H, t, —NH), 11.16 (1H, s, —NH); MS m/z: 490.1 (M⁺ + 1). |
| 154 | 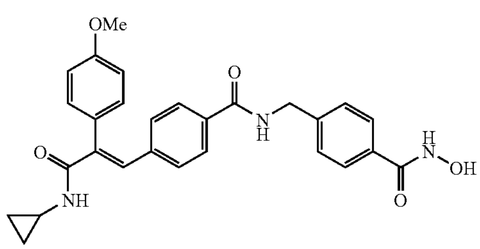 [SMILES: COc1ccc(/C(=C\c2ccc(C(=O)NCc3ccc(C(=O)NO)cc3)cc2)C(=O)NC2CC2)cc1] | ¹H NMR (DMSO-d₆) δ (ppm): 0.50-0.51 (2H, m, —CH₂), 0.61-0.64 (2H, m, —CH₂), 2.74-2.75 (1H, m, —CH), 3.76 (3H, s, —OCH₃), 4.45-4.46 (2H, d, —CH₂), 6.91-6.93 (2H, d, Ar—H), 7.04-7.10 (4H, m, Ar—H), 7.21 (1H, s, =CH), 7.33-7.35 (2H, d, Ar—H), 7.67-7.69 (2H, d, Ar—H), 7.73-7.74 (3H, d, —NH), 8.99-9.03 (2H, m, —NH and —OH), 11.16 (1 H, s, —NH); MS m/z: 486.2 (M⁺ + 1). |
| 155 | 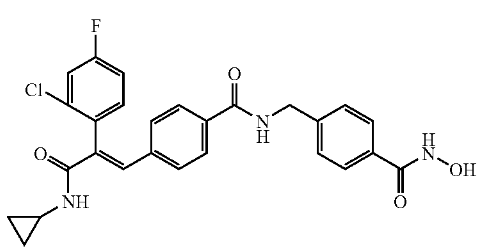 [SMILES: O=C(NC1CC1)/C(=C/c1ccc(C(=O)NCc2ccc(C(=O)NO)cc2)cc1)c1ccc(F)cc1Cl] | ¹H NMR (DMSO-d₆) δ (ppm): 0.56-0.59 (2H, m, —CH₂), 0.61-0.66 (2H, m, —CH₂), 2.72-2.76 (1H, m, —CH), 4.44-4.46 (2H, d, —CH₂), 7.02-7.04 (2H, d, Ar—H), 7.15-7.24 (2H, m, Ar—H), 7.33-7.35 (2H, d, Ar—H), 7.54 (1H, s, =CH), 7.56 (1H, d, Ar—H), 7.67-7.72 (4H, t, Ar—H), 7.85-7.86 (1H, d, —NH), 9.03-9.05 (2H, m, —NH and —OH), 11.16 (1H, s, —NH); MS m/z: 508.1 (M⁺ + 1). |

| Ex. No | Structure | Analytical data |
|---|---|---|
| 156 | 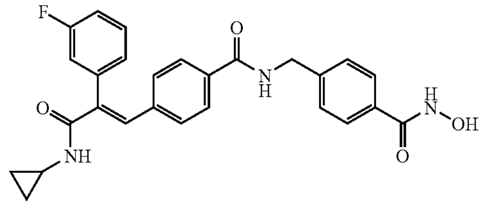 [SMILES: O=C(NC1CC1)/C(=C/c1ccc(C(=O)NCc2ccc(C(=O)NO)cc2)cc1)c1cccc(F)c1] | $^1$H NMR (DMSO-d$_6$) δ (ppm): 0.52-0.53 (2H, m, —CH$_2$), 0.62-0.65 (2H, m, —CH$_2$), 2.73-2.77 (1H, m, —CH), 4.45-4.46 (2H, d, —CH$_2$), 6.95-6.99 (2H, t, Ar—H), 7.07-7.09 (2H, d, Ar—H), 7.18-7.22 (1H, t, Ar—H), 7.32 (1H, s, =CH), 7.34 (2H, m, Ar—H), 7.38-7.43 (1H, m, Ar—H), 7.67-7.70 (4H, m, Ar—H), 7.93-7.94 (1H, d, —NH), 8.99-9.01 (1H, t, —NH), 9.03-9.04 (1H, s, —OH), 11.16 (1H.s, —NH); MS m/z: 474.2 (M$^+$ + 1). |
| 157 | 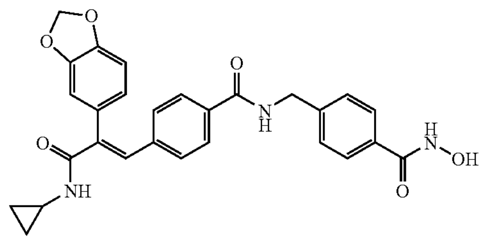 [SMILES: O=C(NC1CC1)/C(=C/c1ccc(C(=O)NCc2ccc(C(=O)NO)cc2)cc1)c1ccc2c(c1)OCO2] | $^1$H NMR (DMSO-d$_6$) δ (ppm): 0.50-0.51 (2H, m, —CH$_2$), 0.62-0.63 (2H, m, —CH$_2$), 2.74-2.75 (1H, m, —CH), 4.45-4.47 (2H, d, —CH$_2$), 6.04 (2H, s, —CH$_2$), 6.57-6.59 (1H, d, Ar—H), 6.67 (1H, s, Ar—H), 6.89-6.91 (1H, d, Ar—H), 7.11-7.13 (2H, d, Ar—H), 7.26 (1H, s, =CH), 7.33-7.35 (2H, d, Ar—H), 7.67-7.71 (5H, m, Ar—H and —NH), 8.99-9.03 (2H, m, —NH and —OH), 11.16 (1H.s, —NH); MS m/z: 500.3 (M$^+$ + 1). |
| 158 | 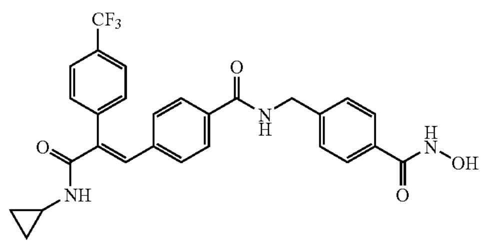 [SMILES: O=C(NC1CC1)/C(=C/c1ccc(C(=O)NCc2ccc(C(=O)NO)cc2)cc1)c1ccc(C(F)(F)F)cc1] | $^1$H NMR (DMSO-d$_6$) δ (ppm): 0.53-0.54 (2H, m, —CH$_2$), 0.64-0.66 (2H, m, —CH$_2$), 2.75-2.76 (1H, m, —CH), 4.44-4.46 (2H, d, —CH$_2$), 7.05-7.06 (2H, d, Ar—H), 7.32 (1H, s, =CH), 7.34-7.37 (4H, t, Ar—H), 7.67-7.69 (3H, d, Ar—H), 7.71-7.73 (3H, d, Ar—H), 8.08-8.09 (1H, d, —NH), 8.99 (1H, s, —OH), 9.01-9.04 (1H.t, —NH), 11.15 (1H.s, —NH); MS m/z: 524.2 (M$^+$ + 1). |
| 159 | 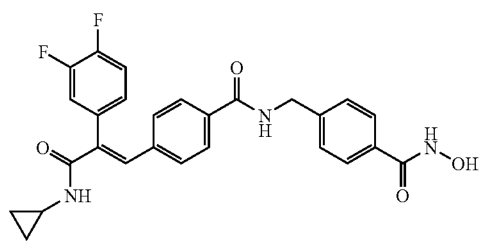 [SMILES: O=C(NC1CC1)/C(=C/c1ccc(C(=O)NCc2ccc(C(=O)NO)cc2)cc1)c1ccc(F)c(F)c1] | $^1$H NMR (DMSO-d$_6$) δ (ppm): 0.52-0.53 (2H, m, —CH$_2$), 0.62-0.65(2H, m, —CH$_2$), 2.74-2.75 (1H, m, —CH), 4.45-4.46 (2H, d, —CH$_2$), 6.95 (1H, M, —Ar—H), 7.08-7.10 (2H, d, Ar—H), 7.24 (1H, t, Ar—H), 7.33-7.35 (2H, d, Ar—H), 7.39-7.43 (2H, d, =CH and Ar—H), 7.67-7.73 (4H, m, Ar—H), 7.86-7.87 (1H, d, —NH), 8.99 (1H, s, —OH), 9.01-9.04 (1H.t, —NH), 11.16 (1H.s, —NH); MS m/z: 492.2 (M$^+$ + 1). |

Example 160

Synthesis of 4-(3-(cyclopropylamino)-2-(4-fluorophenyl)-3-oxoprop-1-en-1-yl)-N-(6-(hydroxyamino)-6-oxohexyl)benzamide

Step-I

Preparation of methyl 6-(4-(3-(cyclopropylamino)-2-(4-fluorophenyl)-3-oxoprop-1-en-1-yl)benzamido)hexanoate

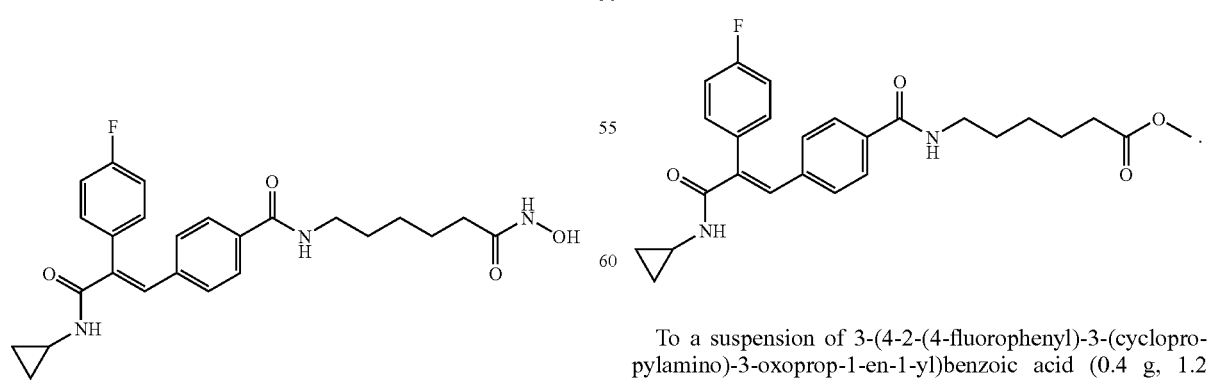

To a suspension of 3-(4-2-(4-fluorophenyl)-3-(cyclopropylamino)-3-oxoprop-1-en-1-yl)benzoic acid (0.4 g, 1.2 mmol, prepared according to the procedure described in Example 99, step-III) in DMF (5 mL), EDCl (0.47 g, 2.4 mmol), HOBt (0.17 g, 1.2 mmol), methyl 6-amino caproate (0.27 g, 1.4 mmol), were added followed by triethylamine (0.5 mL, 3.6 mmol). The reaction mixture was stirred for 8 hours after which the mixture was added to cold water (50 mL). The aqueous layer was extracted with ethyl acetate (1×150 mL), washed with water (2×50 mL) and brine (1×100 mL). The organic layer was dried over anhydrous $Na_2SO_4$ and concentrated to get the crude compound, which was washed with hexane (2×20 mL) to afford the title compound as white solid (0.5 g, 89% yield).

Step-II

Preparation of 4-(3-(cyclopropylamino)-2-(4-fluorophenyl)-3-oxoprop-1-en-1-yl)-N-(6-(hydroxyamino)-6-oxohexyl)benzamide

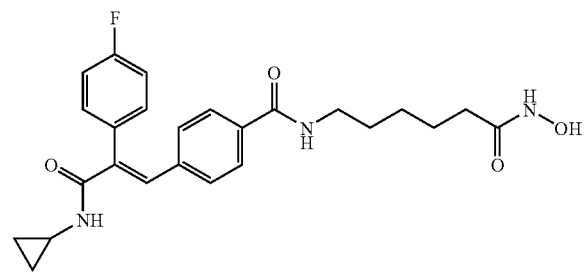 [SMILES: O=C(CCCCCNC(=O)c1ccc(/C=C(/C(=O)NC2CC2)c2ccc(F)cc2)cc1)NO]

Hydroxylamine hydrochloride (0.55 g, 8 mmol) in methanol (3 mL) was mixed with KOH (0.45 g, 8 mmol) in methanol (3 mL) at 0° C., and sonicated for 2 minutes and the white precipitate formed was filtered. The filtrate was added to the methyl 6-(4-(3-(cyclopropylamino)-2-(4-fluorophenyl)-3-oxoprop-1-enyl)benzamido)hexanoate (0.2 g, 0.4 mmol) in DCM (1.5 mL) and the mixture was stirred at room temperature, for 30 minutes. The reaction mixture was diluted with water (200 mL) and extracted with ethyl acetate (3×100 mL). The ethyl acetate layer was washed with water (100 mL), dried over anhydrous $Na_2SO_4$ and concentrated to afford the title compound (0.040 g, 20% yield). $^1H$ NMR (DMSO-$d_6$) δ (ppm): 0.52 (2H, m, 0.63-0.64 (2H, m, —$CH_2$), 1.23-1.25 (2H, m, $CH_2$), 1.44-1.50 (4H, m, $CH_2$), 1.90-1.94 (2H, m, $CH_2$), 2.74-2.75 (1H, m, —CH), 3.17-3.19 (2H, m, $CH_2$), 7.04 (2H, d, Ar—H), 7.16-7.22 (4H, m, Ar—H), 7.28 (1H, s, =C), 7.63 (2H, d, Ar—H), 7.89 (1H, d, NH), 8.36 (1H, t, NH), 8.66 (1H, s, —OH), 10.32 (1H, s, NH), MS m/z: 452.2 ($M^+$−1).

The following compounds were prepared according to the procedure given in Example 160.

| Ex. No | Structure | Analytical data |
|---|---|---|
| 161 | 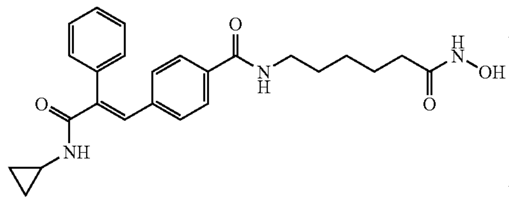 [SMILES: O=C(CCCCCNC(=O)c1ccc(/C=C(/C(=O)NC2CC2)c2ccccc2)cc1)NO] | $^1H$ NMR (DMSO-$d_6$) δ (ppm): 0.51 (2H, m, —$CH_2$), 0.62-0.65 (2H, m, —$CH_2$), 1.23-1.24 (2H, m, $CH_2$), 1.44-1.49 (4H, m, $CH_2$), 1.90-1.92 (2H, m, $CH_2$), 2.74-2.75 (1H, m, —CH), 3.16-3.18 (2H, m, $CH_2$), 7.03 (2H, d, Ar—H), 7.14 (2H, t, Ar—H), 7.24 (1H. s, =CH), 7.37 (3H, m, Ar—H), 7.60 (2H, s, Ar—H), 7.86 (1H, d, —NH), 8.36 (1H, t, —NH), 8.66 (1H, s, —OH), 10.32 (1H, s, —NH), MS m/z: 436.2 ($M^+$ + 1). |
| 162 | 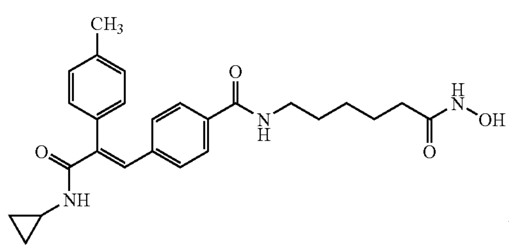 [SMILES: Cc1ccc(/C(=C\c2ccc(C(=O)NCCCCCC(=O)NO)cc2)C(=O)NC2CC2)cc1] | $^1H$ NMR (DMSO-$d_6$) δ (ppm): 0.49-0.50 (2H, m, —$CH_2$), 0.62-0.64 (2H, m, —$CH_2$), 1.23-1.25 (2H, m, $CH_2$), 1.44-1.48 (4H, m, $CH_2$), 1.90-1.92 (2H, m, $CH_2$), 2.32 (3H, s, $CH_3$), 2.74-2.75 (1H, m, —CH), 3.17-3.18 (2H, m, $CH_2$), 7.01-7.06 (4H, m, Ar—H), 7.17-7.21 (3H, m, Ar—H and =CH), 7.61 (2H, d, Ar—H), 7.76 (1H, d, NH), 8.36 (1H, t, NH), 8.67 (1H, s, —OH), 10.34 (1H, s, NH), MS m/z: 450.3 ($M^+$ + 1). |
| 163 | 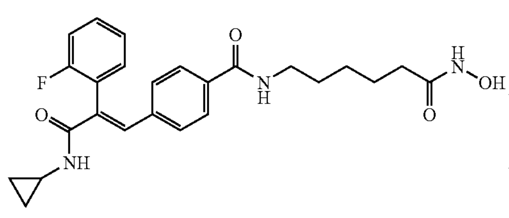 | $^1H$ NMR (DMSO-$d_6$) δ (ppm): 0.52 (2H, m, $CH_2$), 0.64 (2H, m, —$CH_2$), 1.22-1.24 (2H, m, $CH_2$), 1.43-1.48 (4H, m, $CH_2$), 1.89-1.93 (2H, m, $CH_2$), 2.74-2.75 (1H, m, —CH), 3.15-3.17 (2H, m, $CH_2$), 7.05 (2H, d, Ar—H), 7.12-7.21 (2H, m, Ar—H), 7.43 (1H, s, =CH), 7.62 (2H, d, Ar—H), 7.76 (2H, m, Ar—H), 8.03 (1H, d, NH), 8.38 (1H, t, NH), 8.65 (1H, s, —OH), 10.32 (1H, s, NH), MS m/z: 45.3.9 ($M^+$ + 1). |
| 164 | 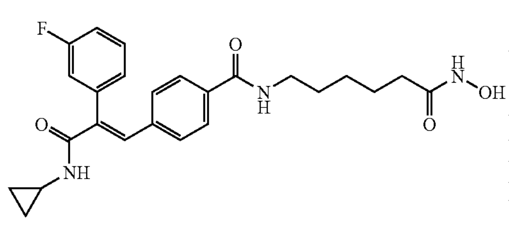 [SMILES: O=C(CCCCCNC(=O)c1ccc(/C=C(/C(=O)NC2CC2)c2cccc(F)c2)cc1)NO] | $^1H$ NMR (DMSO-$d_6$) δ (ppm): 0.52 (2H, m, —$CH_2$), 0.63-0.64 (2H, m, —$CH_2$), 1.24-1.27 (2H, m, $CH_2$), 1.48-1.62 (4H, m, $CH_2$), 1.90-1.94 (2H, m, $CH_2$), 2.74-2.75 (1H, m, —CH), 3.15-3.17 (2H, m, $CH_2$), 6.95 (2H, d, Ar—H), 7.05-7.09 (2H, m, Ar—H), 7.11 (1H, m, Ar—H), 7.26 (1H, s, =CH), 7.45 (1H, m, Ar—H), 7.64 (2H, m, Ar—H), 7.98 (1H, d, —NH), 8.38 (1H, t, —NH), 8.75 (1H, s, —OH), 10.35 (1H, s, —NH). MS m/z: 453.9 ($M^+$ + 1). |

Example 165

Synthesis of N-(4-(3-(cyclopropylamino)-2-(4-fluorophenyl)-3-oxoprop-1-enyl)phenyl)-N-hydroxyoctanediamide

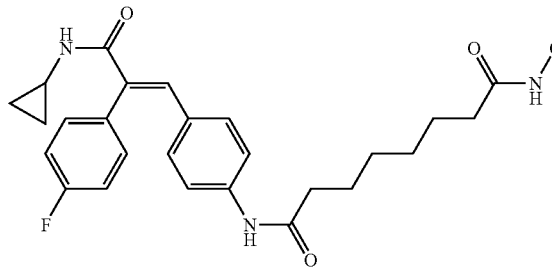

Step-I

Preparation of 2-(4-aminophenyl)-N-cyclopropyl-3-(4-fluorophenyl)acrylamide

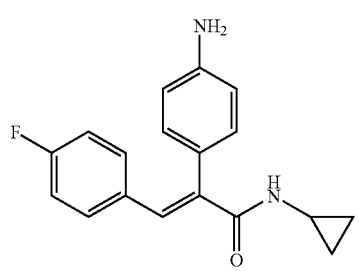 [SMILES: Nc1ccc(/C(=C\c2ccc(F)cc2)C(=O)NC2CC2)cc1]

To a solution of t-butyl 4-(3-(cyclopropylamino)-1-(4-fluorophenyl)-3-oxoprop-1-en-1-yl)phenylcarbamate (0.8 g, 2 mmol, prepared similar to the procedure described in Example 1, stepII-III using appropriate reactants) in dichloromethane (10 mL) trifluoroacetic acid (0.44 mL, 6 mmol) was added. The reaction mixture was stirred for 2 hours, subsequently DCM was evaporated and it was diluted with ethyl acetate (100 mL) and washed with 10% sodium bicarbonate solution (3×50 mL), water (3×50 mL). The organic layer was dried using anhydrous $Na_2SO_4$ and evaporated to afford the crude title compound (0.53 g, 90% yield).

Step-II

Preparation of ethyl 8-(4-(3-(cyclopropylamino)-2-(4-fluorophenyl)-3-oxoprop-1-en-2-yl)phenylamino)-8-oxooctanoate

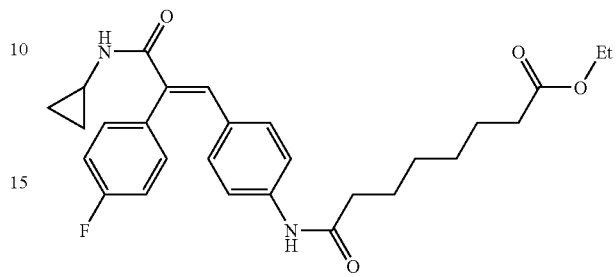

To a suspension of 2-(4-aminophenyl)-N-cyclopropyl-3-(4-fluorophenyl)acrylamide (0.53 g, 1.7 mmol) in DMF (6 mL), BOP reagent (1.5 g. 3.4 mmol), HOBt (0.2 g, 1.7 mmol), ethyl suberate (0.34 g, 1.7 mmol), were added followed by triethylamine (0.7 mL, 5.1 mmol). The reaction mixture was stirred at room temperature for 2.5 hours. After completion of the reaction, the mixture was added to cold water (50 mL). The aqueous layer was extracted with ethyl acetate (1×150 mL), washed with water (2×50 mL), and brine (1×100 mL). The organic layer was dried over anhydrous $Na_2SO_4$ and concentrated to give the crude compound (0.3 g, 35% yield).

Step-II

Preparation of N-(4-(3-(cyclopropylamino)-2-(4-fluorophenyl)-3-oxoprop-1-enyl) phenyl)-N'-hydroxyoctanediamide

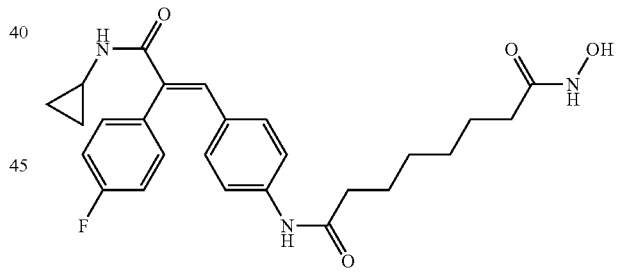

Hydroxylamine hydrochloride (0.78 g, 11.2 mmol) in methanol (2 mL) was mixed with KOH (0.63 g, 11.2 mmol) in methanol (2 mL) at 0° C., the reaction mixture was sonicated for 2 minutes and the white precipitate formed was filtered. The filtrate was added to ethyl 8-(4-(3-(cyclopropylamino)-2-(4-fluorophenyl)-3-oxoprop-1-en-2-yl)phenylamino)-8-oxooctanoate (0.3 g, 0.62 mmol) in methanol (1.5 mL) and the mixture was stirred at room temperature for 1.5 hours. Subsequently the reaction mixture was diluted with water (200 mL) and extracted with ethyl acetate (1×200 mL). The ethyl acetate layer was washed with water (100 mL), dried over anhydrous $Na_2SO_4$ and concentrated to obtain a crude compound, which was purified by flash chromatography using 1.2% MeOH/DCM as eluent, evaporation of the pure fraction afforded the title compound (0.056 g, 20% yield). $^1$H NMR (DMSO-$d_6$) δ (ppm): 0.47-0.51 (2H, m, —$CH_2$), 0.60-0.64 (2H, m, —$CH_2$), 1.25-1.29 (4H, m, —$CH_2$), 1.48-1.53

(2H, m, —CH₂), 1.54-1.59 (2H, m, —CH₂), 1.92-1.96 (2H, t, —CH₂), 2.29-2.32 (2H, t, —CH₂), 2.73-2.74 (1H, m, —CH), 7.04-7.06 (6H, m, Ar—H), 7.21 (1H, s, =CH), 7.58-7.60 (3H, m, Ar—H and NH), 8.66 (1H, s, —NH), 9.97 (1H, s, —OH), 10.34 (1H, s, —NH), MS m/z: 468.3 (M⁺+1).

Example 166

Synthesis of N-(2-aminophenyl)-4-((4-(3-(cyclopropylamino)-1-(4-fluorophenyl)-3-oxoprop-1-en-2-yl)phenylamino)methyl)benzamide

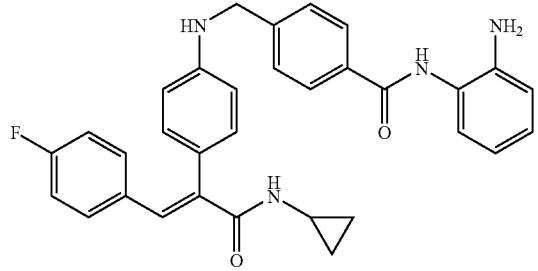 [SMILES: Nc1ccccc1NC(=O)c1ccc(CNc2ccc(/C(=C\c3ccc(F)cc3)C(=O)NC3CC3)cc2)cc1]

Step-I

Preparation of methyl 4-((4-(3-(cyclopropylamino)-1-(4-fluorophenyl)-3-oxoprop-1-en-2-yl)phenylamino)methyl)benzoate

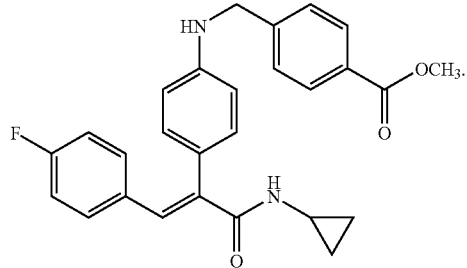 [SMILES: COC(=O)c1ccc(CNc2ccc(/C(=C\c3ccc(F)cc3)C(=O)NC3CC3)cc2)cc1]

To a solution of 2-(4-aminophenyl)-N-cyclopropyl-3-(4-fluorophenyl)acrylamide (0.34 g, 1.15 mmol, prepared according to the procedure described in Example 165, step-I) in dichloroethane (25 mL), methyl-4-formylbenzoate (0.185 g, 1.15 mmol) was added under stirring at 37° C. After stirring for 5 minutes, sodium triacetoxy borohydride (0.39 g, 1.85 mmol) was added to reaction mixture followed by acetic acid (0.3 mL). The reaction mixture was stirred for 8 hours at room temperature. Subsequently the reaction mixture was treated with ethyl acetate:water (1:1, 100 mL) and extracted with ethyl acetate (3×50 mL). The organic layer was washed with brine (100 mL) and dried over anhydrous sodium sulphate and evaporation afforded the title compound (0.42 g, 80% yield)

Step-II

Preparation of 4-((4-(3-(cyclopropylamino)-1-(4-fluorophenyl)-3-oxoprop-1-en-2-yl)phenylamino)methyl)benzoic acid

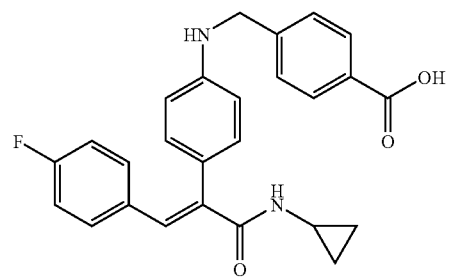 [SMILES: O=C(NC1CC1)/C(=C/c1ccc(F)cc1)c1ccc(NCc2ccc(C(=O)O)cc2)cc1]

To a solution methyl 4-((4-(3-(cyclopropylamino)-1-(4-fluorophenyl)-3-oxoprop-1-en-2-yl)phenylamino)methyl)benzoate (0.42 g, 0.9 mmol) in methanol (10 mL), a solution of NaOH (0.075 g, 18 mmol) in water (0.5 mL) was added. The reaction mixture was refluxed for 1 hour at 70° C. The solvent was removed by evaporation and the remainder was poured to ice cold water. The aqueous layer was acidified to pH 3 with citric acid and allowed to stand at 4° C. for 30 minutes, the solid precipitated was filtered and dried under vacuum to give a pale yellow solid (0.22 g, 51% yield).

Step-III

Preparation of N-(2-aminophenyl)-4-((4-(3-(cyclopropylamino)-1-(4-fluorophenyl)-3-oxoprop-1-en-2-yl)phenylamino)methyl)benzamide

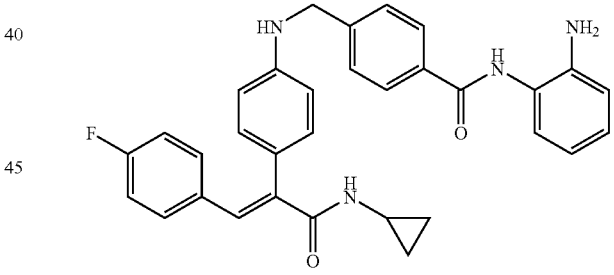

To a suspension of 4-((4-(3-(cyclopropylamino)-1-(4-fluorophenyl)-3-oxoprop-1-en-2-yl)phenylamino)methyl)benzoic acid (0.215 g, 0.5 mmol) in DMF (3 mL) EDCl (0.23 g, 1.1 mmol), HOBt (0.08 g, 0.55 mmol), o-phenylene diamine (0.086 g, 0.7 mmol), were added followed by TEA (0.2 mL, 1.5 mmol). The reaction mixture was stirred for 4 hours after which the mixture was added to cold water (100 mL) and kept at 0° C. for 1 hour. The pale yellow solid formed was filtered and washed with ethyl acetate (15 mL) dried under vacuum to afford the title compound (0.020 g, 8% yield). ¹H NMR (DMSO-d₆) δ (ppm): 0.46-0.47 (2H, m, —CH₂), 0.60-0.62 (2H, m, —CH₂), 2.70-2.71 (1H, m, —CH), 4.36-4.37 (2H, d, —CH₂), 4.88 (2H, s, —NH₂), 6.55-6.61 (4H, m, Ar—H and —NH), 6.76-6.82 (3H, m, Ar—H), 6.93-6.94 (1H, t, Ar—H), 6.98-7.04 (3H, m, Ar—H), 7.06-7.17 (3H, m, Ar—H), 7.48-7.50 (3H, m, Ar—H and =CH), 7.93-7.95 (2H, d, Ar—H and —NH), 9.61 (1H, s, —NH), MS m/z: 521.1 (M⁺+1).

Anti-Cancer Experimental Methods

Anti-Cancer Screen:

Experimental drugs were screened for anti-cancer activity in three cell lines using five concentrations for each compound. The cell lines—HCT 116 (colon), NClH460 (lung) and U251 (glioma) were maintained in DMEM containing 10% fetal bovine serum. 96-well microtiter plates are inoculated with cells in 100 µL of cell suspension ($5 \times 10^4$ cells/mL) for 24 hours at 37° C., 5% $CO_2$, 95% air and 100% relative humidity. A separate plate with these cell lines is also inoculated to determine cell viability before the addition of the compounds ($T_0$)

Addition of Experimental Drugs:

Following 24-hour incubation, test compounds were added to the 96 well plates. Each plate contains one of the above cell lines and the following samples in triplicate: five different dilutions (0.01, 0.1, 1, 10 and 100 µM) of four test compounds, appropriate dilutions of a cytotoxic standard and growth medium (untreated) wells. Test compounds were dissolved in DMSO to prepare 20 mM stock solutions on the day of drug addition and serial dilutions were carried out in complete growth medium at 2× strength such that 100 µL added to wells gave final concentrations (0.01, 0.1, 1, 10 and 100 µM) in the well. SAHA was used as standard drug in these experiments.

End-Point Measurement:

For $T_0$ measurement, 24 hours after seeding the cells, 20 µL of 3-(4.5-dimethyl-2-thiazolyl)-2,5-diphenyl-2H-tetrazolium (MTT) solution per well was added to the '$T_0$' plate and incubated for 3 hours at 37° C. in a $CO_2$ incubator. The plate containing cells and test compounds was treated similarly after 48 hours of incubation. After 3 hours of MTT addition, well contents were aspirated carefully followed by addition of 150 µL DMSO per well. Plates were agitated to ensure dissolution of the formazan crystals in DMSO and absorbance was read at 570 nm ($A_{570}$).

Calculation of $GI_{50}$, TGI and $LC_{50}$:

Percent growth (PG) is calculated relative to the control and zero measurement wells ($T_0$) as follows:

$$PG=(A_{570}\text{test}-A_{520}T_0)/(A_{520}\text{control}-A_{570}T_0) \times 100$$
(If $A_{570}$ test>$A_{570}T_0$)

$$PG=(A_{570}\text{test}-A_{570}T_0)/(A_{570}T_0) \times 100$$
(If $A_{570}$ test<$A_{570}T_0$), PG values are plotted against drug concentration to derive the following: $GI_{50}$ is the concentration required to decrease PG by 50% vs control; TGI is the concentration required to decrease PG by 100% vs control and $LC_{50}$ is the concentration required to decrease PG by 50% vs $T_0$. (Mosmann T. Rapid colorimetric assay for cellular growth and survival: application to proliferation and cytotoxicity assays. (*J. Immunol. Methods.* 1983, 65 (1-2), 55-63; Anne Monks et al). Feasibility of high-flux anticancer drug screen using a diverse panel of cultured human tumor cell lines". (*JNCI*, Vol. 83, No. 11, 1991). Results for growth inhibition of the synthesized compounds are given in Table-1.

HDAC Activity Screening:

Histone Deacetylase (HDAC) Inhibition Assay using Boc-Lys (Ac)-AMC Substrate: Inhibition of HDAC has been implicated to modulate transcription and to induce apoptosis or differentiation in cancer cells. The fluorometric assay provides a fast and fluorescence based method that eliminates radioactivity, extractions or chromatography, as used in traditional assays. The assay is based on two steps. First, the HDAC fluorometric substrate, which comprises an acetylated lysine side chain, is incubated with a sample containing HDAC activity (Mouse Liver Extract). Deacetylation of the substrate sensitizes the substrate, in the second step; treatment with the Trypsin stop solution produces a fluorophore that can be easily analyzed using fluorescence plate reader.

Assay was done in 96-well black microplate and total volume of the assay was 100 µL. Mouse liver enzyme (10 mg/ml) was diluted 1:6 with HDAC buffer. Enzyme cocktail was made of 10 µL of diluted enzyme and 30 µL of HDAC buffer. 40 µl of enzyme cocktail followed by 10 µL of test compound (1 µM and 10 µM) or buffer (control) was added to each well. The plate was pre-incubated at 37° C. for 5 minutes. The HDAC reaction was started by adding 50 µl of HDAC substrate Boc-Lys (Ac)-AMC (Bachem AG, Switzerland). The plate was incubated at 37° C. for 30 minutes. The reaction was stopped by adding 100 µL of Trypsin stop solution and incubating at 37° C. for 15-30 minutes. Measuring the fluorescence at excitation wavelength of 360 nm and emission wavelength of 460 nm monitored the release of AMC. Buffer alone and substrate alone served as blank. For selected compounds, $IC_{50}$ (50% HDAC inhibitory concentration) was determined by testing in a broad concentration range of 0.001, 0.01, 0.1, 1 and 10 µM. (Dennis Wegener et al, *Anal. Biochem*, 321, 2003, 202-208).

Results for HDAC inhibition at 1 and 10 µM and $IC_{50}$ values are indicated in Table-1

TABLE 1

Inhibition of cancer cell growth and HDAC enzyme activity:

| Ex. No | NCI-H460 $GI_{50}$ µM | HCT-116 $GI_{50}$ µM | U-251 $GI_{50}$ µM | HDAC Inhibition % (1 µM) | HDAC Inhibition % (10 µM) | HDAC Inhibition $IC_{50}$ (µM) |
|---|---|---|---|---|---|---|
| 1 | 1.8 | 1.4 | 0.02 | 71.4 | 89.9 | 0.048 |
| 2 | 28.0 | 7.8 | 4.5 | 79.1 | 95.9 | — |
| 3 | 48.0 | 8.5 | 21.8 | 73.4 | 95.5 | — |
| 4 | 35.0 | 7.3 | 11.0 | 75.0 | 97.8 | — |
| 5 | 10.0 | 2.9 | 2.3 | 89.6 | 100.0 | 0.45 |
| 6 | 4.4 | 2.3 | 1.5 | 87.1 | 99.8 | 0.35 |
| 7 | 3.9 | 1.5 | 0.5 | 84.1 | 100.0 | 0.1 |
| 8 | 25.0 | 14.0 | >100 | 84.3 | 100.0 | — |
| 9 | 15.0 | 15.0 | 0.7 | 91.7 | 99.5 | — |
| 10 | 32.0 | 0.8 | 1.5 | 85.8 | 100.0 | — |
| 11 | 13.0 | 6.0 | 7.0 | 85.6 | 95.2 | 0.09 |
| 12 | 0.5 | 0.5 | 1.0 | 89.7 | 96.8 | 0.03 |
| 13 | 0.7 | 0.4 | 3.2 | 87.6 | 96.8 | 0.034 |
| 14 | 0.4 | 0.5 | 0.8 | 82.8 | 96.7 | 0.034 |
| 15 | 10.0 | 12.0 | 10.0 | 96.3 | 99.3 | — |

TABLE 1-continued

Inhibition of cancer cell growth and HDAC enzyme activity:

| Ex. No | NCI-H460 GI$_{50}$ μM | HCT-116 GI$_{50}$ μM | U-251 GI$_{50}$ μM | HDAC Inhibition % (1 μM) | HDAC Inhibition % (10 μM) | HDAC Inhibition IC$_{50}$ (μM) |
|---|---|---|---|---|---|---|
| 16 | 2.1 | 2.8 | 11.0 | 98.1 | 99.9 | 0.35 |
| 18 | 1.1 | 2.7 | 3.5 | 77.5 | 96.0 | 0.1 |
| 19 | 2.1 | 2.8 | 1.8 | 68.6 | 94.4 | 0.99 |
| 20 | 8.0 | 3.0 | 1.8 | 91.2 | 100.0 | 0.068 |
| 21 | 10.1 | 2.0 | 4.2 | 87.9 | 98.0 | 0.04 |
| 22 | 6.0 | 2.6 | 10.5 | 85.5 | 97.9 | 0.09 |
| 23 | 11.0 | 3.0 | 10.5 | 77.0 | 96.2 | 0.08 |
| 24 | 20.0 | 1.2 | 10.5 | 78.3 | 95.0 | — |
| 25 | 9.1 | 1.1 | 3.0 | 91.7 | 100.0 | 0.015 |
| 26 | 7.5 | 2.1 | 3.5 | 88.2 | 99.1 | 0.043 |
| 27 | 8.0 | 1.8 | 4.0 | 88.2 | 100.0 | 0.03 |
| 28 | 30.0 | 6.0 | 6.1 | 80.5 | 100.0 | — |
| 29 | 4.0 | 0.2 | 1.1 | 52.7 | 60.2 | 0.2 |
| 30 | 10.2 | 5.5 | 2.8 | 72.4 | 90.3 | 0.41 |
| 31 | 0.7 | 0.2 | 0.1 | 87.2 | 95.2 | 0.004 |
| 32 | 2.5 | 2.0 | 2.0 | 80.0 | 96.9 | 0.039 |
| 33 | 0.8 | 1.0 | 1.0 | 87.4 | 95.0 | 0.018 |
| 34 | 1.2 | 1.3 | 1.5 | 64.8 | 94.3 | 0.19 |
| 35 | 6.8 | 1.8 | 2.1 | 89.7 | 98.0 | 0.09 |
| 36 | 1.5 | 3.1 | 2.1 | 86.9 | 93.5 | 0.042 |
| 37 | 0.03 | 3.5 | 1.6 | 91.2 | 98.7 | 0.044 |
| 38 | 0.1 | 2.9 | 1.5 | 84.4 | 95.5 | 0.21 |
| 39 | 11 | 0.01 | 4 | 92.9 | 98.3 | 0.052 |
| 40 | 13 | 29 | 10.1 | 85.3 | 97.9 | |
| 41 | 4.6 | 3 | 5 | 85.5 | 98.2 | 0.077 |
| 42 | 2.6 | 5.2 | 5 | 81.4 | 97.6 | 0.28 |
| 43 | 7 | 6 | 6 | 84.9 | 98.1 | 0.056 |
| 44 | 6.3 | 7 | 5 | 77.4 | 95.9 | 0.37 |
| 45 | 1.1 | 0.01 | 1.7 | 95.6 | 99.3 | 0.01 |
| 46 | 0.8 | 1.6 | 2.8 | 73.5 | 98.5 | 0.019 |
| 47 | 14 | 15 | 20 | 89.3 | 97.1 | |
| 48 | 4 | 1 | 2.8 | 91.8 | 98.8 | 0.005 |
| 49 | 30 | 1 | 19 | 55.7 | 92.1 | 0.14 |
| 50 | 2 | 0.7 | 1.2 | 81.8 | 94.4 | 0.083 |
| 55 | 0.3 | 0.02 | 0.28 | 96.3 | 97.9 | 0.006 |
| 59 | 59.2 | 20 | — | 11.5 | 49.9 | |
| 60 | 29.0 | 23.0 | 22.0 | 28.3 | 34.2 | — |
| 61 | >100 | 68.0 | — | 12.3 | 14.6 | — |
| 62 | >100 | 64.0 | — | 27.1 | 58.0 | — |
| 63 | 32.0 | 30.0 | >100 | 27.5 | 49.2 | — |
| 64 | 52.0 | 44.0 | 78.0 | 22.6 | 48.8 | — |
| 65 | 80.0 | >100 | 82.0 | 31.2 | 56.2 | — |
| 66 | >100 | >100 | >100 | 41.6 | 72.4 | — |
| 67 | 40.0 | 36.0 | >100 | 31.5 | 59.5 | — |
| 68 | 80.0 | — | — | 19.1 | 21.1 | — |
| 69 | 74.0 | 94.0 | >100 | 25.5 | 54.4 | — |
| 70 | >100 | >100 | >100 | 34.0 | 36.0 | — |
| 71 | >100 | >100 | 0.6 | 28.0 | 37.0 | — |
| 72 | 50.0 | 20.0 | 20.0 | 24.8 | 52.0 | — |
| 73 | >100 | 10.1 | >100 | 12.0 | 21.8 | — |
| 74 | >100 | 100 | 90 | 12.3 | 12.1 | — |
| 75 | 38 | 23 | 30 | 70.3 | 94.4 | — |
| 76 | 20.0 | 10.0 | — | 91.4 | 96.5 | — |
| 77 | 2.3 | 5.0 | 10.5 | 97.8 | 100.0 | 0.003 |
| 78 | 10.3 | 5.6 | 22.0 | 98.1 | 99.9 | — |
| 79 | 2.2 | 8.2 | 3.2 | 99.1 | 100.0 | 0.014 |
| 80 | 19.0 | 4.0 | 0.8 | 100.0 | 100.0 | <0.001 |
| 81 | 11.0 | 5.0 | 0.4 | 97.0 | 100.0 | 0.01 |
| 82 | 1.0 | 3.0 | 7.0 | 93.2 | 98.6 | 0.0085 |
| 83 | 10.5 | 6.0 | 10.0 | 98.8 | 99.6 | 0.001 |
| 84 | 70.0 | 24.0 | 24.0 | 93.5 | 96.5 | — |
| 85 | 69.0 | 26.0 | 10.1 | 96.0 | 100.0 | — |
| 86 | 50.0 | 19.0 | 10.5 | 95.6 | 98.6 | — |
| 87 | 70.0 | 40.0 | 20.0 | 91.0 | 98.6 | — |
| 88 | >100 | 11.0 | 18.0 | 97.9 | 98.8 | — |
| 89 | >100 | 40 | 13 | 42.1 | 70.3 | — |
| 90 | 11.0 | 3.5 | 4.5 | 94.6 | 100.0 | 0.013 |
| 91 | 25.0 | 0.2 | 0.2 | 99.8 | 100.0 | <0.001 |
| 92 | 0.1 | 3.0 | 24.0 | 85.8 | 99.7 | 0.0017 |
| 93 | 32.0 | 35.0 | 52.0 | 74.0 | 91.6 | — |
| 94 | 20.0 | 8.0 | 1.8 | 99.8 | 100 | <0.001 |
| 95 | 90.0 | 4.0 | 15.0 | 97.6 | 100.0 | — |
| 96 | >100 | 85.0 | 5.0 | 100.0 | 100.0 | — |
| 97 | 7.5 | 6.5 | 2.3 | 100.0 | 100.0 | 0.0025 |

TABLE 1-continued

Inhibition of cancer cell growth and HDAC enzyme activity:

| Ex. No | NCI-H460 $GI_{50}$ μM | HCT-116 $GI_{50}$ μM | U-251 $GI_{50}$ μM | HDAC Inhibition % (1 μM) | HDAC Inhibition % (10 μM) | HDAC Inhibition $IC_{50}$ (μM) |
|---|---|---|---|---|---|---|
| 98 | >100 | 9.0 | 18.0 | 91.5 | 98.8 | — |
| 99 | 66.00 | 32.00 | 12.00 | 40.2 | 59.0 | — |
| 100 | 67.0 | 58.0 | — | 39.8 | 76.2 | — |
| 101 | 60.0 | 44.0 | — | 44.6 | 84.9 | — |
| 102 | 48.0 | 17.0 | 19.0 | 50.1 | 80.4 | — |
| 103 | 68.0 | 29.0 | 20.0 | 43.6 | 80.0 | — |
| 104 | 5.00 | 6.00 | 7.00 | 44.7 | 58.4 | — |
| 105 | 0.9 | 1.0 | 4.8 | 46.0 | 71.3 | 15.8 |
| 106 | 20.0 | 4.0 | 15.0 | 35.8 | 42.9 | — |
| 107 | 5.0 | 2.0 | 4.5 | 34.1 | 58.4 | 12.0 |
| 108 | 80.0 | >100 | 82.0 | 39.1 | 61.7 | — |
| 109 | 6.5 | 4.1 | 21.0 | 35.8 | 66.8 | — |
| 110 | 5.5 | 0.3 | 5.0 | 45.7 | 71.4 | 5.0 |
| 111 | 2.1 | 1.1 | 1.5 | 24.8 | 52.2 | 8.0 |
| 112 | 1.1 | 6.0 | 20.0 | 29.9 | 55.7 | 4.5 |
| 113 | 25.0 | 11.0 | 20.0 | 34.6 | 51.8 | — |
| 114 | 5.0 | 0.4 | 4.0 | 34.5 | 59.0 | 5.5 |
| 115 | 6.0 | 0.1 | 15.0 | 31.1 | 50.1 | 8.3 |
| 116 | 6.1 | 0.4 | 11.0 | 32.4 | 55.7 | 9.0 |
| 117 | 10.0 | 68.0 | 3.8 | 36.2 | 66.6 | — |
| 118 | 90.0 | 10.0 | 4.2 | 21.0 | 46.0 | — |
| 119 | 28.0 | 32.0 | 18.0 | 28.9 | 33.9 | — |
| 120 | 21.0 | 10.5 | 10.0 | 36.9 | 59.3 | — |
| 121 | 3.1 | 1.7 | 9 | 35.0 | 63.5 | — |
| 122 | 11 | 2.6 | 50 | 28.9 | 54.1 | — |
| 123 | 28 | 16 | 20 | 19.0 | 50.7 | — |
| 124 | 4.5 | 2 | 2.6 | 34.7 | 63.2 | — |
| 125 | 35 | 3.6 | 20 | 31.5 | 45.4 | — |
| 126 | 40 | 14 | 22 | 36.9 | 53.9 | — |
| 127 | 12 | 22 | 40 | 36.9 | 55.4 | — |
| 128 | 26 | 24 | 28 | 31.8 | 55.1 | — |
| 129 | 12 | 3.5 | 22 | 30.0 | 54.6 | — |
| 130 | 9 | 5.8 | 16 | 34.7 | 56.0 | — |
| 131 | 18 | 4 | 19 | 28.6 | 57.4 | — |
| 132 | >100 | >100 | >100 | 23.5 | 25.3 | — |
| 133 | 6.6 | 2.8 | 12 | 39.6 | 56.7 | — |
| 134 | 12 | 6 | 7.5 | 38.2 | 63.3 | — |
| 135 | 76 | 6.8 | 9.8 | 8.6 | 16.6 | — |
| 136 | 80 | 40 | 21 | 36.1 | 67.9 | — |
| 137 | >100 | 17 | 58 | 2.7 | 40.8 | — |
| 138 | >100 | 60 | 60 | 6.2 | 26.5 | — |
| 144 | 10 | 5.5 | 8 | 36.3 | 62.3 | — |
| 145 | 0.50 | 1.6 | 0.08 | 94.7 | 100 | 0.044 |
| 146 | 1.3 | 3.0 | 0.8 | 86.8 | 99.8 | 0.008 |
| 147 | 95.0 | 20.0 | 19.0 | 94.6 | 100.0 | — |
| 148 | 0.10 | 2.00 | 0.08 | 86.9 | 97.8 | 0.022 |
| 149 | 52.0 | 12.0 | 12.0 | 61.7 | 88.0 | — |
| 150 | 45.0 | 31.0 | 21.0 | 91.7 | 98.1 | — |
| 151 | 40.0 | 10.0 | 12.0 | 92.3 | 99.4 | — |
| 152 | 25 | 30 | 22 | 88.7 | 98.0 | — |
| 153 | 19 | 10.2 | 21 | 87.5 | 97.1 | — |
| 154 | 33 | 27 | 20 | 87.2 | 97.5 | — |
| 155 | 16 | 30 | 26 | 88.8 | 99.3 | — |
| 156 | 26 | 26 | 26 | 88.4 | 98.1 | — |
| 157 | 18 | 19 | 60 | 82.2 | 96.6 | — |
| 158 | 25 | 30 | 22 | 88.7 | 98.0 | — |
| 159 | 20 | 12 | 11 | 89.3 | 97.0 | — |
| 160 | 0.30 | 20.00 | 0.10 | 86.0 | 98.0 | — |
| 161 | 5.3 | 8.2 | 3.2 | 87.8 | 97.5 | 0.006 |
| 162 | 46.0 | 19.0 | 2.0 | 86.1 | 95.7 | — |
| 163 | 10.0 | 32.0 | 41.0 | 81.7 | 97.7 | — |
| 164 | 28.0 | 15.0 | 30.0 | 91.9 | 100.0 | — |
| 165 | 15 | 5.6 | 11 | 91.5 | 96.8 | — |

— Not tested

HDAC Isoform Selectivity:

Since the benzamide type compounds are known to have potential for HDAC class 1 specificity, active compounds were tested for HDAC1 inhibitory activity. The assay was carried out, as previously described using recombinant HDAC1 enzyme (BIOMOL, USA) and following manufacturer's instructions. For determination of $IC_{50}$ values compounds were tested at five different concentrations (0.001, 0.01, 0.1, 1 and 10 μM). The results shown in Table-2 indicate that these compounds inhibit HDAC1 enzyme at nanomolar concentrations, which are much lower as compared to pan HDAC activity in mouse liver enzyme, indicating HDAC isoform specific activity.

TABLE 2

HDAC isoform specific activity

| Test Compound | HDAC1 inhibition ($IC_{50}$, nM) |
|---|---|
| 105 | 77.0 |
| 107 | 180.0 |
| 110 | 150.0 |
| 111 | 100.0 |
| 112 | 49.0 |
| 114 | 44.0 |
| 115 | 68.0 |
| 116 | 60.0 |

Detection of Histone (H3) Acetylation, Tubulin Acetylation and p21 Induction:

Acetylated histone (H3), acetylated Tubulin and p21 levels were detected in cell lysate by sandwich ELISA method (Cell Signaling Technology, USA, Cat No: 7232, 7204 and 7167 respectively) by following manufacturer's instructions. Briefly, colon cancer cells (HCT116, 10,000/well) were incubated with test compound (1 and 10 μM) or medium (control) for 4 hours at 37° C. in $CO_2$ incubator. The incubation lasted 18 hours for p21 induction. After incubation, cell lysates were prepared in cell lysis buffer by sonication on ice. The lysates were collected after centrifugation and subjected to ELISA test procedure. 100 μL of each diluted cell lysate in dilution buffer (1:1) was added to appropriate capture antibody coated microwells and incubated overnight at 4° C. After washing, 100 μL of detection antibody was added for 1 hour at 37° C. After second washing, 100 μL of HRP-linked secondary antibody was added for 30 minutes at 37° C. Finally, after appropriate washing, 100 μL of TMB substrate was added for 10 minutes at 37° C. followed by 100 μL, of stop solution. The absorbance of individual wells was read using a spectrophotometer at 450 nm ($A_{450}$). Results were expressed as fold increase ($A_{450}$test/$A_{450}$ control) as compared to control and shown in Table-3. Selected compounds were tested in these assays and were found to cause histone and tubulin acetylation and induce p21 expression several fold higher as compared to untreated control in colon cancer cells. Thus, these compounds demonstrated good cellular HDAC activity in addition to activity in the isolated enzyme preparations.

TABLE 3

Effect of HDAC inhibition in cells (Histone acetylation, Tubulin acetylation and p21 induction)

| Test Compound | Cellular effects of HDAC Inhibition (Fold Increase) | | | | | |
|---|---|---|---|---|---|---|
| | H3 Acetylation | | μ-Tubulin Acetylation | | P21 Induction | |
| | 1 μM | 10 μM | 1 μM | 10 μM | 1 μM | 10 μM |
| 105 | 1.24 | 6.67 | 2.22 | 8.98 | 1.05 | 2.50 |
| 12 | 10.63 | 15.69 | 12.00 | 16.35 | 1.95 | 2.93 |
| 14 | 8.46 | 15.52 | 9.00 | 14.02 | 1.07 | 3.28 |

In Vitro Metabolic Stability in Liver Microsomes:

Metabolic stability is defined as the percentage of parent compound lost over time in the presence of liver microsomes, liver S9, or hepatocytes, depending on the goal of the assay. By understanding the metabolic stability of compounds early in discovery, compounds can be ranked for further studies, and the potential for a drug candidate to fail in development as a result of pharmacokinetic reasons may be reduced.

Preparation of phosphate buffer (pH 7.4) and stock solutions of test compound (usually in DMSO or water). Incubation of reaction mix including cryopreserved mouse or human liver microsomes (1 mg/mL), test compound (50 μM), and NADPH for different time points, e.g. 10, 15, 30, and 60 minutes or single time points, e.g. 60 minutes. Reaction is started by the addition of NADPH and stopped either immediately or after 60 minutes for screening assay or at 5, 15, 30 and 60 minutes for a more precise estimate of clearance by addition of ice-cold acetonitrile, followed by sample preparation. Determination of loss of parent compound (compared to zero time point control and/or no NADPH-control) was done using HPLC or LC-MS methods. Metabolism was expressed as percentage of test compound metabolized after a certain time). A marker reaction and marker substrate (e.g. testosterone) was employed as quality criteria of the metabolic capability of the microsomes. (Rodrigues, A. D., Use of in vitro human metabolism studies in drug development. An industrial perspective. *Biochem Pharm,* 48(12): 2147-2156, 1994). Metabolic stability was expressed as % metabolism of the compound after 30 minutes of incubation in the presence of active microsomes. Compound that had a % metabolism less than 30% were defined as highly stable. Compound that had a metabolism between 30% and 60% were defined as moderately stable and compounds that showed a % metabolism higher than 60% were defined as less stable. Several compounds have been found to be highly to moderately stable.

In Vivo Anti-Tumor Activity:

Experiments were carried out using 6-8 week old female athymic SCID (Severe Combined Immune Deficient) mice. The mice were housed in Individually Ventilated Cages (IVC) at constant temperature (22±3° C.) and humidity (50±20%). They had free access to food and water. Tumors were obtained from ATCC, USA and maintained in vivo by subcutaneous (s.c.) passage of tumor fragments (appx30 mg) in healthy mice according to standard reported procedures. All the animal protocols were approved by the Institutional Animal Ethics Committee, ORLL, Chennai. Each experimental group included 6-8 mice bearing s.c. tumors. Tumors were implanted into the axillary region by puncturing using a Trocar, and tumor growth was monitored by measurement of tumor diameters with a Vernier caliper. Tumor Volume (TV) was calculated according to the following formula:

$$TV\ (mm^3) = L \times W^2 \times 0.5,$$

Where L and W are the longest diameter and shortest diameter of the tumor, respectively. The compound treatment started when tumors were palpable (150-200 $mm^3$).

Test compound was administered by oral gavage in a volume of 5-10 ml/kg. Drugs were administered once every day for a period of 21 days. Control mice were administered the vehicle at equivalent volume. Tumor size was measured twice every week and body weight was recorded daily prior to dosing.

Test compound (T) efficacy was assessed by calculating several parameters based on tumor volume (TV) with respect to untreated control (C). Parameters routinely assessed were T/C % [$TV_{test}/TV_{control} \times 100$] and Tumor Volume Inhibition (TVI=1−T/C %). Other parameters were Relative Tumor Volume, Percent Tumor volume change, Tumor Delay and Log Cell Kill.

Toxic effects of drug treatment were assessed by Body Weight Loss %. Lethal toxicity was defined as any death in treated groups occurring before any control death. Mice were inspected daily for mortality and toxic clinical signs.

Results of the Xenograft Study:

The compound 105 showed good in-vivo anti-cancer activity in HCT116 (colon) xenograft model. Treatment with compound 105 (100 mg/kg p.o. qdx21) resulted in maximum Tumor Volume Inhibition (TVI) of 39.4% as compared to vehicle treated control during the course of the study (FIG. 1). Furthermore, the compound treatment did not result in significant body weight loss or treatment related mortality as compared to control.

We claim:

1. A compound of formula (I):

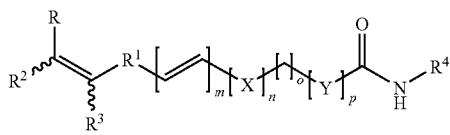

(I)

their tautomeric form, stereoisomer, pharmaceutically acceptable salt, or pharmaceutical composition thereof; wherein, the configuration around the double bonds may be E/Z;

R represents substituted or unsubstituted groups selected from aryl, cycloalkyl, heteroaryl, arylalkyl, heterocyclyl and heteroarylalkyl;

$R^1$ represents substituted or unsubstituted aryl;

$R^2$ and $R^3$ independently represents hydrogen, alkyl, —$COOR^5$, —$CONR^5R^6$, —$CH_2NR^5R^6$, —$CH_2CH_2NR^5R^6$, —$CH_2CH_2OR^5$, —$CH_2OR^5$, —$CH_2OCONR^5R^6$ and —$CH_2NR^5COR^6$; wherein when one of $R^2$ or $R^3$ is hydrogen or unsubstituted alkyl, the other is neither of hydrogen nor of unsubstituted alkyl;

$R^5$ and $R^6$ independently represents hydrogen, substituted or unsubstituted groups selected from alkyl, cycloalkyl, heterocyclyl, aryl, arylalkyl, arylalkenyl, arylalkynyl, heteroaryl, heteroarylalkyl, heteroarylalkenyl and heteroarylalkynyl; or $R^5$ and $R^6$ may be combined to form 3-8 membered saturated or unsaturated ring having 0-2 hetero atoms comprising N, O or S;

$R^4$ represents —$OR^7$, aryl, ortho substituted aniline, amino aryl and amino heteroaryl, which may be further substituted; wherein, $R^7$ represents hydrogen, —$COR^8$, optionally substituted alkyl, cycloalkyl, aryl, heteroaryl and heterocyclyl; wherein, $R^8$ represents optionally substituted alkyl, aryl, heteroaryl and heterocyclyl;

X represents —O—, —$NR^7$—, —$CONR^7$—, —$NR^7SO_2$—, —$SO_2NR^7$—, —$SO_2O$—, —O—$SO_2$—, —$CH_2NR^7$—, —$NR^7CONR^7$— and —$NR^7CO$—;

Y represents aryl and arylalkenyl;

m is an integer from 0-3; n is an integer from 0-1; o is an integer from 0-7 and p is an integer from 0-1, when the groups R, $R^1$, $R^5$, $R^6$, $R^7$ and $R^8$ are substituted, the substituents which are one or more selected from halogens comprising fluorine, chlorine, bromine, or iodine; hydroxy; nitro; cyano; oxo (=O); thioxo (=S); azido; nitroso; amino; hydrazino; formyl; alkyl; alkoxy; aryl; haloalkyl group comprising trifluoromethyl, tribromomethyl or trichloromethyl; haloalkoxy comprising —$OCH_2Cl$; arylalkoxy comprising benzyloxy or phenylethoxy; cycloalkyl; —O-cycloalkyl; aryl; alkoxy; heterocyclyl; heteroaryl; alkylamino; —O—$CH_2$-cycloalkyl; —$COOR^a$; —$C(O)R^b$; —$C(S)R^a$; —$C(O)NR^aR^b$; —$NR^aC(O)NR^bR^c$; —$N(R^a)SOR^b$; —$N(R^a)SO_2R^b$; —$NR^aC(O)OR^b$; —$NR^aR^b$; —$NR^aC(O)R^b$; $NR^aC(S)R^b$; —$SONR^aR^b$; —$SO_2NR^aR^b$; —$OR^a$; —$OR^aC(O)OR^b$; —$OC(O)NR^aR^b$; $OC(O)R^a$; —$OC(O)NR^aR^b$—; —$R^aNR^bR^c$; —$R^aOR^b$; —$SR^a$; —$SOR^a$ or —$SO_2R^3$; $R^a$, $R^b$ and $R^c$ each independently represents hydrogen atom; substituted or unsubstituted groups selected from alkyl; aryl; arylalkyl; cycloalkyl; heterocyclyl; heteroaryl or heteroarylalkyl;

the substituents which in turn are further optionally substituted by halogens comprising fluorine, chlorine, bromine or iodine; hydroxy, nitro, cycloalkyl, cyano, azido, nitroso, amino, hydrazino, formyl, alkyl, or haloalkyl group comprising trifluoromethyl or tribromoethyl;

with the proviso that, if n, o and p=0, then m=0-1; and with the proviso that, if n=1, o=3-7 and p=0, then m=0-1; and with the proviso that, if n, o and p=1, then m=0-1.

2. A compound according to claim 1 wherein,

R represents substituted or unsubstituted groups selected from aryl group comprising phenyl, naphthyl, biphenyl or indanyl; cycloalkyl group comprising cyclopropyl, cyclobutyl, cyclopentyl, cyclohexyl or cyclooctyl; heteroaryl group comprising pyridinyl, pyridazinyl, pyrimidyl, triazinyl, pyrrolyl, indolyl, pyrazolyl, imidazolyl, pyrazinyl, pyrimidinyl, tetrazolyl, furyl, thienyl, thiazolyl, isoxazolyl, oxazolyl or quinolinyl; arylalkyl group comprising benzyl or phenylethyl; heterocyclyl group comprising azetidinyl, acridinyl, benzodioxolyl, benzodioxanyl, benzofuranyl or carbazolyl; and heteroarylalkyl group comprising thienylpropyl, pyridinylethyl or indolylpropyl;

$R^1$ represents substituted or unsubstituted aryl group comprising phenyl, naphthyl, biphenyl or indanyl;

$R^2$ and $R^3$ independently represents hydrogen, alkyl group comprising methyl, ethyl, n-propyl, isopropyl, butyl, isobutyl, t-butyl, pentyl, hexyl, heptyl or octyl; —$COOR^5$, —$CONR^5R^6$, —$CH_2NR^5R^6$; —$CH_2CH_2NR^5R^6$, —$CH_2CH_2OR^5$, —$CH_2OR^5$, —$CH_2OCONR^5R^6$ and —$CH_2NR^5COR^6$; wherein when one of $R^2$ or $R^3$ is hydrogen or unsubstituted alkyl, the other is neither of hydrogen nor of unsubstituted alkyl;

$R^5$ and $R^6$ independently represents hydrogen, substituted or unsubstituted groups selected from alkyl group comprising methyl, ethyl, n-propyl, isopropyl, butyl, isobutyl, t-butyl, pentyl, hexyl, heptyl or octyl; cycloalkyl group comprising cyclopropyl, cyclobutyl, cyclopentyl, cyclohexyl or cyclooctyl; heterocyclyl group comprising azetidinyl, acridinyl, benzodioxolyl, benzodioxanyl, benzofuranyl or carbazolyl; aryl group comprising phenyl, naphthyl, biphenyl or indanyl; arylalkyl group comprising benzyl or phenylethyl; arylalkenyl group comprising phenylethenyl or phenylpropenyl; arylalkynyl group comprising phenylethynyl or phenylpropynyl; heteroaryl group comprising pyridinyl, pyridazinyl, pyrimidyl, triazinyl, pyrrolyl, pyrazolyl, imidazolyl, pyrazinyl, pyrimidinyl, tetrazolyl, furyl, thienyl, thiazolyl, isoxazolyl, oxazolyl, indolyl or quinolinyl; heteroarylalkyl group comprising thienylpropyl, pyridinylethyl or indolylpropyl; heteroarylalkenyl group comprising thienylpropenyl, pyridinylethenyl or indolylpropenyl; and heteroarylalkynyl group comprising thienylpropynyl, pyridinylethynyl or indolylpropynyl; or $R^5$ and $R^6$ may be combined to form 3-8 membered saturated or unsaturated ring having 0-2 hetero atoms comprising N, O or S;

$R^4$ represents —$OR^7$, aryl comprising phenyl, naphthyl, biphenyl or indanyl; ortho substituted aniline, amino aryl and amino heteroaryl, which is optionally substituted;

wherein, $R^7$ represents hydrogen, —$COR^8$, substituted or unsubstituted groups selected from alkyl group comprising methyl, ethyl, n-propyl, isopropyl, butyl, isobutyl, t-butyl, pentyl, hexyl, heptyl or octyl; cycloalkyl group comprising cyclopropyl, cyclobutyl, cyclopentyl, cyclohexyl or cyclooctyl; aryl group comprising phenyl, naphthyl, biphenyl or indanyl; heteroaryl group comprising pyridinyl, pyridazinyl, pyrimidyl, triazinyl, pyrrolyl, pyrazolyl, imidazolyl, pyrazinyl, pyrimidinyl, tetrazolyl, furyl, thienyl, thiazolyl, isoxazolyl, oxazolyl or quinolinyl; and heterocyclyl group comprising azetidinyl, acridinyl, benzodioxolyl, benzodioxanyl, benzofuranyl or carbazolyl;

wherein, $R^8$ represents substituted or unsubstituted groups selected from alkyl group comprising methyl, ethyl, n-propyl, isopropyl, butyl, isobutyl, t-butyl, pentyl, hexyl, heptyl or octyl; aryl group comprising phenyl, naphthyl, biphenyl or indanyl; heteroaryl group comprising pyridinyl, pyridazinyl, pyrimidyl, triazinyl, pyrrolyl, pyrazolyl, imidazolyl, pyrazinyl, pyrimidinyl, tetrazolyl, furyl, thienyl, thiazolyl, isoxazolyl, oxazolyl or quinolinyl and heterocyclyl group comprising azetidinyl, acridinyl, benzodioxolyl, benzodioxanyl, benzofuranyl or carbazolyl;

X represents —O—, —$NR^7$—, —$CONR^7$—, —$NR^7SO_2$—, —$SO_2NR^7$—, —$SO_2O$—, —O—$SO_2$—, —$CH_2NR^7$—, —$NR^7CONR^7$— and —$NR^7CO$—;

Y represents aryl group comprising phenyl, naphthyl, biphenyl or indanyl; arylalkenyl group comprising phenylethenyl or phenylpropenyl;

when the groups R, $R^1$, $R^5$, $R^6$, $R^7$ and $R^8$ are substituted, the substituents which are one or more selected from halogens comprising fluorine, chlorine, bromine, or iodine; hydroxy; nitro; cyano; azido; nitroso; amino; hydrazino; formyl: alkyl; alkoxy; aryl; haloalkyl group comprising trifluoromethyl, tribromomethyl or trichloromethyl; haloalkoxy comprising —$OCH_2Cl$; arylalkoxy comprising benzyloxy or phenylethoxy; cycloalkyl; —O-cycloalkyl; heterocyclyl; heteroaryl; alkylamino; —O—$CH_2$-cycloalkyl; —$COOR^a$; —$C(O)R^b$; —$C(S)R^a$; —$C(O)NR^aR^b$; —$NR^aC(O)NR^bR^c$; —$N(R^a)SOR^b$; —$N(R^a)SO_2R^b$; —$NR^aC(O)OR^b$; —$NR^aR^b$; —$NR^aC(O)R^b$; —$NR^aC(S)R^b$; —$SONR^aR^b$; —$SO_2NR^aR^b$; —$OR^a$; —$OR^aC(O)OR^b$; —$OC(O)NR^aR^b$; —$OC(O)R^a$; —$R^aNR^bR^c$; —$R^aOR^b$; —$SR^a$; —$SOR^a$ and —$SO_2R^a$; $R^a$, $R^b$ and $R^c$ in each of the above groups can be hydrogen atom; substituted or unsubstituted groups selected from alkyl; aryl; arylalkyl; cycloalkyl; heterocyclyl; heteroaryl; and heteroarylalkyl;

the substituents which in turn are further optionally substituted by halogens comprising fluorine, chlorine, bromine or iodine; hydroxy; nitro; cycloalkyl; cyano; azido; nitroso: amino; hydrazino; formyl; alkyl; and haloalkyl group comprising trifluoromethyl or tribromoethyl.

3. The compound according to claim 1 selected from the compounds consisting of:

N-Cyclopropyl-2-(4-fluorophenyl)-3-(4-((1E)-3-(hydroxyamino)-3-oxoprop-1-en-1-yl)phenyl)acrylamide;

N-Methyl-2-(4-fluorophenyl)-3-(4-((1E)-3-(hydroxyamino)-3-oxoprop-1-en-1-yl)phenyl)acrylamide;

N,N-Dimethyl-2-(4-fluorophenyl)-3-(4-((1E)-3-(hydroxyamino)-3-oxoprop-1-en-1-yl)phenyl)acrylamide;

2-Phenyl-3-(4-((1E)-3-(hydroxyamino)-3-oxoprop-1-en-1-yl)phenyl)acrylamide;

N-Cyclopropyl-2-(thiophen-2-yl)-3-(4-((1E)-3-(hydroxyamino)-3-oxoprop-1-en-1-yl)phenyl)acrylamide;

N-Cyclopropyl-2-phenyl-3-(4-((1E)-3-(hydroxyamino)-3-oxoprop-1-en-1-yl)phenyl)acrylamide;

N-Cyclopropyl-2-(4-trifluoromethylphenyl)-3-(4-((1E)-3-(hydroxyamino)-3-oxoprop-1-en-1-yl)phenyl)acrylamide;

N-Cyclopropyl-2-(pyridin-3-yl)-3-(4-((1E)-3-(hydroxyamino)-3-oxoprop-1-en-1-yl)phenyl)acrylamide;

N-Cyclopropyl-2-(4-methoxyphenyl)-3-(4-((1E)-3-(hydroxyamino)-3-oxoprop-1-en-1-yl)phenyl)acrylamide;

N-Cyclopropyl-2-(2-chlorophenyl)-3-(4-((1E)-3-(hydroxyamino)-3-oxoprop-1-en-1-yl)phenyl)acrylamide;

N-Cyclopropyl-2-(2-fluorophenyl)-3-(4-((1E)-3-(hydroxyamino)-3-oxoprop-1-en-1-yl)phenyl)acrylamide;

N-Cyclopropyl-2-(3-chlorophenyl)-3-(4-((1E)-3-(hydroxyamino)-3-oxoprop-1-en-1-yl)phenyl)acrylamide;

N-Cyclopropyl-2-[benzodioxol-5-yl]-3-(4-((1E)-3-(hydroxyamino)-3-oxoprop-1-en-1-yl)phenyl)acrylamide;

N-Cyclopropyl-2-(4-methylphenyl)-3-(4-((1E)-3-(hydroxyamino)-3-oxoprop-1-en-1-yl)phenyl)acrylamide;

(E)-3-(4-(2-(4-Fluorophenyl)-3-morpholino-3-oxoprop-1-enyl)phenyl)-N-hydroxyacrylamide;

(E)-3-(4-(2-(2-Fluorophenyl)-3-morpholino-3-oxoprop-1-enyl)phenyl)-N-hydroxyacrylamide;

(E)-N-Hydroxy-3-(4-(2-(3-methoxyphenyl)-3-morpholino-3-oxoprop-1-enyl)phenyl)acrylamide;

(E)-3-(4-(2-(4-Fluorophenyl)-3-oxo-3-thiomorpholinoprop-1-enyl)phenyl)-N-hydroxyacrylamide;

N-Cyclooctyl-2-(4-fluorophenyl)-3-(4-((1E)-3-(hydroxyamino)-3-oxoprop-1-en-1-yl)phenyl)acrylamide;

N-Cyclopropyl-2-(3-methoxyphenyl)-3-(4-((1E)-3-(hydroxyamino)-3-oxoprop-1-en-1-yl)phenyl)acrylamide;

N-Cyclopropyl-2-(3-fluorophenyl)-3-(4-((1E)-3-(hydroxyamino)-3-oxoprop-1-en-1-yl)phenyl)acrylamide;

N-Isopropyl-2-(3-fluorophenyl)-3-(4-((1E)-3-(hydroxyamino)-3-oxoprop-1-en-1-yl)phenyl)acrylamide;

N-Isopropyl-2-(4-fluorophenyl)-3-(4-((1E)-3-(hydroxyamino)-3-oxoprop-1-en-1-yl)phenyl)acrylamide;

N-Isopropyl-2-(3,4-difluorophenyl)-3-(4-((1E)-3-(hydroxyamino)-3-oxoprop-1-en-1-yl)phenyl)acrylamide;

N-Cyclopropyl-2-(3-fluoro-4-methoxyphenyl)-3-(4-((1E)-3-(hydroxyamino)-3-oxoprop-1-en-1-yl)phenyl)acrylamide;

N-Isopropyl-2-(3-fluoro-4-methoxyphenyl)-3-(4-((1E)-3-(hydroxyamino)-3-oxoprop-1-en-1-yl)phenyl)acrylamide;

N-Cyclopropyl-2-(3,4-difluorophenyl)-3-(4-((1E)-3-(hydroxyamino)-3-oxoprop-1-en-1-yl)phenyl)acrylamide;

2-(4-Fluorophenyl)-3-(4-((1E)-3-(hydroxyamino)-3-oxoprop-1-en-1-yl)phenyl)acrylamide;

2-(4-Fluorophenyl)-3-(4-((1E)-3-(hydroxyamino)-3-oxoprop-1-en-1-yl)phenyl)-N-phenylacrylamide;

(E)-3-(4-(2-(4-Fluorophenyl)-3-oxo-3-(pyrrolidin-1-yl)prop-1-enyl)phenyl)-N-hydroxyacrylamide;

N-Cyclopropyl-2-(4-cyclopropylmethoxyphenyl)-3-(4-((1E)-3-(hydroxyamino)-3-oxoprop-1-en-1-yl)phenyl)acrylamide;

N-Cyclopropyl-2-(4-benzyloxyphenyl)-3-(4-((1E)-3-(hydroxyamino)-3-oxoprop-1-en-1-yl)phenyl)acrylamide;

N-Cyclopropyl-2-(4-cyclopentyloxyphenyl)-3-(4-((1E)-3-(hydroxyamino)-3-oxoprop-1-en-1-yl)phenyl)acrylamide;

N-(4-Fluorobenzyl)-2-(4-fluorophenyl)-3-(4-((1E)-3-(hydroxyamino)-3-oxoprop-1-en-1-yl)phenyl)acrylamide;

N-Cyclopropyl-2-(2,4-dimethoxyphenyl)-3-(4-((1E)-3-(hydroxyamino)-3-oxoprop-1-en-1-yl)phenyl)acrylamide;
N-Cyclopropyl-2-(3,4-dimethoxyphenyl)-3-(4-((1E)-3-(hydroxyamino)-3-oxoprop-1-en-1-yl)phenyl)acrylamide;
N-Cyclopropyl-2-(indol-3-yl)-3-(4-((1E)-3-(hydroxyamino)-3-oxoprop-1-en-1-yl)phenyl)acrylamide;
N-Cyclopropyl-2-(thiophen-3-yl)-3-(4-((1E)-3-(hydroxyamino)-3-oxoprop-1-en-1-yl)phenyl)acrylamide;
N-Cyclopropyl-3-(4-fluorophenyl)-2-(4-((1E)-3-(hydroxyamino)-3-oxoprop-1-en-1-yl)phenyl)acrylamide;
N-Cyclopropyl-3-(4-fluorophenyl)-2-(3-((1E)-3-(hydroxyamino)-3-oxoprop-1-en-1-yl)phenyl)acrylamide:
N-Cyclopropyl-2-(3-(cyclopropylmethoxy)phenyl)-3-(4-((1E)-3-(hydroxyamino)-3-oxoprop-1-en-1-yl)phenyl)acrylamide;
2-(3-(Cyclopropylmethoxy)phenyl)-3-(4-((1E)-3-(hydroxyamino)-3-oxoprop-1-en-1-yl)phenyl)-N-phenylacrylamide;
N-Cyclopropyl-2-(3-cyclopentyloxyphenyl)-3-(4-((1E)-3-(hydroxyamino)-3-oxoprop-1-en-1-yl)phenyl)acrylamide;
2-(3-Cyclopentyloxyphenyl)-3-(4-((1E)-3-(hydroxyamino)-3-oxoprop-1-en-1-yl)phenyl)-N-phenylacrylamide;
N-Cyclopropyl-2-(biphenyl-4-yl)-3-(4-((1E)-3-(hydroxyamino)-3-oxoprop-1-en-1-yl)phenyl)acrylamide;
2-(4-Cyclopropylmethoxyphenyl)-3-(4-((1E)-3-(hydroxyamino)-3-oxoprop-1-en-1-yl)phenyl)-N-phenylacrylamide;
N-Cyclopropyl-3-(3,4-dimethoxyphenyl)-2-(3-((1E)-3-(hydroxyamino)-3-oxoprop-1-en-1-yl)phenyl)acrylamide;
N-Cyclopropyl-3-(4-methoxyphenyl)-2-(4-((1E)-3-(hydroxyamino)-3-oxoprop-1-en-1-yl)phenyl)acrylamide;
N-Cyclopropyl-3-(4-cyclopropylmethoxyphenyl)-2-(4-((1E)-3-(hydroxyamino)-3-oxoprop-1-en-1-yl)phenyl)acrylamide;
N-Cyclopropyl-3-(4-cyclopentyloxyphenyl)-2-(4-((1E)-3-(hydroxyamino)-3-oxoprop-1-en-1-yl)phenyl)acrylamide;
N-Cyclopropyl-2-(4-fluorophenyl)-3-(4-((1E)-3-(hydroxyamino)-3-oxoprop-1-en-1-yl)phenyl)but-2-enamide;
2-[4-(Dimethylamino)phenyl]-3-(4-((1E)-3-(hydroxyamino)-3-oxoprop-1-en-1-yl)phenyl)-N-cyclopropylacrylamide,
N-Cyclopropyl-3-(4-fluorophenyl)-2-(4-(3-(hydroxyamino)-3-oxopropyl)phenyl)acrylamide;
N-Cyclopropyl-2-(4-fluorophenyl)-3-(3-((1E)-3-(hydroxyamino)-3-oxoprop-1-en-1-yl)phenyl)acrylamide;
3-(4-((1E)-3-(Cyclopropylamino)-2-(4-fluorophenyl)prop-1-en-1-yl)phenyl)-N-hydroxyacrylamide;
3-(4-((1E)-3-(Cyclopropylamino)-2-phenylprop-1-en-1-yl)phenyl)-N-hydroxyacrylamide;
3-(4-((1E)-2-(3-Cyclopentyloxyphenyl)-3-(cyclopropylamino)prop-1-en-1-yl)phenyl)-N-hydroxyacrylamide;
3-(4-((1E)-2-(3-Chlorophenyl)-3-(cyclopropylamino)prop-1-en-1-yl)phenyl)-N-hydroxyacrylamide;
N-Cyclopropyl-3-(4-(3-(2-aminophenylamino)-3-oxoprop-1-en-1-yl)phenyl)-2-(4-fluorophenyl)acrylamide;
3-(4-((1E)-3-(2-Aminophenylamino)-3-oxoprop-1-en-1-yl)phenyl)-2-(4-fluoro phenyl)-N,N-dimethylacrylamide;
N-Cyclopropyl-3-(4-((1E)-3-(2-aminophenylamino)-3-oxoprop-1-en-1-yl)phenyl)-2-(4-(trifluoromethyl)phenyl)acrylamide;
N-Cyclopropyl-3-(4-((1E)-3-(2-aminophenylamino)-3-oxoprop-1-en-1-yl)phenyl)-2-(pyridin-3-yl)acrylamide;
N-Cyclopropyl-3-(4-((1E)-3-(2-aminophenylamino)-3-oxoprop-1-en-1-yl)phenyl)-2-(2-chlorophenyl)acrylamide;
N-Cyclopropyl-3-(4-((1E)-3-(2-aminophenylamino)-3-oxoprop-1-en-1-yl)phenyl)-2-[benzodioxol-5-yl]-acrylamide;
N-Cyclopropyl-3-(4-((1E)-3-(2-aminophenylamino)-3-oxoprop-1-en-1-yl)phenyl)-2-(2-fluorophenyl)acrylamide;
N-Cyclopropyl)-3-(4-((1E)-3-(2-aminophenylamino)-3-oxoprop-1-en-1-yl)phenyl)-2-(3-chlorophenyl)acrylamide;
(E)-N-Cyclopropyl-3-(4-((1E)-3-(2-aminophenylamino)-3-oxoprop-1-en-1-yl)phenyl)-2-(4-methylphenyl)acrylamide;
(E)-N-(2-Aminophenyl)-3-(4-(2-(4-fluorophenyl)-3-morpholino-3-oxoprop-1-enyl)phenyl)acrylamide;
N-Cyclopropyl-3-(4-((1E)-3-(2-aminophenylamino)-3-oxoprop-1-en-1-yl)phenyl)-2-(3-methoxyphenyl)acrylamide;
N-Cyclopropyl-3-(4-((1E)-3-(2-aminophenylamino)-3-oxoprop-1-en-1-yl)phenyl)-2-phenylacrylamide;
N-Cyclopropyl-3-(4-((1E)-3-(2-aminophenylamino)-3-oxoprop-1-en-1-yl)phenyl)-2-(thiophen-2-yl)acrylamide;
(E)-N-(2-Aminophenyl)-3-(4-(2-(2-fluorophenyl)-3-morpholino-3-oxoprop-1-enyl)phenyl)acrylamide;
N-Cyclopropyl-3-(4-((1E)-3-(2-aminophenylamino)-3-oxoprop-1-en-1-yl)phenyl)-2-(3,4-difluorophenyl)acrylamide;
N-Cyclopropyl-3-(4-((1E)-3-(2-aminophenylamino)-3-oxoprop-1-en-1-yl)phenyl)-2-(3,4-dimethoxyphenyl)acrylamide;
6-((1E)-3-(4-(3-(Cyclopropylamino)-2-(4-fluorophenyl)-3-oxoprop-1-en-1-yl)phenyl)acrylamido)-N-hydroxyhexanamide;
6-((1E)-3-(4-(3-(N,N-Dimethylamino)-2-(4-fluorophenyl)-3-oxoprop-1-en-1-yl)phenyl)acrylamido)-N-hydroxyhexanamide;
6-((1E)-3-(4-(3-(Cyclopropylamino)-2-(2-chlorophenyl)-3-oxoprop-1-en-1-yl)phenyl)acrylamido)-N-hydroxyhexanamide;
6-((1E)-3-(4-(3-(Cyclopropylamino)-2-(2-fluorophenyl)-3-oxoprop-1-en-1-yl)phenyl)acrylamido)-N-hydroxyhexanamide;
6-((1E)-3-(4-(3-(Cyclopropylamino)-2-[benzodioxol-5-yl]-3-oxoprop-1-en-1-yl)phenyl)acrylamido)-N-hydroxyhexanamide;
6-((1E)-3-(4-(3-(Cyclopropylamino)-2-(3-chlorophenyl)-3-oxoprop-1-en-1-yl)phenyl)acrylamido)-N-hydroxyhexanamide;
6-((1E)-3-(4-(3-(Cyclopropylamino)-2-(4-methylphenyl)-3-oxoprop-1-en-1-yl)phenyl)acrylamido)-N-hydroxyhexanamide;
6-((1E)-3-(4-(3-(cyclopropylamino)-2-phenyl-3-oxoprop-1-enyl)phenyl)acrylamido)-N-hydroxyhexanamide;
6-((1E)-3-(4-(3-(Cyclopropylamino)-2-(thiophen-2-yl)-3-oxoprop-1-enyl)phenyl)acrylamido)-N-hydroxyhexanamide;

6-((1E)-3-(4-(3-(Cyclopropylamino)-2-(4-methoxyphenyl)-3-oxoprop-1-en-1-yl)phenyl)acrylamido)-N-hydroxyhexanamide;

6-((1E)-3-(4-(3-(Cyclopropylamino)-2-(3-methoxyphenyl)-3-oxoprop-1-en-1-yl)phenyl)acrylamido)-N-hydroxyhexanamide;

6-((1E)-3-(4-(3-(Morpholino)-2-(4-fluorophenyl)-3-oxoprop-1-enyl)phenyl)acrylamido)-N-hydroxyhexanamide;

6-((1E)-3-(4-(3-(Morpholino)-2-(2-fluorophenyl)-3-oxoprop-1-en-1-yl)phenyl)acrylamido)-N-hydroxyhexanamide;

6-((1E)-3-(4-(3-(Cyclopropylamino)-2-(3-fluoro-4-methoxyphenyl)-3-oxoprop-1-en-1-yl)phenyl)acrylamido)-N-hydroxyhexanamide;

4-(((1E)-3-(4-(3-(Cyclopropylamino)-2-(4-fluorophenyl)-3-oxoprop-1-en-1-yl)phenyl)acrylamido)methyl)-N-hydroxybenzamide;

4-(((1E)-3-(4-(3-(Cyclopropylamino)-2-(2-chlorophenyl)-3-oxoprop-1-en-1-yl)phenyl)acrylamido)methyl)-N-hydroxybenzamide;

4-(((1E)-3-(4-(3-(Cyclopropylamino)-2-(3-chlorophenyl)-3-oxoprop-1-en-1-yl)phenyl)acrylamido)methyl)-N-hydroxybenzamide;

4-(((1E)-3-(4-(3-(Cyclopropylamino)-2-(4-methylphenyl)-3-oxoprop-1-en-1-yl)phenyl)acrylamido)methyl)-N-hydroxybenzamide;

4-(((1E)-3-(4-(3-(Cyclopropylamino)-2-phenyl-3-oxoprop-1-en-1-yl)phenyl)acrylamido)methyl)-N-hydroxybenzamide;

4-(((1E)-3-(4-(3-(Cyclopropylamino)-2-(thiophen-2-yl)-3-oxoprop-1-en-1-yl)phenyl)acrylamido)methyl)-N-hydroxybenzamide;

4-(((1E)-3-(4-(3-(Cyclopropylamino)-2-(4-methoxyphenyl)-3-oxoprop-1-en-1-yl)phenyl)acrylamido)methyl)-N-hydroxybenzamide;

4-(((1E)-3-(4-(3-(Morpholino)-2-(4-fluorophenyl)-3-oxoprop-1-en-1-yl)phenyl)acrylamido)methyl)-N-hydroxybenzamide;

4-(((1E)-3-(4-(3-(Cyclopropylamino)-2-(3-methoxyphenyl)-3-oxoprop-1-en-1-yl)phenyl)acrylamido)methyl)-N-hydroxybenzamide;

4-(((1E)-3-(4-(3-(Morpholino)-2-(2-fluorophenyl)-3-oxoprop-1-en-1-yl)phenyl)acrylamido)methyl)-N-hydroxybenzamide;

4-(3-(Cyclopropylamino)-2-(4-methylphenyl)-3-oxoprop-1-en-1-yl)-N-hydroxybenzamide;

4-(3-(Cyclopropylamino)-2-(4-methoxyphenyl)-3-oxoprop-1-en-1-yl)-N-hydroxybenzamide;

4-(3-(Cyclopropylamino)-2-(3-methoxyphenyl)-3-oxoprop-1-en-1-yl)-N-hydroxybenzamide;

4-(3-(Cyclopropylamino)-2-phenyl-3-oxoprop-1-en-1-yl)-N-hydroxybenzamide;

4-(3-(Cyclopropylamino)-2-(2-fluorophenyl)-3-oxoprop-1-en-1-yl)-N-hydroxybenzamide;

N-(2-Aminophenyl)-4-(3-(cyclopropylamino)-2-(4-methylphenyl)-3-oxoprop-1-en-1-yl)benzamide;

(E)-N-(2-Aminophenyl)-4-(3-(cyclopropylamino)-2-(4-fluorophenyl)-3-oxoprop-1-en-1-yl)benzamide;

N-(2-Aminophenyl)-4-(3-(cyclopropylamino)-2-(4-trifluoromethylphenyl)-3-oxoprop-1-en-1-yl)benzamide;

N-(2-Aminophenyl)-4-(3-(cyclopropylamino)-2-phenyl-3-oxoprop-1-en-1-yl)benzamide;

N-(2-Aminophenyl)-4-(3-(cyclopropylamino)-2-(3-methoxyphenyl)-3-oxoprop-1-en-1-yl)benzamide;

N-(2-Aminophenyl)-4-(3-(cyclopropylamino)-2-(2-fluorophenyl)-3-oxoprop-1-en-1-yl)benzamide;

N-(2-Aminophenyl)-4-(3-(cyclopropylamino)-2-(3-fluorophenyl)-3-oxoprop-1-en-1-yl)benzamide;

N-(2-Aminophenyl)-4-(3-(cyclopropylamino)-2-(benzodioxol-5-yl)-3-oxoprop-1-en-1-yl)benzamide;

N-(2-Aminophenyl)-4-(3-(cyclopropylamino)-2-(2-chlorophenyl)-3-oxoprop-1-en-1-yl)benzamide;

N-(2-Aminophenyl)-4-(3-(cyclopropylamino)-2-(thiophen-2-yl)-3-oxoprop-1-en-1-yl)benzamide;

N-(2-Aminophenyl)-4-(3-(cyclopropylamino)-2-(3-chlorophenyl)-3-oxoprop-1-en-1-yl)benzamide;

N-(2-Aminophenyl)-4-(3-(cyclopropylamino)-2-(3,4-difluorophenyl)-3-oxoprop-1-en-1-yl)benzamide;

N-(2-Aminophenyl)-4-(3-(cyclopropylamino)-2-(4-methoxyphenyl)-3-oxoprop-1-en-1-yl)benzamide;

N-(2-Aminophenyl)-4-(3-(cyclopropylamino)-2-(2-chloro-4-fluorophenyl)-3-oxoprop-1-en-1-yl)benzamide;

N-(2-Aminophenyl)-4-(3-(phenylamino)-2-(3,4-dimethoxyphenyl)-3-oxoprop-1-en-1-yl)benzamide;

N-(2-Aminophenyl)-4-(3-(cyclopropylamino)-2-(3,4-dimethoxyphenyl)-3-oxoprop-1-en-1-yl)benzamide;

N-(2-Aminophenyl)-4-(3-(cyclopropylamino)-2-(2,4-dimethoxyphenyl)-3-oxoprop-1-en-1-yl)benzamide;

N-(2-Aminophenyl)-4-(3-(cyclopropylamino)-2-(2-naphthyl)-3-oxoprop-1-en-1-yl)benzamide;

N-(2-Aminophenyl)-4-(3-phenylamino-2-(2,4-dimethoxyphenyl)-3-oxoprop-1-en-1-yl)benzamide;

N-(2-Amino-5-fluorophenyl)-4-(2-(4-fluorophenyl)-3-(cyclopropylamino)-3-oxoprop-1-en-1-yl)benzamide;

N-(2-Aminophenyl)-4-(3-(cyclopropylamino)-3-oxo-2-(1H-indol-3-yl)prop-1-en-1-yl)benzamide;

N-(2-Aminophenyl)-4-(3-(cyclopropylamino)-3-oxo-2-biphenyl-4-yl-prop-1-en-1-yl)benzamide;

4-(2-(4-Fluorophenyl)-3-(cyclopropylamino)-3-oxoprop-1-en-1-yl)-N-(2-hydroxy phenyl)benzamide;

N-(2-Aminophenyl)-4-[3-(cyclopropylamino)-3-oxo-2-pyridin-3-yl-prop-1-en-1-yl]benzamide;

N-(2-Aminophenyl)-4-(2-(4-hydroxyphenyl)-3-(cyclopropylamino)-3-oxoprop-1-en-1-yl)benzamide;

N-(2-Aminophenyl)-4-(2-(2,6-difluorophenyl)-3-(cyclopropylamino)-3-oxoprop-1-en-1-yl)benzamide;

N-(2-Aminophenyl):4-(2-(2,5-difluorophenyl)-3-(cyclopropylamino)-3-oxoprop-1-en-1-yl)benzamide;

N-(2-Aminophenyl)-4-(2-(4-fluorophenyl)-3-(isopropylamino)-3-oxoprop-1-en-1-yl)benzamide;

N-(4-Aminobiphenyl-3-yl)-4-(3-(cyclopropylamino)-2-(4-fluorophenyl)-3-oxo prop-1-enyl)benzamide;

N-(2-Aminophenyl)-4-(3-(cyclopropylamino)-2-(2-methylphenyl)-3-oxoprop-1-en-1-yl)benzamide;

N-(2-Aminophenyl)-4-(3-(methylamino)-2-(4-fluorophenyl)-3-oxoprop-1-en-1-yl)benzamide;

(Z)—N-(2-Aminophenyl)-4-(2-(4-fluorophenyl)-3-(cyclopropylamino)-3-oxoprop-1-en-1-yl)benzamide;

N-(2-Aminophenyl)-4-[2-(4-fluorophenyl)-3-morpholin-4-yl-3-oxoprop-1-en-1-yl]benzamide;

N-(2-Aminophenyl)-4-(3-(cyclopropylamino)-1-(4-fluorophenyl)-3-oxoprop-1-en-1-yl)benzamide;

N-(2-Aminophenyl)-3-(3-(cyclopropylamino)-1-(4-fluorophenyl)-3-oxoprop-1-en-1-yl)benzamide;

N-(2-Aminophenyl)-4-(3-(phenylamino)-2-(4-fluorophenyl)-3-oxoprop-1-en-1-yl)benzamide;

4-[3-Amino-2-(4-fluorophenyl)-3-oxoprop-1-en-1-yl]-N-(2-aminophenyl)benzamide;

N-(2-Aminophenyl)-4-(2-(4-cyclopentyloxyphenyl)-3-(cyclopropylamino)-3-oxoprop-1-en-1-yl)benzamide;

N-(2-Aminophenyl)-4-(2-(4-cyclopropylmethoxyphenyl)-3-(cyclopropylamino)-3-oxoprop-1-en-1-yl)benzamide;

N-(2-Aminophenyl)-4-(3-(benzylamino)-2-(4-fluorophenyl)-3-oxoprop-1-en-1-yl)benzamide;

N-(2-Aminophenyl)-4-(3-(cyclopropylamino)-2-(4-fluorophenyl)prop-1-en-1-yl)benzamide;

4-(3-(Cyclopropylamino)-2-(4-fluorophenyl)-3-oxoprop-1-en-1-yl)-N-(4-((E)3-(hydroxyamino)-3-oxoprop-1-en-1-yl)benzyl)benzamide;

4-(3-(Cyclopropylamino)-2-phenyl-3-oxoprop-1-en-1-yl)-N-(4-((E)-3-(hydroxyamino)-3-oxoprop-1-en-1-yl)benzyl)benzamide;

4-(3-(Cyclopropylamino)-2-[benzodioxol-5-yl]-3-oxoprop-1-en-1-yl)-N-(4-((E)-3-(hydroxyamino)-3-oxoprop-1-en-1-yl)benzyl)benzamide;

4-(3-(Cyclopropylamino)-2-(4-methylphenyl)-3-oxoprop-1-en-1-yl)-N-(4-(hydroxycarbamoyl)benzyl)benzamide;

4-(3-(Cyclopropylamino)-2-phenyl-3-oxoprop-1-en-1-yl)-N-(4-(hydroxycarbamoyl)benzyl)benzamide;

4-(3-(Cyclopropylamino)-2-(2-fluorophenyl)-3-oxoprop-1-en-1-yl)-N-(4-(hydroxycarbamoyl)benzyl)benzamide;

4-(3-(Cyclopropylamino)-2-(2-chlorophenyl)-3-oxoprop-1-en-1-yl)-N-(4-(hydroxycarbamoyl)benzyl)benzamide;

4-(3-(Cyclopropylamino)-2-(4-fluorophenyl)-3-oxoprop-1-en-1-yl)-N-(4-(hydroxycarbamoyl)benzyl)benzamide;

4-(3-(Cyclopropylamino)-2-(3-chlorophenyl)-3-oxoprop-1-en-1-yl)-N-(4-(hydroxycarbamoyl)benzyl)benzamide;

4-(3-(Cyclopropylamino)-2-(4-methoxyphenyl)-3-oxoprop-1-en-1-yl)-N-(4-(hydroxycarbamoyl)benzyl)benzamide;

4-(3-(Cyclopropylamino)-2-(2-chloro-4-fluorophenyl)-3-oxoprop-1-en-1-yl)-N-(4-(hydroxycarbamoyl)benzyl)benzamide;

4-(3-(Cyclopropylamino)-2-(3-fluorophenyl)-3-oxoprop-1-en-1-yl)-N-(4-(hydroxy carbamoyl)benzyl)benzamide;

4-(3-(Cyclopropylamino)-2-[benzodioxol-5-yl]-3-oxoprop-1-en-1-yl)-N-(4-(hydroxycarbamoyl)benzyl)benzamide;

4-(3-(Cyclopropylamino)-2-(4-trifluoromethylphenyl)-3-oxoprop-1-en-1-yl)-N-(4-(hydroxycarbamoyl)benzyl)benzamide;

4-(3-(Cyclopropylamino)-2-(3,4-difluorophenyl)-3-oxoprop-1-en-1-yl)-N-(4-(hydroxycarbamoyl)benzyl)benzamide;

4-(3-(Cyclopropylamino)-2-(4-fluorophenyl)-3-oxoprop-1-en-1-yl)-N-(6-(hydroxyamino)-6-oxohexyl)benzamide;

4-(3-(Cyclopropylamino)-2-phenyl-3-oxoprop-1-en-1-yl)-N-(6-hydroxyamino-6-oxohexyl)benzamide;

4-(3-(Cyclopropylamino)-2-(4-methylphenyl)-3-oxoprop-1-en-1-yl)-N-(6-(hydroxyamino)-6-oxohexyl)benzamide;

4-(3-(Cyclopropylamino)-2-(2-fluorophenyl)-3-oxoprop-1-en-1-yl)-N-(6-(hydroxyamino)-6-oxohexyl)benzamide;

4-(3-(Cyclopropylamino)-2-(3-fluorophenyl)-3-oxoprop-1-en-1-yl)-N-(6-(hydroxyamino)-6-oxohexyl)benzamide;

N-(4-(3-(Cyclopropylamino)-2-(4-fluorophenyl)-3-oxoprop-1-en-1-yl)phenyl)-N'-hydroxyoctanediamide;

N-(2-Aminophenyl)-4-((4-(3-(cyclopropylamino)-1-(4-fluorophenyl)-3-oxoprop-1-en-2-yl)phenylamino)methyl)benzamide; and their pharmaceutically acceptable salts.

4. The compound according to claim 1 selected from:

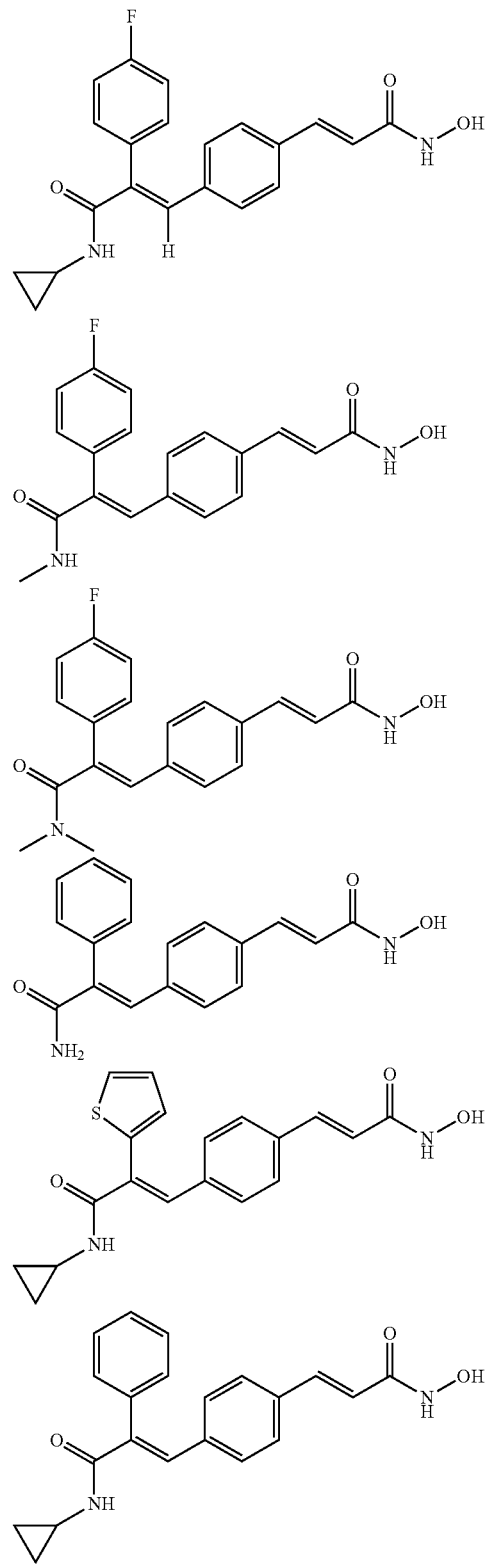

125
-continued
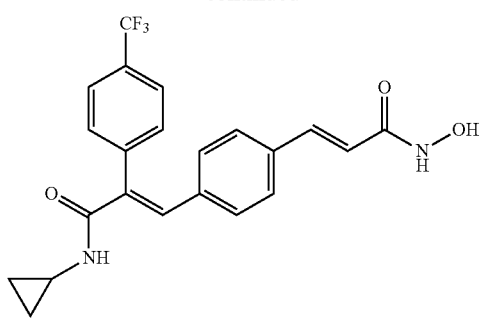
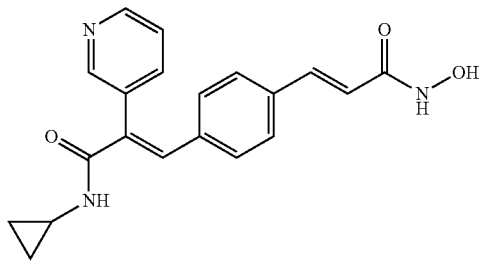
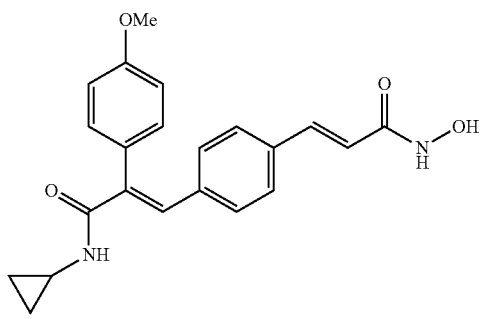
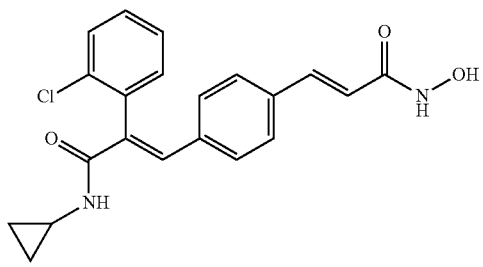
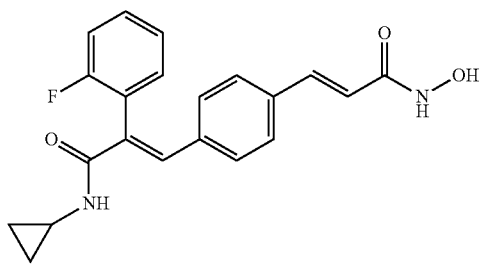
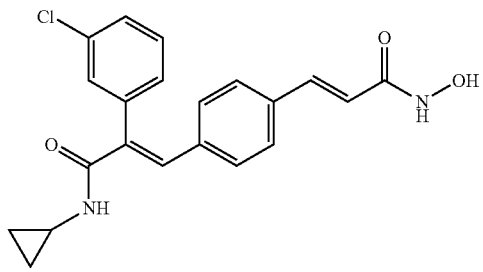
126
-continued
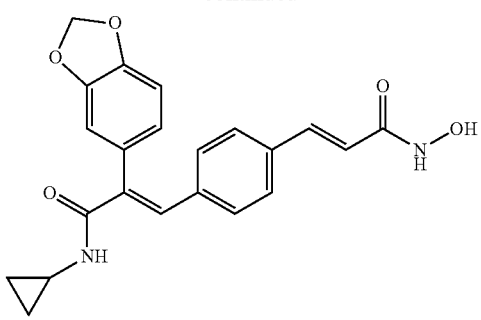
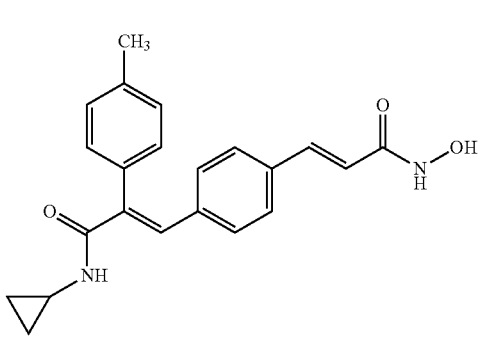
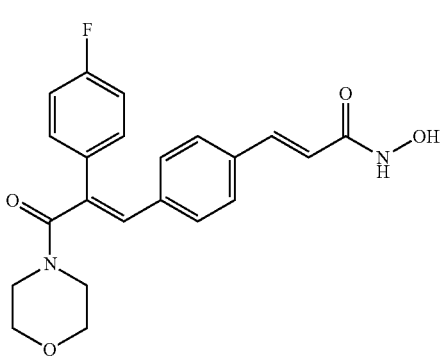
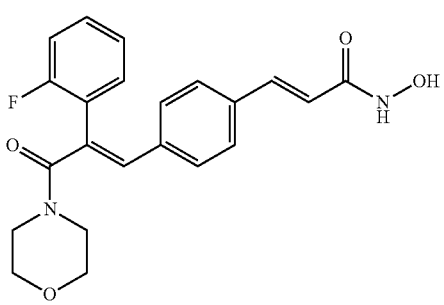
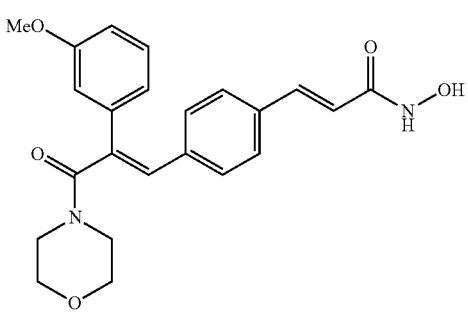

127
-continued
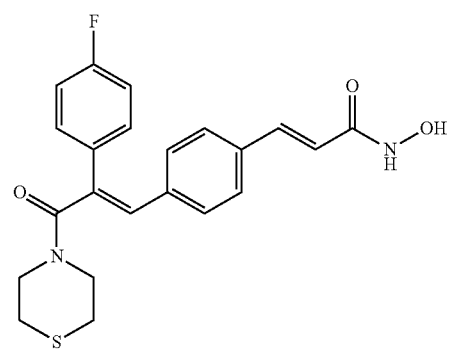
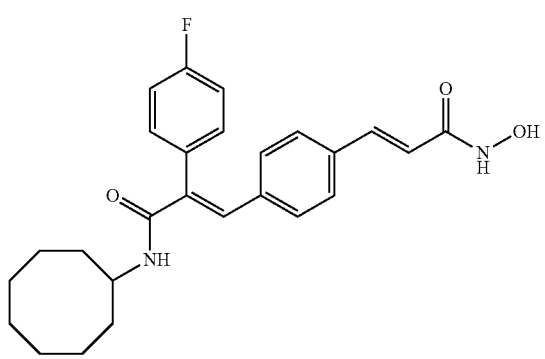
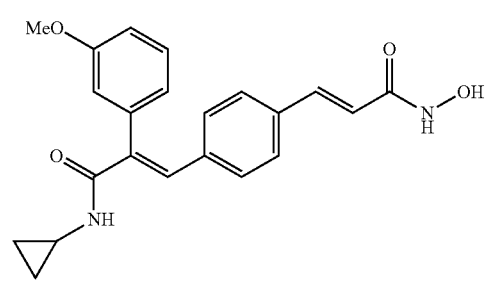
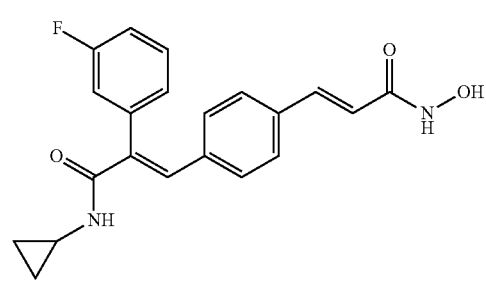
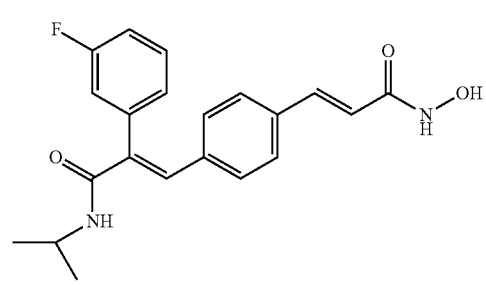
128
-continued
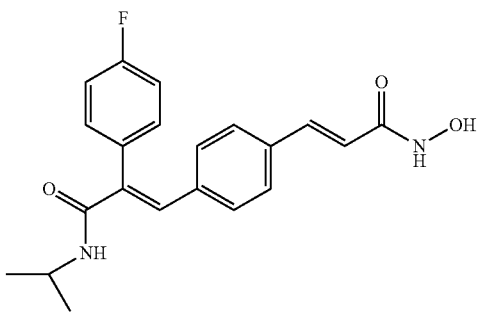
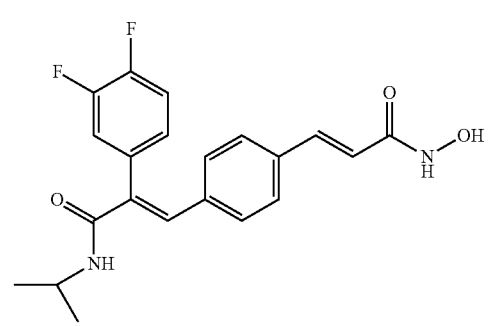
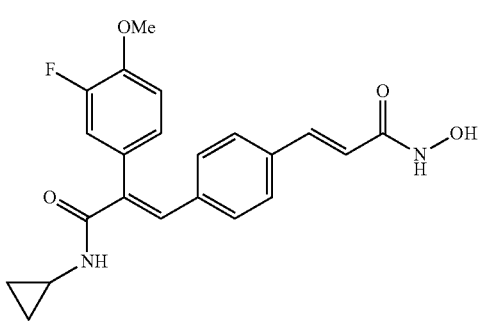
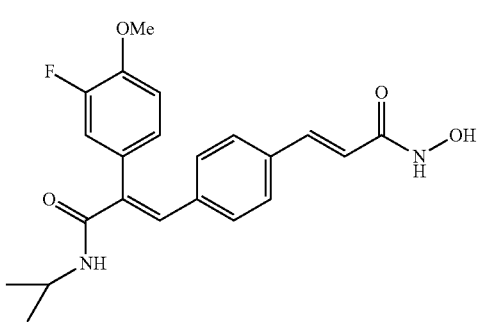
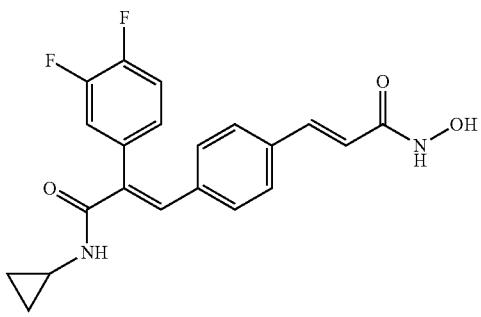

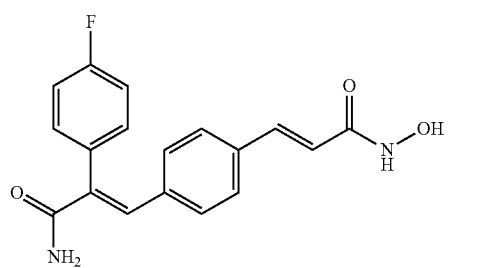
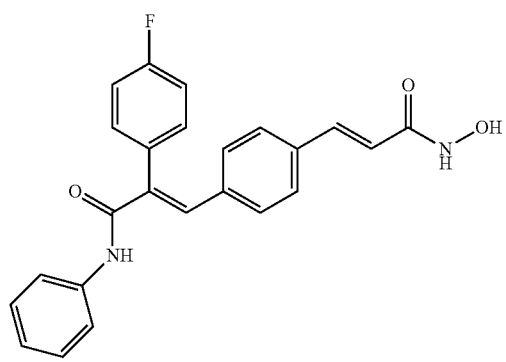
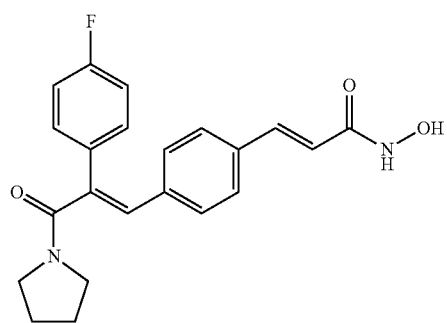
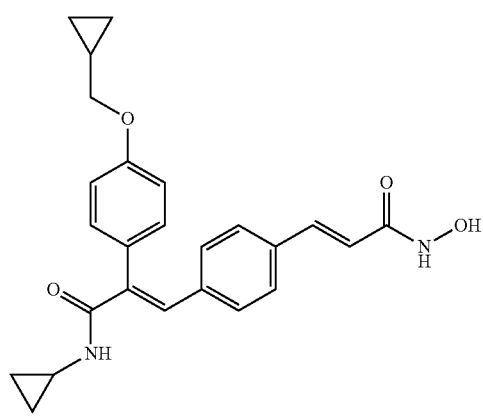
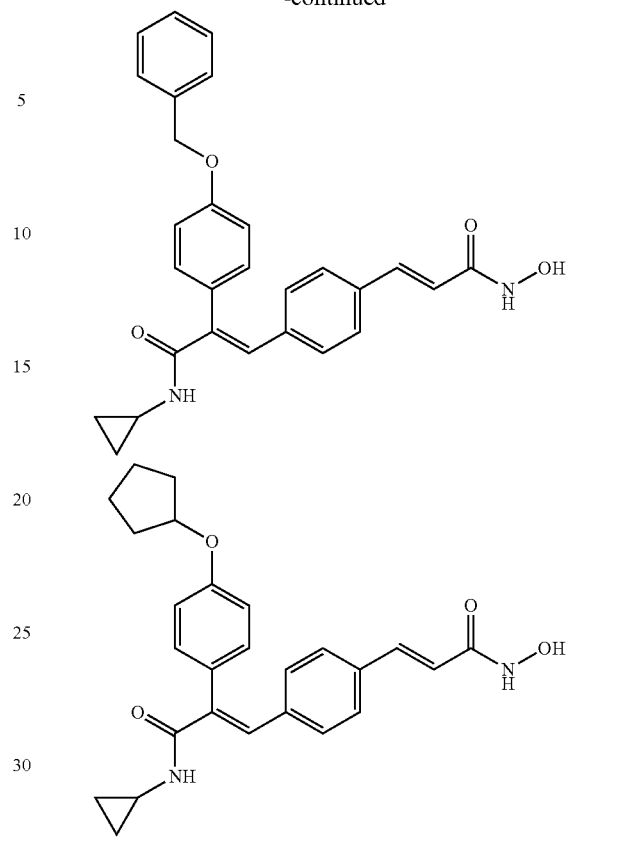
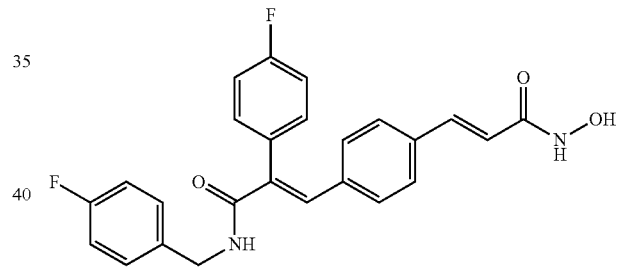
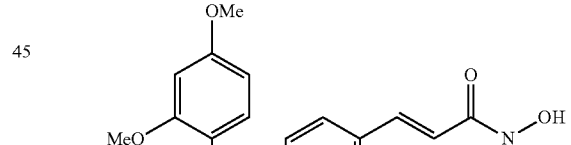
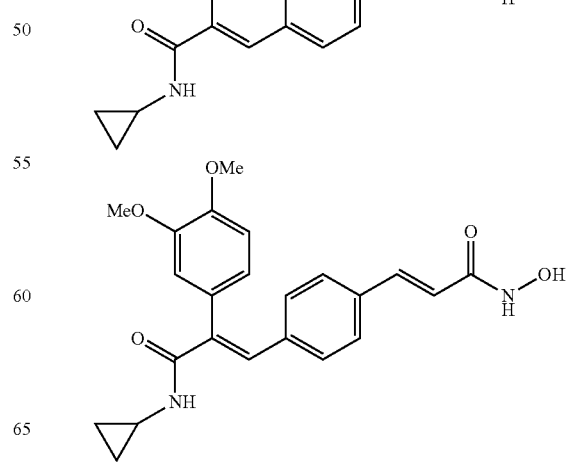

131
-continued
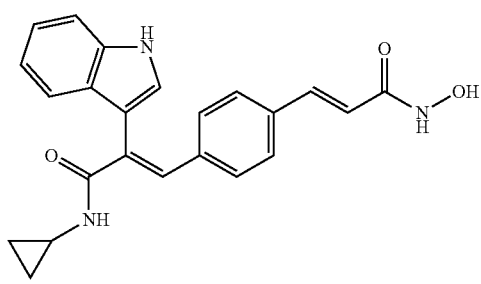
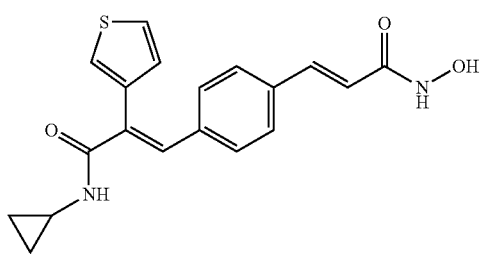
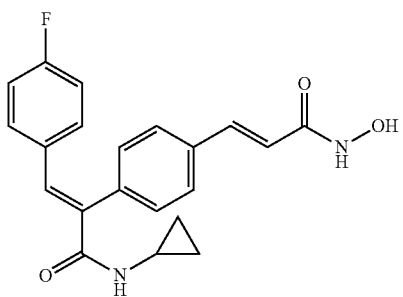
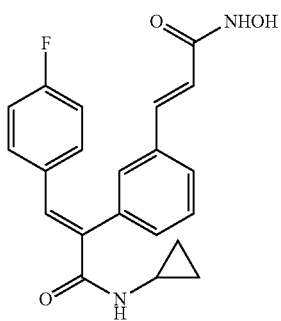
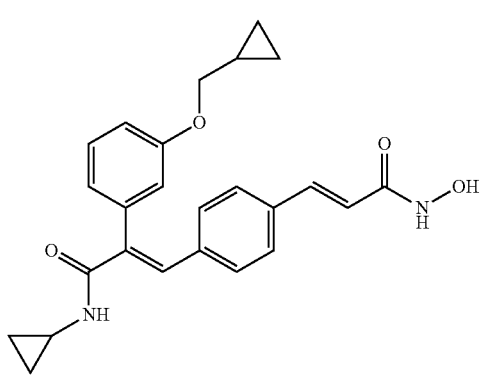
132
-continued
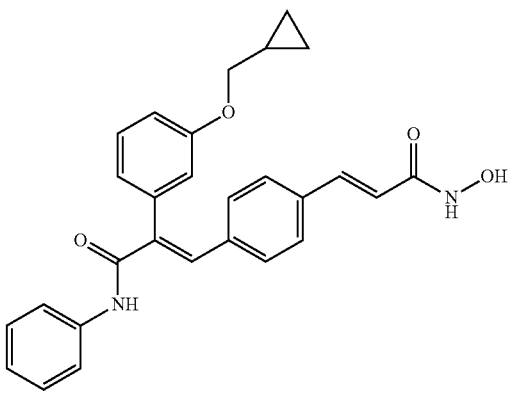
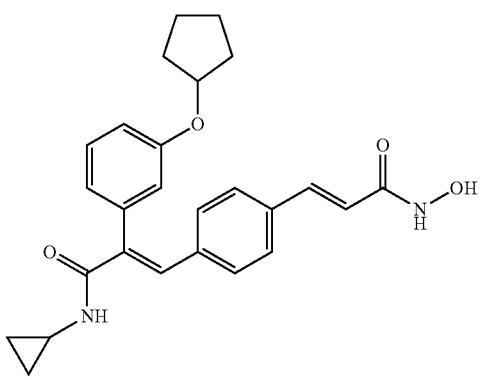
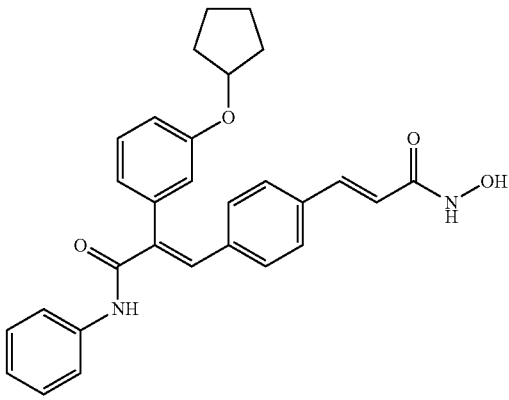
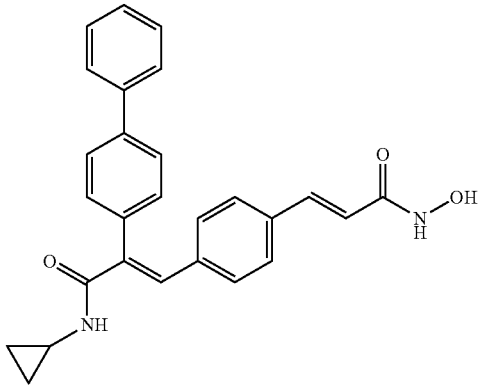

133
-continued
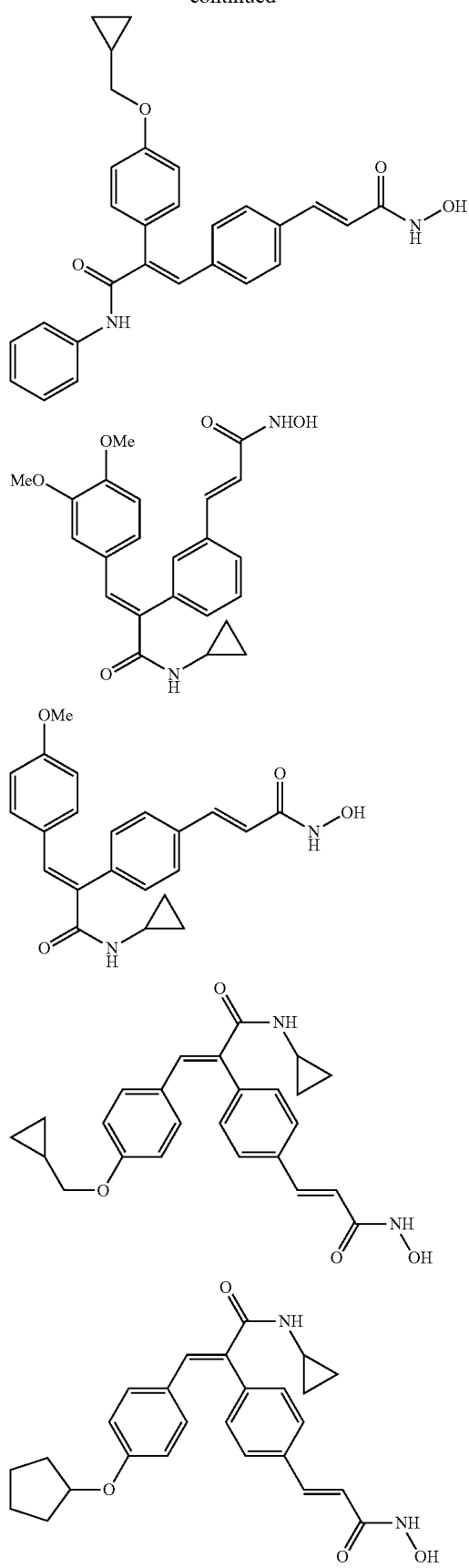
134
-continued
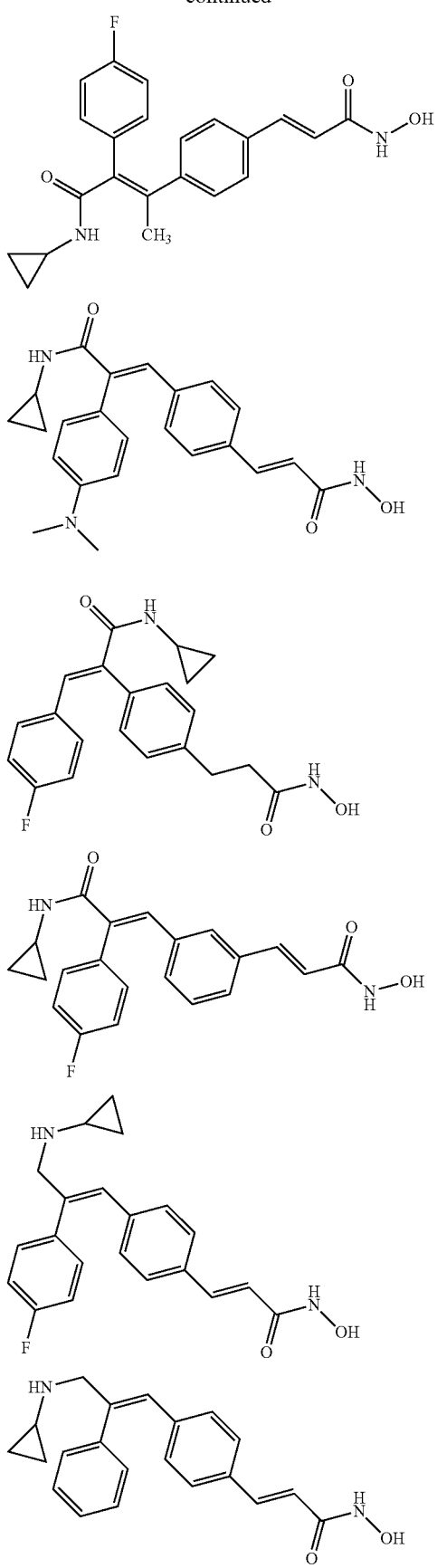

135
-continued
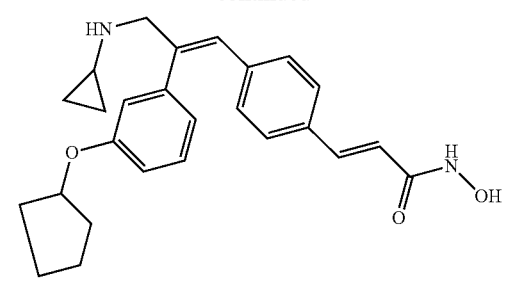
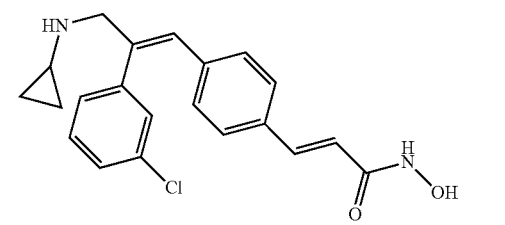
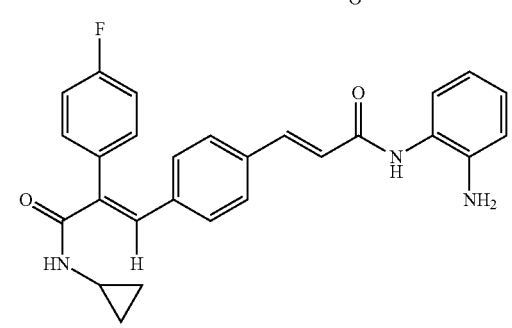
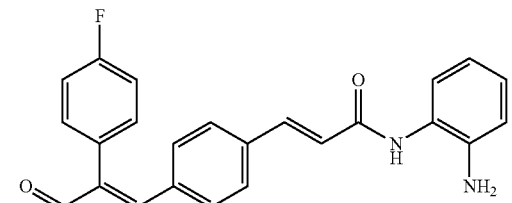
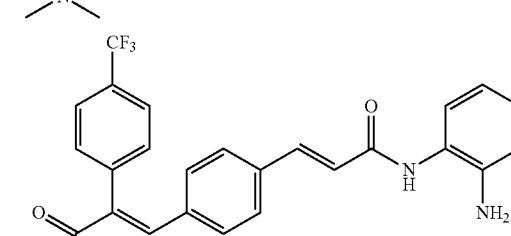
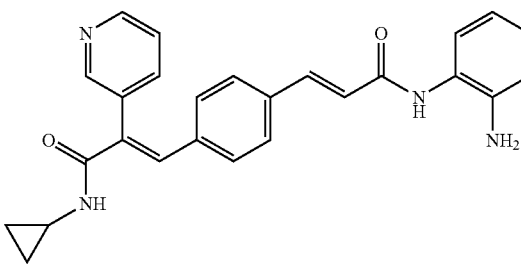
136
-continued
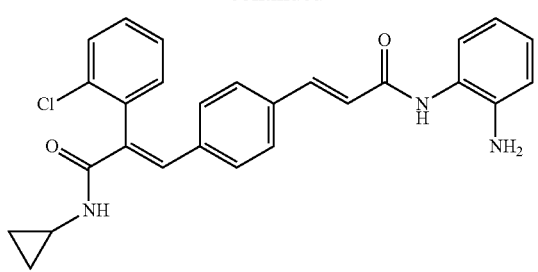
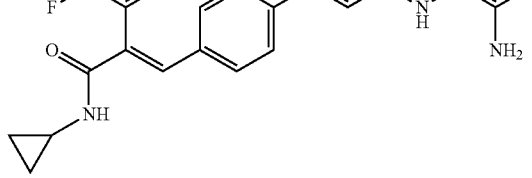
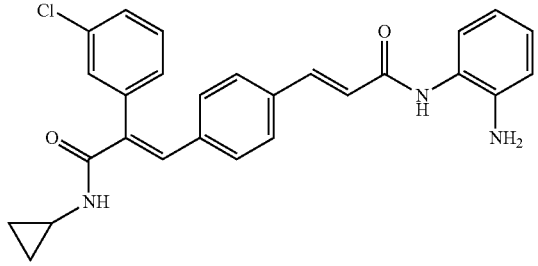
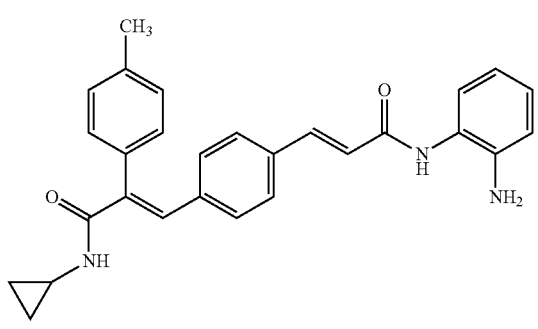

137
-continued
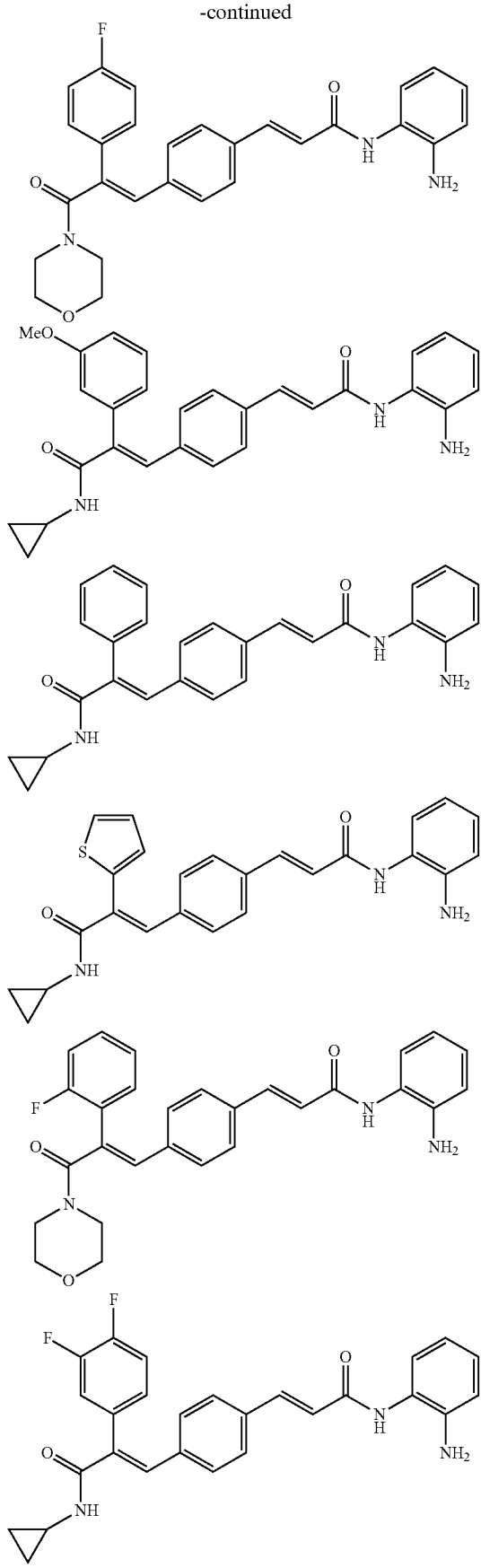
138
-continued
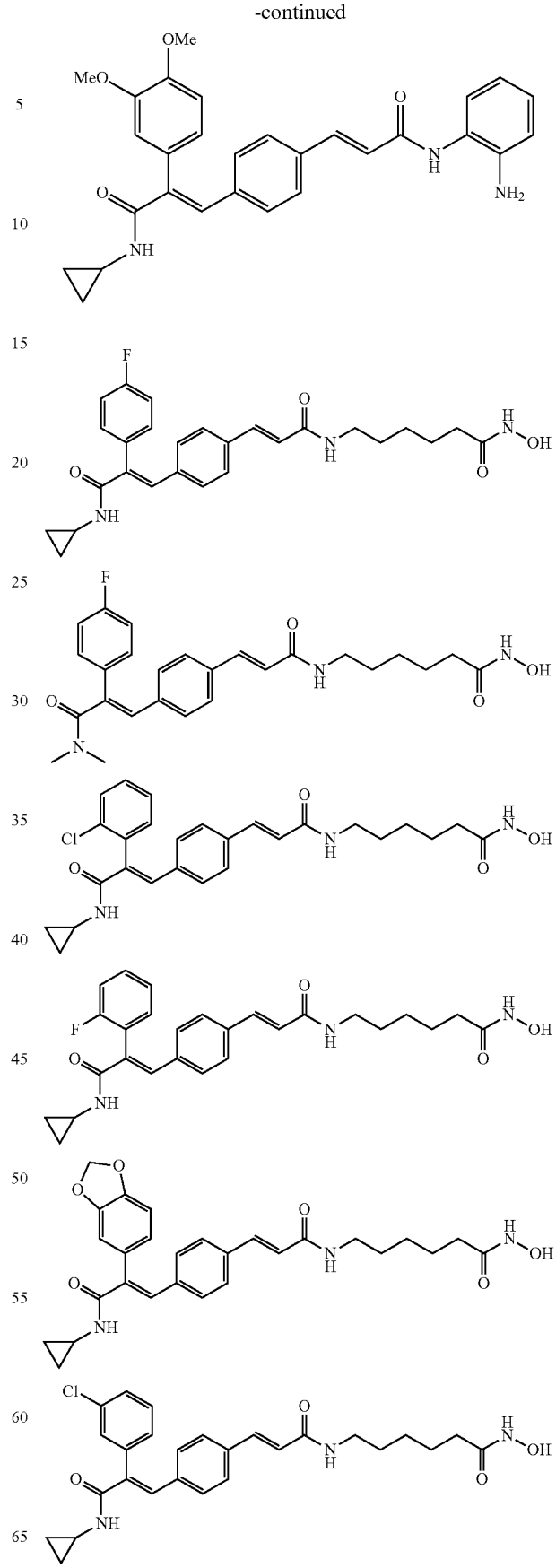

139
-continued
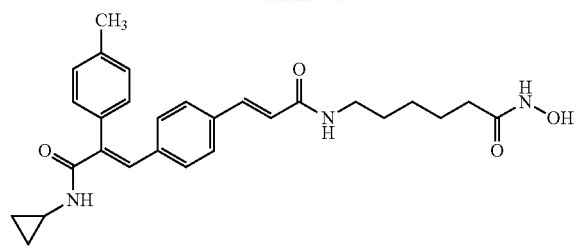
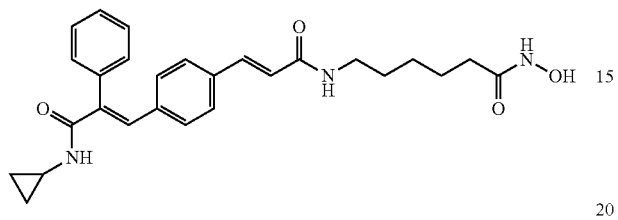
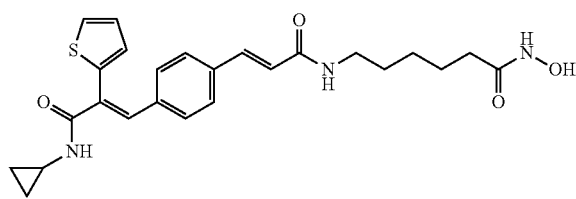
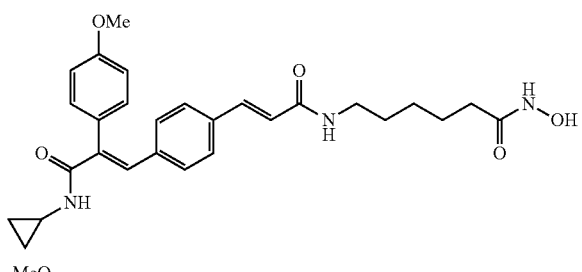
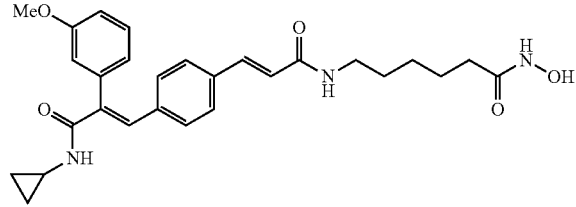
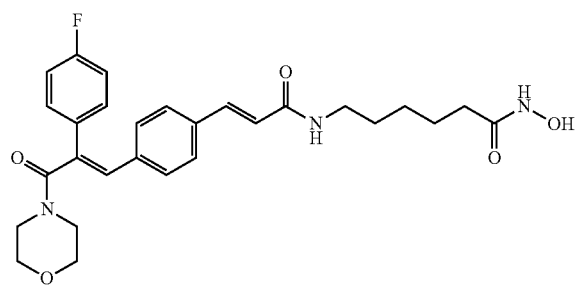
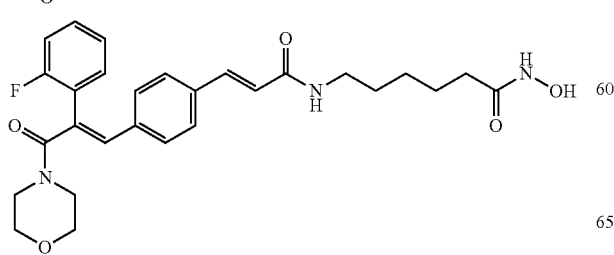
140
-continued
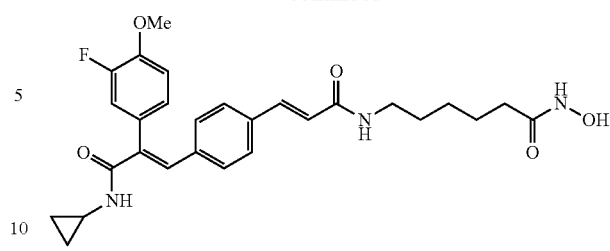
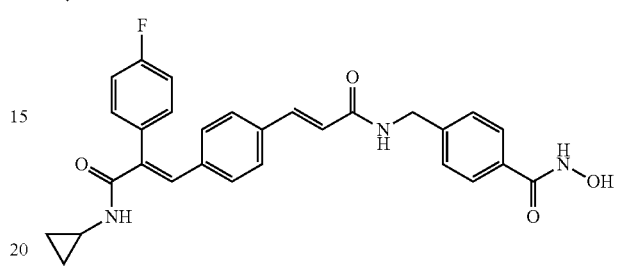
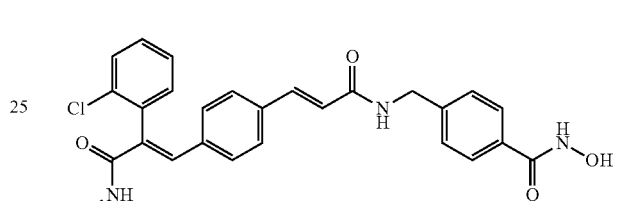
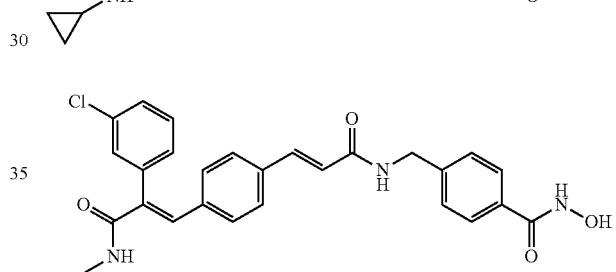
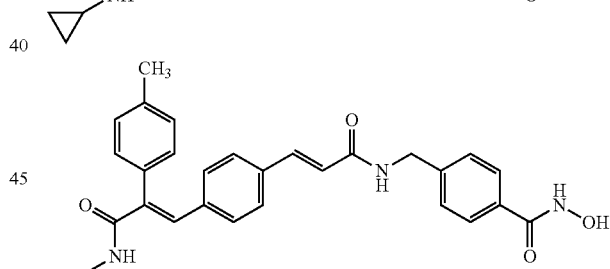
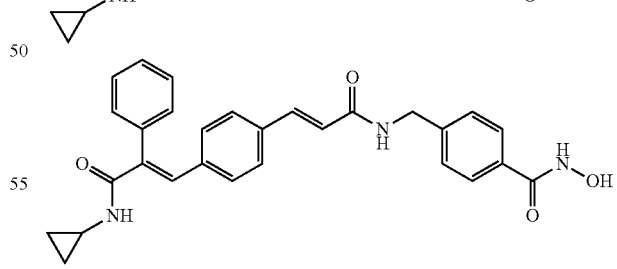
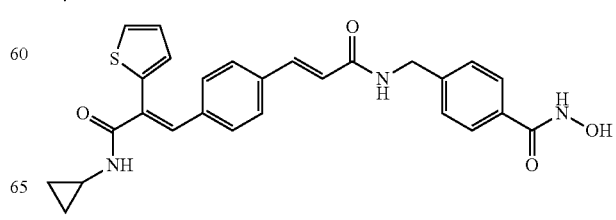

-continued
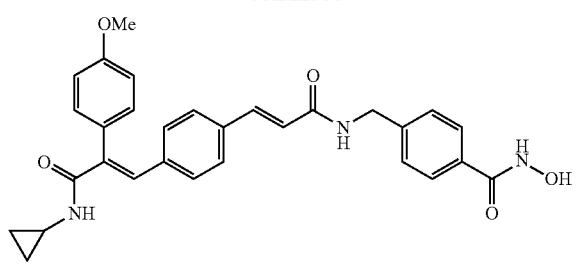
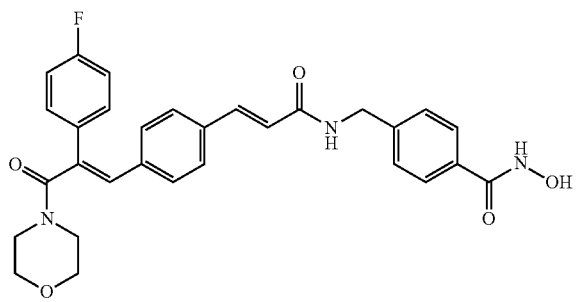
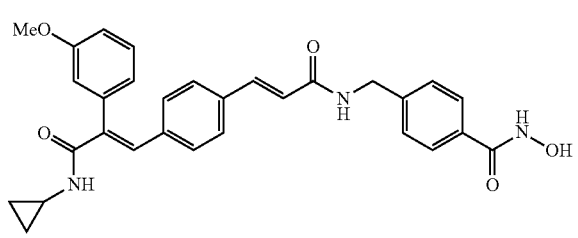
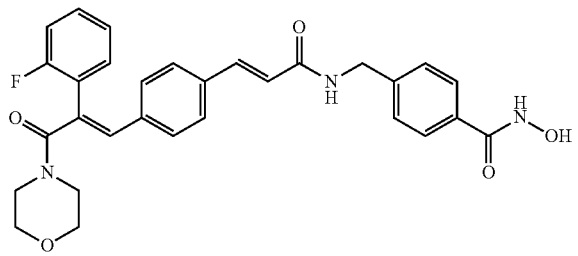
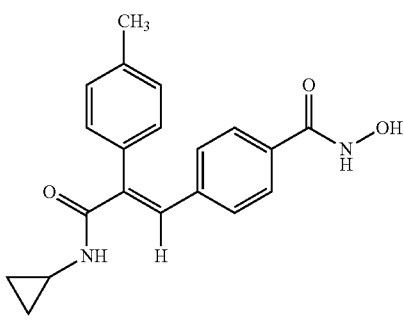
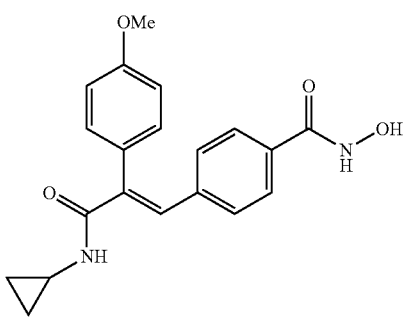
-continued
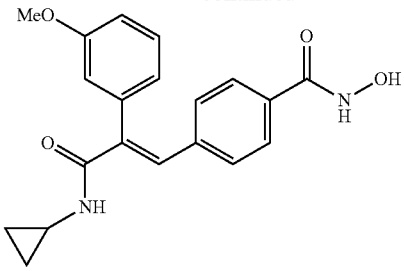
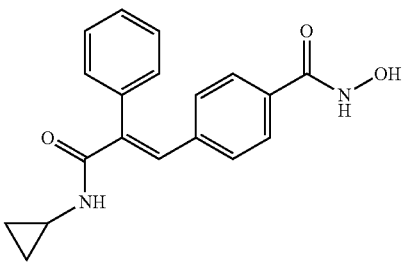
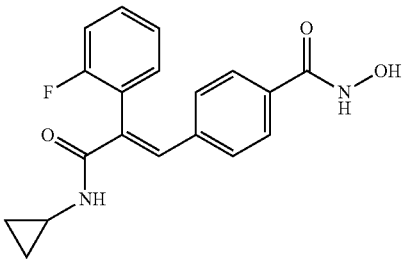
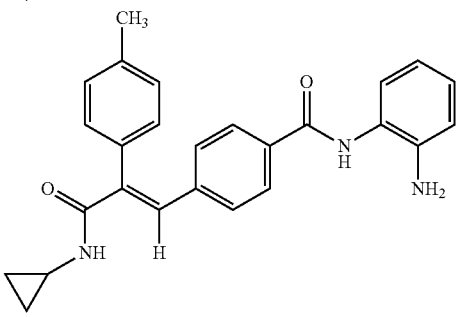
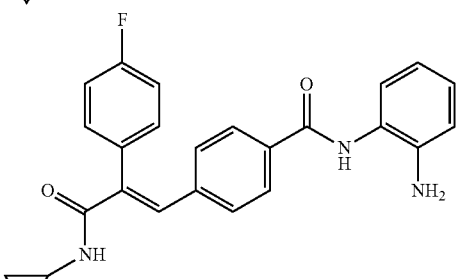
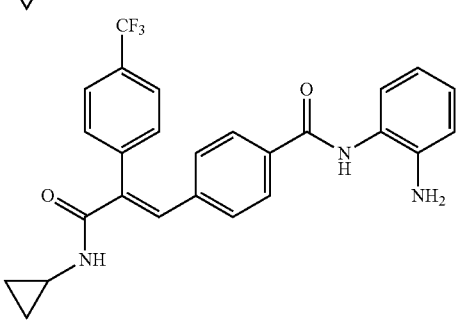

143
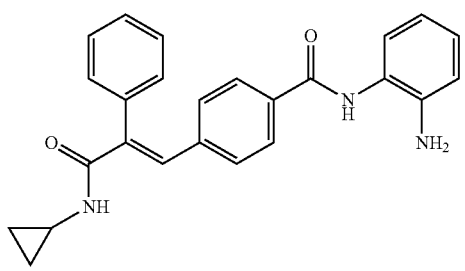
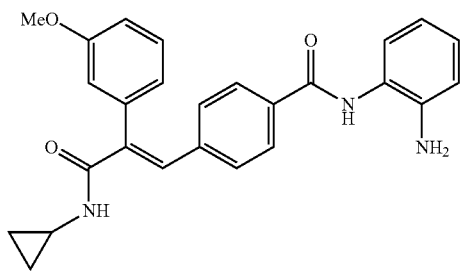
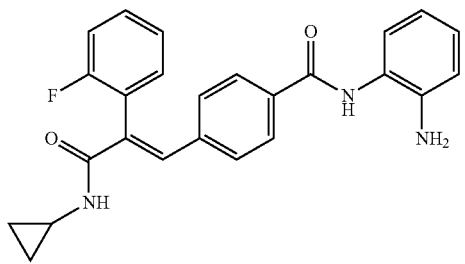
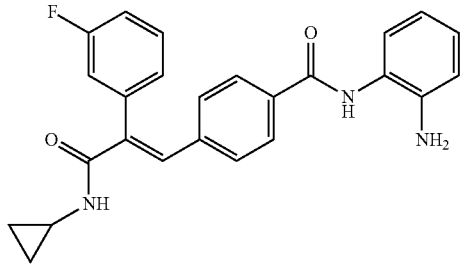
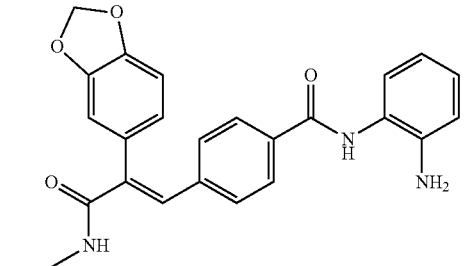
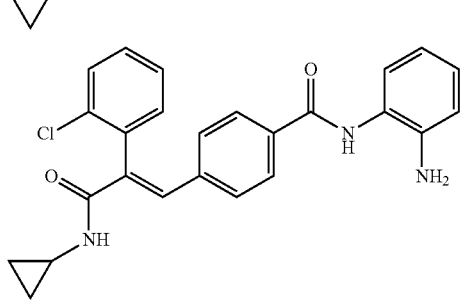
144
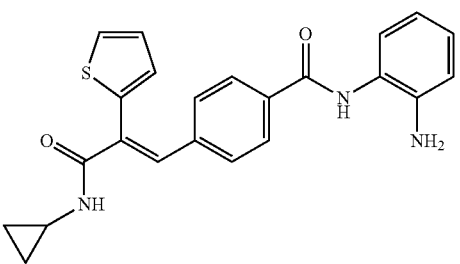
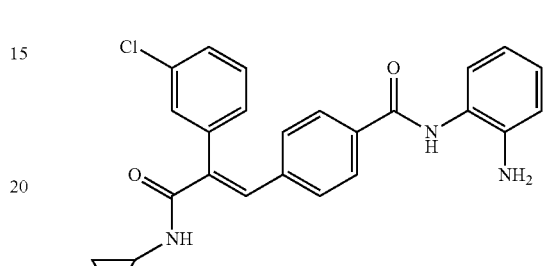
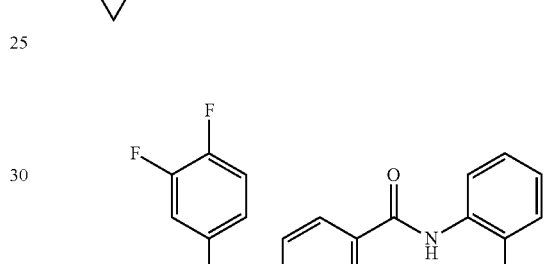
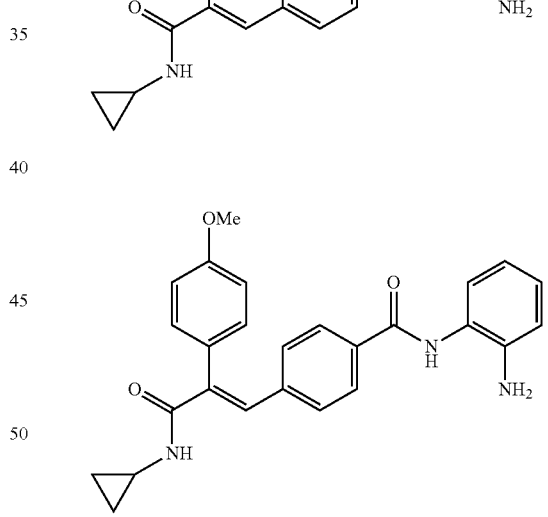
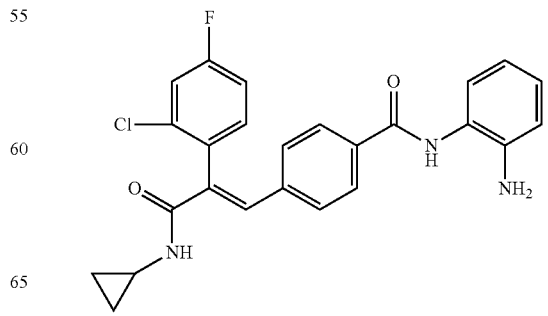

145
-continued
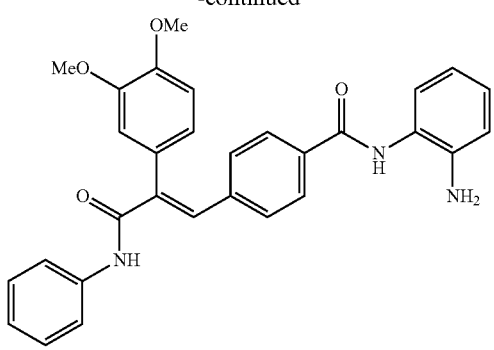
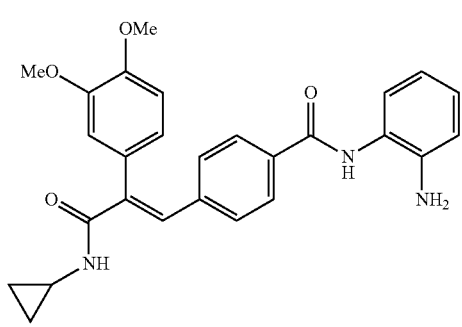
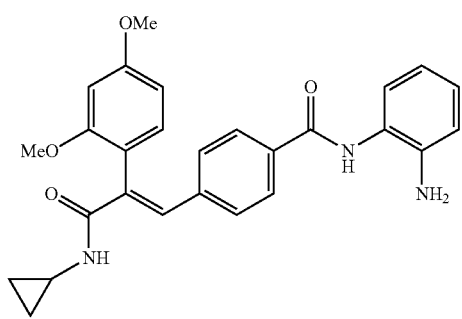
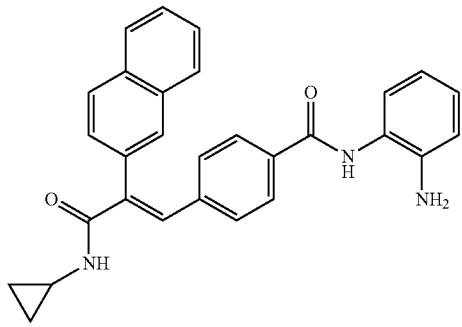
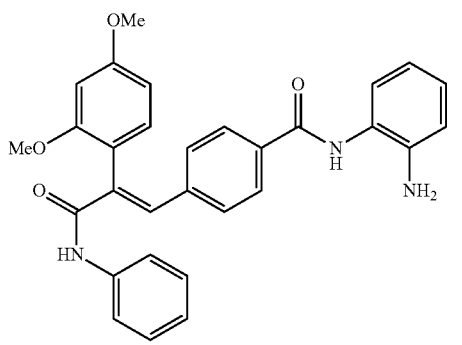
146
-continued
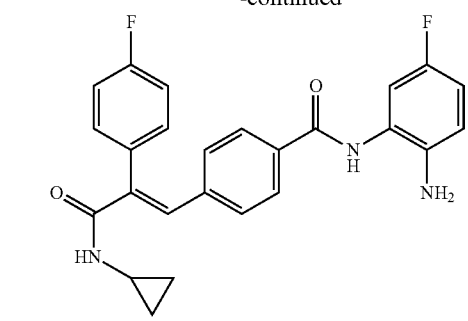
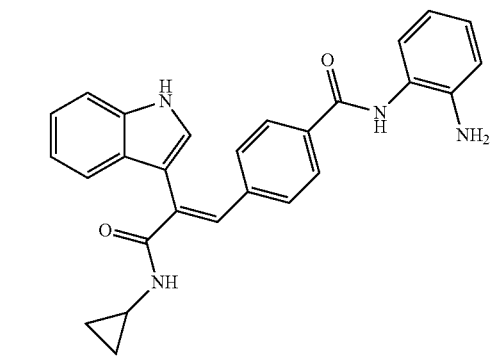
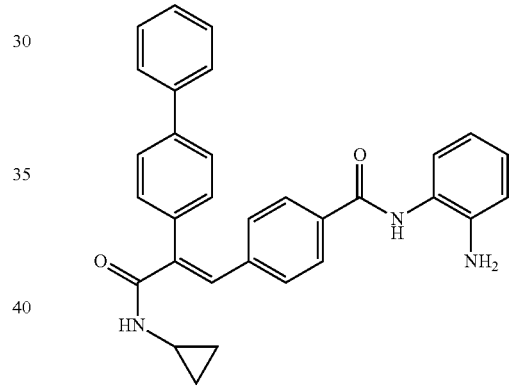
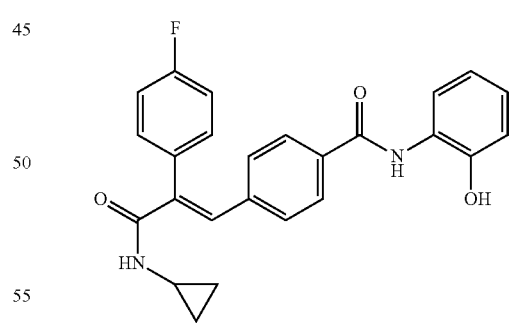
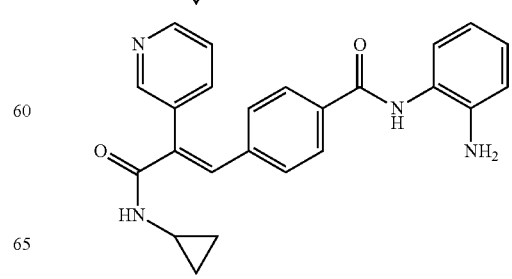

147
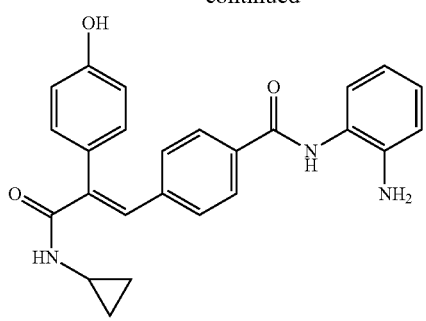
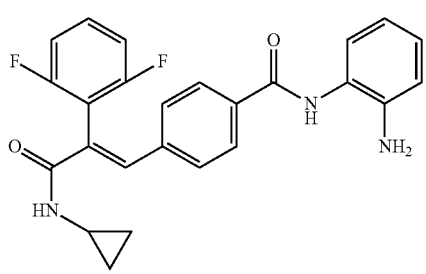
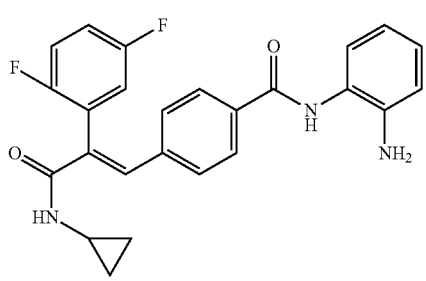
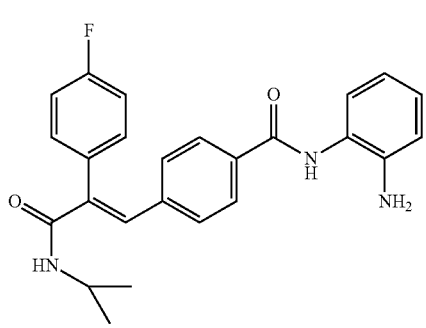
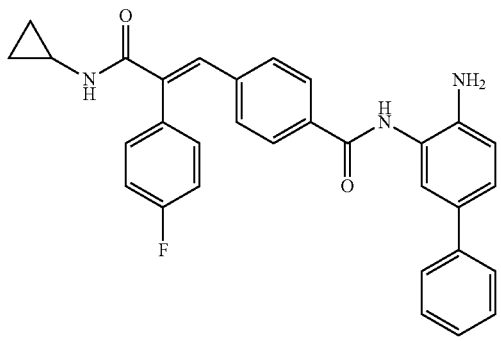
148
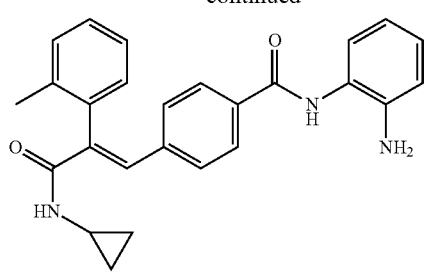
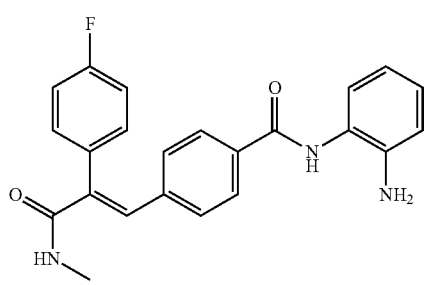
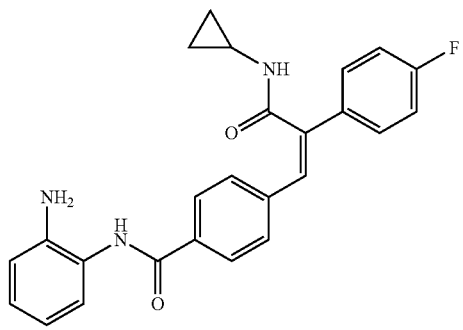
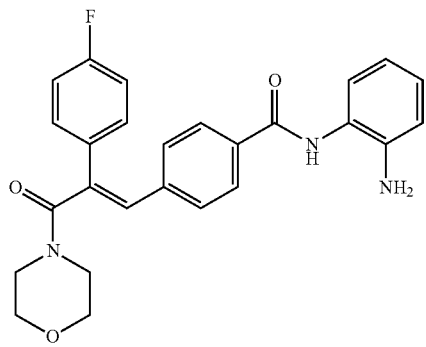
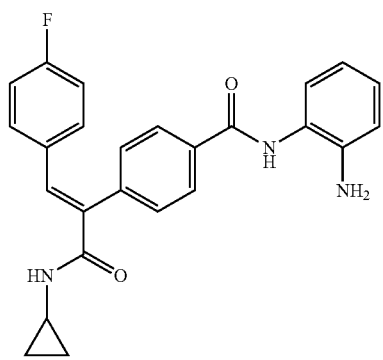

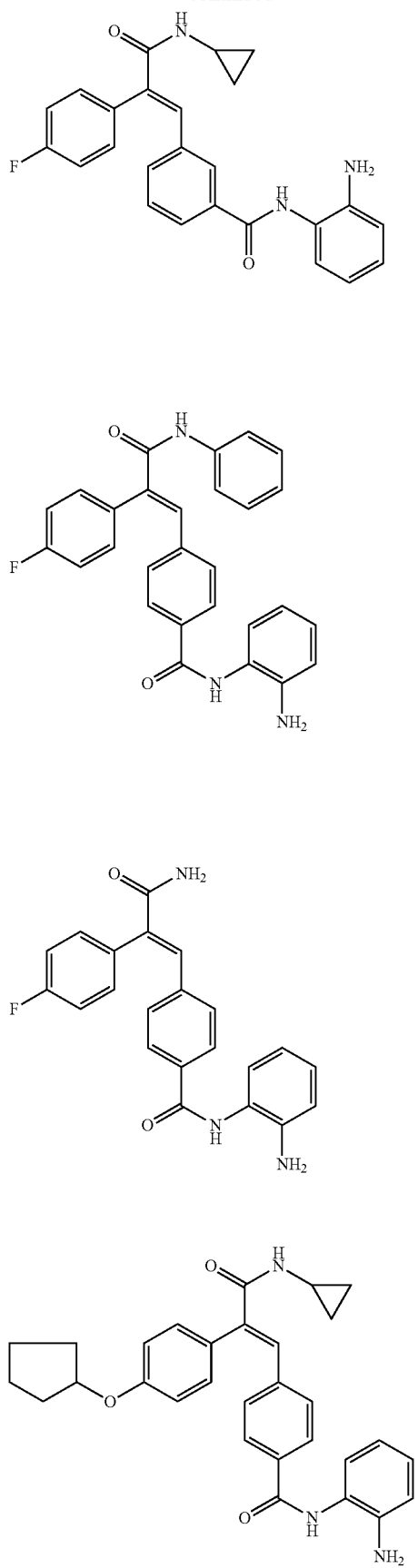

151
-continued
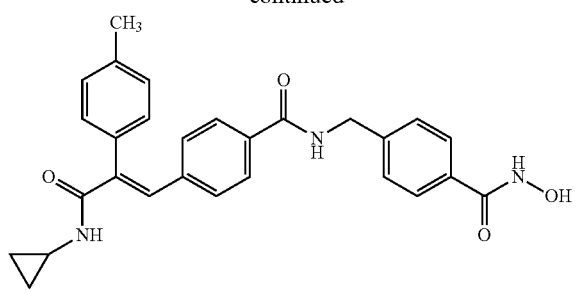
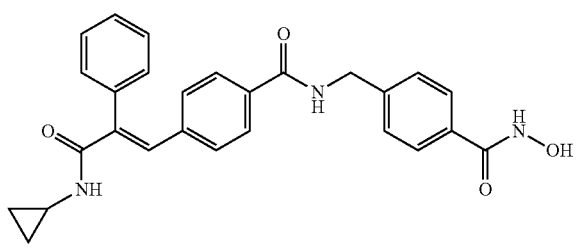
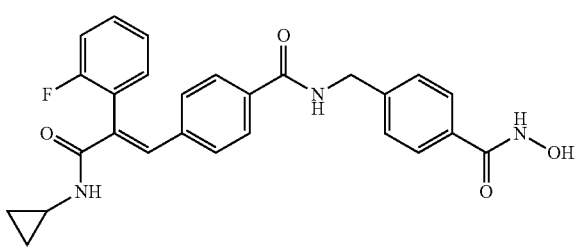
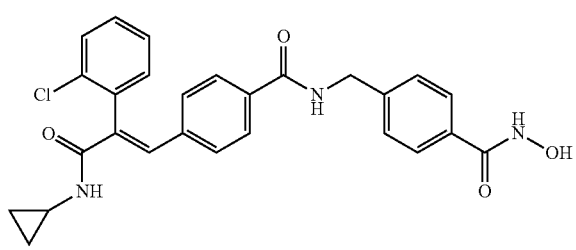
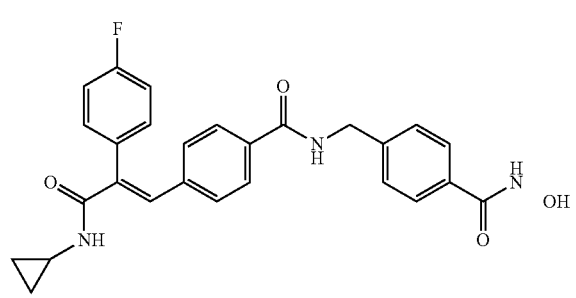
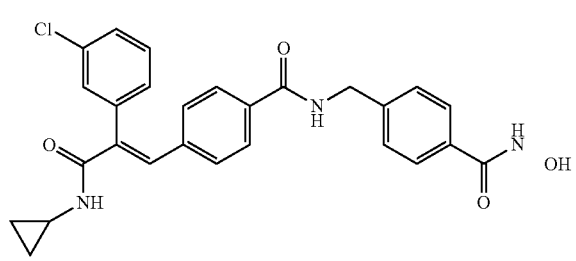
152
-continued
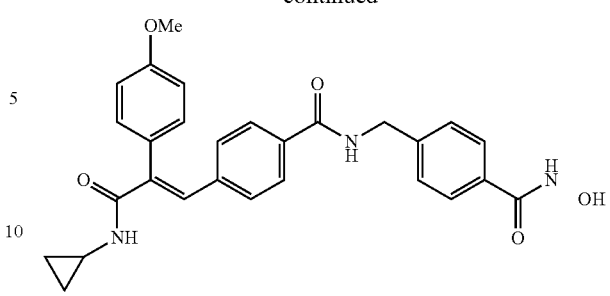
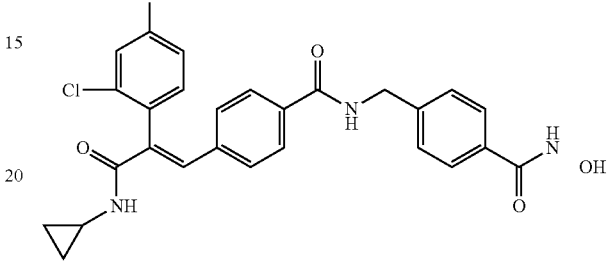
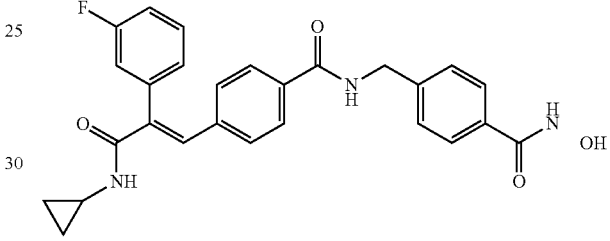
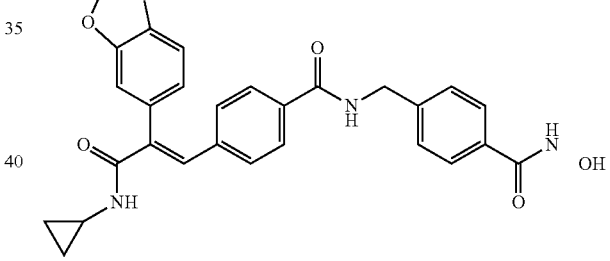
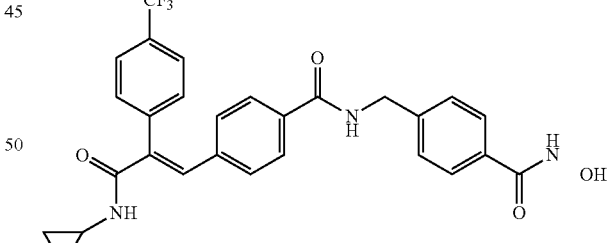
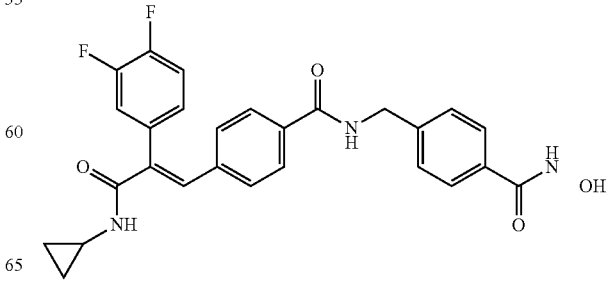

-continued

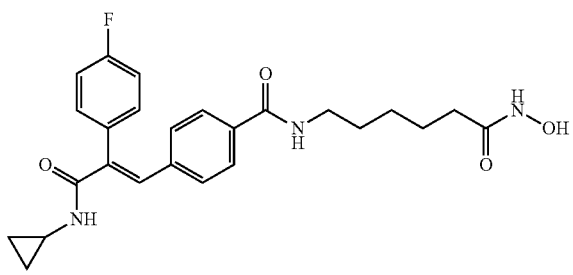

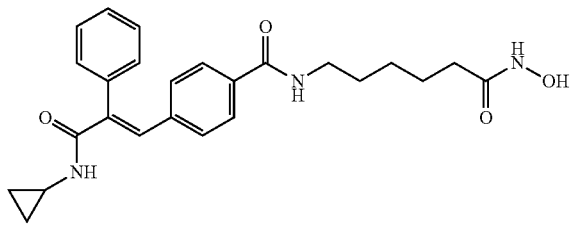

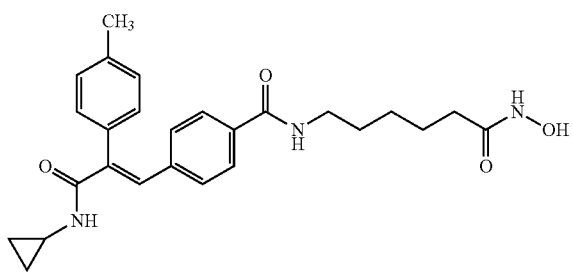

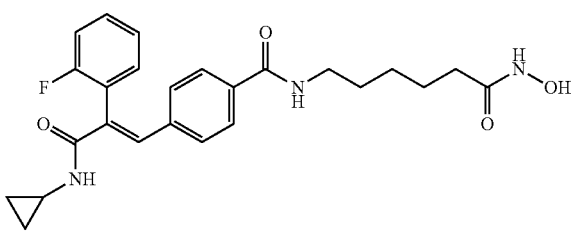

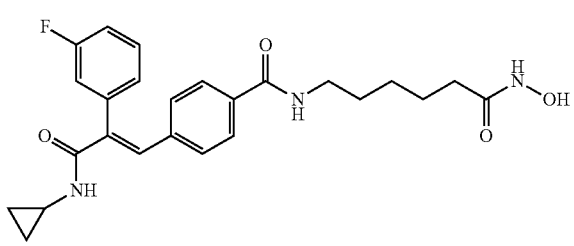

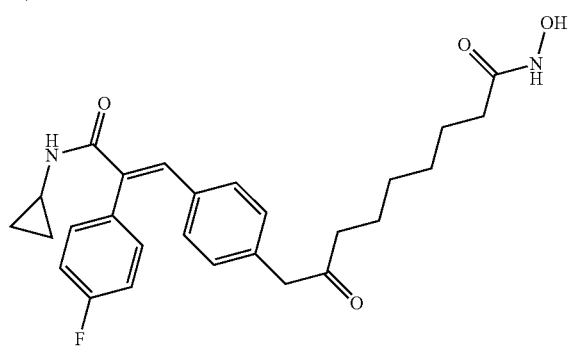

-continued

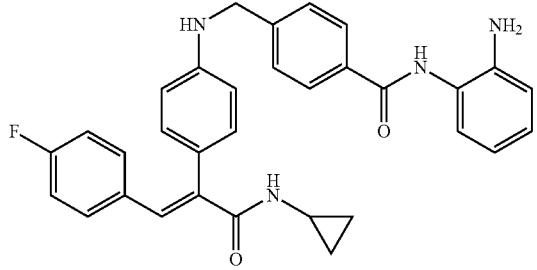 [SMILES: Nc1ccccc1NC(=O)c1ccc(CNc2ccc(/C(=C\c3ccc(F)cc3)C(=O)NC3CC3)cc2)cc1]

and their pharmaceutically acceptable salts.

5. The compound as claimed in claim 3, wherein the pharmaceutically acceptable salt is hydrochloride acid salt.

6. A process for the preparation of the compound of formula (I) as claimed in claim 1, from the compound of formula (II) reacting with $R^4NH_2$, wherein, when one of $R^2$ or $R^3$ is hydrogen or unsubstituted alkyl, the other is neither of hydrogen nor of unsubstituted alkyl and $R^4$, $R^3$, $R^2$, $R^1$, R, X, Y, m, n, o, p are as defined earlier.

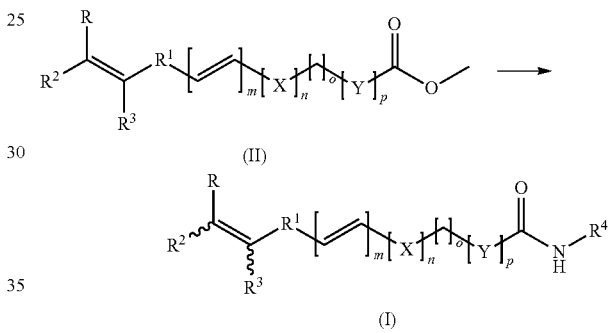

7. A compound of formula (II), or its stereoisomer, enantiomer, diastereomer or pharmaceutically acceptable salt thereof, for the preparation of the compound of formula (I) as claimed in claim 6, wherein, when one of $R^2$ or $R^3$ is hydrogen or unsubstituted alkyl, the other is neither of hydrogen nor of unsubstituted alkyl and $R^3$, $R^2$, $R^1$, R, X, Y, m, n, o, p are as defined earlier

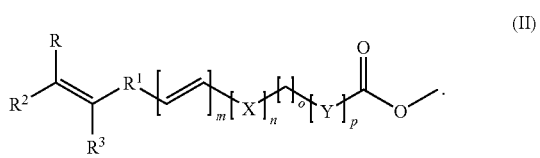

8. A pharmaceutical composition comprising the compound of formula (I), according to claim 1, as an active ingredient, along with a pharmaceutically acceptable carrier, diluent, excipient or solvate.

9. The pharmaceutical composition according to claim 8, wherein the composition is in the form of a tablet, capsule, powder, syrup, solution, aerosol or suspension.

10. A method for inhibiting HDAC in a cell comprising treating the cell with an effective amount of the compound according to claim 1.

11. A method for the treatment of a proliferative condition or cancer selected from colon cancer, lung cancer and glioma cancer, comprising administering to a subject suffering from the proliferative condition or cancer, a therapeutically effective amount of the compound according to claim 1.

12. A pharmaceutical composition comprising the compound of formula (I), according to claim 3, as an active ingredient, along with a pharmaceutically acceptable carrier, diluent, excipient or solvate.

13. A method for the treatment of a proliferative condition or cancer selected from B-cell lymphoma, T-cell lymphoma, leukemia, breast cancer, lung cancer, ovarian cancer, prostate cancer, head cancer, neck cancer, renal cancer, gastric cancer, colon cancer, pancreatic cancer and brain cancer, comprising administering to a subject suffering from the proliferative condition or cancer, a therapeutically effective amount of the compound according to claim 1.

14. A method for the treatment of a proliferative condition or cancer selected from lung cancer, colon cancer, renal cancer, ovarian cancer, breast cancer, leukemia, glioma cancer and prostate cancer, comprising administering to a subject suffering from the proliferative condition or cancer, a therapeutically effective amount of the compound according to claim 3, selected from the group consisting of:

- 4-(3-(Cyclopropylamino)-2-(4-methylphenyl)-3-oxoprop-1-en-1-yl)-N-hydroxybenzamide;
- 4-(3-(Cyclopropylamino)-2-(4-methoxyphenyl)-3-oxoprop-1-en-1-yl)-N-hydroxybenzamide;
- 4-(3-(Cyclopropylamino)-2-(3-methoxyphenyl)-3-oxoprop-1-en-1-yl)-N-hydroxybenzamide;
- 4-(3-(Cyclopropylamino)-2-phenyl-3-oxoprop-1-en-1-yl)-N-hydroxybenzamide;
- 4-(3-(Cyclopropylamino)-2-(2-fluorophenyl)-3-oxoprop-1-en-1-yl)-N-hydroxybenzamide;
- N-(2-Aminophenyl)-4-(3-(cyclopropylamino)-2-(4-methylphenyl)-3-oxoprop-1-en-1-yl)benzamide;
- (E)-N-(2-Aminophenyl)-4-(3-(cyclopropylamino)-2-(4-fluorophenyl)-3-oxoprop-1-en-1-yl)benzamide;
- N-(2-Aminophenyl)-4-(3-(cyclopropylamino)-2-(4-trifluoromethylphenyl)-3-oxoprop-1-en-1-yl)benzamide;
- N-(2-Aminophenyl)-4-(3-(cyclopropylamino)-2-phenyl-3-oxoprop-1-en-1-yl)benzamide;
- N-(2-Aminophenyl)-4-(3-(cyclopropylamino)-2-(3-methoxyphenyl)-3-oxoprop-1-en-1-yl)benzamide;
- N-(2-Aminophenyl)-4-(3-(cyclopropylamino)-2-(2-fluorophenyl)-3-oxoprop-1-en-1-yl)benzamide;
- N-(2-Aminophenyl)-4-(3-(cyclopropylamino)-2-(3-fluorophenyl)-3-oxoprop-1-en-1-yl)benzamide;
- N-(2-Aminophenyl)-4-(3-(cyclopropylamino)-2-(1,3-benzodioxol-5-yl)-3-oxoprop-1-en-1-yl)benzamide;
- N-(2-Aminophenyl)-4-(3-(cyclopropylamino)-2-(2-chlorophenyl)-3-oxoprop-1-en-1-yl)benzamide;
- N-(2-Aminophenyl)-4-(3-(cyclopropylamino)-2-(thiophen-2-yl)-3-oxoprop-1-en-1-yl)benzamide;
- N-(2-Aminophenyl)-4-(3-(cyclopropylamino)-2-(3-chlorophenyl)-3-oxoprop-1-en-1-yl)benzamide;
- N-(2-Aminophenyl)-4-(3-(cyclopropylamino)-2-(3,4-difluorophenyl)-3-oxoprop-1-en-1-yl)benzamide;
- N-(2-Aminophenyl)-4-(3-(cyclopropylamino)-2-(4-methoxyphenyl)-3-oxoprop-1-en-1-yl)benzamide;
- N-(2-Aminophenyl)-4-(3-(cyclopropylamino)-2-(2-chloro-4-fluorophenyl)-3-oxoprop-1-en-1-yl)benzamide;
- N-(2-Aminophenyl)-4-(3-(phenylamino)-2-(3,4-dimethoxyphenyl)-3-oxoprop-1-en-1-yl)benzamide;
- N-(2-Aminophenyl)-4-(3-(cyclopropylamino)-2-(3,4-dimethoxyphenyl)-3-oxoprop-1-en-1-yl)benzamide;
- N-(2-Aminophenyl)-4-(3-(cyclopropylamino)-2-(2,4-dimethoxyphenyl)-3-oxoprop-1-en-1-yl)benzamide;
- N-(2-Aminophenyl)-4-(3-(cyclopropylamino)-2-(2-naphthyl)-3-oxoprop-1-en-1-yl)benzamide;
- N-(2-Aminophenyl)-4-(3-phenylamino-2-(2,4-dimethoxyphenyl)-3-oxoprop-1-en-1-yl)benzamide;
- N-(2-Amino-5-fluorophenyl)-4-(2-(4-fluorophenyl)-3-(cyclopropylamino)-3-oxoprop-1-en-1-yl)benzamide;
- N-(2-Aminophenyl)-4-(3-(cyclopropylamino)-3-oxo-2-(1H-indol-3-yl)prop-1-en-1-yl)benzamide;
- N-(2-Aminophenyl)-4-(3-(cyclopropylamino)-3-oxo-2-biphenyl-4-yl-prop-1-en-1-yl)benzamide;
- 4-(2-(4-Fluorophenyl)-3-(cyclopropylamino)-3-oxoprop-1-en-1-yl)-N-(2-hydroxyphenyl)benzamide;
- N-(2-Aminophenyl)-4-[3-(cyclopropylamino)-3-oxo-2-pyridin-3-yl-prop-1-en-1-yl]benzamide;
- N-(2-Aminophenyl)-4-(2-(4-hydroxyphenyl)-3-(cyclopropylamino)-3-oxoprop-1-en-1-yl)benzamide;
- N-(2-Aminophenyl)-4-(2-(2,6-difluorophenyl)-3-(cyclopropylamino)-3-oxoprop-1-en-1-yl)benzamide;
- N-(2-Aminophenyl)-4-(2-(2,5-difluorophenyl)-3-(cyclopropylamino)-3-oxoprop-1-en-1-yl)benzamide;
- N-(2-Aminophenyl)-4-(2-(4-fluorophenyl)-3-(isopropylamino)-3-oxoprop-1-en-1-yl)benzamide;
- N-(4-Aminobiphenyl-3-yl)-4-(3-(cyclopropylamino)-2-(4-fluorophenyl)-3-oxoprop-1-enyl)benzamide;
- N-(2-Aminophenyl)-4-(3-(cyclopropylamino)-2-(2-methylphenyl)-3-oxoprop-1-en-1-yl)benzamide;
- N-(2-Aminophenyl)-4-(3-(methylamino)-2-(4-fluorophenyl)-3-oxoprop-1-en-1-yl)benzamide;
- (Z)—N-(2-Aminophenyl)-4-(2-(4-fluorophenyl)-3-(cyclopropylamino)-3-oxoprop-1-en-1-yl)benzamide;
- N-(2-Aminophenyl)-4-[2-(4-fluorophenyl)-3-morpholin-4-yl-3-oxoprop-1-en-1-yl]benzamide;
- N-(2-Aminophenyl)-4-(3-(cyclopropylamino)-1-(4-fluorophenyl)-3-oxoprop-1-en-1-yl)benzamide;
- N-(2-Aminophenyl)-3-(3-(cyclopropylamino)-1-(4-fluorophenyl)-3-oxoprop-1-en-1-yl)benzamide;
- N-(2-Aminophenyl)-4-(3-(phenylamino)-2-(4-fluorophenyl)-3-oxoprop-1-en-1-yl)benzamide;
- 4-[3-Amino-2-(4-fluorophenyl)-3-oxoprop-1-en-1-yl]-N-(2-aminophenyl)benzamide;
- N-(2-Aminophenyl)-4-(2-(4-cyclopentyloxyphenyl)-3-(cyclopropylamino)-3-oxoprop-1-en-1-yl)benzamide;
- N-(2-Aminophenyl)-4-(2-(4-cyclopropylmethoxyphenyl)-3-(cyclopropylamino)-3-oxoprop-1-en-1-yl)benzamide;
- N-(2-Aminophenyl)-4-(3-(benzylamino)-2-(4-fluorophenyl)-3-oxoprop-1-en-1-yl)benzamide;
- N-(2-Aminophenyl)-4-(3-(cyclopropylamino)-2-(4-fluorophenyl)prop-1-en-1-yl)benzamide;

and their pharmaceutically acceptable salts.

15. The compound according to claim 4, wherein the pharmaceutically acceptable salt is hydrochloride acid salt.

* * * * *